(12) United States Patent
Tehrani et al.

(10) Patent No.: US 12,318,224 B2
(45) Date of Patent: Jun. 3, 2025

(54) WEARABLE BIOSENSOR DEVICE

(71) Applicant: AQUILX INCORPORATED, Bonsall, CA (US)

(72) Inventors: Farshad Tehrani, Bonsall, CA (US); Hazhir Teymourian, San Diego, CA (US); Brian Wuerstle, Pacifica, CA (US)

(73) Assignee: AQUILX INCORPORATED, Bonsall, CA (US)

( * ) Notice: Subject to any disclaimer, the term of this patent is extended or adjusted under 35 U.S.C. 154(b) by 0 days.

(21) Appl. No.: 18/586,283

(22) Filed: Feb. 23, 2024

(65) Prior Publication Data

US 2024/0285236 A1 Aug. 29, 2024

Related U.S. Application Data

(63) Continuation-in-part of application No. PCT/US2024/010775, filed on Jan. 8, 2024, which is
(Continued)

(51) Int. Cl.
*A61B 5/1486* (2006.01)
*A61B 5/00* (2006.01)
*A61B 5/145* (2006.01)

(52) U.S. Cl.
CPC ............ *A61B 5/685* (2013.01); *A61B 5/0004* (2013.01); *A61B 5/14865* (2013.01); *A61B 5/6833* (2013.01); *A61B 5/6885* (2013.01)

(58) Field of Classification Search
CPC . A61B 5/1473; A61B 5/0022; A61B 5/14514; A61B 5/14865; A61B 5/685; A61M 2037/0023
(Continued)

(56) References Cited

U.S. PATENT DOCUMENTS 4,969,468 A 11/1990 Byers et al.
6,312,612 B1 11/2001 Sherman et al.
(Continued)

FOREIGN PATENT DOCUMENTS

AU 2004200303 A1 2/2004
CN 108404286 A 8/2018
(Continued)

OTHER PUBLICATIONS

ISA, International Search Report and Written Opinion for PCT Application No. PCT/US2022/036424. Mail Date: Oct. 14, 2022. 13 pages.
(Continued)

*Primary Examiner* — Navin Natnithithadha
(74) *Attorney, Agent, or Firm* — Joseph S. Bird, III; Maynard Nexsen PC

(57) ABSTRACT

An improved wearable biosensor device having emergent properties such as extended wear life, elimination or significant reduction of warm-up time, a user-friendly insertion process that ensures secure skin-locking immediately post-insertion, enhanced durability of microneedles against breakage, superior user experience and comfort during wear, and improved scalable manufacturability. Together, these innovations not only elevate the sensor's overall performance but also its accuracy, functionality, and reliability. This novel design and functionality guarantees that the wearable biosensor device is more efficient, provides a better experience for users and establishes a new benchmark in the industry.

25 Claims, 80 Drawing Sheets

Related U.S. Application Data a continuation-in-part of application No. 18/528,763, filed on Dec. 4, 2023, which is a continuation-in-part of application No. 18/513,424, filed on Nov. 17, 2023.

(60) Provisional application No. 63/548,793, filed on Feb. 1, 2024, provisional application No. 63/447,851, filed on Feb. 23, 2023.

(58) Field of Classification Search
USPC .......................................... 600/309, 345–366
See application file for complete search history.

(56) References Cited

U.S. PATENT DOCUMENTS

| | | | |
|---|---|---|---|
| 6,611,707 | B1 | 8/2003 | Prausnitz et al. |
| 7,785,301 | B2 | 8/2010 | Yuzhakov et al. |
| 8,088,321 | B2 | 1/2012 | Ferguson et al. |
| 8,506,529 | B1 | 8/2013 | Yang et al. |
| 8,708,966 | B2 | 4/2014 | Allen et al. |
| 8,986,256 | B2 | 3/2015 | Scholten et al. |
| 9,008,745 | B2 | 4/2015 | Pushpala et al. |
| 9,182,368 | B2 | 11/2015 | Pushpala et al. |
| 9,743,870 | B2 | 8/2017 | Wang et al. |
| 9,933,387 | B1 | 4/2018 | McCanna et al. |
| 10,034,636 | B2 | 7/2018 | Huang |
| 10,092,207 | B1 | 10/2018 | Windmiller |
| 10,492,708 | B1 | 12/2019 | Windmiller |
| 10,524,730 | B2 | 1/2020 | Reitz et al. |
| 10,549,080 | B2 | 2/2020 | Pushpala et al. |
| 10,820,860 | B2 | 11/2020 | Pushpala et al. |
| 10,835,163 | B2 | 11/2020 | Haghgooie et al. |
| 10,980,448 | B2 | 4/2021 | Ebeje |
| 10,987,039 | B2 | 4/2021 | Di Palma et al. |
| 11,045,142 | B1 | 6/2021 | Windmiller et al. |
| 11,172,851 | B2 | 11/2021 | Pushpala et al. |
| 11,272,866 | B2 | 3/2022 | Pushpala et al. |
| 11,478,194 | B2 | 10/2022 | Windmiller et al. |
| 11,684,298 | B2 | 6/2023 | Tehrani et al. |
| 11,877,846 | B2* | 1/2024 | Tehrani ................. A61B 5/0022 |
| 2003/0078549 | A1 | 4/2003 | Stupar et al. |
| 2005/0013753 | A1 | 1/2005 | Eaton et al. |
| 2008/0213461 | A1* | 9/2008 | Gill ...................... A61K 9/0021 |
| | | | 427/2.3 |
| 2009/0062752 | A1 | 3/2009 | Gonnelli |
| 2011/0237925 | A1 | 9/2011 | Yue et al. |
| 2013/0197338 | A1 | 8/2013 | Yu et al. |
| 2014/0336487 | A1* | 11/2014 | Wang ................... A61B 5/6833 |
| | | | 600/352 |
| 2016/0029966 | A1 | 2/2016 | Salas-Boni et al. |
| 2017/0007813 | A1 | 1/2017 | Negi et al. |
| 2017/0128009 | A1 | 5/2017 | Pushpala et al. |
| 2017/0164881 | A1 | 6/2017 | Fujita et al. |
| 2018/0338712 | A1 | 11/2018 | Cass et al. |
| 2019/0001108 | A1 | 1/2019 | Ono |
| 2019/0125223 | A1 | 5/2019 | Wang et al. |
| 2019/0240469 | A1 | 8/2019 | McAllister et al. |
| 2019/0309433 | A1 | 10/2019 | Sattayasamitsathit et al. |
| 2020/0085341 | A1 | 3/2020 | Windmiller |
| 2020/0101286 | A1 | 4/2020 | Windmiller et al. |
| 2020/0254240 | A1 | 8/2020 | Windmiller et al. |
| 2020/0297997 | A1 | 9/2020 | Windmiller et al. |
| 2021/0060322 | A1 | 3/2021 | Burton |
| 2021/0100504 | A1 | 4/2021 | Pushpala et al. |
| 2021/0187286 | A1 | 6/2021 | Windmiller et al. |
| 2021/0204878 | A1* | 7/2021 | Huang ................. A61B 5/1473 |
| 2021/0228115 | A1 | 7/2021 | Prais et al. |
| 2021/0321942 | A1 | 10/2021 | Pushpala et al. |
| 2021/0353229 | A1* | 11/2021 | Pierart ................. A61B 5/6833 |
| 2021/0379370 | A1 | 12/2021 | Windmiller et al. |
| 2021/0386373 | A1 | 12/2021 | Kendall et al. |
| 2021/0393201 | A1 | 12/2021 | Morelock et al. |
| 2022/0031209 | A1* | 2/2022 | Windmiller .......... A61B 5/0022 |
| 2022/0031244 | A1* | 2/2022 | Windmiller ........ A61B 5/14865 |
| 2022/0054813 | A1 | 2/2022 | Pushpala et al. |
| 2022/0087610 | A1 | 3/2022 | Pushpala et al. |
| 2022/0151518 | A1 | 5/2022 | Pushpala et al. |
| 2022/0151558 | A1 | 5/2022 | Pushpala et al. |
| 2022/0175278 | A1 | 6/2022 | Campbell et al. |
| 2022/0178867 | A1 | 6/2022 | Wang et al. |
| 2022/0241569 | A1* | 8/2022 | Quan ................. A61M 37/0015 |
| 2022/0249002 | A1 | 8/2022 | Chapman et al. |
| 2022/0257181 | A1 | 8/2022 | Wang et al. |
| 2022/0287598 | A1 | 9/2022 | Pierart |
| 2022/0287638 | A1 | 9/2022 | Pierart |
| 2022/0346679 | A1 | 11/2022 | Kendall et al. |
| 2022/0361776 | A1 | 11/2022 | Wang et al. |
| 2022/0370011 | A1 | 11/2022 | Windmiller et al. |
| 2023/0003725 | A1 | 1/2023 | Wang et al. |
| 2023/0012662 | A1* | 1/2023 | Tehrani .............. A61B 5/14735 |
| 2023/0099617 | A1* | 3/2023 | Mansfield, III ... A61M 37/0015 |
| 2023/0111253 | A1 | 4/2023 | Wang et al. |
| 2023/0190147 | A1 | 6/2023 | Campbell et al. |
| 2023/0277759 | A1 | 9/2023 | Kamen et al. |
| 2023/0301552 | A1* | 9/2023 | Mallires ................. A61B 5/165 |
| 2023/0320636 | A1* | 10/2023 | Tehrani .............. A61B 5/14735 |
| | | | 600/345 |
| 2024/0172973 | A1* | 5/2024 | Tehrani ................. A61B 5/0022 |
| 2024/0180459 | A1* | 6/2024 | Tehrani .............. A61B 5/14546 |

FOREIGN PATENT DOCUMENTS

| | | |
|---|---|---|
| CN | 113352654 A | 9/2021 |
| CN | 113648529 A | 11/2021 |
| CN | 114010934 A | 2/2022 |
| CN | 114129503 A | 3/2022 |
| DE | 102008048984 A1 | 4/2010 |
| EP | 1377338 A2 | 1/2004 |
| EP | 2359885 A1 | 8/2011 |
| EP | 2898821 A1 | 7/2015 |
| EP | 3285851 A1 | 2/2018 |
| EP | 3772329 A1 | 2/2021 |
| EP | 3861933 A1 | 11/2021 |
| FR | 3099696 A1 | 2/2021 |
| JP | 5053330 B2 | 10/2012 |
| KR | 100793615 B1 | 1/2008 |
| KR | 20080074058 A | 8/2008 |
| KR | 101621945 B1 | 5/2016 |
| WO | 2016/009228 A1 | 1/2016 |
| WO | 2020/186118 A1 | 9/2020 |
| WO | 2021007344 A1 | 1/2021 |
| WO | 2021/081456 A1 | 4/2021 |
| WO | 2021/119546 A1 | 6/2021 |
| WO | 2021/216186 A2 | 10/2021 |
| WO | 2021216744 A2 | 10/2021 |
| WO | 2022/170283 A1 | 8/2022 |

OTHER PUBLICATIONS

ISA, International Search Report and Written Opinion for PCT Application No. PCT/US2023/08405. Mail Date: Apr. 12, 2024. 7 pages.

ISA, International Search Report and Written Opinion for PCT Application No. PCT/US2023/82392. Mail Date: Apr. 4, 2024. 7 pages.

ISA, International Search Report and Written Opinion for PCT Application No. PCT/US2024/10775. Mail Date: Apr. 26, 2024. 7 pages.

Al Sulaiman, D. et al. Hydrogel-Coated Microneedle Arrays for Minimally Invasive Sampling and Sensing of Specific Circulating Nucleic Acids from Skin Interstitial Fluid, ACS Nano, vol. 13, 9620-9628 (2019).

Arroyo-Currás, N. et al. Real-time measurement of small molecules directly in awake, ambulatory animals, PNAS, vol. 114(4), 645-650 (2017).

Babity, S. et al. Advances in the Design of Transdermal Microneedles for Diagnostic and Monitoring Applications, Advanced Science News, vol. 14, 1-16 (2018).

Bandodkar, A. J. et al. Tattoo-Based Noninvasive Glucose Monitoring: A Proof-of-Concept Study. Anal. Chem. 87, 394-398 (2015).

(56) References Cited

OTHER PUBLICATIONS

Bollella, P. et al. Microneedle-based biosensor for minimally-invasive lactate detection, Biosensors and Bioelectronics, vol. 123, 152-159 (2019).

Bollella, P. et al. Minimally Invasive Glucose Monitoring Using a Highly Porous Gold Microneedles-Based Biosensor: Characterization and Application in Artificial Interstitial Fluid, Catalysts, vol. 9, 1-14, (2019).

Campbell, A. et al. Wearable Electrochemical Alcohol Biosensors, Curr Opin Electrochem, 1-17 (2018).

Chinnadayyala, S. et al. Review—In Vivo and In Vitro Microneedle Based Enzymatic and Non-Enzymatic Continuous Glucose Monitoring Biosensors. ECS Journal of Solid State Science and Technology, vol. 7, Q3159-Q3171 (2018).

Ciui, B. et al. Wearable Wireless Tyrosinase Bandage and Microneedle Sensors: Toward Melanoma Screening. Advanced Healthcare Materials, 1-9 (2018).

Dunn, J., et al. Wearables and the medical revolution. Per. Med. 15, 429-448 (2018).

El-Laboudi, A. et al. Use of Microneedle Array Devices for Continuous Glucose Monitoring: A Review. Diabetes Technology & Therapeutics, vol. 15(1), 101-115 (2013).

Fairbairn, C. E. et al. Temporal Dynamics of Transdermal Alcohol Concentration Measured via New-Generation Wrist-Worn Biosensor. Alcohol. Clin. Exp. Res. 43, 2060-2069 (2019).

Gao, J., et al. Simultaneous detection of glucose, uric acid and cholesterol using flexible microneedle electrode array-based biosensor and multi-channel portable electrochemical analyzer. Sensors Actuators, B Chem. 287, 102-110 (2019).

García-López, E. et al. Study of the fabrication of AISI 316L microneedle arrays. Science Direct, Procedia Manufacturing vol. 26, 117-124 (2018).

Goud, K. et al. Wearable Electrochemical Microneedle Sensor for Continuous Monitoring of Levodopa: Toward Parkinson Management. ACS Sensors, vol. 4, 2196-2204 (2019).

Gowers, S. et al. Development of a Minimally Invasive Microneedle-Based Sensor for Continuous Monitoring of β-Lactam Antibiotic Concentrations in Vivo. ACS Publications, 1072-1080 (2019).

Heikenfeld, J. et al. Accessing analytes in biofluids for peripheral biochemical monitoring. Nat. Biotechnol. 37, 407-419 (2019).

Ingrole, R. et al. Trends of microneedle technology in the scientific literature, patents, clinical trials and internet activity. Biomaterials 267, 1-24 (2021).

Jiang, X. et al. Microneedle-based skin patch for blood-free rapid diagnostic testing. Microsystems and Nanoengineering, 1-11 (2020).

Jina, A. et al. Design, Development, and Evaluation of a Novel Microneedle Array-based Continuous Glucose Monitor, Journal of Diabetes Science and Technology, vol. 8(3), 483-487 (2014).

Kathuria, H. et al. Polymeric Microneedle Array Fabrication by Photolithography. Journal of Visualized Experiments, vol. 105, 1-8 (2015).

Khezrian, S. et al. Label-free electrochemical IgE aptasensor based on covalent attachment of aptamer onto multiwalled carbon nanotubes/ionic liquid/chitosan nanocomposite modified electrode. Biosensors and Bioelectronics, vol. 43, 218-225 (2013).

Kim, J. et al. Simultaneous Monitoring of Sweat and Interstitial Fluid Using a Single Wearable Biosensor Platform, Advanced Science, 1-11 (2018).

Kim, J., et al. Wearable biosensors for healthcare monitoring. Nature Biotechnology vol. 37 389-406 (2019).

Kolluru, C. et al. Recruitment and Collection of Dermal Interstitial Fluid Using a Microneedle Patch, Adv. Healthc Mater, 1-19 (2019).

Kolluru, C. et al. Monitoring drug pharmacokinetics and immunologic biomarkers in dermal interstitial fluid using a microneedle patch, Biomed Microdevices, vol. 21(1), 1-16 (2020).

Lee, S.J. et al. A patch type non-enzymatic biosensor based on 3D SUS micro-needle electrode array for minimally invasive continuous glucose monitoring, Sensors and Actuators B: Chemical, 1144-1151 (2016).

Lipani, L. et al. Non-invasive, transdermal, path-selective and specific glucose monitoring via a graphene-based platform. Nat. Nanotechnol. 13, 504-511 (2018).

Liu, G. et al. Microneedles for transdermal diagnostics: Recent advances and new horizons, Biomaterials, 1-16 (2020).

Madden, J. et al. Biosensing in dermal interstitial fluid using microneedle based electrochemical devices. Sensing and Bio-Sensing Research, vol. 29, 1-17 (2020).

Menon, I. et al. Microneedles: A New Generation Vaccine Delivery System. Micromachines. 1-18 (2021).

Miller, P. et al. Multiplexed microneedle-based biosensor array for characterization of metabolic acidosis. Talanta, vol. 88. 739-742 (2012).

Miller, P. et al. Microneedle-based sensors for medical diagnosis. Journals of Materials Chemistry B, vol. 4, No. 8, 6 pages (2016).

Miller, P. et al. Extraction and biomolecular analysis of dermal interstitial fluid collected with hollow microneedles. Communications Biology. 1-11 (2018).

Min, J. et al. Wearable electrochemical biosensors in North America. Biosensors and Bioelectronics, vol. 172, 1-16 (2021).

Mishra, R. et al. A microneedle biosensor for minimally-invasive transdermal detection of nerve agents. Royal Society of Chemistry. 918-924 (2017).

Mishra, R. et al. Continuous Opioid Monitoring along with Nerve Agents on a Wearable Microneedle Sensor Array. Journal of the American Chemical Society, vol. 142, 5991-5995 (2020).

Mohan, A.M. et al. Continuous minimally-invasive alcohol monitoring using microneedle sensor arrays. Biosensors and Bioelectronics, vol. 91, 574-579 (2017).

Ruiz-Valdepeñas Montiel, V. et al. Delayed Sensor Activation Based on Transient Coatings: Biofouling Protection in Complex Biofluids. Journal of the American Chemical Society. vol. 140, 14050-14053 (2018).

Parrilla, M. et al. Wearable All-Solid-State Potentiometric Microneedle Patch for Intradermal Potassium Detection. Analytical Chemistry, vol. 91, 1578-1586 (2019).

Rawson, T. et al. Towards a minimally invasive device for beta-lactam monitoring in humans. Electrochem commun. 1-12 (2017).

Rawson, T. M. et al. Microneedle biosensors for real-time, minimally invasive drug monitoring of phenoxymethylpenicillin: a first-in-human evaluation in healthy volunteers. Lancet Digit. Heal. 1, e335-e343 (2019).

Ribet, F. et al. Real-time intradermal continuous glucose monitoring using a minimally invasive microneedle-based system, Biomedical Microdevices, 1-10 (2018).

Samant, P. P. et al. Sampling interstitial fluid from human skin using a microneedle patch. Sci. Transl. Med. 12, eaaw0285 (2020).

Shao, Y. et al. Recent advances in solid-contact ion-selective electrodes: functional materials, transduction mechanisms, and development trends, Chem. Soc. Rev. 4405-4465 (2020).

Sharma, S. et al. Evaluation of a minimally invasive glucose biosensor for continuous tissue monitoring, Anal Bioanal Chem, 8427-8435 (2016).

Sharma, S. et al. Rapid, low cost prototyping of transdermal devices for personal healthcare monitoring, Sens Biosensing Res. 104-108 (2017).

Sharma, S. et al. A pilot study in humans of microneedle sensor arrays for continuous glucose monitoring, Analytical Methods, 2088-2095 (2018).

Takeuchi, K. et al. Functionalized microneedles for continuous glucose monitoring, Nano Convergence, 1-10 (2018).

Tasca, F. et al. Microneedle-based electrochemical devices for transdermal biosensing: a review, Electrochemistry, 42-49 (2019).

Tehrani, F. et al. An integrated wearable microneedle array for the continuous monitoring of multiple biomarkers in interstitial fluid, Nature Biomedical Engineering, 1-14 (2021).

Tehrani, F. Doctoral Dissertation—Lab Under the Skin: a Microneedle Platform for Electrochemical Wearable Sensing 1-165 (2021).

Teymourian, H. et al. Closing the loop for patients with Parkinson disease: where are we?, Nature Reviews| Neurology, 1-11 (2022).

Teymourian, H. et al. Wearable Electrochemical Sensors for the Monitoring and Screening of Drugs, ACS Sensors, vol. 5, 2679-2700 (2020).

(56) References Cited

OTHER PUBLICATIONS

Teymourian, H. et al. Electrochemical glucose sensors in diabetes management: an updated review (2010-2020). Royal Society of Chemistry, Chem. Soc. Rev., vol. 49, 7671-7709 (2020).
Teymourian, H. et al. Microneedle-Based Detection of Ketone Bodies along with Glucose and Lactate: Toward Real-Time Continuous Interstitial Fluid Monitoring of Diabetic Ketosis and Ketoacidosis. Anal. Chem., vol. 92, 2291-2300 (2020).
Teymourian, H., et al. Lab under the Skin: Microneedle Based Wearable Devices. Adv. Healthc. Mater. n/a, 2002255 (2021).
Tran, B. Q. et al. Proteomic Characterization of Dermal Interstitial Fluid Extracted Using a Novel Microneedle-Assisted Technique. Journal of Proteome Research, vol. 17, 479-485 (2018).
Tu, J. et al. The Era of Digital Health: A Review of Portable and Wearable Affinity Biosensors. Advanced Functional Materials. 1-30 (2019).
Valdés-Ramírez, G. et al. Microneedle-based self-powered glucose sensor. Electrochemistry Communications, vol. 47, 58-62 (2014).
Vargas, E. et al. Enzymatic/Immunoassay Dual-Biomarker Sensing Chip: Towards Decentralized Insulin/Glucose Detection. Angew. Chem. Int. Ed. 6376-6379 (2019).
Ventrelli, L. et al. Microneedles for Transdermal Biosensing: Current Picture and Future Direction. Advanced Healthcare Materials. 2606-2640 (2015).
Venugopal, M. et al. Clinical Evaluation of a Novel Interstitial Fluid Sensor System for Remote Continuous Alcohol Monitoring. IEEE Sensors Journal, vol. 8, No. 1, 71-80 (2008).
Waltz, E. Sweet sensation. Nat. Biotechnol. 37, 340-344 (2019).
Wang, J. Electrochemical Glucose Biosensors. Chem. Rev. vol. 108, 814-825 (2008).
Wang, F. et al. Living Bacterial Microneedles for Fungal Infection Treatment. Research Article, vol. 2020, 1-9 (2020).
Wang, M. et al. Recent advances in the design of polymeric microneedles for transdermal drug delivery and biosensing. Lab on a Chip, vol. 17, 1373-1387 (2017).
Wang, Z. et al. Microneedle patch for the ultrasensitive quantification of protein biomarkers in interstitial fluid. Nature Biomedical Engineering, vol. 5, 64-76 (2021).
Windmiller J.R. et al. Bicomponent Microneedle Array Biosensor for Minimally-Invasive Glutamate Monitoring. Electroanalysis, vol. 23, 2302-2309 (2011).
Windmiller, J.R. et al. Microneedle array-based carbon paste amperometric sensors and biosensors. Analyst, vol. 136, 1846-1851 (2011).
Wolkowicz, K. L. et al. A review of biomarkers in the context of type 1 diabetes: Biological sensing for enhanced glucose control. Bioeng. Transl. Med. 6, e10201 (2021).
Xie, L. et al. Engineering Microneedles for Therapy and Diagnosis: A Survey. Micromachines. 1-28 (2020).
Yáñez-Sedeño, P. et al. Multiplexed Electrochemical Immunosensors for Clinical Biomarkers. Sensors, vol. 17, 1-30 (2017).
Yang, B. et al. In Situ Sampling and Monitoring Cell-Free DNA of the Epstein-Barr Virus from Dermal Interstitial Fluid Using Wearable Microneedle Patches. ACS Applied Materials & Interfaces, vol. 11, 38448-38458 (2019).
Yu, G. et al. Utility of the early lactate area score as a prognostic marker for septic shock patients in the emergency department. Acute Crit Care 34, 126-132 (2019).
Zhang, B.L. et al. Microneedle-assisted technology for minimally invasive medical sensing. Microchemical Journal, vol. 162, 1-12 (2021).
Zhang, X. et al. Encoded Microneedle Arrays for Detection of Skin Interstitial Fluid Biomarkers. Advanced Materials, vol. 31, 1-8 (2019).
Zhang, X. et al. Bio-inspired clamping microneedle arrays from flexible ferrofluid-configured moldings. Science Bulletin, vol. 64, 1110-1117 (2019).

* cited by examiner

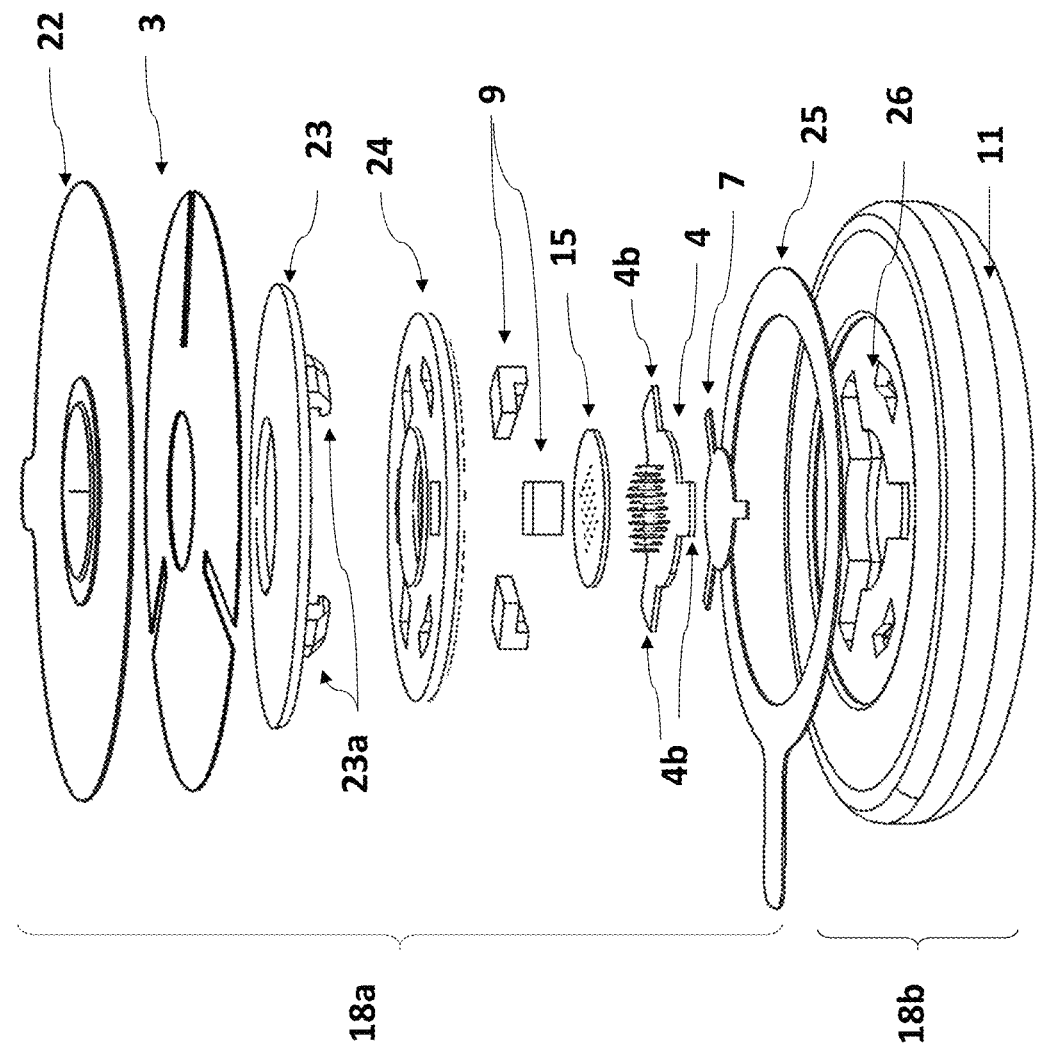

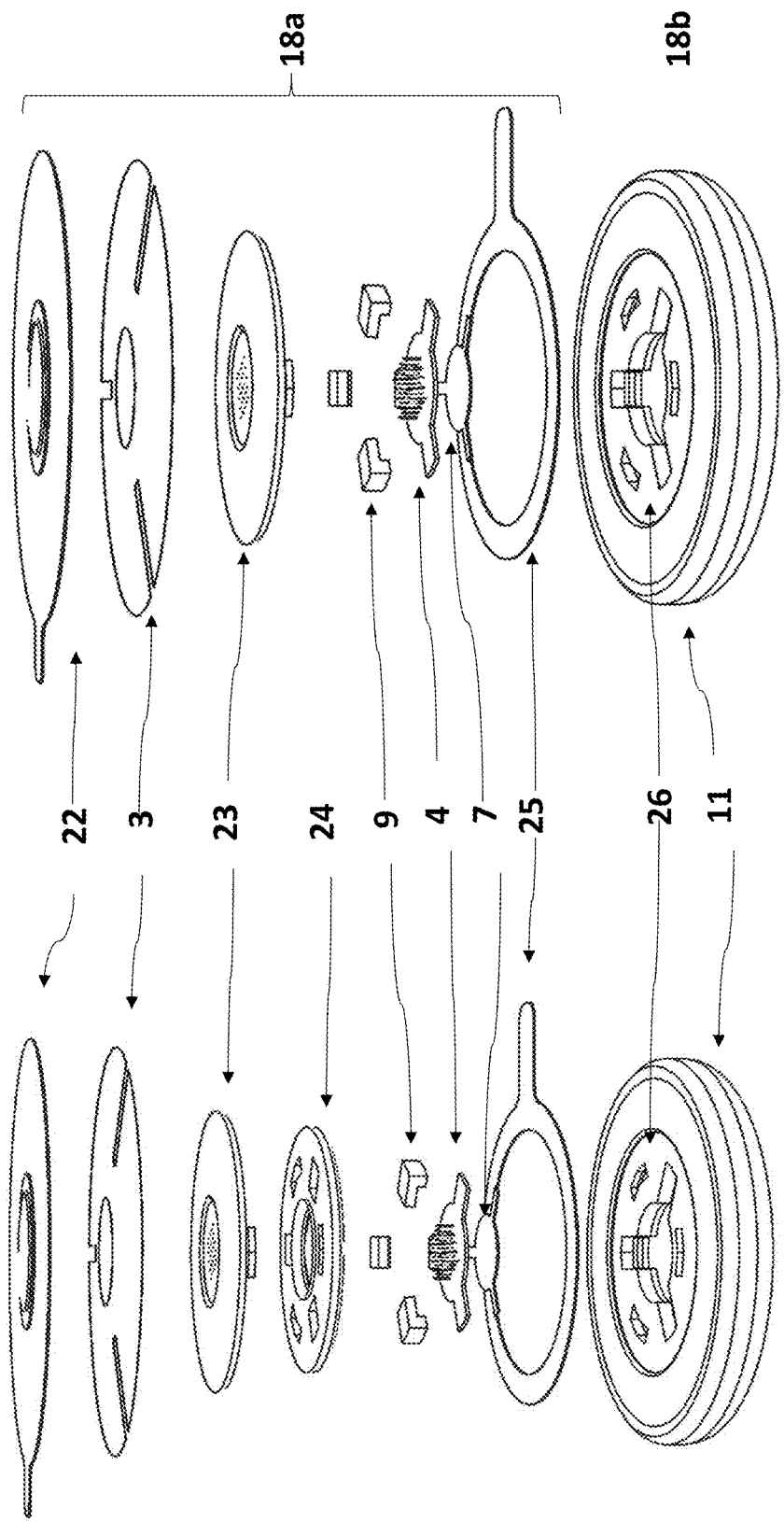

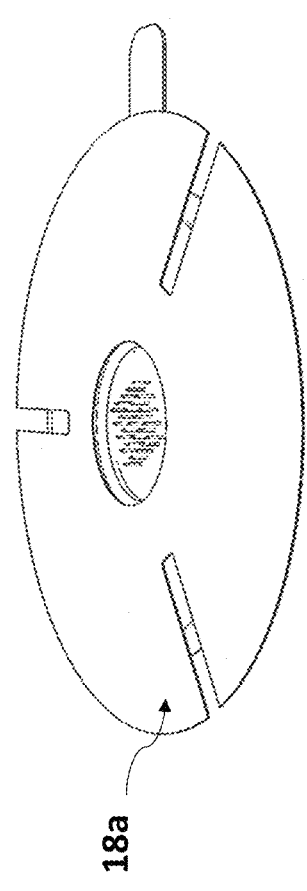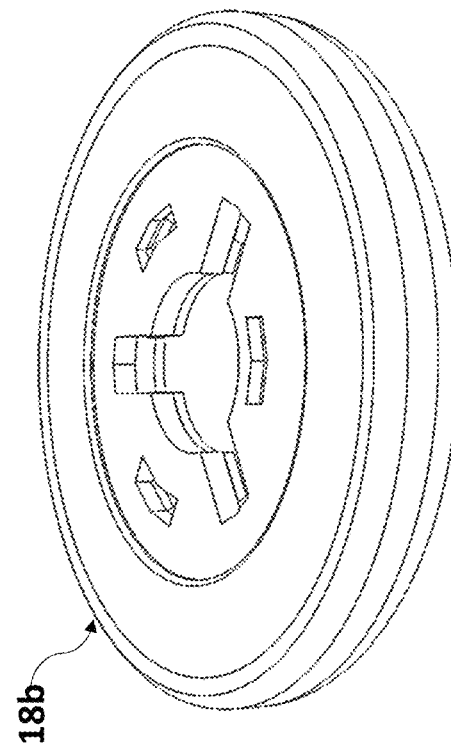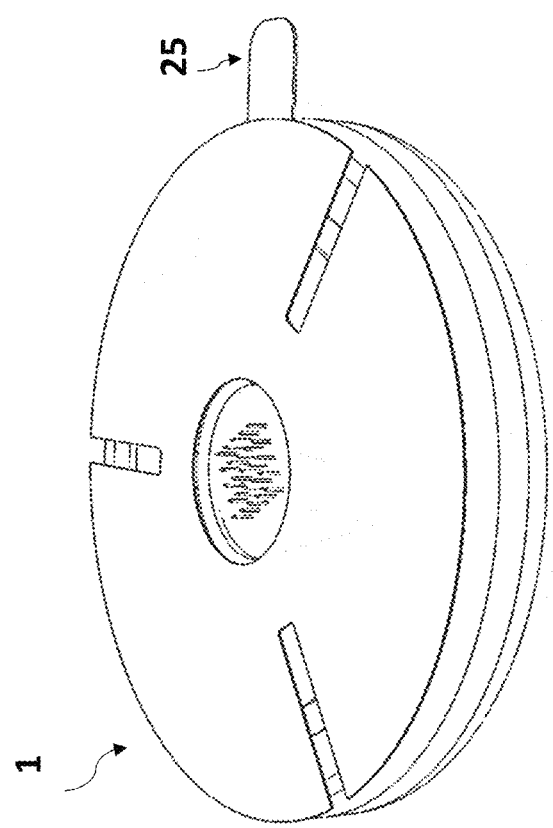

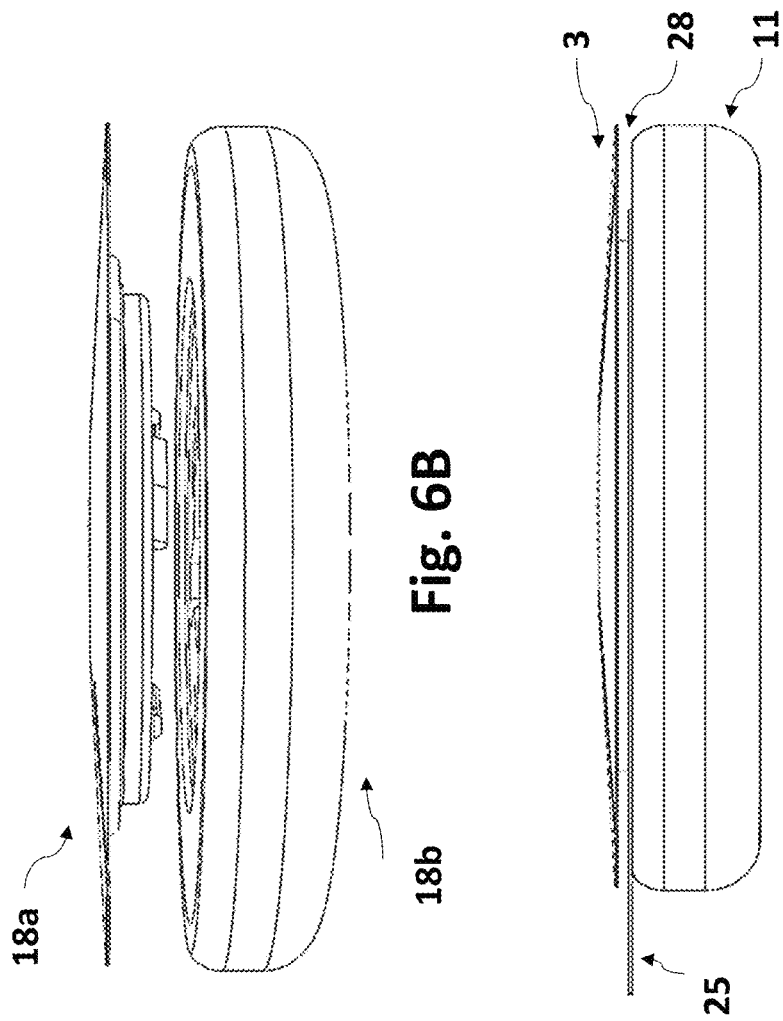
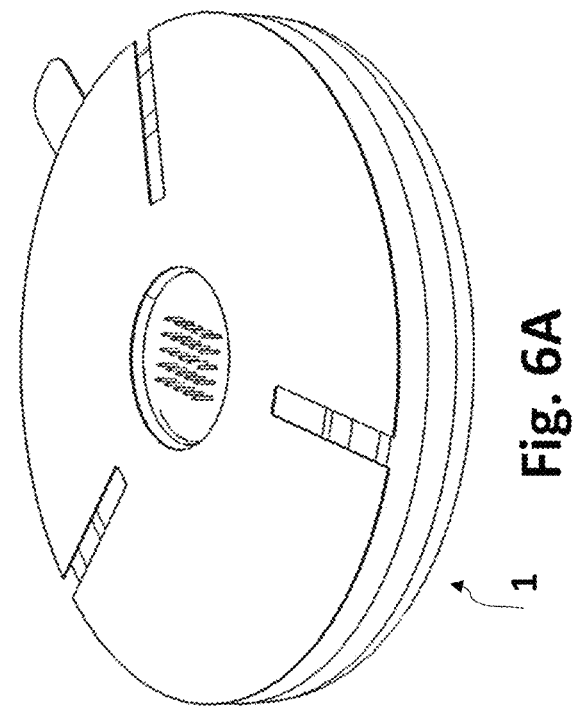

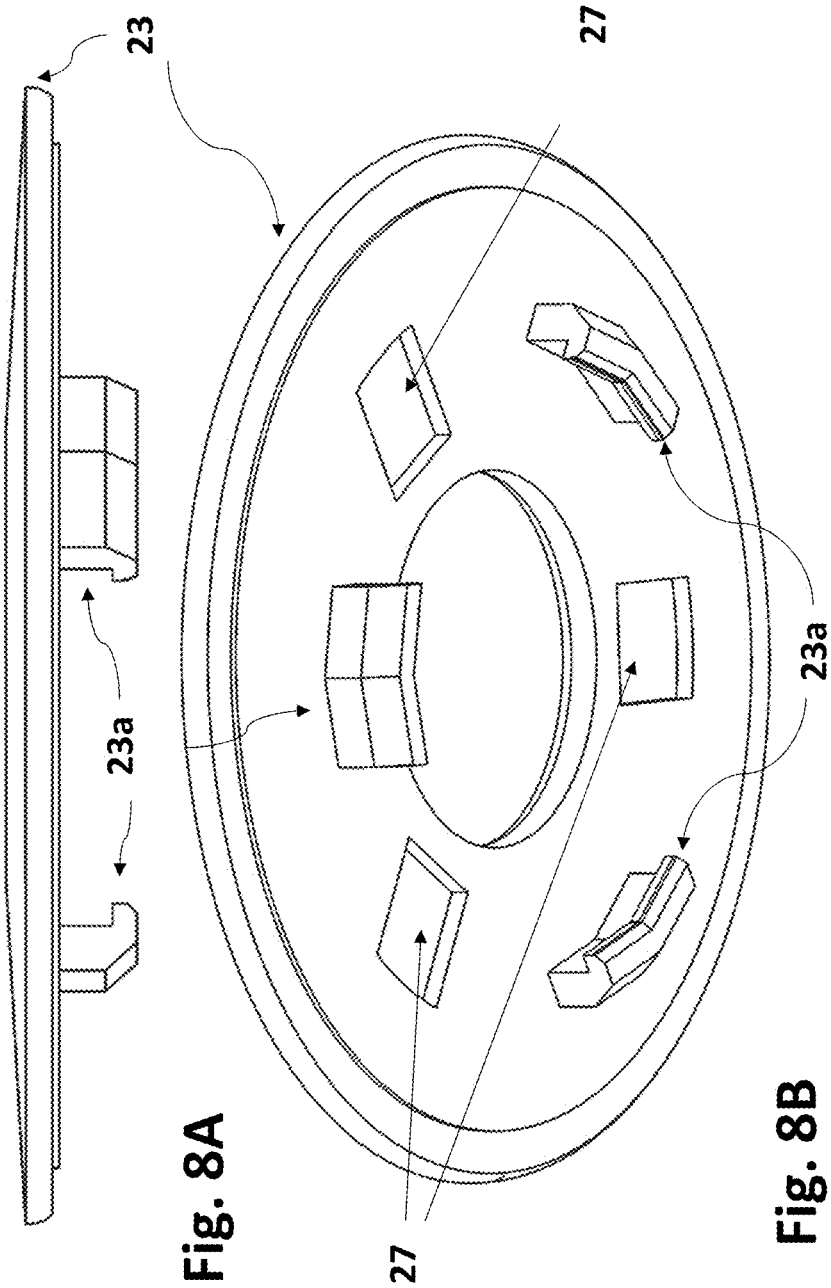

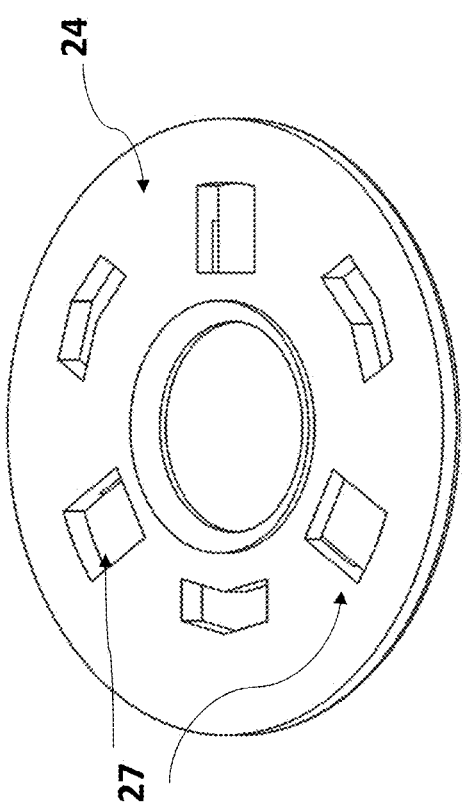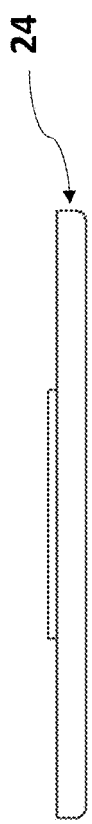

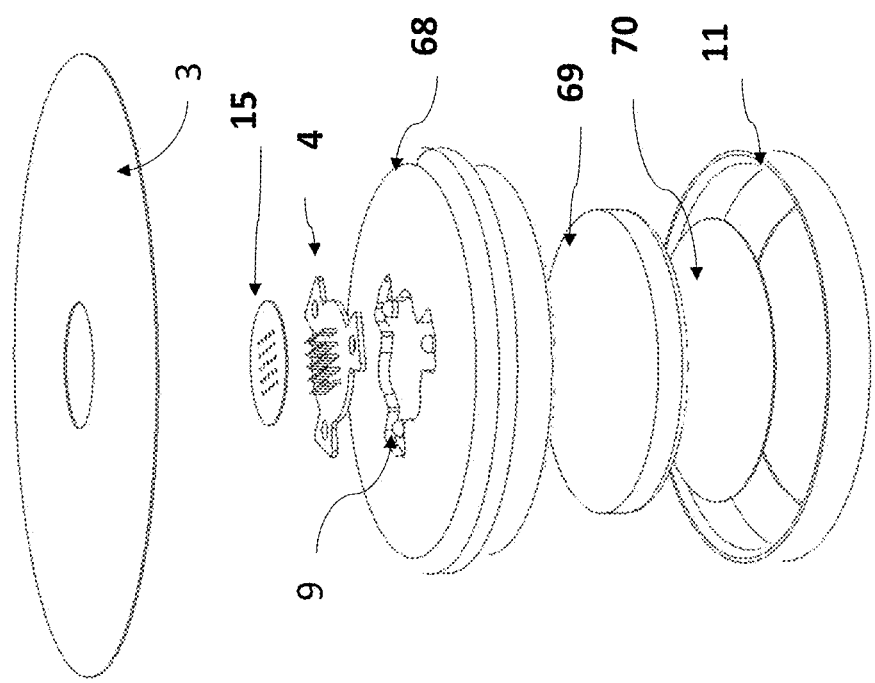

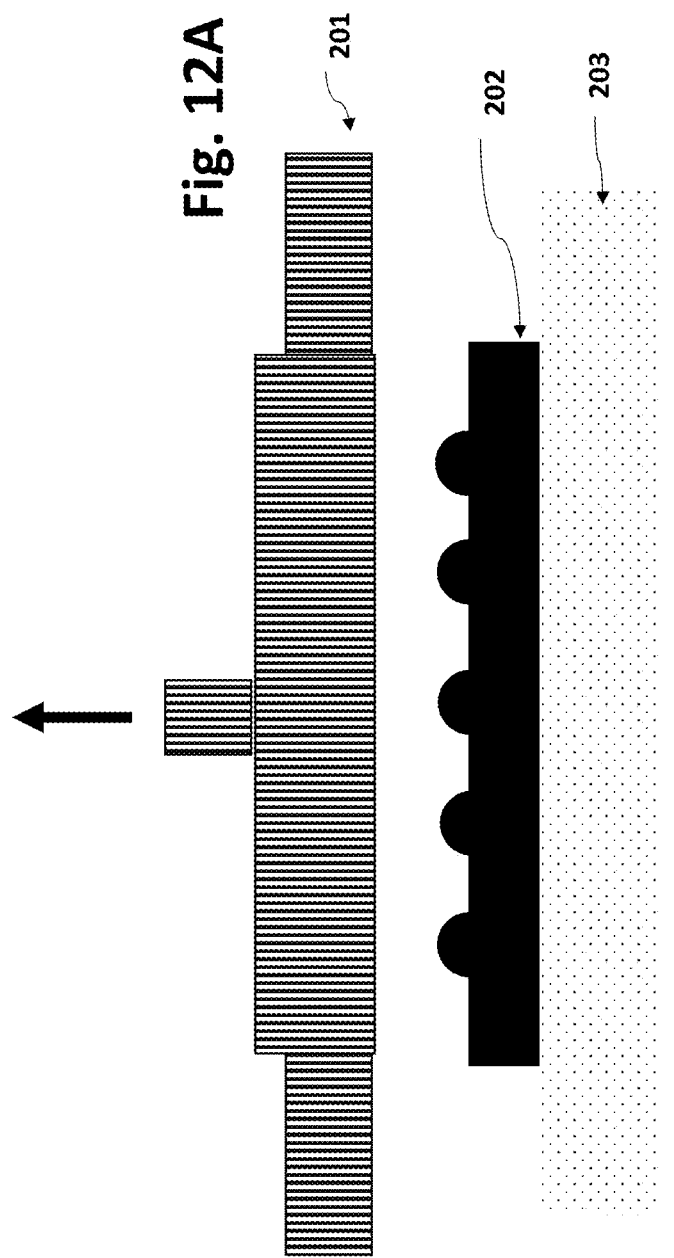

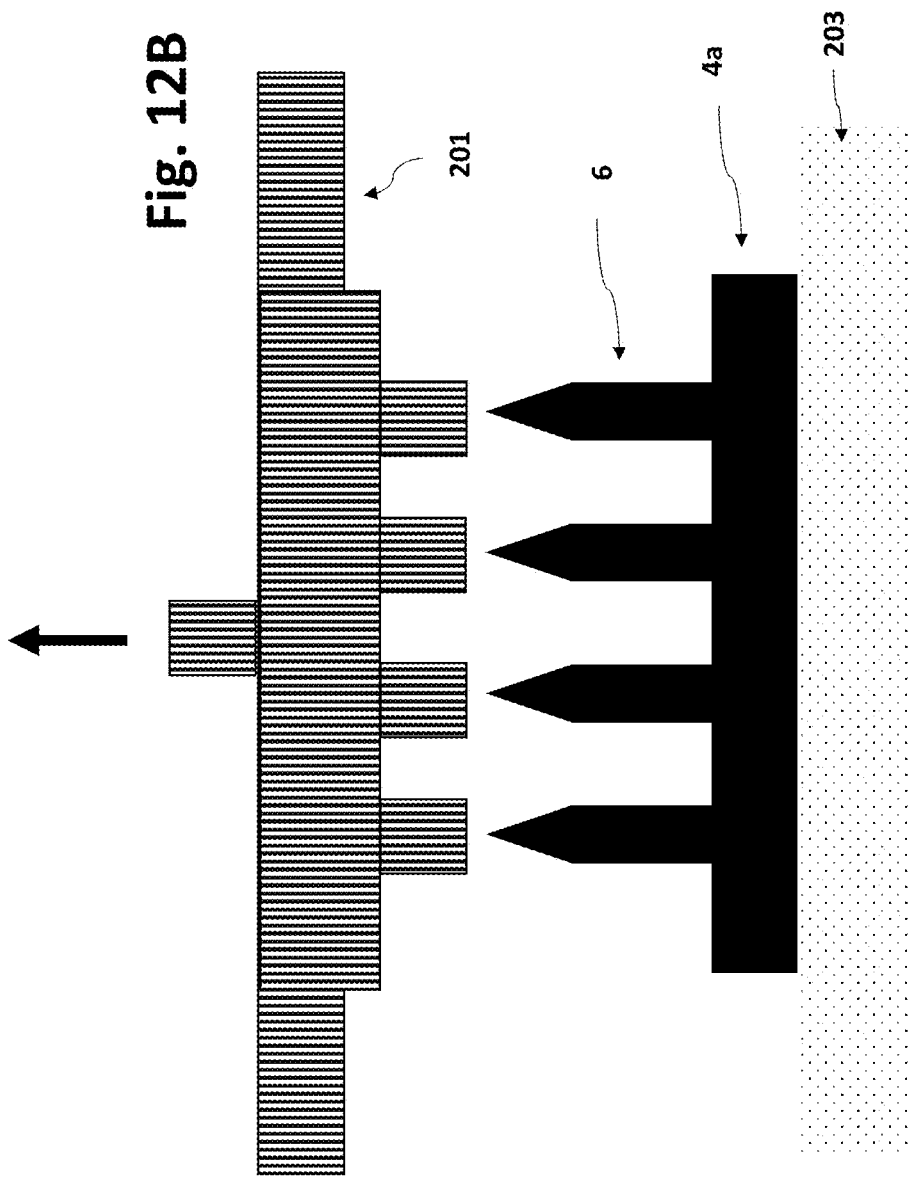

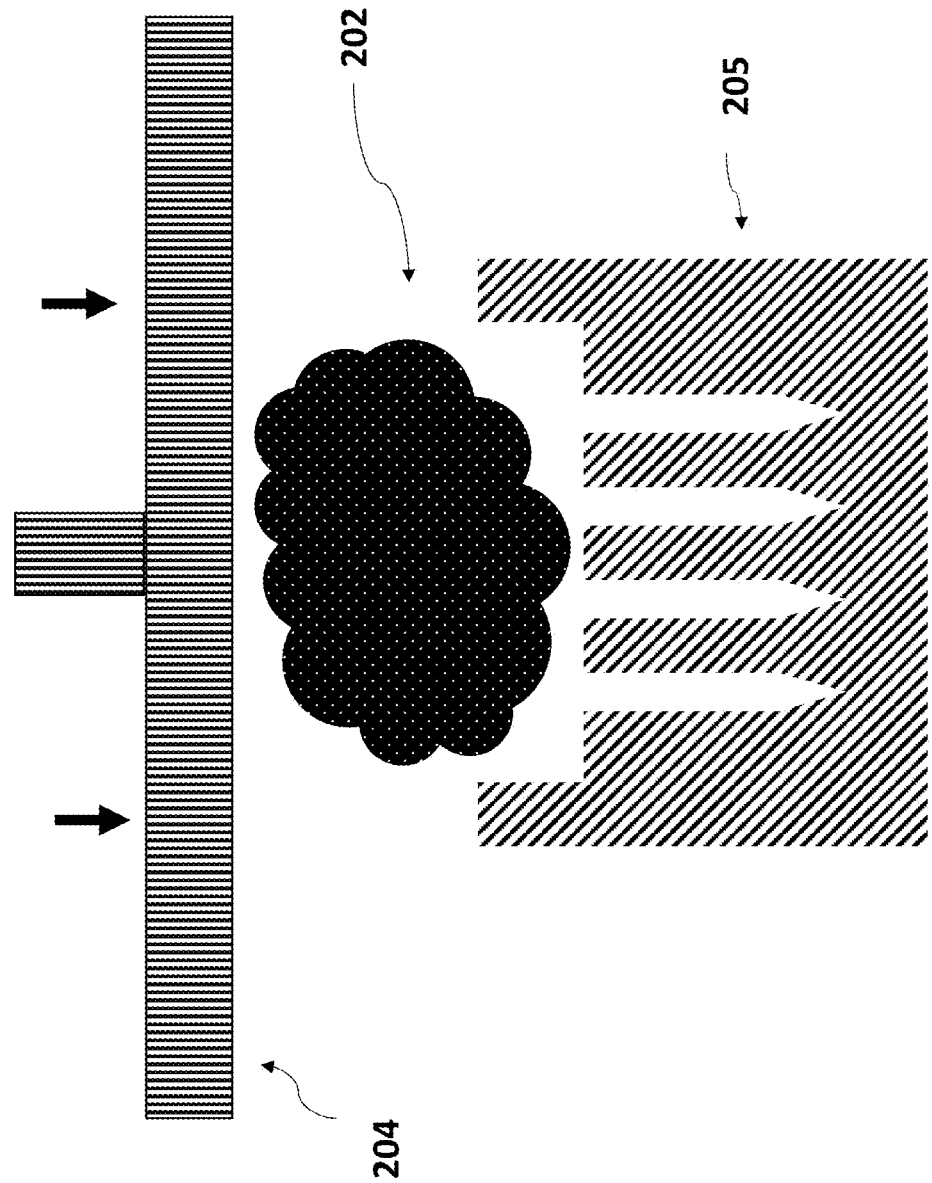

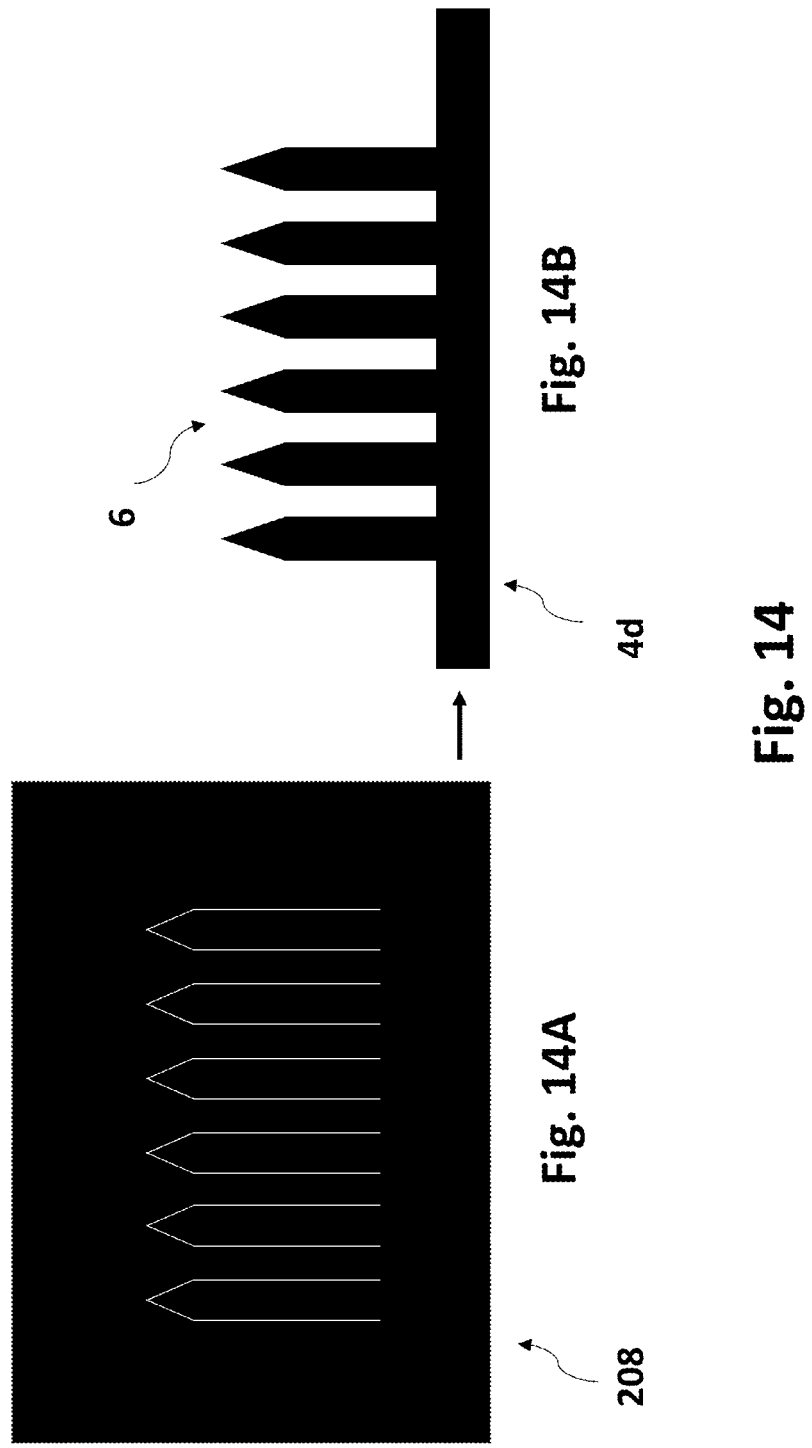

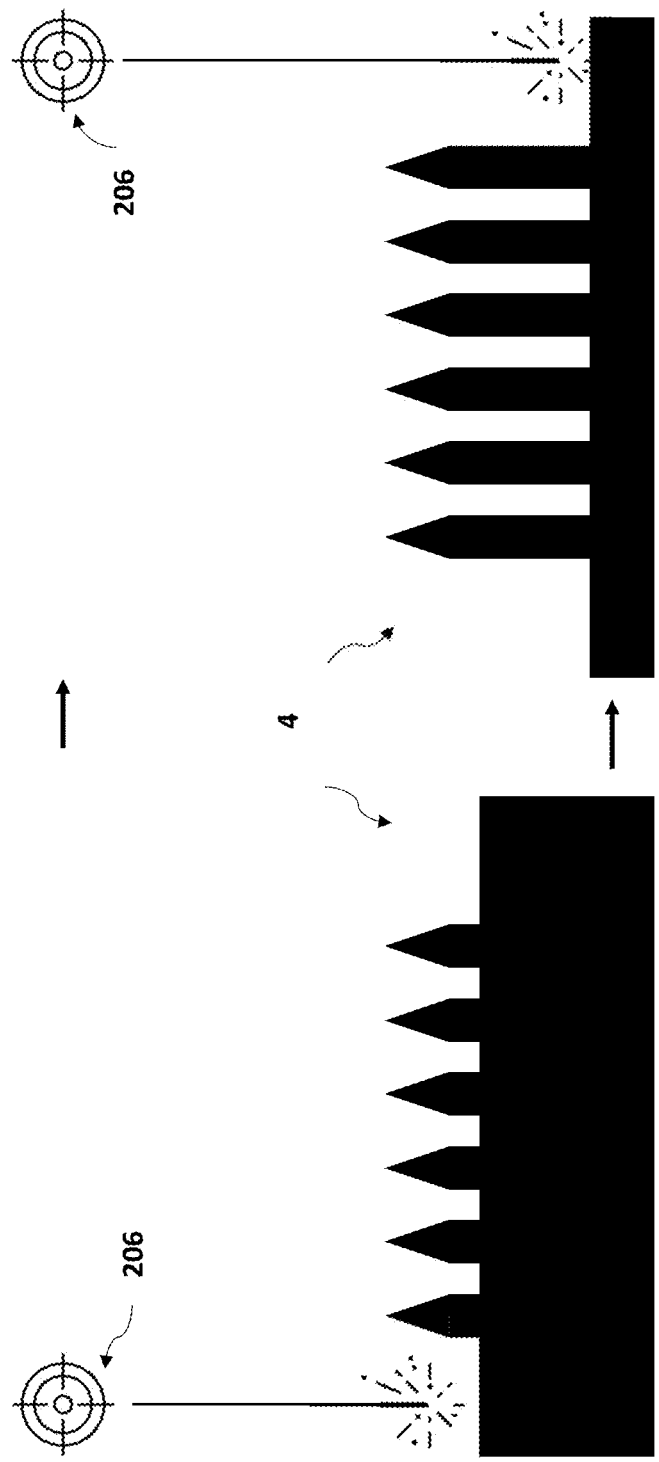

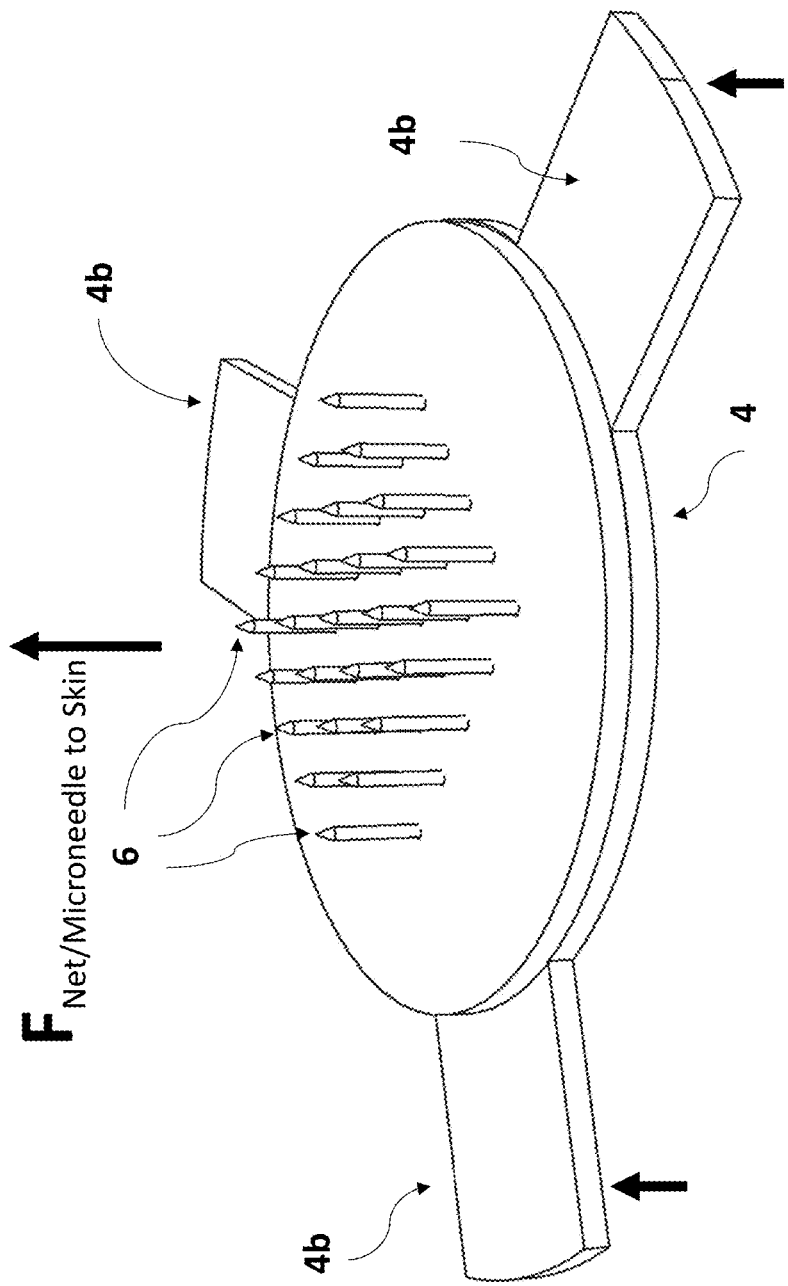

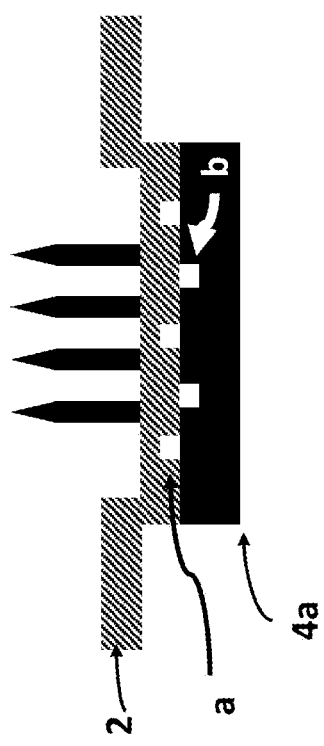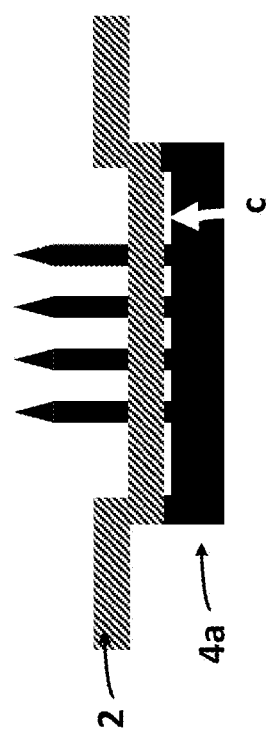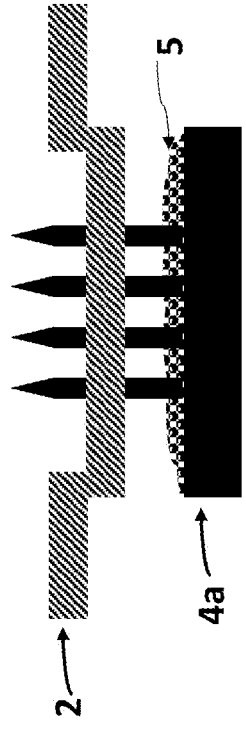

Fig. 9 from US Patent # 11,877,846

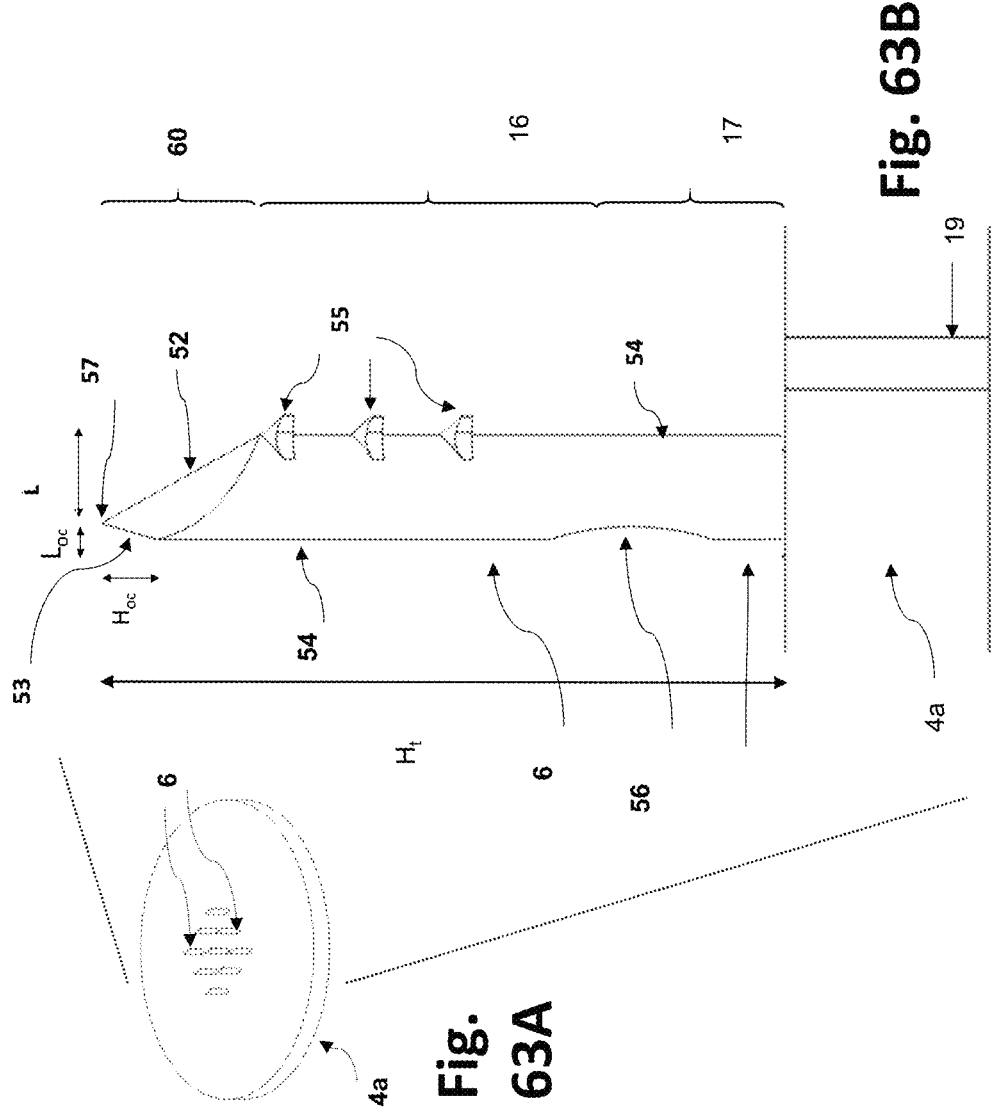

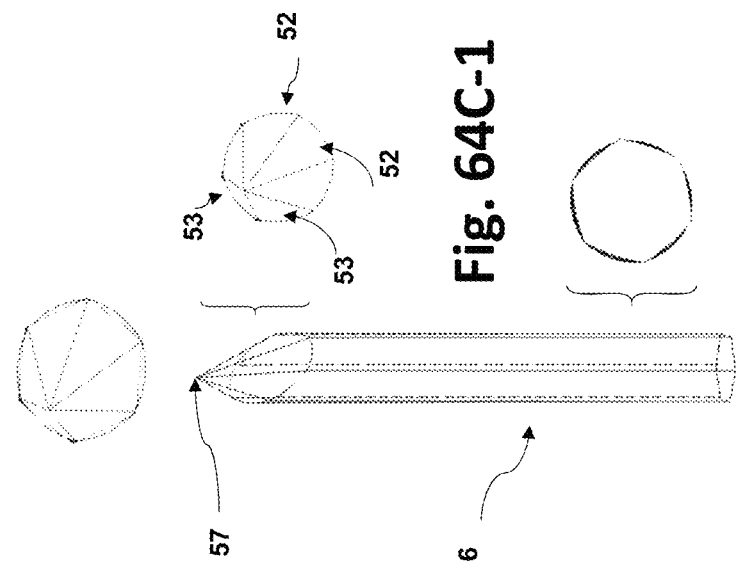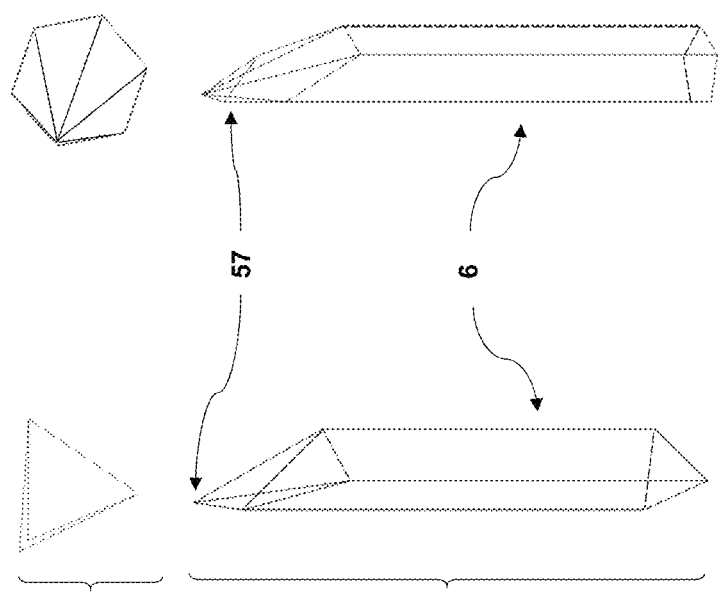

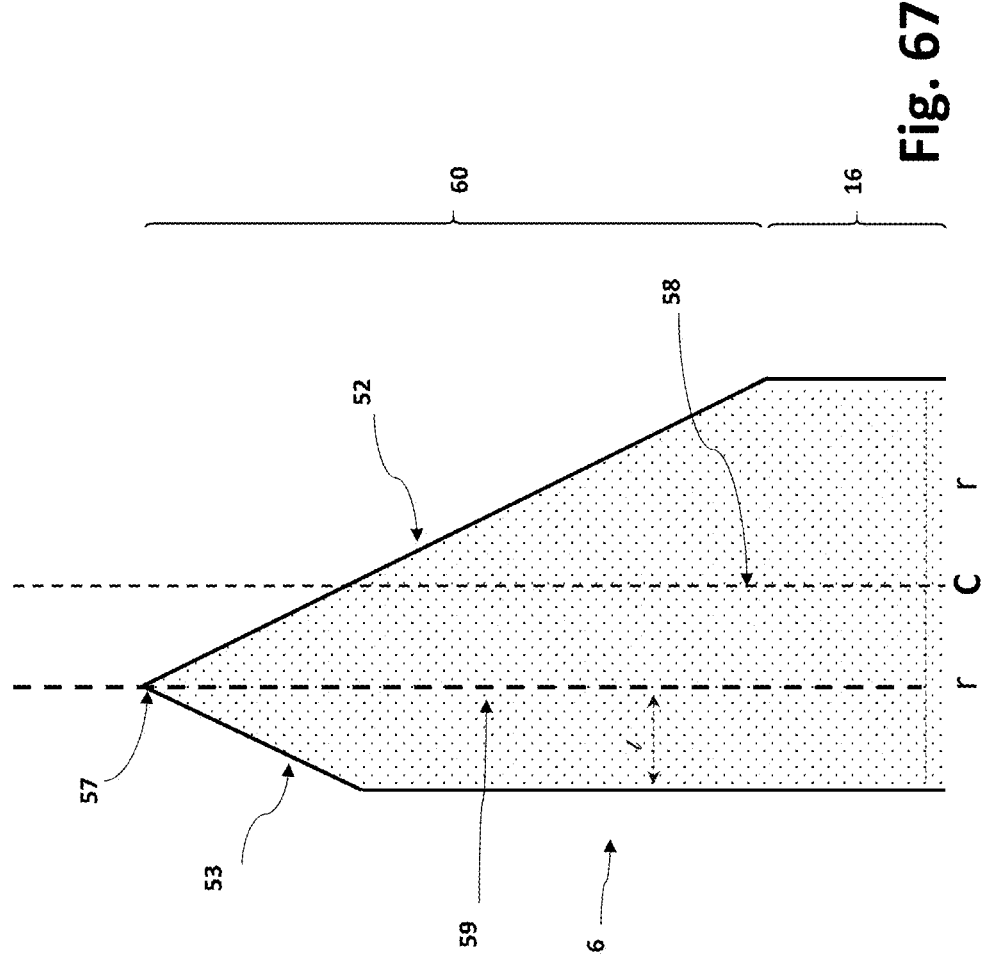

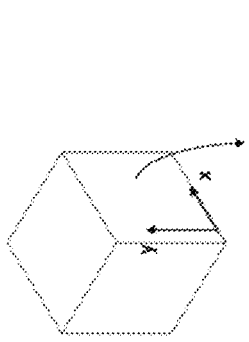
Fig. 68C1
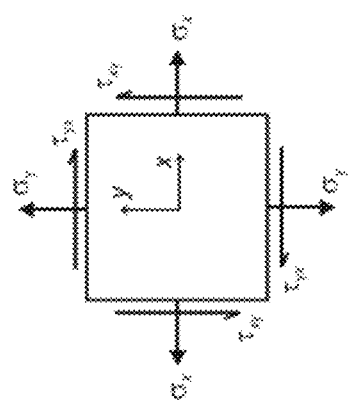
Fig. 68C2
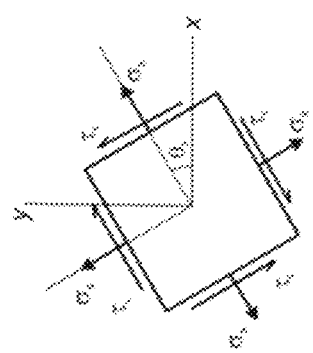
Fig. 68C3

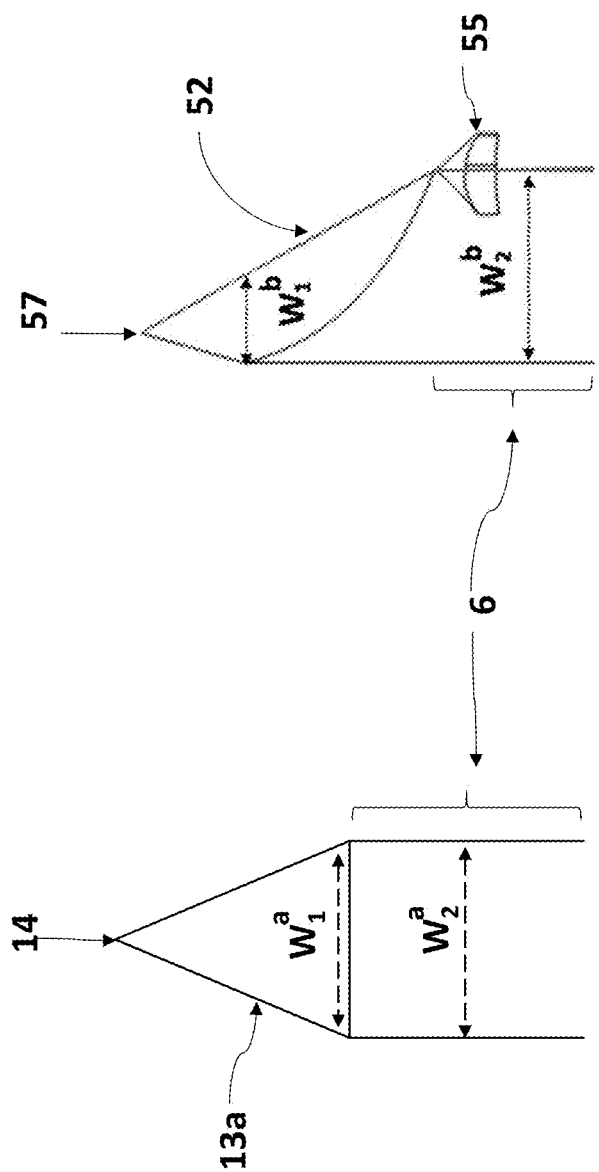

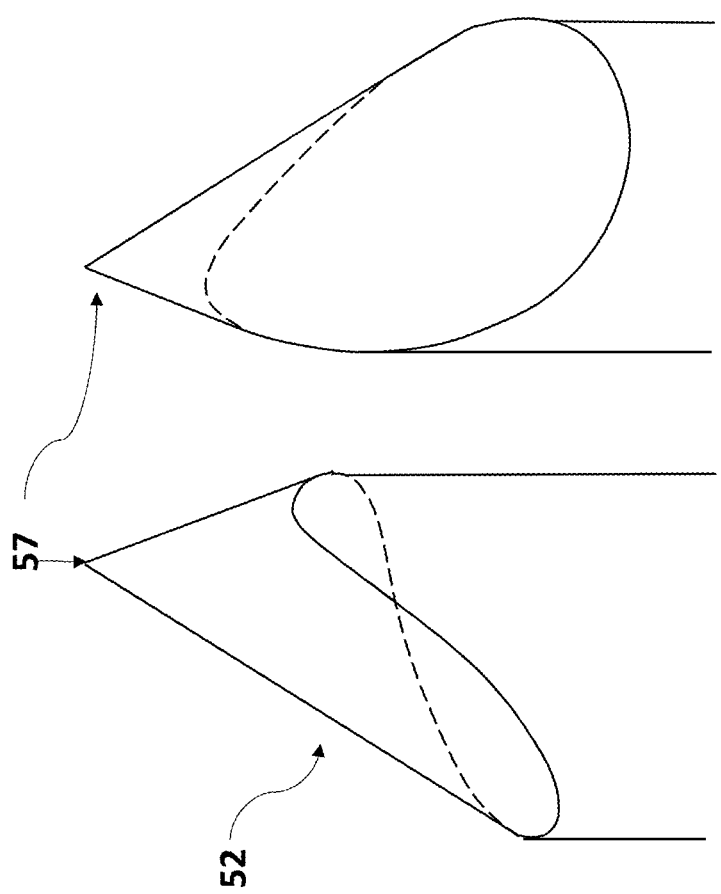

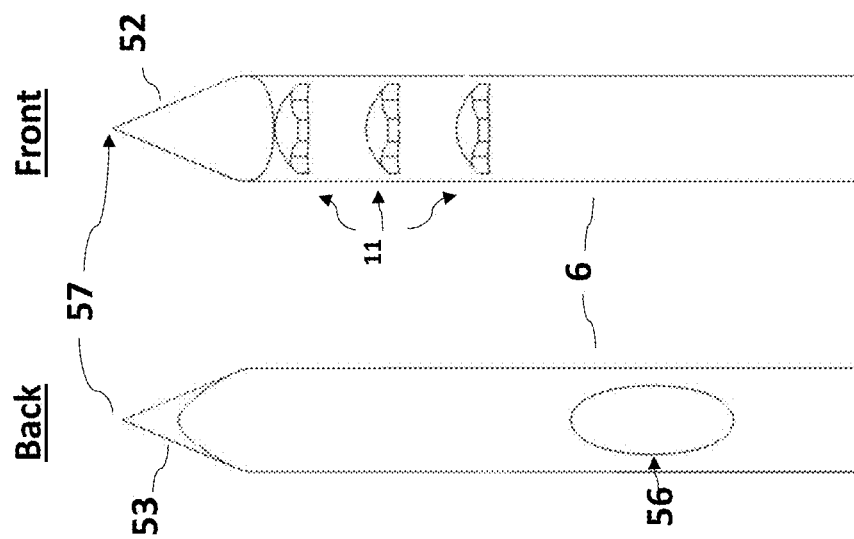
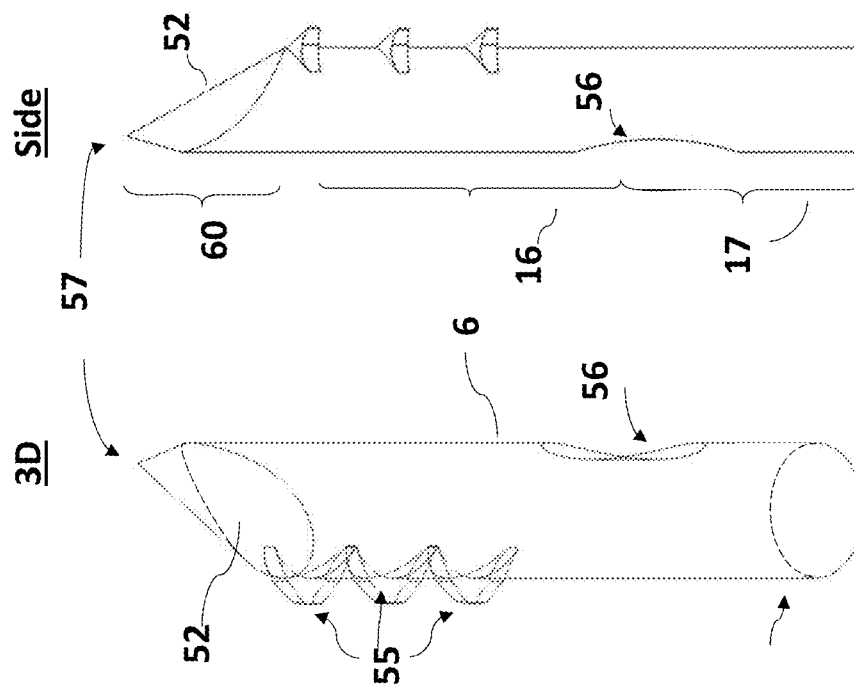
Fig. 71A Fig. 71B Fig. 71C Fig. 71D

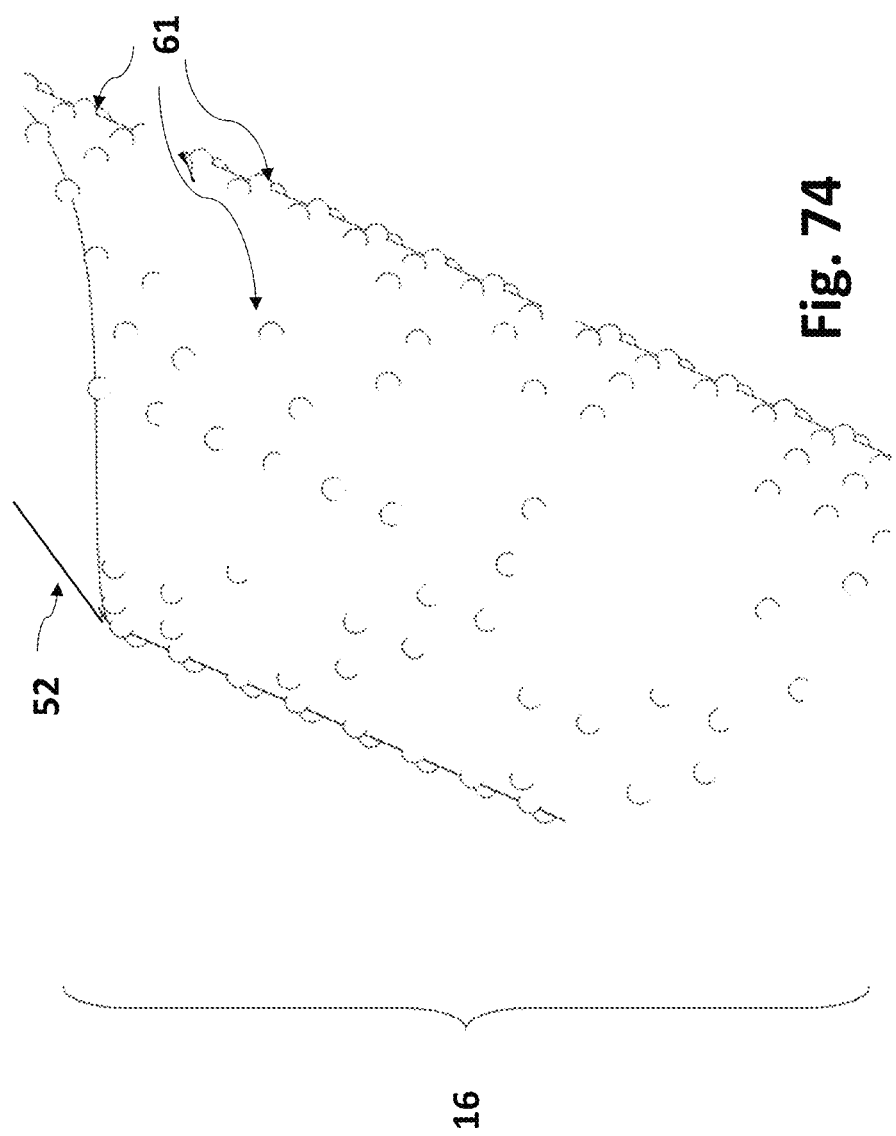

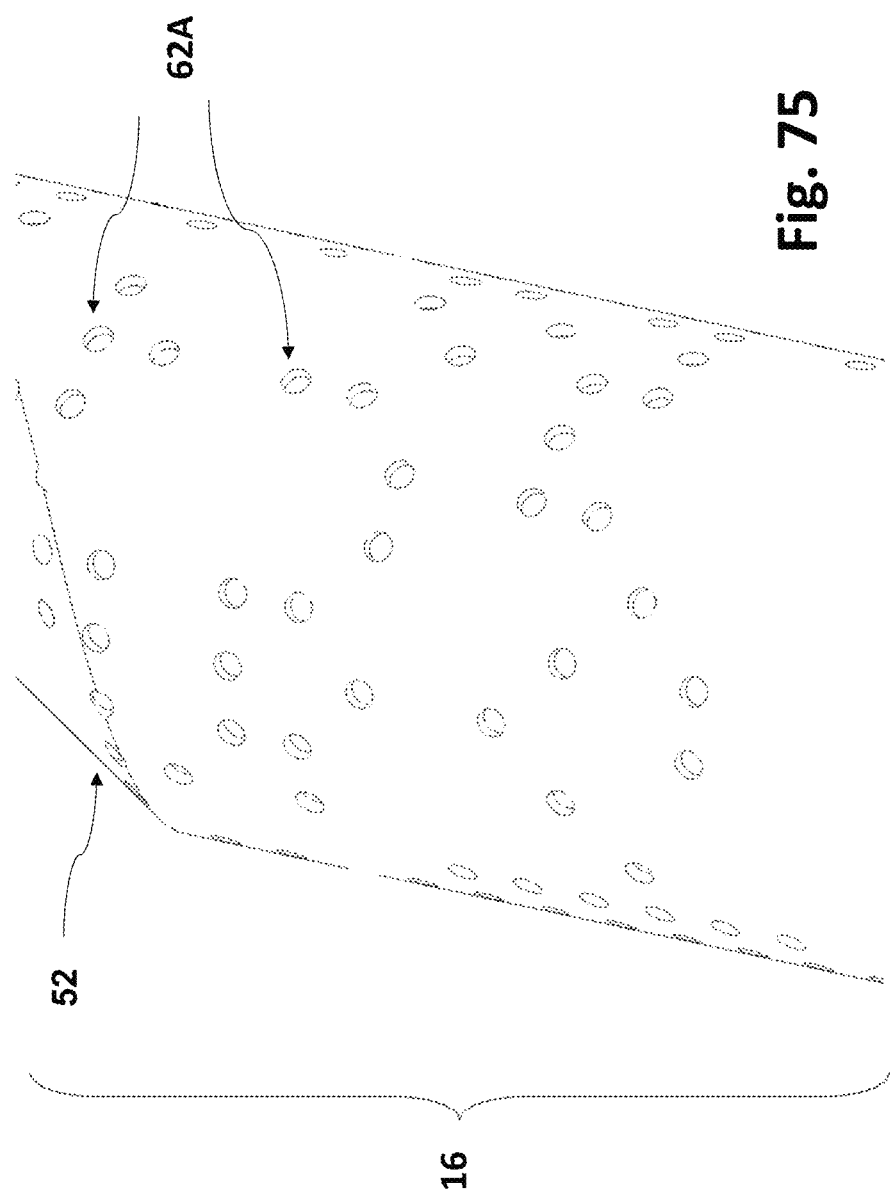

WEARABLE BIOSENSOR DEVICE

STATEMENT REGARDING PRIORITY AND RELATED APPLICATIONS

This application claims priority to and the full benefit of U.S. provisional application No. 63/548,793 filed Feb. 1, 2024 and U.S. provisional patent application No. 63/447,851 filed Feb. 23, 2023. This application also claims priority to and the full benefit of, and is a continuation-in-part of, the following three applications: international patent application PCT/US24/10775 filed Jan. 8, 2024; U.S. nonprovisional patent application Ser. No. 18/528,763 filed Dec. 4, 2023 and U.S. nonprovisional patent application Ser. No. 18/513,424 filed Nov. 17, 2023. This application also incorporates by reference U.S. Pat. No. 11,877,846 issued Jan. 23, 2024 ("the '846 patent"), in its entirety and as if set forth fully herein.

GOVERNMENT LICENSE RIGHTS

This invention was made with US government support under Grant Number: 5R44AA030231-03 awarded by the National Institute on Alcohol Abuse and Alcoholism. The US government has certain rights in the invention.

ASPECTS OF THE INVENTION

Overview of the Invention

The present invention represents novel aspects of the wearable biosensor device of the '846 patent. The novel aspects of the present invention provide better aspects and solutions for, without limitation, placement and anchoring of the microneedles in the skin, skin conformance and flexibility, and manufacturing, all producing emergent properties producing significant improvement for the user over the invention of the '846 patent.

The present is an improved wearable biosensor device 1 for continuous monitoring of analytes in a biofluid such as interstitial fluid (ISF), blood and the like. The device comprises a microneedle array and associated components having new aspects and architecture over the prior art. The microneedle array, comprising nonconductive material such as polymer, has various aspects and embodiments but is distinct from devices with silicon-based microneedle arrays made by a MEMS manufacturing process. Applicant hereby disclaims from the invention any use of microneedle arrays made by a MEMS manufacturing process. (Other components of the present invention may be made by a MEMS manufacturing process.)

The microneedle array comprises a nonconductive material comprising a substrate integral with microneedles on a top surface of the substrate, which are first covered by an electrically conductive layer such as metal or conductive polymer. As used herein throughout, "top" of the device means the part closest to the skin when the device is applied to the skin, and "below" means further from the skin in this setting. The nonconductive material is selected from the group consisting of polymer and ceramic which is cast in a mold, coated by a layer of electrically conductive material, and then coated by at least one chemical layer on top of the electrically conductive layer. The nonconductive material can form the basis of a conductive microneedle array and microneedles because the electrically conductive layer on the microneedles is thin and applied by techniques selected from the group consisting of sputtering or other physical vapor deposition, chemical vapor deposition, electroplating and the like. In other embodiments, a conductive material such as a metal may form a foundational structure for the microneedle array which is then covered by a nonconductive layer before application of the electrically conductive layer.

The microneedles comprise a tip in a tip region, a body region and a base integral to the substrate. At least one of the microneedles is configured as a working electrode functionalized with at least one chemical layer in at least one sensing region to detect an electrical signal from a reaction with a target analyte in a biofluid exposed to the microneedle tip, tip region or body region. Fitted over the microneedles (with at least one chemical layer) is a cover formed of the nonconductive material having a set of first openings configured to align with the array of microneedles on the substrate, such that the tip region and at least a distal portion of the body region of the microneedles pass through the set of first openings of the cover. A cured custom resin is positioned between the microneedle array and the cover and also extends upward to surround the bases of at least some of the microneedles, and the cured custom resin prevents leakage of fluid to the substrate and also secures the cover to the substrate and to the microneedles, and also defines reproducibly the electrochemically active surface area on the microneedles. A plurality of electrical connections connect the electrically conductive layer to an electronics unit. The cured custom resin is pushed as a flowable liquid into a gap between the microneedle array and the cover with or without microfluidic channels on the cover or the microneedle array. In contrast, the '846 patent requires microfluidic channels.

A "cover" herein is made of a nonconductive material which has a set of first openings and has a number of embodiments. As with the microneedle array, though, the cover can also comprise a conductive material such as metal as long as it is covered with a layer of nonconductive material. The basic cover has a mostly flat surface throughout the bottom and the top. An extended cover, with different levels, can be either recessed or elevated. A recessed cover has a lower surface where the set of first openings is located, and the lower surface is surrounded by an upper surface. An elevated cover has a raised panel where the set of first openings is located, and the raised panel is surrounded by a bottom panel. Some embodiments in this paragraph may have a sidewall and some may not. Any of the cover embodiments can have cover enhancements including without limitation sleeves, bodily features, conductive traces and other sensors. The foldable cover differs from the other embodiments in its foldability. Except for the differences as stated clearly in this written description and in the figures, "cover" herein can refer to any of the embodiments, even when designated by a different reference number (e.g., 2, 15, 33, 65).

The electrically conductive layer connects the microneedles to pins connected to an electronics unit which receives and processes electrical signals from interactions of the microneedles at the least one chemical layer with analytes in a bodily fluid. The at least one chemical layer may comprise a material selected from the group consisting of an enzyme, an ionophore, an antibody, a peptide nucleic acid (PNA), a DNA aptamer, a RNA aptamer, a molecularly imprinted polymer (MIP), and a cell.

The electronics unit comprises a power source, a data processing unit in communication with a signal processing circuit, the data processing unit comprising a processor and a memory and configured to process the electrical signal as data representative of one or more parameters of the target analyte. The signal processing circuit is configured to process the electrical signals generated at the least one chemical layer by one or more of amplifying the electrical signals, filtering the electrical signals, or converting the electrical signals from analog to digital, and the data processing unit is configured to process the electrical signals after processing by the signal processing circuit. The electronics unit further comprises a wireless communication unit in communication with one or both of the signal processing circuit and the data processing unit, and the wireless communication unit comprises a wireless transmitter and/or wireless transceiver to at least transmit one or both of the data (the processed electrical signals) to an external computing device such as the user's mobile device, and to receive instructions from an external computing device (e.g., a user's smart phone).

Several embodiments herein are fully disposable or partially reusable.

Although the invention of the '846 patent requires microfluidic channels in the substrate or the cover for distributing the curable resin, inclusion of microfluidic channels in the present invention is optional. In some embodiments, a bottom portion of the cover and/or the substrate comprise microfluidic channels through which the curable resin flows to seal and strengthen the microneedles, and extends through the gap between the set of first openings and the microneedles and then moves upward, in some embodiments to a cut-off fluidic line on the microneedles designed to halt the upward capillary flow of the curable resin. In other embodiments microfluidic channels, vertical or diagonal, are also included on the bases of at least some of the microneedles to assist with capillary flow. In these embodiments, microfluidic channels help distribute curable resin as it flows before curing. In embodiments with the foldable cover, the cured custom resin rises by capillary flow to the tips of petal-like sleeves surrounding a center opening of a set of complex openings, without the need for microfluidic channels. Other embodiments do not require microfluidic channels on the microneedles even without the complex openings.

The present invention has at least one sensing region and may have two or more such sensing regions, each sensing region comprising at least one working electrode having at least one chemical layer targeting analytes which are different than the analyte targeted by the at least one chemical layer targeted by all of other sensing regions. That is, each sensing region may be configured to target an analyte different from the analyte targeted by the other sensing regions. For each of two or more sensing regions, the electrically conductive layer for that sensing region is electrically isolated from the other sensing regions as described herein.

The electrical connections can include conductive pins (flexible or rigid) connecting at a substrate contact on one end at walls covered by the electrically conductive layer in a frictionous hole in the substrate, and at the other end to an electrical contact on the electronics unit. In another embodiment, elastic conductive pins connect at the substrate contact and at the electrical contact on the electronics unit. In another embodiment, the electrical connections comprise L-shaped pins with one surface contacting the electrically conductive layer on the substrate, at least one L-shaped pin per sensing region, and another surface contacting the electronics unit. Other kinds of electrical contacts for the invention include, without limitation, solder and conductive glue.

Additional sensors (in addition to those on the microneedles themselves) may be added in embodiments with conductive traces on the top surface of the cover for reporting skin temperature, perspiration and the like.

In other embodiments a force touch sensor is built into the wearable device between the bottom surface of the substrate and the electronics unit for sensing the amount of force during insertion, and converting this force into electrical parameters which are transmitted to a circuit in the electronics unit to generate feedback to the user that the microneedles have been properly inserted.

The properties of the microneedles may vary. The body region of the microneedles may be symmetrical having symmetrical tips (e.g., cylindrical body and conical tip), or have the shape of a prism which is triangular, rectangular, pentagonal and hexagonal, with the tip having a similar number of surfaces, or the surfaces in the tip region may be uncorrelated to the shape of the body region. Symmetrical body regions may have an asymmetrical (off-center) tip and tip regions having at least one major surface and one major surface. Asymmetrical body regions can have asymmetrical (off-center) tips having at least one major surface and at least one minor surface, such as cylindrical with conical tips. To enable the microneedles to bend upon insertion into the skin, in some embodiments the base or lower body region of the microneedle can have an indention which serves to weaken the microneedle and bend in the direction of the indention, especially with an off-center tip whose major surface is on the opposite of the microneedle from the indention. This produces beneficial distribution of forces to pierce the skin. The indentions and off-center tips are configured, together or separately, to guide deflection of the microneedles during insertion into a tissue. One or more sills placed on the side of the major surface on a body region (and opposite the side with the indention) near the tip can be present to assist with locking the microneedles into the skin to reduce movement relative to the skin. In other embodiments, there can be spiral protrusions around the body region. Pores can be applied after casting of the microneedle array by machining in order to provide extra surface area for chemical layer materials or for securing them to the microneedle, or both. Microanomalies selected from the group consisting of knobs, cavities, liquids curable into an etchable solid and solid additives, can also be formed in the microneedles as they are being cast in a mold to produce random patterns of holes or weaknesses or useful substances which are embedded in the microneedles. Enteric coatings on top of the at least one chemical layer can be applied in uniform thicknesses to extend the life of microneedles, or the thicknesses of enteric coatings can be varied to extend the life of the microneedle array as a whole, i.e., microneedles with thicker coatings will be activated later than ones with no coating or a thinner coating, and so will be active longer than the microneedles with no or thinner coatings. Staggering thickness and composition of the enteric layer on different microneedles can extend the life of the device as a whole by bringing "on line" microneedles in different stages after insertion into the skin. Additionally, the microneedles can be warm-up free on insertion if they are contained within a hydration chamber to keep them moist and hydrated.

All of the foregoing and those aspects described elsewhere herein, in various combinations, produce emergent properties such as extended wear life, elimination or significant reduction of warm-up time, a user-friendly insertion process that ensures secure skin-locking immediately post-insertion, enhanced durability of microneedles against breakage, superior user experience and comfort during wear, and improved scalable manufacturability. Together, these innovations not only elevate the sensor's overall performance but also its accuracy, functionality, and reliability. This novel design and functionality guarantees that the wearable biosensor device is more efficient, provides a better experience for users and establishes a new benchmark in the industry.

A portion of the microneedle array 4 of the wearable biosensor device 1 in FIG. 1 shows the tips of the microneedles when inserted pierce the skin to the area when the epidermis 40, borders the inner skin layer, the dermis 41. In this embodiment for detection of three different analytes with one working electrode for each molecule of lactate, (Lac), Alcohol (Alc) and glucose, there are also a counter electrode (CE) and a reference electrode (RE). The shallow location of the microneedle tips is made possible by the correlation between the ISF and blood as established by studies, particularly by F. Tehrani, H. Teymourian, B. Wuerstle, . . . J. Wang, An integrated wearable microneedle array for the continuous monitoring of multiple biomarkers in interstitial fluid, *Nature Biomedical Engineering* volume 6, pages 1214-1224 (2022).

Data collected using embodiments of the present invention are found in the '846 patent and F. Tehrani, et al. *Nature Biomedical Engineering* cited above.

BRIEF DESCRIPTION OF THE FIGURES

FIG. 3 is an exploded view of another embodiment of the device with disposable and reusable modules having a basic cover.

FIG. 4A is an exploded view of an embodiment of the device with disposable and reusable modules with an elastic insulative base, and FIG. 4B is the same but without the elastic insulative base.

FIGS. 5A-5C a perspective view showing the reusable and disposable modules assembled and combined and then separated.

FIGS. 6A-6C is similar to 5A-5C but with two side views.

FIGS. 8A and 8B respectively are a side and underneath perspective view of the rigid base.

FIGS. 9A and 9B respectively are a side view and perspective view of the elastic insulative base.

FIG. 11 is an exploded view of the device embodiment with an alternate top enclosure.

FIGS. 12A and 12B are schematics of a method of drawing microneedles from a moldable material.

FIG. 13 is a schematic of a method of making a microneedle array with compression molding.

FIGS. 14A and 14B are schematics of a row of microneedles cut from a sheet of material by laser or water jet cutting.

FIGS. 15A and 15B are schematics of a method of making a microneedle array by laser engraving.

FIG. 16 is a perspective view of a microneedle array with cantilevered arms.

FIG. 17A-17C are schematics showing ways to apply curable resin with or without microfluidic channels.

FIG. 63A is a perspective view of one embodiment of a basic cover with microneedles inserted and FIG. 63B is an enlargement of one of the microneedles showing one embodiment of the off-center tip and tip region, sills and an indention.

FIGS. 64A-C are perspective and 3D views of embodiments of microneedles in the shapes of triangular, pentagonal and hexagonal prisms, and FIG. 64C-1 includes a top down of the tip region and a section view of the hexagonal shape.

FIG. 67 is a section view of one embodiment of an off-center tip and tip region and upper body region of a microneedle herein.

FIGS. 68C1, 68C2 and 68C3 are block diagrams of the forces in FIGS. 68A-68B.

FIGS. 69A-69B show relative safety factors for microneedle tips of a prior art off-center and the present invention's off-center tip.

FIG. 70 includes 3D side and front views of an off-center tip showing major and (in dotted lines) minor surfaces.

FIGS. 71A-71D are perspective and side views of one embodiment of a cylindrical microneedle with an off-center tip and tip region, sills and an indention.

FIG. 74 is a perspective view of a portion of one embodiment of a microneedle with an off-center tip region and knobs on the surface of the upper body region.

FIG. 75 is similar to FIG. 74 but instead shows regular shaped cavities on the surface of the upper body region and the tip region.

Figure 2:
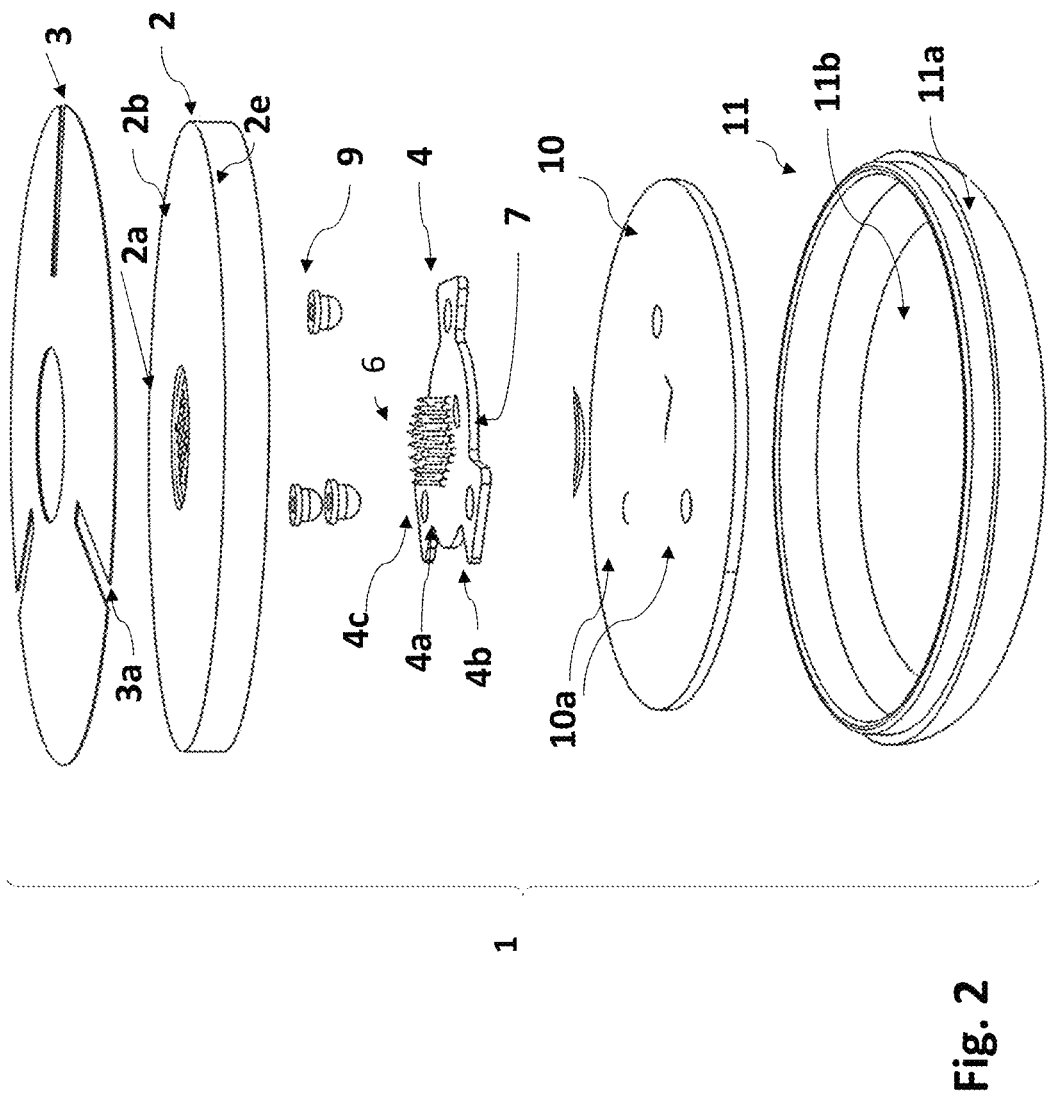
FIG. 2 is an exploded view of one embodiment of the wearable biosensor device with disposable and reusable modules having a recessed cover.

An exploded view of a fully disposable embodiment of the invention is shown in FIG. 2 and, as further described in this application comprises a recessed cover 2 which connects to a lower enclosure 11, and the microneedle array 4, and the electronics unit 10 and other components are enclosed therein. This embodiment is intended to be replaceable at the end of the life of the device, that is, it is a single unit which is fully disposable. A recessed cover 2 comprises a lower surface 2a, here in the center (without sleeves), surrounded by an upper surface 2b. At a fillet 2c, shown for example in FIG. 27, a rounded annular junction at the inner boundary of the upper surface, a downward slope 2d of the recessed cover descends to the lower surface. The recessed cover in this embodiment also has at least one sidewall 2e which secures and seals it in complementary fashion to a sidewall 11a of the lower enclosure 11 which has a bottom 11b. The lower surface of the recessed cover has a set of first openings 12 (holes) which are complementary to, and correspond with, microneedles 6 of the microneedle array 4. The set of first openings can be seen clearly in FIG. 28. A flexible microneedle array 4 comprises in its center a substrate 4a and microneedles 6 which at their bases 16 are integral with the substrate. In the embodiment of FIG. 2, a force touch sensor 7 underneath the microneedle array is shown, for example, in FIG. 3. An electronics unit 10 here is either a printed circuit board (PCB) or application specific integrated circuit (ASIC). Conductive pins 9 at the cantilevered arms 4b of the microneedle array attach to substrate contacts and to contacts on the electronics unit. Connection holes 4c allow a connection to contacts 10a on the electronics unit by conductive pins 9 which may be flexible and elastic or rigid. A skin adhesive layer 3 is attached to the upper surface of the recessed cover, that is, there is an opening in the skin adhesive layer 3 above the microneedles as they would appear through the first openings in the lower surface. The skin adhesive layer may have slots 3a to prevent wrinkling.

An embodiment which is partially reusable is shown in FIG. 3. Here the disposable module 18a comprising the microneedle array can be separated after usage for the recommended period and a replacement disposable module can be affixed to the reusable module 18b. FIG. 3 is an exploded perspective view of the two modules 18a, 18b of the device with a removable microneedle protector 22, a skin adhesive layer 3, a rigid base 23, an optional elastic insulative base 24, pins 9 (here, compression pins in an L-shape), a basic cover 15, a microneedle array 4 with microneedles 6 and cantilevered arms 4b, a force touch sensor 7. All the above is in module 18a and removable with an eject plastic sheet 25. This disposable module sits above the reusable module 18b with a lower rigid base 26 with an electronics unit (enclosed but not visible) inside a lower enclosure 11.

FIG. 4A is similar to FIG. 3, except that a recessed cover 2 (without a sidewall) is substituted for the basic cover 15. An elastic insulative base 24 is present to give greater flexibility and conformability to the microneedle array, for better contact and retention on the skin without movement. FIG. 4A is similar to FIG. 4B except that the latter has no elastic insulative base. FIG. 5A is a perspective view of one embodiment of the wearable biosensor device 1 as a two module device, with the replaceable module 18a in FIG. 5B and the reusable module 18b in FIG. 5C.

FIG. 6A is similar to FIG. 5A, with FIG. 6B showing the two modules 18a, 18b separated, and FIG. 6C showing them joined with a maneuvering gap 28 between them. The eject plastic sheet 25 enables removal of the disposable module 18a.

Figure 7:
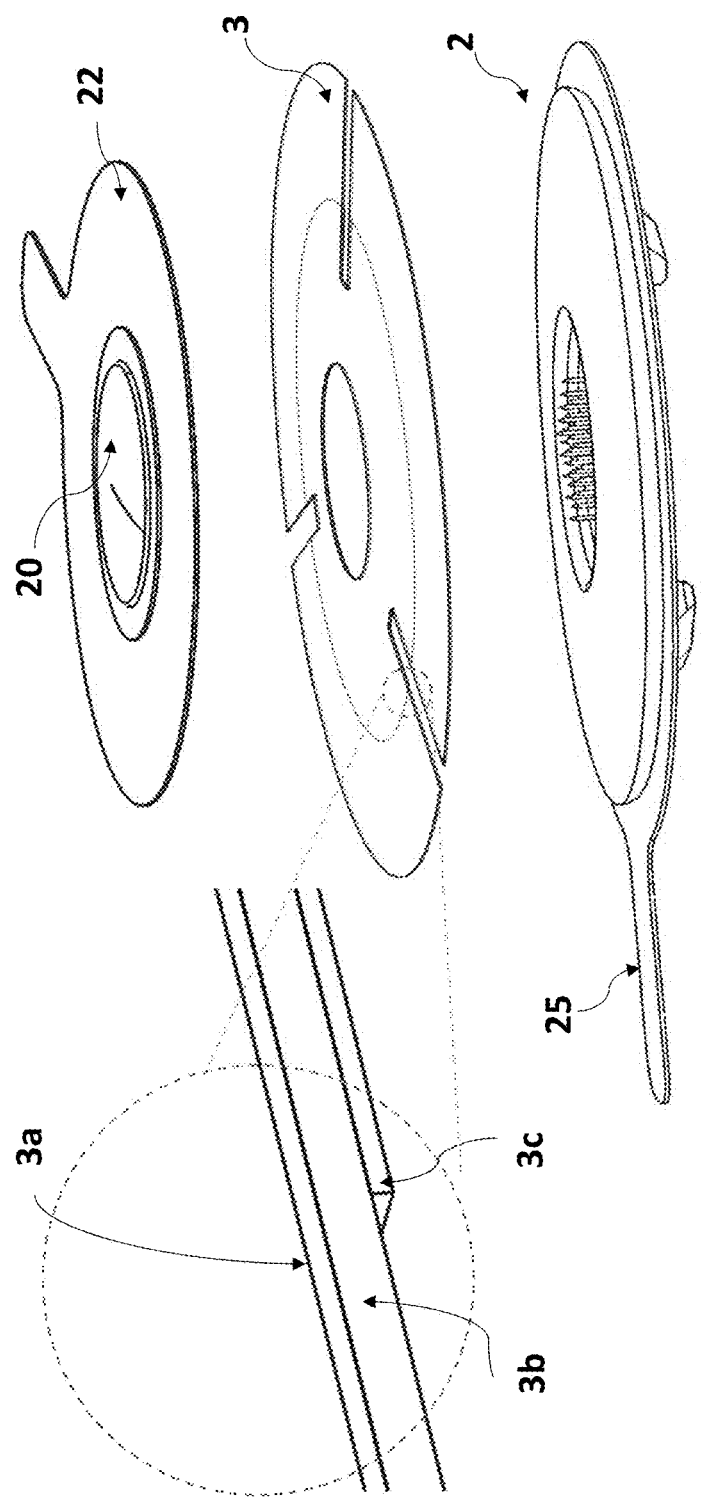
FIG. 7 is an exploded perspective view of the disposable module with an inset showing a close-up of the adhesive layer.

FIG. 7 is an exploded view of the reusable module 18a with a recessed cover 2 and a close up of one embodiment of the skin adhesive layer in three parts: the skin facing adhesive 3a, a non adhesive filament 3b, and adhesive 3c to attach to the recessed cover 2. A protective plastic bubble 20 is removed before usage. The skin adhesive layer can be used in all the embodiments of the invention.

FIG. 8A is a side view of the rigid base 23 and FIG. 8B is a perspective view underneath, with the rigid base integrated with the elastic insulative and the electrically conductive elastic e-contacts 9. The rigid base creates a robust connection between the disposable 18a and reusable 18b modules of the invention with rigid hooks 23a, which interlock with the top of the electronics (i.e., the lower rigid base 26). Openings 27 allow pins 9 to pass through to connect to the electronics unit.

FIG. 9A is a side view and FIG. 9B is a perspective view of the elastic insulative base 24, as also shown in FIG. 4A integrated between the rigid base (FIG. 8B). The microneedle array creates insulation and sensor conformability to the skin. Due to its intrinsic elastic and hydrophobic materials properties, the elastic insulative base 24 contributes to the following: a) provides sealing of the entire device against moisture, vapor, dust and liquids reaching electronics, and b) allows for reversible mechanical flexibility (spring-like reversibility) of the disposable module 18a during wear. Additionally, the piece provides micro motion/shock absorbance (i.e., mechanical damping), reducing motion-based artifacts that would otherwise corrupt an acquired biosensor signal.

Figure 10:
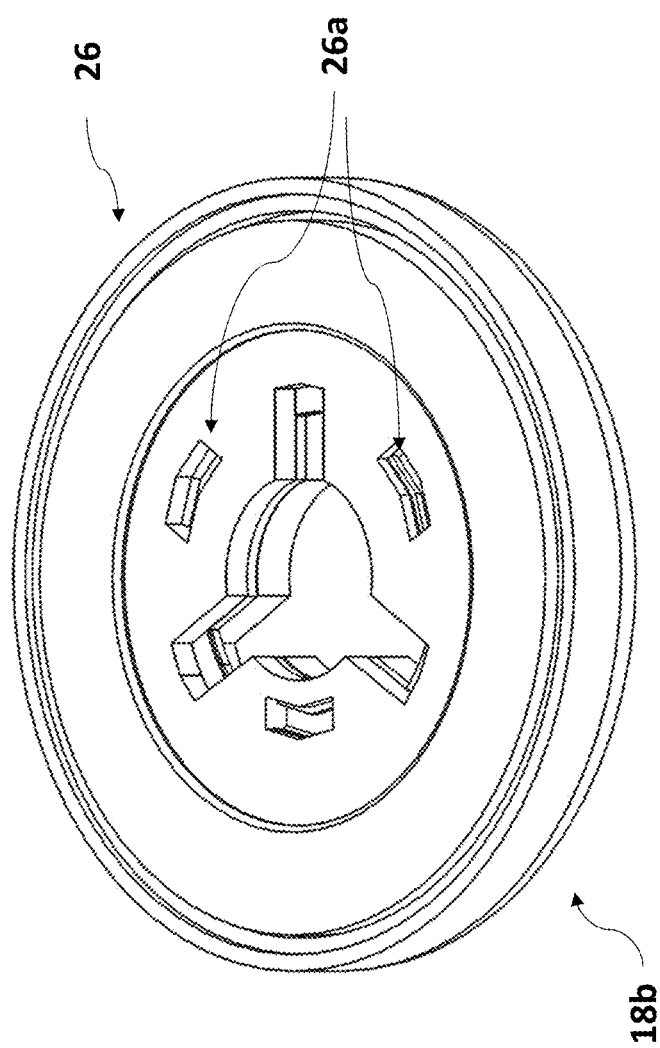
FIG. 10 is a perspective view of the assembled reusable module.
Figure 22:
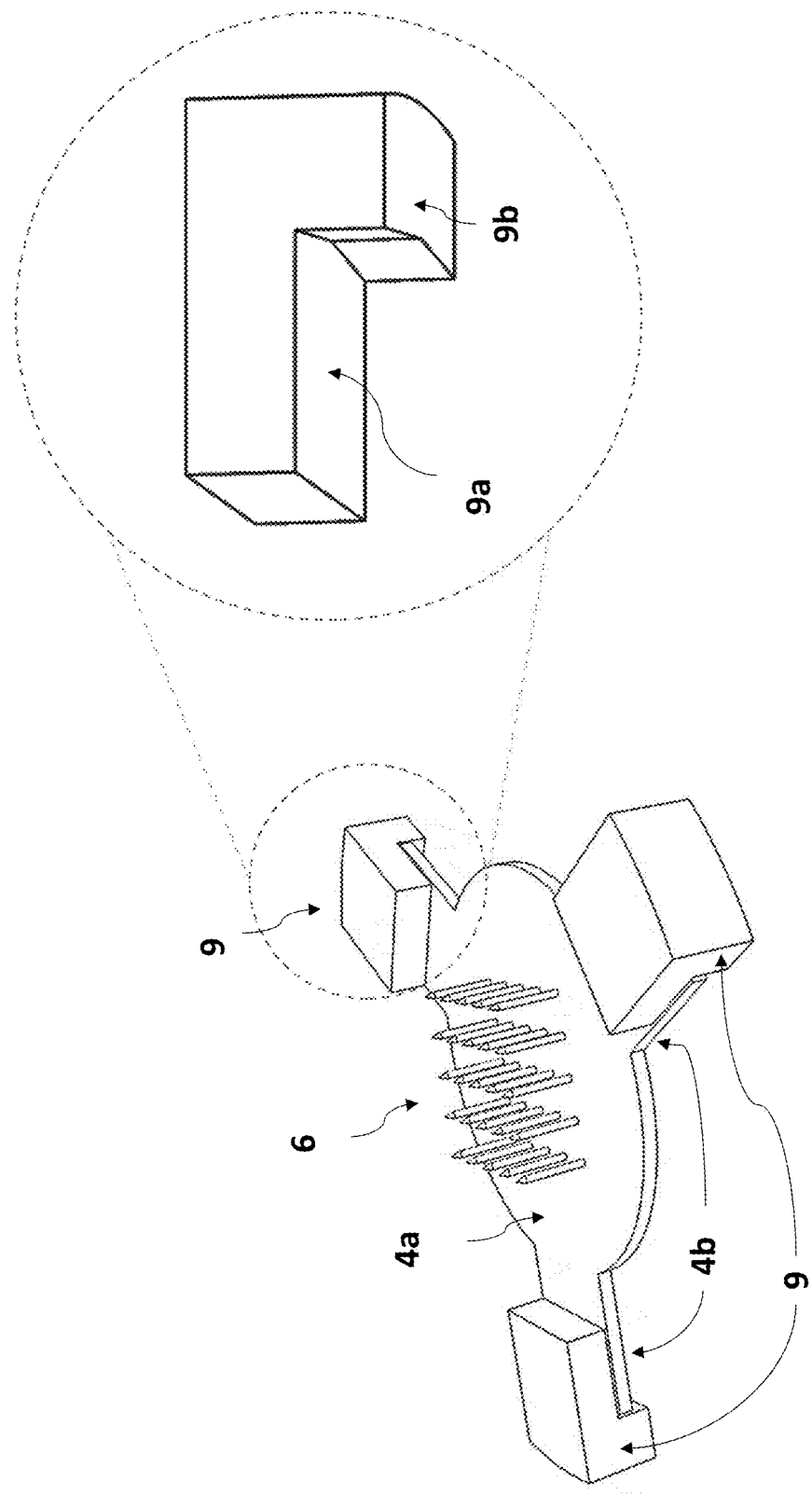
FIG. 22 is a perspective view an embodiment of a microneedle array with cantilevered arms and L-shaped pins.

FIG. 10 is a perspective view of the reusable module 18b with the lower rigid base 26. The lower rigid base 26, depicted in FIG. 31, mechanically and electrically interfacing with the disposable module 18a (not shown), comprises electronic hardware, such as an electronics unit assembled with components, which perform various functions including: a) acquire data from the biosensor (located on the disposable module 18a), b) to sense mechanical interferences sources which cause artifacts upon the biosensor data, and c) apply artifact removal algorithms to cleanse the biosensor data of artifacts. An example of a mechanical interference sources is a (quasi-) static force applied to the integrated device thereby pushing the microneedles toward the skin. FIG. 10 shows the lower rigid base 26 with connection sites 26a to the disposable piece, namely the rigid hooks 23a, a cavity for the microneedle array and cover to insert into. This provides an electrical connection between the electronic unit and the functionalized microneedle array via the L-shape conductive elastic pins 9 (as shown in FIG. 22) on the substrate.

The reusable module 18a has mechanical features such as a maneuvering gap 28, as shown in FIG. 6C, which allows a tunable degree of freedom for the disposable component to flex and conform at to the skin of the wearer. It also has a waterproof, closed structure. The entire electronics system in all embodiments of the device is water resistant by means of welding (e.g., ultrasonic), use of the photo-, or temperature-curable fluidic resins, or by the use of a double-sided adhesive and/or gluing the upper and lower enclosure piece together. Similarly, all the interfaces involving the PCB/enclosure contact are sealed using mentioned methods. FIG. 6C shows assembled pieces of the disposable module 18a including the array and reusable module 18b with electronics with sealed interfaces.

Another embodiment is depicted in FIG. 11, and it can be fully disposable or partially reusable using the design considerations and strategies described elsewhere herein. As further described herein (including in the description regarding FIG. 7), the topmost layer 3 is a medical-grade adhesive, ensuring the patch securely adheres to the skin with minimal risk of irritation. This adhesive can be peeled off and replaced as needed to maintain optimal skin compatibility and adherence. Just beneath the adhesive layer sits a basic cover 15 shields the microneedle array beneath it. The cover is designed to protect the microneedle array while also allowing for gas exchange, which is essential for skin health during prolonged wear. In this embodiment, the basic cover is level or flush with the alternate top enclosure, but it can also be elevated or recessed as described elsewhere herein. The microneedle array 4 has microneedles complementary to the set of first openings on the cover. Pins 9 connect the microneedle array and the electronics unit the including signal processing unit and wireless communication modules (not shown) housed within the alternate top enclosure 68. This alternate top enclosure is accessible for servicing or upgrading the electronics, which is crucial for the longevity and up-to-date functionality of the device. Beneath the alternate top enclosure is the rechargeable battery 69 which powers the electronics unit. The rechargeable design underscores the patch's sustainability by eliminating the need for disposable batteries. Lastly, the charging coil 70, which is part of the power management system, enables wireless recharging of the battery, adding a layer of convenience for the user by simplifying the recharging process. The bottommost layer is the lower enclosure 11, which serves as the base of the patch and provides structural integrity. It protects the charging coil and the battery from environmental elements and mechanical impacts.

Layout of Microneedle Array

In various embodiments of a manufacturing method, the cover and microneedle array are assembled with the photo-curable resin being introduced to the interface between the cover and the microneedle array followed by spontaneously forming a resin layer at the interface and surround the bases of the microneedles up to the microneedles' cutoff line 8.

The substrate 4a comprises an electrically insulative material which can be rigid, flexible or foldable in various embodiments, for example, it may be polymethyl methacrylate (PMMA) or other electrically insulative polymer, e.g., including UV curable polymers; whereas in other embodiments, the substrate 4a can include an electrically insulative ceramic and/or metallic material, including a composite material, which may include a polymeric material. The base of the microneedle 6 is integral to the substrate 4a; and the base 17 of the microneedle can be surrounded, at least partially, by the cured custom resin.

In some embodiments of the custom resin material, the resin material is formed of a polymer that is modified by a non-ionic surfactant and thermal treatment to render the desired viscosity and capillary properties. For example, the custom resin material can include a biomedical grade polymer composed of a mixture of acrylate and methacrylate based monomers and oligomers and a benzil ketal compound, e.g., Irgacur 651, as the photoinitiator, in which the polymer has an initial viscosity of 5 Pa·s. This polymer can be modified by adding the non-ionic surfactant (e.g., Triton X-100, 0.1-1% wt) that is thermally treated (e.g., thermal procuring at 65° C. for 20 min) to significantly decrease the viscosity, such that the final, custom resin material includes a viscosity within the range of 0.01 to 0.5 Pa·s. The low viscosity of the example custom resin material can considerably enhance the dynamic flowability of the overall polymer in the microfluidic channels 200. In implementations, for example, lowering the viscosity can result in more efficient crosslinking performance of the curable custom resin and thus create a highly chemically-resistant and biologically-resistant sealant material, which is an important factor during sensor modification, sterilization, and sensor use/application (e.g., in vivo and in vitro applications). In some embodiments of the custom resin material, the resin material can be configured to have resolution (size) lower than 500 nm. (Example images of microneedle arrays produced by this low temperature casting process are found in FIG. 7 of the '846 patent.)

Notably, in the course of refining this technique, a few key parameters regarding the post-processing of the photo-curable resin polymer that were found to solve the common problems of low-temperature casting methods. For example, these problems include the incomplete filling of the resin, low resolution and lack of forming a nanoscale surface roughness, usual adhesion problems between the mold and the final microstructure, lack of tip sharpness, gas bubble formation and other issues—all of which are successfully addressed by the use of the newly developed polymeric photocurable resin with optimal characteristic, as well as manufacturing process parameters tailored to the custom-made resin.

In some embodiments of the curable resin material, for example, the resin was prepared to an optimal viscosity by addition of nonionic surfactant (e.g., Triton X-100, in a concentration range of 0.1-1 wt %) to a biocompatible polymer, which included a biomedical-grade photocurable polymer resin. The surfactant additive, along with thermal treatment of the polymer mixture (e.g., at 65° C. for 20 min), resulted in enhancing the flowability (e.g., by reducing viscosity and enhancing surface energy) of the resin and led to nanoscale resolution of the method, without affecting the photo-crosslinking process and mechanical robustness of the finished material.

Any curable resin which meets the needs for manufacturability, strength and sealing is acceptable, in addition to the examples which are disclosed herein.

Using the curable resin material in the fabrication method, the final manufactured microneedles shows excellent solvent compatibility against both organic and inorganic harsh solutions, such as acetone, isooctane, ethanol, bleach, concentrated NaOH and HCl solution, hydrogen peroxide (3%) and saline water (3.5% NaCl), even up to 24 hours. Furthermore, these microneedles have demonstrated a remarkable compatibility to sterilization methods (e.g., Gamma radiation, ethylene oxide, autoclave treatments up to 125° C. for an hour, or UVc treatment). This fabrication method identified manufacturing process parameters that mitigate various problems, like incomplete filling, bubble formation, and low resolution, by combined use of the customized low-viscosity resin material, vacuumed pouring of the custom resin at an elevated temperature (e.g., 70° C. for 6 hours) followed by UV curing (e.g., 90° C. UV curing for 90 minutes). The example results produce a nanometer-precision replica with superior mechanical fracture toughness, e.g., with <5 microns of tip sharpness as shown in FIG. 7 of the '846 patent.

FIG. 33B of the '846 patent shows an illustrated flow diagram of an example embodiment of a fabrication method 3320 for microcasting of a microneedle sensor array in accordance with the present technology. In some implementations of the method 3320, the method 3320 is used to micro-cast an array of microneedles protruding from a substrate structure with an array of microchannels formed on the surface or within the substrate, which involves a three-phase process including a first phase to create a master structure for a mold of the microneedle array, a second phase to create a mold of the microneedle array for repeatable micro-casting manufacturing, and a third phase of producing units of the microneedle array via micro-casting from the mold. This method in the '846 patent also enables production of an array without microfluidic channels.

In various embodiments of a manufacturing method, the cover and microneedle array are assembled with the photo-curable resin being introduced to the interface between the cover and the microneedle array followed by spontaneously forming a resin layer at the interface and surround the bases of the microneedles up to the microneedles' cutoff line 8.

The substrate 4a comprises an electrically insulative material which can be rigid, flexible or foldable in various embodiments, for example, it may be polymethyl methacrylate (PMMA) or other electrically insulative polymer, e.g., including UV curable polymers; whereas in other embodiments, the substrate 4a can include an electrically insulative ceramic and/or metallic material, including a composite material, which may include a polymeric material. The base of the microneedle 6 is integral to the substrate 4a; and the base 17 of the microneedle can be surrounded, at least partially, by the cured custom resin.

In some embodiments of the custom resin material, the resin material is formed of a polymer that is modified by a non-ionic surfactant and thermal treatment to render the desired viscosity and capillary properties. For example, the custom resin material can include a biomedical grade polymer composed of a mixture of acrylate and methacrylate based monomers and oligomers and a benzil ketal compound, e.g., Irgacur 651, as the photoinitiator, in which the polymer has an initial viscosity of 5 Pa·s. This polymer can be modified by adding the non-ionic surfactant (e.g., Triton X-100, 0.1-1% wt) that is thermally treated (e.g., thermal procuring at 65° C. for 20 min) to significantly decrease the viscosity, such that the final, custom resin material includes a viscosity within the range of 0.01 to 0.5 Pa·s. The low viscosity of the example custom resin material can considerably enhance the dynamic flowability of the overall polymer in the microfluidic channels 200. In implementations, for example, lowering the viscosity can result in more efficient crosslinking performance of the curable custom resin and thus create a highly chemically-resistant and biologically-resistant sealant material, which is an important factor during sensor modification, sterilization, and sensor use/application (e.g., in vivo and in vitro applications). In some embodiments of the custom resin material, the resin material can be configured to have resolution (size) lower than 500 nm. (Example images of microneedle arrays produced by this low temperature casting process are found in FIG. 7 of the '846 patent.)

Notably, in the course of refining this technique, a few key parameters regarding the post-processing of the photo-curable resin polymer that were found to solve the common problems of low-temperature casting methods. For example, these problems include the incomplete filling of the resin, low resolution and lack of forming a nanoscale surface roughness, usual adhesion problems between the mold and the final microstructure, lack of tip sharpness, gas bubble formation and other issues-all of which are successfully addressed by the use of the newly developed polymeric photocurable resin with optimal characteristic, as well as manufacturing process parameters tailored to the custom-made resin.

In some embodiments of the curable resin material, for example, the resin was prepared to an optimal viscosity by addition of nonionic surfactant (e.g., Triton X-100, in a concentration range of 0.1-1 wt %) to a biocompatible polymer, which included a biomedical-grade photocurable polymer resin. The surfactant additive, along with thermal treatment of the polymer mixture (e.g., at 65° C. for 20 min), resulted in enhancing the flowability (e.g., by reducing viscosity and enhancing surface energy) of the resin and led to nanoscale resolution of the method, without affecting the photo-crosslinking process and mechanical robustness of the finished material.

Using the curable resin material in the fabrication method, the final manufactured microneedles show excellent solvent compatibility against both organic and inorganic harsh solutions, such as acetone, isooctane, ethanol, bleach, concentrated NaOH and HCl solution, hydrogen peroxide (3%) and saline water (3.5% NaCl), even up to 24 hours. Furthermore, these microneedles have demonstrated a remarkable compatibility to sterilization methods (e.g., Gamma radiation, ethylene oxide, autoclave treatments up to 125° C. for an hour, or UVc treatment). This fabrication method identified manufacturing process parameters that mitigate various problems, like incomplete filling, bubble formation, and low resolution, by combined use of the customized low-viscosity resin material, vacuumed pouring of the custom resin at an elevated temperature (e.g., 70° C. for 6 hours) followed by UV curing (e.g., 90° C. UV curing for 90 minutes). The example results produce a nanometer-precision replica with superior mechanical fracture toughness, e.g., with <5 microns of tip sharpness as shown in FIG. 7 of the '846 patent.

FIG. 33B of the '846 patent shows an illustrated flow diagram of an example embodiment of a fabrication method 3320 for microcasting of a microneedle sensor array in accordance with the present technology. In some implementations of the method 3320, the method 3320 is used to micro-cast an array of microneedles protruding from a substrate structure with an array of microchannels formed on the surface or within the substrate, which involves a three-phase process including a first phase to create a master structure for a mold of the microneedle array, a second phase to create a mold of the microneedle array for repeatable micro-casting manufacturing, and a third phase of producing units of the microneedle array via micro-casting from the mold. This method in the '846 patent also enables production of an array without microfluidic channels.

The method 3320 includes a process 3321 to create or obtain a computer-aided model/design (e.g., CAM/CAD design in a 3D modeling software, such as Fusion 360, Solidworks, etc.) for a microneedle array, including 3D structures including microneedles (and optionally, micro-channels). The method 3320 can include a process 3322 to create a master structure for the microneedle array in accordance with the computer-aided model/design. In some implementations of the process 3322, for example, where the features of the microneedle array include high resolution features (e.g., 5 μm or less), the process 3322 can include utilizing an ultra-high resolution 3D printing technique, a CNC technique (e.g., as in the process 3312), or two-photon lithography technique to create the master structure for the array. In some implementations of the process 3322, for example, where the features of the microneedle array do not include ultra-high resolution features, the process 3322 can include utilizing a micro-machining technique or a photolithography technique.

The method 3320 includes a process 3324 to create a mold for the microneedle array using the master structure of the microneedle array. In some implementations of the process 3324, for example, the process 3324 includes creating the mold using molding material (e.g., including but not limited to polydimethylsiloxane (PDMS) or a silicone-based elastomer) by depositing the molding material onto and/or into the master structure; degassing and heat treating the molding material on/in the master structure to produce the mold of the microneedle array, and removing the master structure from the produced mold. In implementations of the method 3320, for example, the process 3324 can be repeated to make multiple molds from a single master structure produced in the process 3322. The method 3320 includes a process 3326 to cast a substrate structure in the created mold to form an array of microneedles on a substrate. In some implementations of the process 3326, for example, the process 3326 includes casting a biocompatible polymer material (e.g., UV-curable resin) by depositing the biocompatible material into the mold, degassing the deposited biocompatible material in the mold, and curing the degassed biocompatible material, e.g., by UV light and/or heat. In implementations of the method 3320, for example, the process 3326 can be repeated to make multiple microneedle array units from a single mold produced in the process 3324.

In some aspects, a method for fabricating a wearable, non-intrusive microneedle sensor device includes creating or obtaining a computer-aided design of a microneedle sensor array comprising a plurality of microneedles arranged on a substrate, wherein the plurality of microneedles includes a body region, a tip in a tip region; producing a physical rendition of the microneedle sensor array, wherein at least some of the plurality of microneedles of the produced physical rendition of the microneedle sensor array include an electrically-conductive region to form the plurality of microneedles; and attaching a cover to the microneedle array, the cover comprising an electrically insulative material having a set of first openings configured to align with the plurality of microneedles on the substrate, such that the tip region and at least a distal portion of the body region of the microneedles configured to pass through the set of first openings of the cover.

Drawing lithography is a fabrication method for the microneedle array in which a melted material selected from the group consisting of polymer, composite, ceramic and metal is drawn from a planar substrate directly to a 3D microneedle without the need for a mask and light irradiation. It creates microneedles from liquid or soft materials and solidifies them into high aspect structures, offering simplicity and efficiency. These materials include Clary, sheet, molding dough liquid etc. FIGS. 12A and 12B illustrate that a drawing disc 201 draws curing molding materials 202 on a non-stick substrate 203 into microneedles 6 integral to the substrate 4a. This will also include new classes of meltable material, some to be developed in the future, which can solidify in a new shape. FIGS. 12A-12B introduce a "drawing and curing" technique for microneedle fabrication, a method that stands out for its precision and efficacy. In this inventive process, a drawing disc or arm is engaged in a delicate dance of upward motion, exerting a carefully calibrated pull on the moldable materials below. This drawing action is not merely lifting but sculpting—the materials, such as clays, sheets, or molding dough liquids, are coaxed upwards, forming the slender, tapered shapes characteristic of microneedles. As the materials are drawn, they undergo a simultaneous curing process, which may involve heat, UV radiation, or chemical reactions, solidifying the materials into their final, rigid form with pinpoint accuracy. This method allows finesse, allowing for the creation of microneedles with exceptionally fine tips and precise dimensions. This process ensures that the microneedles have the necessary sharpness for penetration with minimal discomfort, and the strength to withstand the forces exerted during use. The curing aspect of the process is equally critical, as it locks in the shape and structural integrity of the needles, ensuring that they are not only functional but also safe and reliable. Also suitable is magnetorheological drawing lithography (MRDL), a modified form of drawing lithography, in which an external magnetic field is used to draw a droplet of a curable magnetorheological fluid to form 3D microneedles with improved sharpness and length of the resulted microneedles.

Another method for making the microneedle array is compression molding using molding clay, biomedical dough or formable thick films. Compression molding uses a compression disc 204 to press a semi-cured or pliable material 202 into a master mold 205 to form microneedles. This versatile technique, depicted in FIG. 13, is effective for creating detailed shapes with consistent quality in mechanical and physical properties. This method applies uniform force via a compression disc, exerting downward pressure to shape materials into a desired form. This process transforms molding materials such as clays, sheets, molding dough, or liquids with precision. The molding materials are placed between the compression disc and the mold. As the compression disc applies force, the materials yield to the contours of the mold, taking on complex geometries with fidelity. This method allows detailed control over the molding process. The uniform force ensures that the materials fill every part of the mold evenly, eliminating air pockets and inconsistencies that could weaken the final product.

FIG. 14 depicts laser or water jet cutting. A first step is cutting a sheet of material 208 as shown in 14A, and bending of the microneedles within the sheet in 14B. Use of these rows of microneedles could be done on one sheet, as long as the rows were folded together at the bottom. Or, the rows can be added to a substrate and secured thereon with the custom cured resin described elsewhere. FIG. 14 shows a two-step microneedle fabrication process that begins with the precision of laser or water jet cutting. In the first step, the cutting technique is employed to intricately carve out a row microneedle profiles from a sheet material. FIG. 14A showcases a series of uniform and sharply defined microneedle outlines, showing the accuracy of the cutting method. This technology allows for the creation of complex, high-precision shapes within the sheet, laying the groundwork for the microneedles' structure. FIG. 14B is a side view of a row of microneedles 4d in which the previously cut microneedles are now bent upwards from within the plane of the sheet, transforming the two-dimensional outlines into three-dimensional functional forms. This bending process is as crucial as the cutting, for it gives the microneedles their characteristic protrusion from the base, allowing for effective skin penetration. The marriage of cutting-edge laser or water jet cutting with meticulous bending results in a sheet densely populated with uniformly shaped microneedles, ready for application. This approach to microneedle fabrication uses the synergy between high-precision cutting technology and material manipulation to produce microneedles.

FIGS. 15A and 15B are successive steps of another lasering method starting with a block of material 207, and the laser beam 206 engraving of the block of material 207 to generate a microneedle array 4. In FIG. 15A the microneedle array is only partially engraved.

3D printing, or additive manufacturing, is a method for fabrication of microneedle arrays. 3D printing is used here as a broad term for stereolithography, fused filament fabrication, digital light processing, and scan, spin, & selectively photocuring (3SP) methods. The materials for 3D printing are selected from the group consisting polymers such as (PLA (polylactic acid)), ABS (acrylonitrile butadiene styrene) and TPU (thermoplastic polyurethane); metals such as titanium, stainless steel and aluminum; ceramics such as zirconia and alumina; composites such as carbon fiber reinforced plastics and glass-fiber reinforced plastics; resins such as photopolymers for SLA (stereolithography) and DLP (digital light processing) and are cured by UV light and epoxy resins; powders such as nylon powder used in SLS (selective laser sintering) and metal powders such as titanium, stainless steel, and aluminum, used in metal 3D printing processes like DMLS (direct metal laser sintering); hybrids such as polymer-metal hybrids and ceramic-polymer hybrids; other specialty materials such as conductive filaments, high-temperature resistant filaments such as PEEK, and biocompatible materials: for medical implants and prosthetics; and new materials and combinations of the above. 3D printing techniques are versatile fabrication methods in terms of microneedle geometry, spacing, height, numbers, and two-photon polymerization (TPP) SLA allows the fabrication of higher resolution. Conductive materials such as the metals in the group are passivated electrically with a nonconductive coating before a microarray with them is used.

Other methods of fabricating microneedle arrays are also within the scope of this application including, without limitation, making a master, e.g. a metal master, (e.g. of aluminum), making a mold, for example a PDMS mold from the master, and then forming a sensor array, for example from epoxy, in the mold. The electrodes are then formed on the sensors by forming a mask on the sensor body defining a number of openings corresponding to the areas to be covered by the electrodes, and then applying the conductive coating to the areas exposed by the mask to form the electrodes.

FIG. 16 is one embodiment of the microneedle array 4 with microneedles 6 on the top surface as manufactured by one of the methods discussed herein. This is an embodiment with cantilevered arms 4b. FIG. 16 is a perspective view of the microneedle array 4 with cantilevered arms 4b. Arrows show $F_{net/Microneedle\ to\ skin}$ which is the amount of net force applied from the microneedles to the skin during the microneedle insertion at the time of sensor application to the wearer's body and also during the sensor wear period.

The following describes fabrication of a cover with conductive traces (see FIG. 48) and its application for sensing and stimulation. The electronic microneedle cover can be fabricated using additive (e.g., sputtering and photolithography) and/or subtractive (e.g., chemical etching) to form electrically conductive patterns. The substrate for the conductive patterns can comprise a variety of materials with various mechanical properties, e.g., a polyimide for a flexible cover. The improved cover can be composed of multiple substrate and conductive layers, with each substrate and/or layer being made of a different material, such as a flexible polyimide bonded to a rigid plastic.

Masks may be used in conjunction with additive and/or subtractive fabrication methods to form patterns of the conductive layers. The conductive material exposed to the skin can be controlled to present different electrical or mechanical coupling to the skin. For example, an exposed circular gold-plated copper pad can touch the skin to form a direct-coupled electrode. In another embodiment a circular copper pad which is covered with a thin polyimide film forms an electrode that is capacitively coupled to the body.

Multiple conductive layers can be interconnected with vias. Sections of the conductive layers can be exposed to allow for electrical connections to electronic hardware, e.g., a printed circuit board (PCB).

The microneedle array and the cover are coupled together by a curable resin in one of several ways. See FIGS. 17A-17C. In one method of sealing the microneedle array to the cover and strengthening both components, the resin is introduced after the cover is coupled with the microneedle array, where microfluidic channels 200 are present (see FIG. 18). These channels are specifically designed to direct the flow of resin in a controlled manner. The resin enters through resin insert holes within the cover or within the microneedle array's substrate, which are located on the cover's bottom surface (labeled 'a') in FIG. 17A, or on the microneedle array substrate's top surface (labeled 'b'), and then are guided into the channels. The resin flows precisely along these predefined paths, allowing for targeted delivery to specific areas on the substrate. In FIG. 17B this controlled flow is further guided horizontally (labeled 'c') to ensure even distribution and accurate placement of the resin around the microneedles, without coating them. The microfluidic channels 200 act as conduits, preventing the resin from spreading randomly and ensuring that it only goes where it is needed. This results in a more efficient use of the resin, improved performance of the microneedles, and enhanced functionality of the overall device due to the precise positioning of the resin. In another method in FIG. 17C, the curable resin is applied before the microneedle array is coupled to a recessed cover 2, which means the resin is applied directly onto the top surface of the microneedle substrate or to the cover's bottom side. Without microfluidic channels to guide and control the flow, the resin spreads out in all directions from the point of application as a result of capillary action and the adhesive properties of the resin. The resin fills the spaces between the microneedles and also surrounds their bases, and is controlled by applied assembly force, resin flow properties and amount applied, and curing rate all resulting in precise distribution of the resin.

Figure 18:
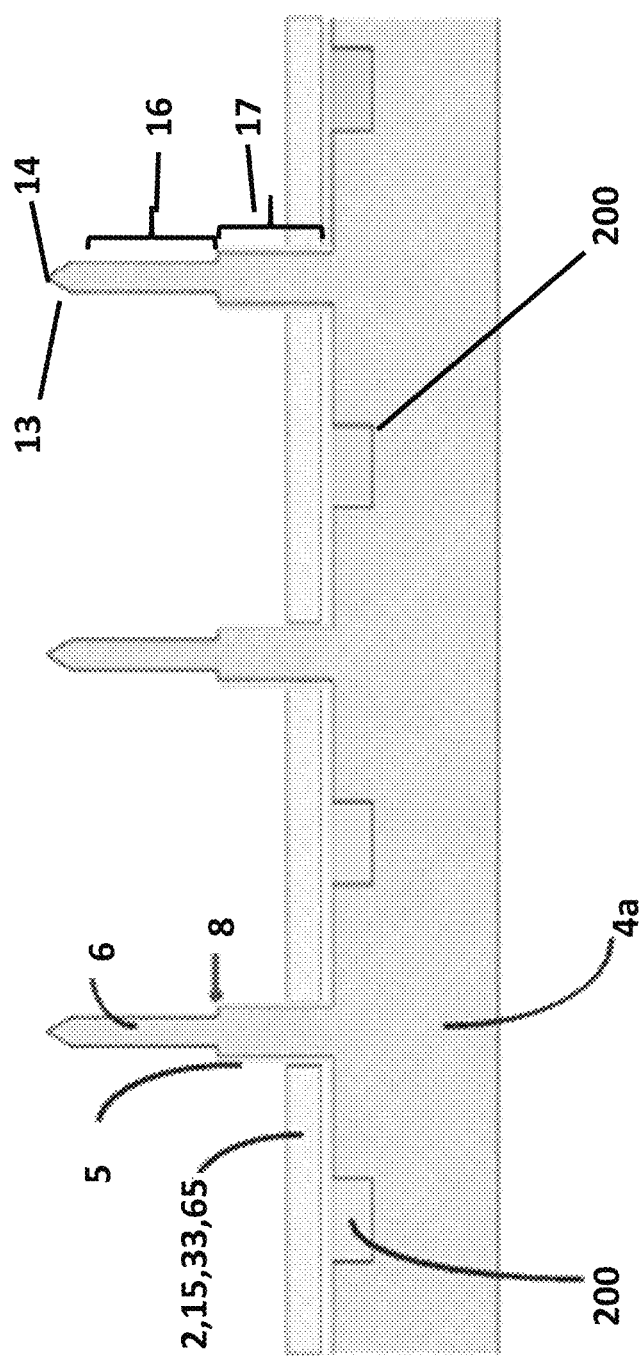
FIG. 18 (FIG. 4B of U.S. Pat. No. 11,877,846) is a section view of a portion of a microneedle array showing microfluidic channels with resin in the channels and up to a cut-off line.

FIG. 18 (adapted from FIG. 4B of the '846 patent) is a cross-sectional view illustrating an example embodiment of microneedles 6 and portion of substrate and covered by an example cover 2, 15, 33, 65 which facilitates the capillary sealing method for flowing the curable resin material 5 through the microfluidic channels 200 and through gaps between the substrate 4a and cover 419 and outward to the cut-off line 8, which can surround the bases 17 of the microneedles (e.g., via photocuring the resin 5). In some embodiments of the method, for example, the cut-off line 8 or area of the microneedle 6 can (i) provide a location where the capillary flow of the curable resin stops flowing upwardly, and (ii) serve as a structure responsible for where the microneedles are to be reproducibly insulated. For further details, see FIGS. 34A-34C of the '846 patent. In some embodiments the microneedle array includes a network of microfluidic channels 200 that are embedded on the top surface of the substrate. In some embodiments microfluidic channels can be tunneled into substrate or the cover with holes to the surface allowing the resin to flow to the surface. The microfluidic channels 200 assist the flowing of a curable resin with optimal viscosity and capillary properties from one or more entry point(s) through the network of microfluidic channels to the interface where the substrate 4a and cover 2, 15, 33, 65 meet. For example, at this cover/microneedle array interface, the resin both (1) seals the microneedle array 4 and the extended, basic or foldable cover 2, 15, 33, 65 together and (2) insulates the microneedles 6 at their base 17. In some embodiments the microfluidic channels can also run vertically, slanted, or otherwise on the microneedles. In the example shown in FIG. 34A of the '846 patent, the plurality of channels (numbered 3414 therein) are configured as vertical channels. Electrical The electrically conductive layer is described in FIG. 19 (FIG. 19 of the '846 patent), and companion text, which sets forth the method 1900 including a process 1920 to carry out thin-film depositions and etching to create an array of microneedles. In some implementations of the process 1920, for example, the process 1920 includes (i) thin film-depositing a first material (e.g., PMMA) to form a batch of a clean microneedles (e.g., PMMA array of microneedles) as shown in panel (bi); (ii) then thin film-depositing a second material to the batch of clean microneedles to form a first coating on the microneedles, e.g., such as by sputtering Cr/Pt/Ag to form a Cr/Pt/Ag-coated array of microneedles as shown in panel (bii); and (iii) followed by etching of a conductive material (e.g., Ag) from the microneedles to be designated as the working and counter microneedle microelectrodes and subsequent reference-electrode prepping, e.g., such as chloritization of the conductive material (e.g., chloritization of Ag to Ag—AgCl as the reference microelectrodes) as shown in panel (biii).

The method 1900 includes a process 1930 to electrically isolate one or more working microelectrode regions (e.g., one or more sets of WE microneedles), at least one counter microelectrode region (e.g., one or more sets of CE microneedles), and at least one reference microelectrode region (e.g., one or more sets of RE microneedles), as shown in panel (biv). In some implementations of the process 1930, formation of the electrically isolated microelectrode regions can be achieved by removal of a thin film metal using mechanical abrasion (e.g., manual or using a CNC) on the traces; and/or removal of the thin film metal using laser machine. Implementations of the process 1930 can complete fabrication of a microneedle array.

Figure 26:
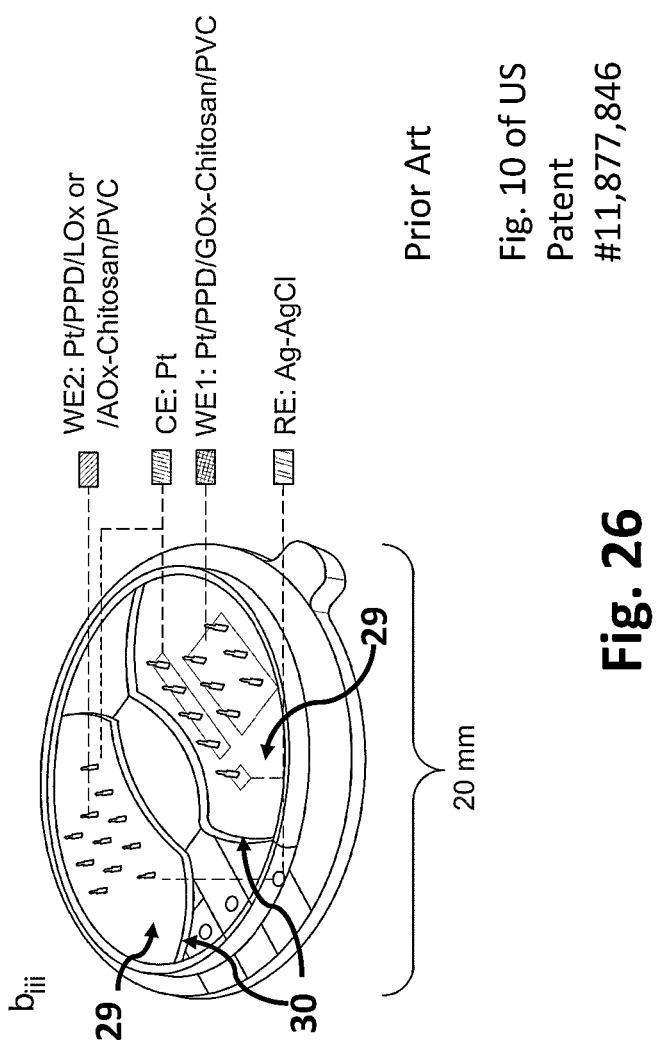
FIG. 26 (FIG. 10 of U.S. Pat. No. 11,877,846) is a perspective view of an embodiment of a microneedle array with two sensing regions.

Also, for example, the microfluidic channels (e.g., which can have a depth and/or width ranging from 100-400 µm) that are created on and/or in the substructure can also serve as electrical isolation channels 30 as shown in FIG. 26 26 (e.g., when masked or engraved to individually addressable electrical regions) for an electrical isolation process step of the fabrication method, which can include (i) guiding the mechanical scraping of the metal sputtered inside the channels (that can leave the rest of the substrate into electrically isolated islands/regions), or (ii) holding solid or liquid-based masks that can be fit inside the channels before any metal deposition and removed after the metal thin film deposition. This can be implemented by laser engraving, micro-CNC machining, or manual scraping of the metal inside of the channel according to the final design of the microneedle regions, as illustrated by the examples in diagram 402, which can leave certain regions to be electrically connected or electrically isolated from each other. Further details about the fabrication method are described later in this patent document.

Figure 19:
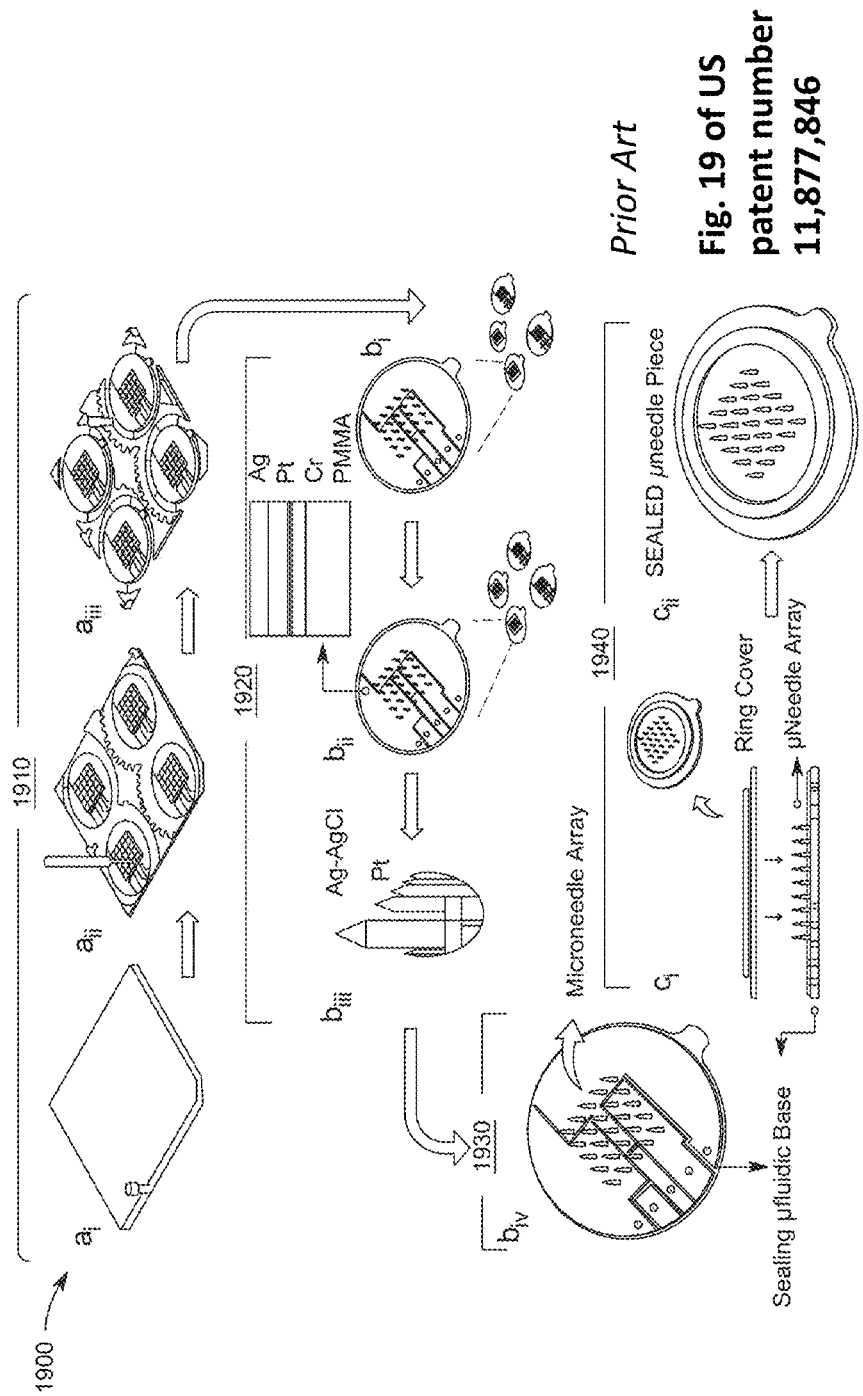
FIG. 19 (FIG. 19 of U.S. Pat. No. 11,877,846) shows aspects of ways to construct an embodiment of a device herein.
Figure 20:
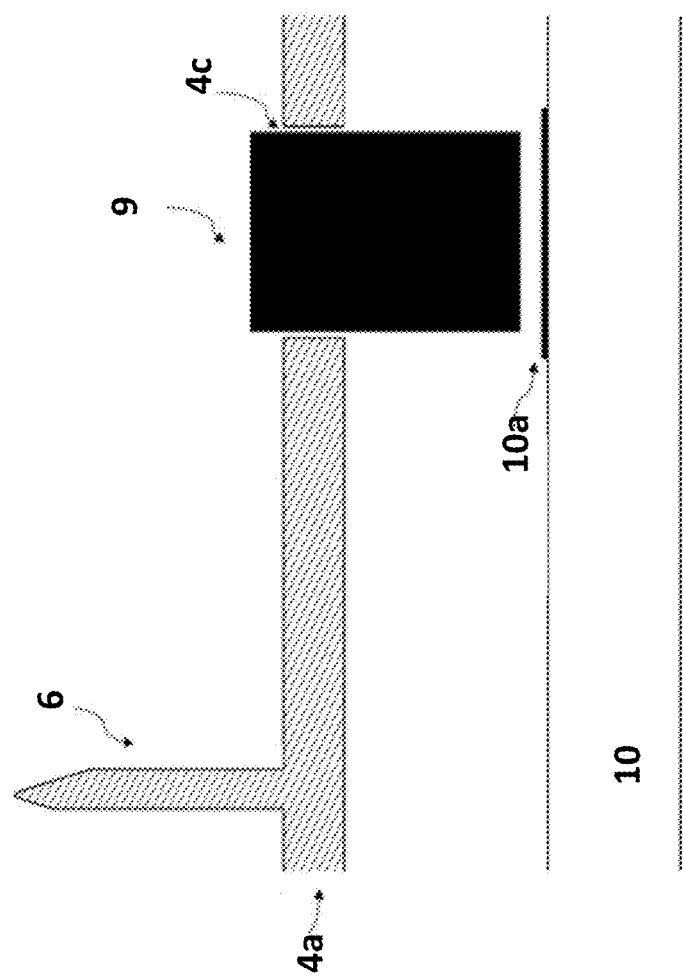
FIGS. 20 and 21 respectively are schematics of a conductive pin connecting a frictionous hole on the substrate to the electronics unit, or a pin which is bonded

Briefly, for the single analyte sensors (e.g., lactate, glucose, alcohol), a 3-electrode electrochemical system was used with the electrodes ratio of 16WE/8CE/1RE (e.g., see FIGS. 19-20 of the '846 patent). The multiplexed sensors (e.g., lactate-glucose, alcohol-glucose), relied on two 3-electrode systems, with two physically isolated working electrodes, two complementary counter electrodes, and two complementary reference electrodes, in the ratio of 6WE/8CE/1RE (e.g., see FIG. 10 of the '846 patent, panel (biii)).

In addition to the electrical connections described herein, the microneedle array, formed as described herein, may also be connected using prior art techniques to the electronics unit of the device for signal processing.

Figure 21:
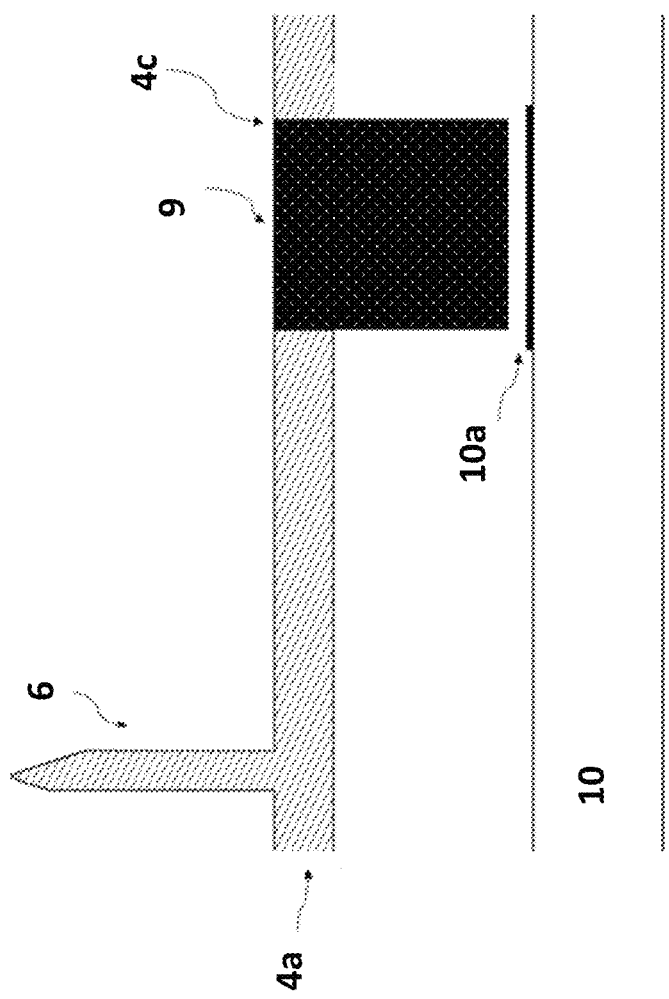

FIGS. 20 and 21 contain different embodiments of the electrical connections between the electrically conductive layer of the microneedles and the electronics unit. The pins 9 used with frictionous contact pads are made of electrically conductive, elastic, or spring-like materials (e.g., pogo pins). These pins 9 at one end push against the electrically conductive layer on the walls in the holes 4c in the substrate and at the other end press against, for example, conductive pads 10 a on the electronics unit 10. The pins 9 in FIGS. 20 and 21 are similar to those disclosed, for example, as elements 526, 510 and 512 in FIG. 5 of the '846 patent, incorporated herein. The pins may be frictionous as in FIG. 20 or bonded or cured into the holes as in FIG. 21.

In another embodiment, pins 9 may be bonded or glued to the electrically conductive layer on the walls of the holes of the substrate 4a, eliminating the need for friction between against the substrate contacts 4c. The materials used in this kind of connection are similar to those mentioned herein. The bonding and gluing process can use curable materials, such as silver epoxy or silicone rubber. In this type of electronic interconnection, either the entire pin or the interface between the pin and the metal layer within the holes in the substrate can be made of elastic conductive materials, as previously mentioned.

FIG. 22 includes an embodiment of the conductive pins 9 as L-shaped having at least two conductive surfaces, 9a which contacts the electrically conductive layer 50 on the microneedle array 4 (here on cantilevered arms 4b) and 9b which contacts the electronics unit (not shown here).

Figure 23:
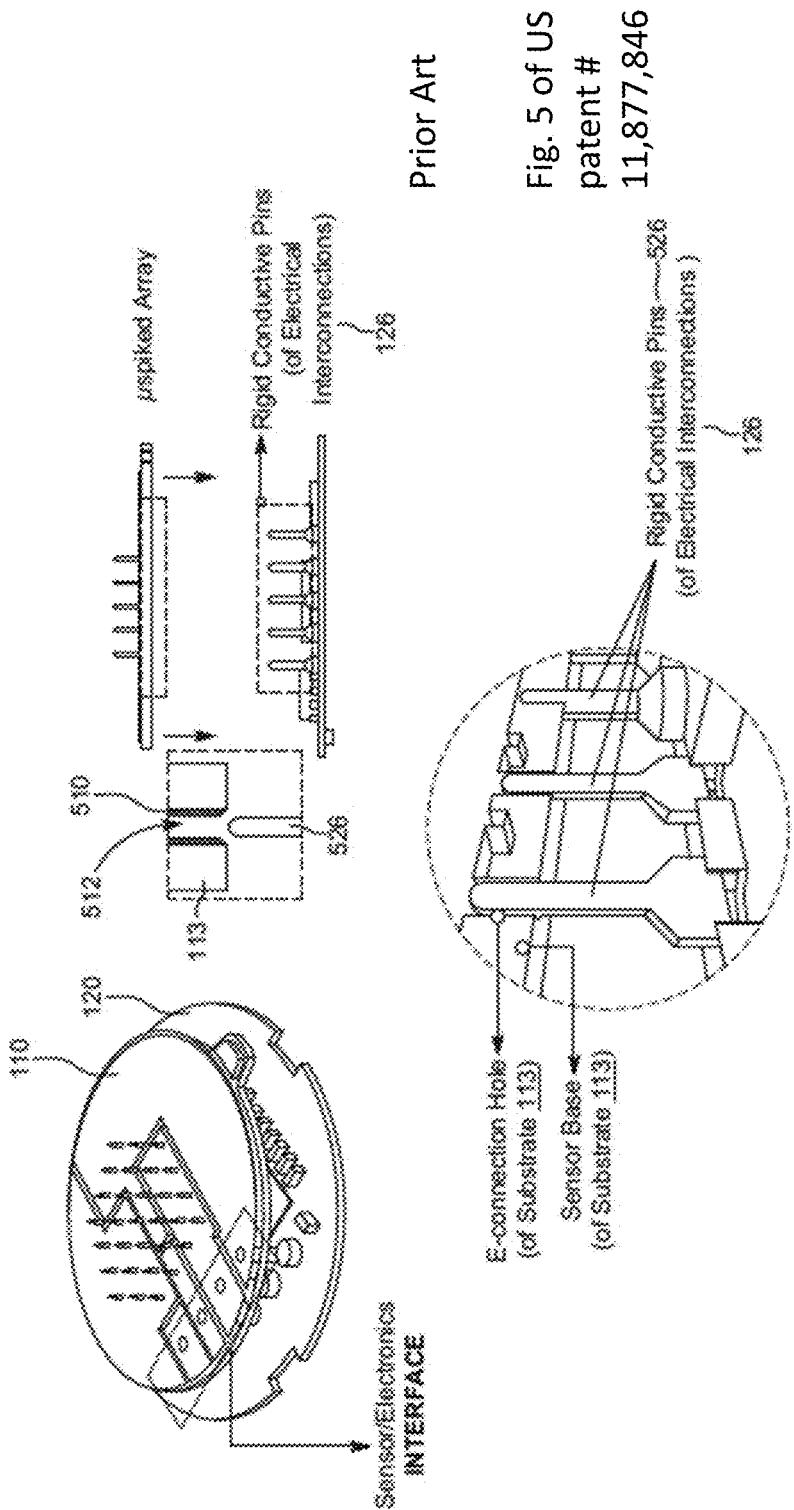
FIG. 23 (FIG. 5 of U.S. Pat. No. 11,877,846) shows aspects of ways to construct an embodiment of a device herein.

FIG. 23 (FIG. 5 of the '846 patent) shows diagrams depicting example embodiments of the substrate of the microneedle array 4 and electrical connection to the electronics unit 100 (e.g., signal conditioning unit, which can provide a potentiostat). In one embodiment the substrate 4a includes a plurality of electrically-conductive, friction-based contacts (e.g., less than 100 nm thickness) that are disposed within openings 4c of the substructure of the substrate 4a. The example openings 4c of the substructure of the substrate 4a, combined with the electrically-conductive, friction-based contacts 510, are sized to receive the conductive pins 9. For example, an advantage of this embodiment is related to the single-step sputtering/metal film deposition process of the microneedle array 4, which allows for top-down sputtering that covers the walls of the openings 4c with the electrically conductive layer to form contacts where the conductive pins 9 of the electronics unit 10 (or an intermediate interface) inserts. The resulting electrically-conductive, friction-based contact 510 provides a relatively low noise and reliable interface, even during high intensity body motions (by the user), which is a challenging objective to achieve (e.g., particularly for nano-ampere sensitivity systems for epidermal analyte-based electrochemical sensing applications). The pins 9 are configured, e.g., on electronic unit 10 to mechanically align with corresponding openings 4c. Such pins 9 can be fabricated using an orientation aligner design and configured to have a round tip at the apex of the pin for smooth insertion to the openings.

Figure 24:
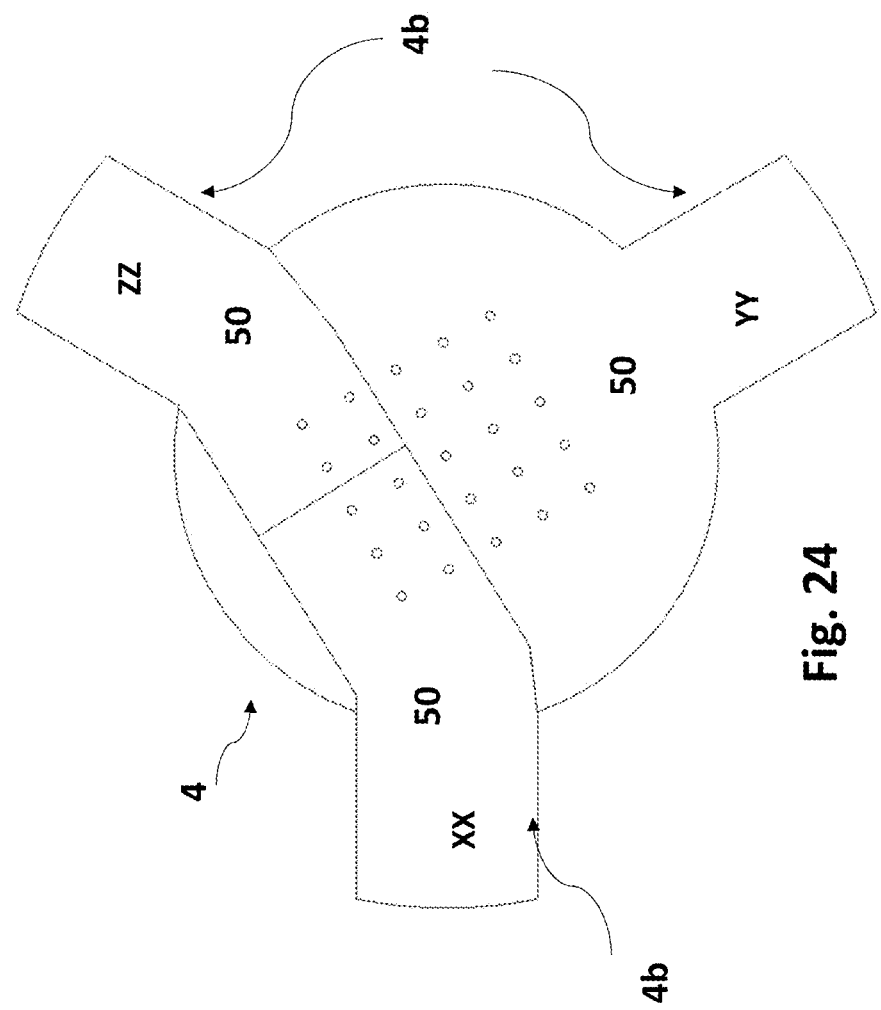
FIG. 24 is a schematic of an embodiment of the microneedle array with cantilevered arms and a three electrode electrochemical sensing system.

FIG. 24 is a top down view of one embodiment of the microneedle array illustrating the central positioning of the microneedles 6 within the substrate 4a. To construct an electrochemical sensor system, one needs a dual-electrode system, which incorporates a working electrode (WE) and a counter/reference electrode (CE/RE), or a tri-electrode system that integrates a WE, a CE, and a separate RE. There can be one or multiple dual- or tri-electrode systems incorporated on a single microneedle array, forming multiple sensors that act concurrently or sequentially constituting the WE, CE, and RE electrodes, each with multiple microneedles, forming electrode regions and are labeled XX, YY, and ZZ. The electrically conductive layer (50) covers each of the isolated regions, and each region is electrically isolated from the others. For an electrode region to be complete, it must have at least one microneedle and a connection to the electronic unit. This connection needs to allow electricity to flow continuously from the microneedle to the electronic unit. For example, in the electrode region YY, several microneedles are electrically connected to each other and to the electronic unit through layer 50, creating a fully functioning electrode region. Together, the YY, XX, and ZZ regions make up a complete tri-electrode electrochemical sensor. This tri-electrode electrochemical sensor can be considered as a single sensing region. There can be one or multiple dual- or tri-electrode systems incorporated on a single microneedle array, forming multiple sensors that act concurrently or sequentially in measuring more than one analyte or biomarker.

Figure 25:
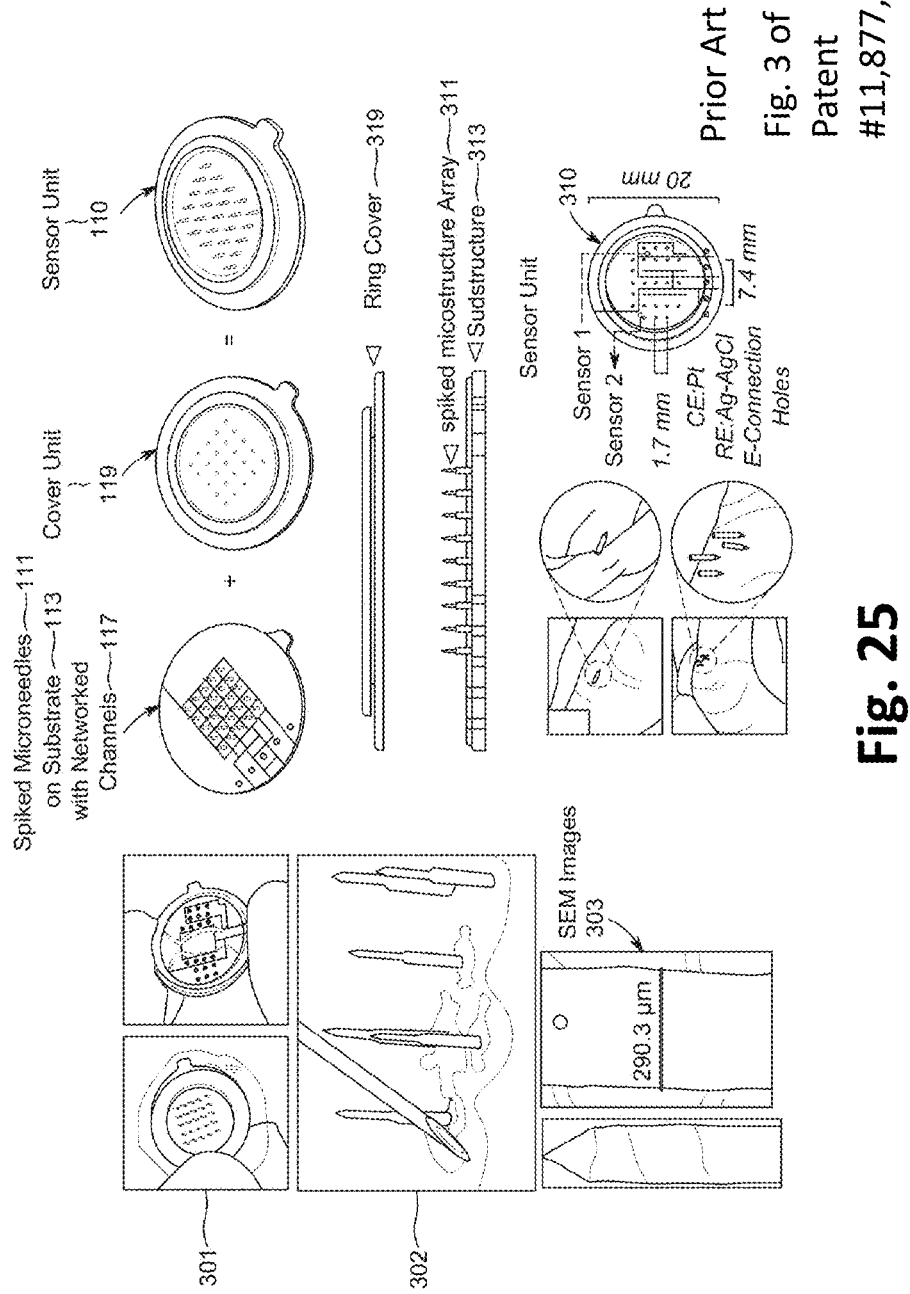
FIG. 25 (FIG. 3 of U.S. Pat. No. 11,877,846) shows aspects of ways to construct an embodiment of a device herein.

FIG. 25 (FIG. 3 of the '846 patent) shows panels of diagrams showing the microneedle sensor unit 110, including an example arrangement of the microneedles 111 on the substrate 113 and substructure of the substrate 113. On the left side of FIG. 25, image 301 shows an example single (left) and multiple (right) analyte sensor unit, respectively; image 302 shows an optical micrograph of an example spiked microneedle array with 150 μm diameter next to a stainless-steel insulin injection nano-pen (34 gauge); and diagrams 303 show zoomed views of an example spiral spiked microneedle 111. On the right side of FIG. 25, a top series of diagrams illustrates an example array of spiked microneedles 111 on the substrate 113 with an example network of microfluidic channels 117 (which can be used to flow insulative material to seal the spiked microneedles 111 and form a sealed base 115), as well as show how this combines with an example cover unit 119 to form an example sensor unit 110. A middle series of diagrams illustrates a side view of the example cover unit 119, configured as a ring cover 319. The lower series of diagrams illustrate an example embodiment of a spiked microneedle sensor unit 310 for multi-analyte simultaneous detection, which includes two sensor regions of spiked microneedles (each with 1.7 mm spacing between spiked microneedles), a reference electrode (e.g., Ag—AgCl), a counter electrode (e.g., Pt), and electronic-connection holes. The lower series of diagrams also includes images showing individual spiked microneedles on a single strand of hair and their penetration to the skin (e.g., on a finger).

FIG. 26 (FIG. 10 of the '846 patent) shows a diagram depicting a multiplexed sensor design for measuring specific analyte parameters in continuous monitoring of two analytes in two sensing regions 29 separated by electrical isolation channels 30. Each sensing region has at least one working electrode (WE), reference electrode (RE) and counter electrode (CE). Example implementations were performed using an example sensor like that in FIG. 26, which demonstrated a cross-talk-free wearable device capable of simultaneous, multiplexed sensing of multiple subdermal analytes with microneedle structures on a substructure with spacing (between target analyte 1 and target analyte 2 sensor regions) of at least 5 mm. For example, the example wearable device is configured to provide two working electrode sensor regions with identical detection mechanisms, such as oxidase-based sensors (which rely on $H_2O_2$ as the sensing molecule). The microneedle array was able to provide a mitigated sensor sensitivity range of at most 10 nA/mM for each sensing region. The microneedle array was also configured for use of common or an individually addressable auxiliary/counter electrode(s), and for use of common or an individually addressable reference electrode(s). Also, in these example implementations, a sealing cover with at least two embedded non-intrusive skin insertion enhancing rings or ring-like elevated surfaces was used.

The device includes the improvement of seating the microneedle array in a lower surface 2*a* of an recessed cover 2, the lower surface of the recessed cover being surrounded by an upper surface 2*b* so that the base of each of the microneedles is recessed below a fillet 2*c* at the inner boundary of the upper surface so that the fillet is configured to pinch a user's skin where the microneedles are inserted into the skin. By mitigating dynamic interference sources (e.g., device movement when the user is moving vigorously) and static/quasi-static interference sources (e.g., the user sleeps on the device). These aspects enable a) dynamic and static artifact mitigation or suppression, b) high accuracy bio-molecular sensing, and c) safe ultra-smooth microneedle insertion.

Figure 27:
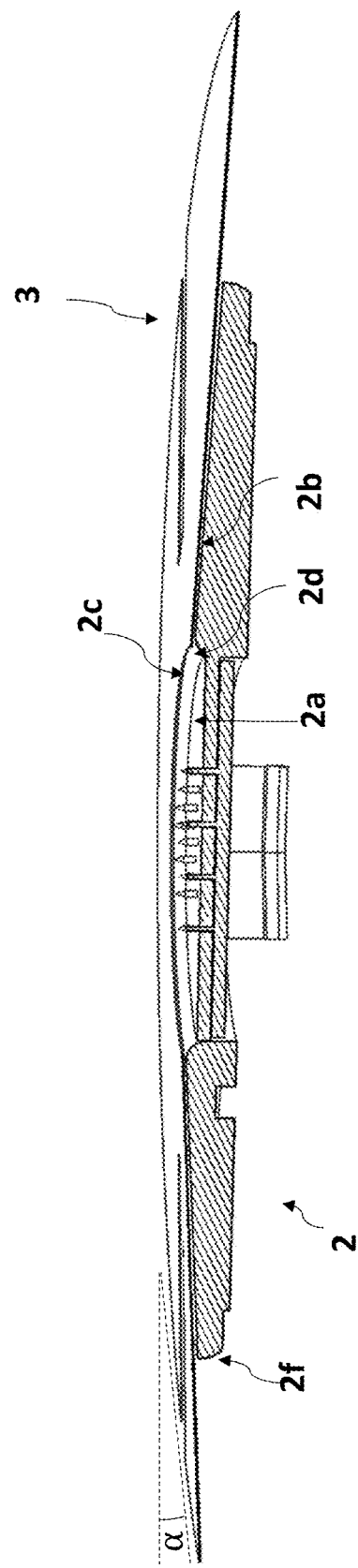
FIG. 27 is a section view of one embodiment of a recessed cover with a microneedle inserted and an adhesive layer.

FIG. 27 is a section view of the recessed cover 2 as used in a disposable module 18*a* (shown for example in FIG. 4A) with the skin adhesive layer 3 attached tightly. This embodiment of the recessed cover has no sidewall as does the embodiment in FIG. 2. An angle alpha α shows the outer portion 2*f* of the upper surface 2*b* is lower than the inner boundary at the fillet 2*c*.

Figure 28:
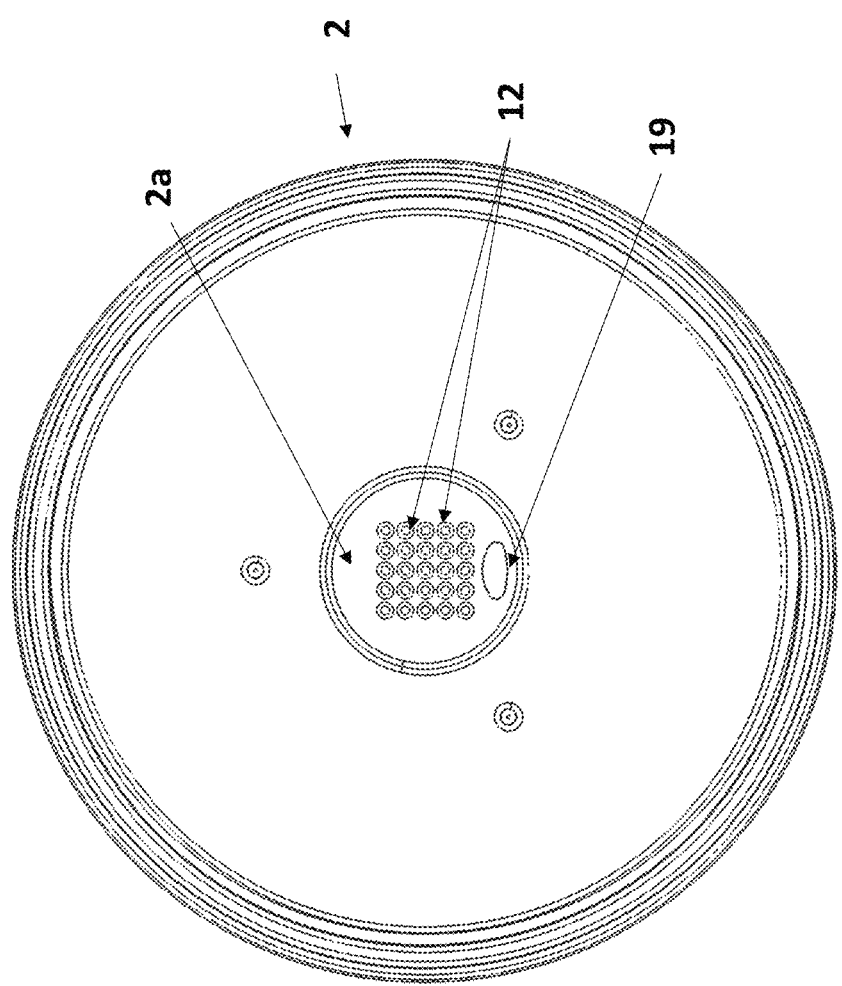
FIG. 28 is an underneath view of one embodiment of a recessed cover showing the set of first openings.

FIG. 28 is the underside of the recessed cover 2 showing the set of first openings 12 in the lower surface 2*a*. An optional second opening 19 allows the flow of curable custom resin in manufacturing. There are pillar-like protrusions sticking out inwardly from the top enclosure to have the elastic conductive pins 9 slipped on in a way analogous to sliding socks onto one's feet. The elastic conductive pins (FIG. 2, feature 9) pull on the pillars from their side with the hole forming an elastic-conductive outer piece, with a robust-rigid core. They are located in alignment to the microneedle array holes, located on each of the cantilevered arms on the microneedle array.

Figure 29:
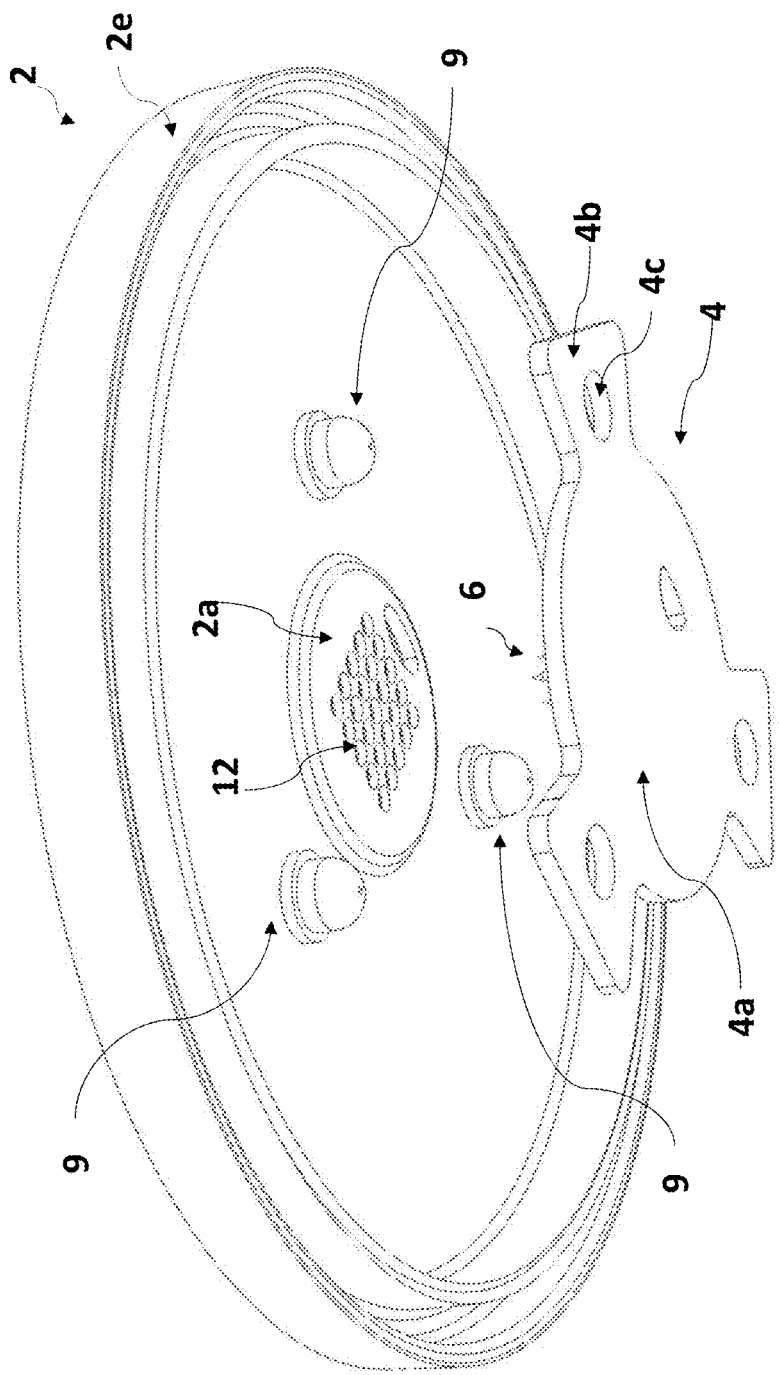
FIG. 29 is a perspective view underneath an embodiment of the recessed cover showing the set of first holes, the conductive pins and the position of the microneedle array ready for insertion into the set of first openings.

FIG. 29 is a perspective view of the underside of the recessed cover 2 with the lower surface 2*a* and the set of first openings 12. The microneedle array 4 is positioned for the microneedles 6 to be inserted through the set of first openings. The cantilevered arms 4*b* having substrate holes 4*c* surround the substrate 4*a* in the center of the microneedle array. Conductive pins 9 are positioned to be inserted through the substrate holes to the electronic unit (not pictured here).

Figure 30:
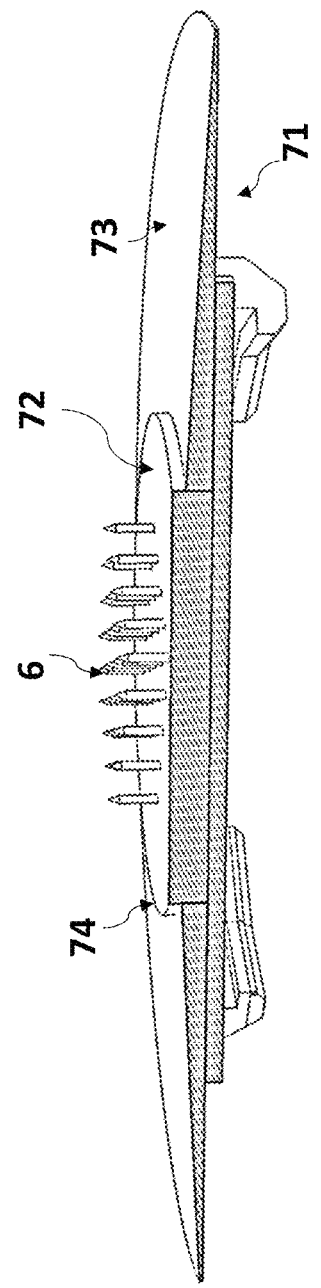
FIG. 30 is a section view of one embodiment of an elevated cover with a microneedle array inserted.
Figure 31:
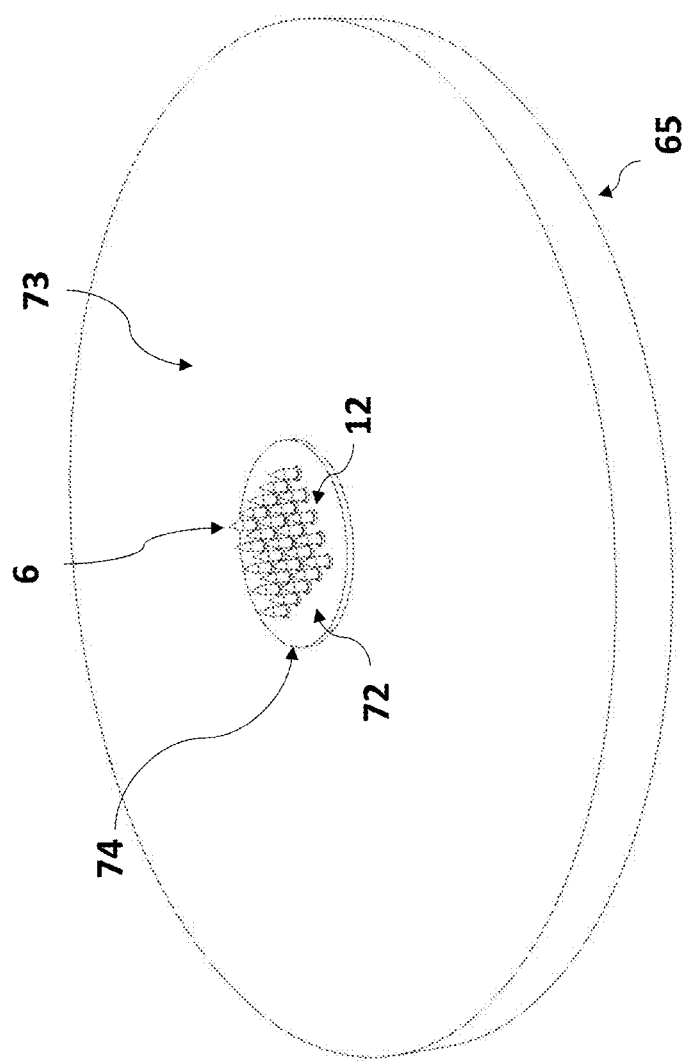
FIG. 31 is a perspective view of one embodiment of an elevated cover with the microneedle array inserted.

The cover may also be an elevated cover 65 in some embodiments. FIG. 30 is a section view of the elevated cover in which the set of first openings 12 is positioned within a raised panel 72, the raised panel being integral with and surrounded by a bottom panel 73, and an outer border 74 of the raised panel is configured to pinch the user's skin, to stretch the user's skin where the microneedles are inserted into the skin and to secure the microneedles at an insertion location of the user's skin. The outer border may be a slope or an angle, and a fillet 2*c* may also be positioned near the outer border of the raised panel. FIG. 31 is a perspective view of the elevated cover.

Figure 32:
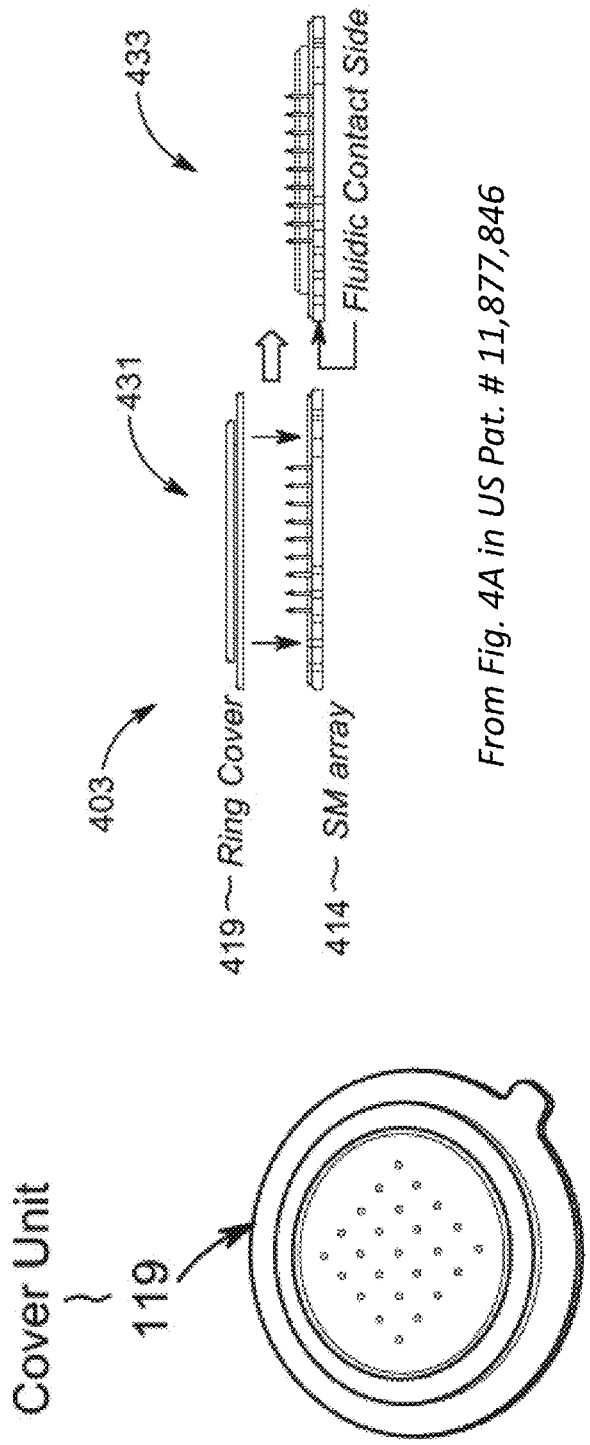
FIG. 32 (FIGS. 3 and 4A of U.S. Pat. No. 11,877,846) are respectively a perspective and side views of embodiments of a basic cover including two side views with microneedle arrays inserted into the cover.

The present invention includes several embodiments of an improved cover over the '846 patent, and two of these are the recessed cover 2 and the elevated cover 65. The '846 patent incorporates a basic cover, for example feature 119 in FIGS. 3 and 4A in the '846 patent, collected here in FIG. 32 for convenient reference. The basic cover is flat as shown in features numbered 119 and 419. The present invention, however, includes a novel improvements over the device with the basic cover.

Figure 33:
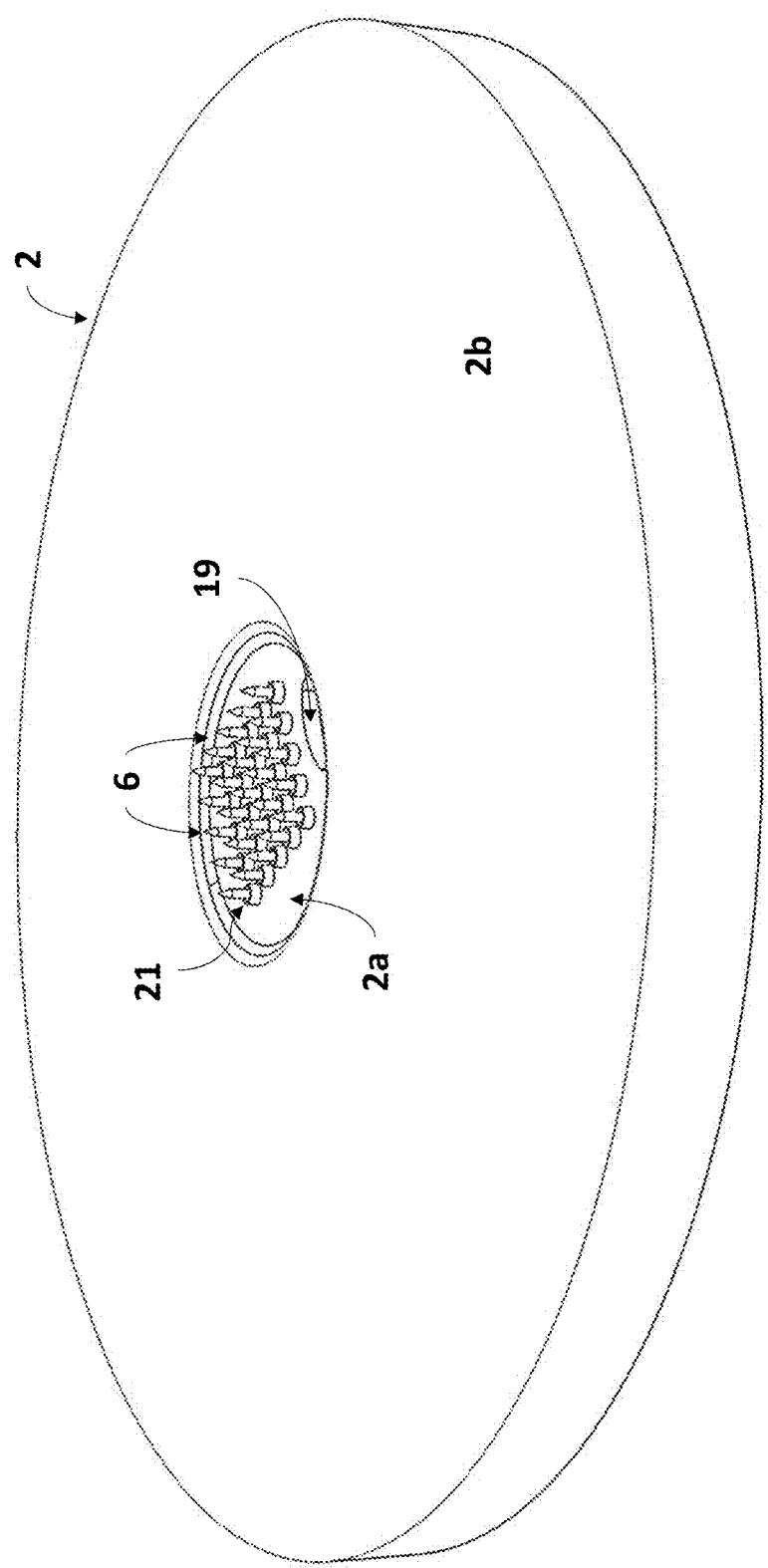
FIG. 33 is a perspective view of one embodiment of a recessed cover with a microneedle array inserted through the set of first openings in the lower surface with sleeves.
Figure 34:
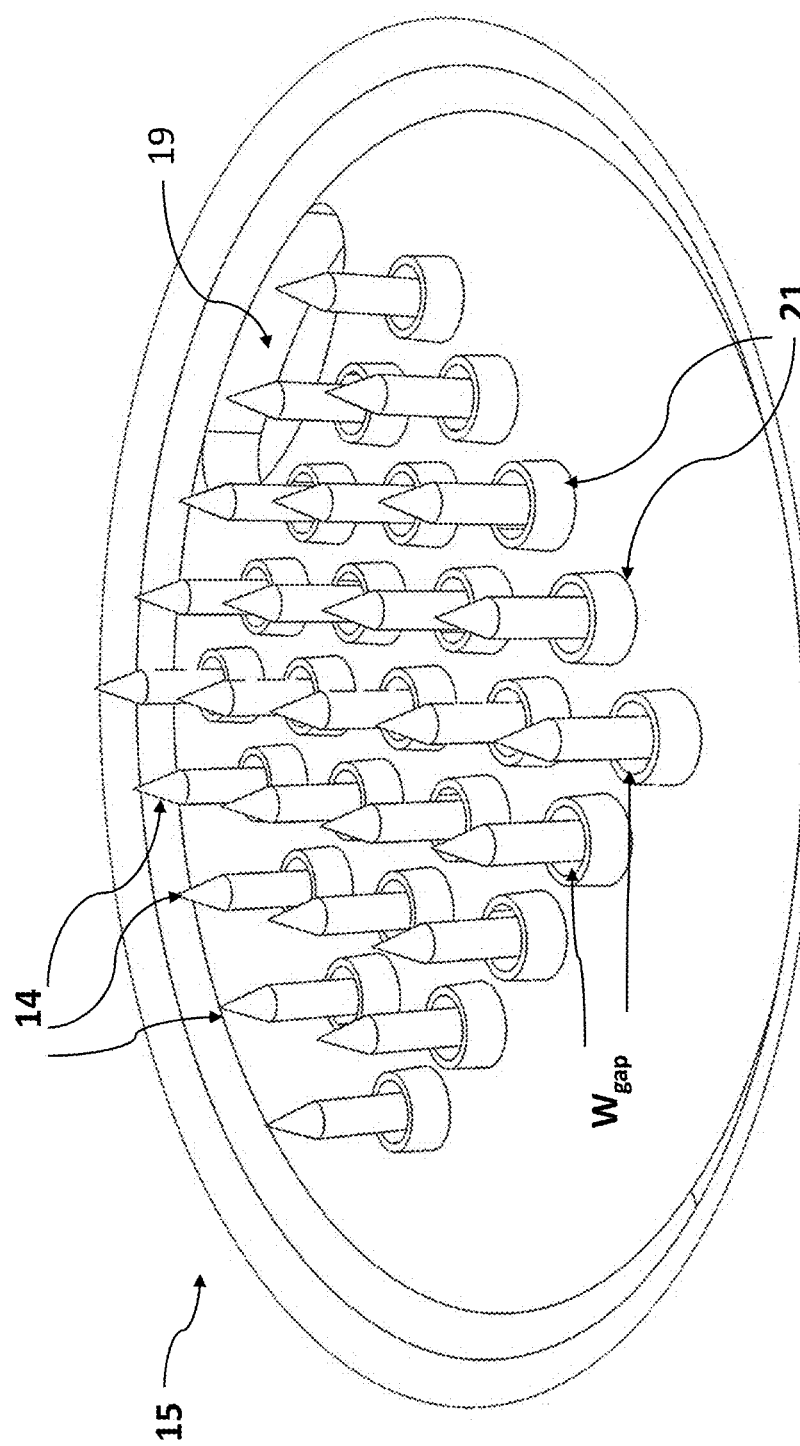
FIG. 34 is a perspective view of one embodiment of the lower surface of a recessed cover with a microneedle array inserted through the set of first openings with sleeves. The outer surface is not shown.

The invention herein includes one or more cover enhancements including sleeves 21 extending upward around the set of first openings 12 through which the microneedles of the microneedle array are pressed. Additional cover enhancements are bodily features 31 which can perform different functions as described further herein. These improvements may be used separately or in tandem. In FIG. 33 sleeves 21 are shown on the lower surface 2a of the recessed cover 2. Microneedles 6 extend above the sleeves. In this embodiment, the sleeves are uniform but they may be varied in shape and size, or may be present only for a portion of the first openings, in various embodiments. An optional second opening 19 is also shown. FIG. 34 shows the embodiment of the basic cover 15 with sleeves 21 for use in the replaceable module 18a, as shown in FIG. 3. Gaps $W_{gap}$, between the sleeves 21 and the microneedles 6 are shown here.

Figure 35:
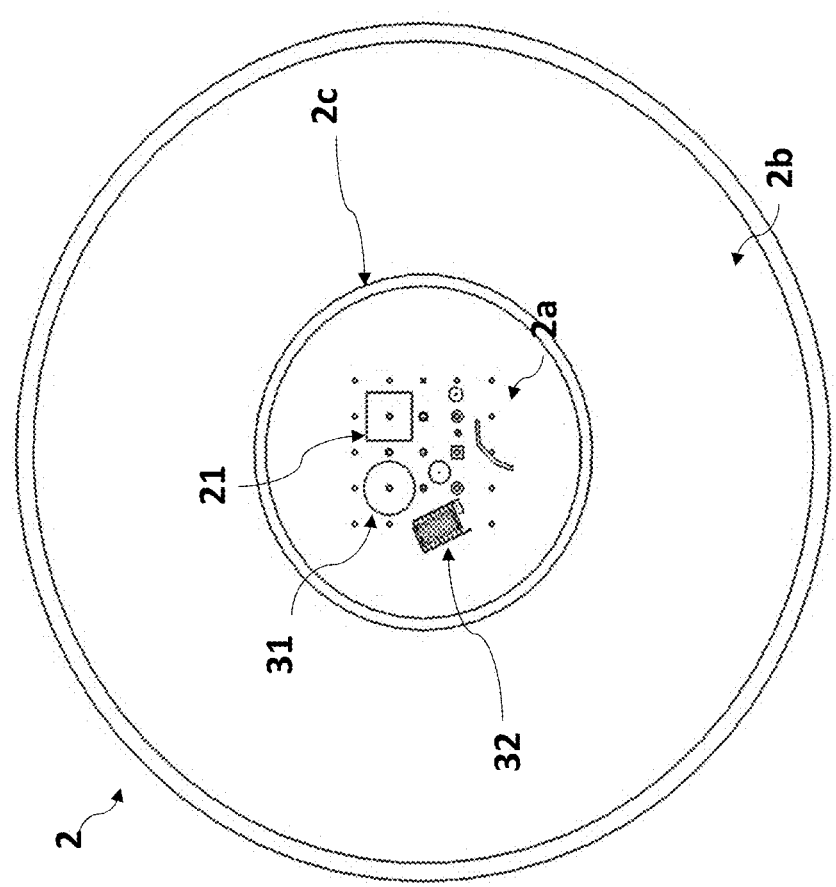
FIG. 35 is a top down view of one embodiment of a recessed cover with cover enhancements including sleeves, bodily features and a conductive trace.
Figure 36:
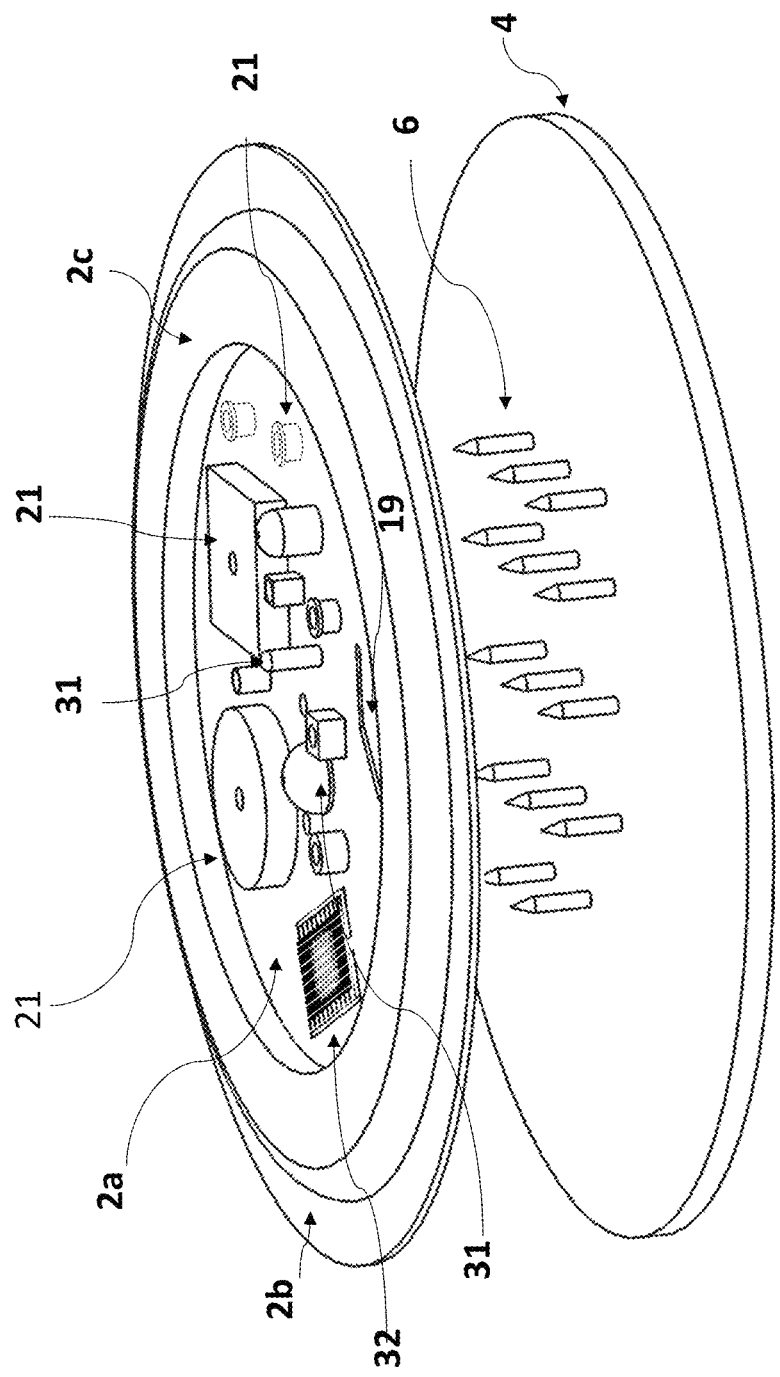
FIG. 36 is a perspective view of one embodiment of a recessed cover with cover enhancements including sleeves, bodily features and a conductive trace, and with a microneedle array underneath positioned for insertion into the set of first openings of the recessed cover. The upper surface of the recessed cover is undersized compared to other embodiments.

FIG. 35 is a top down view of a recessed cover showing different sized and shaped sleeves 21 and bodily features 31. The fillet 2c, first openings 12, conductive trace 32 and optional second opening 19 are also shown. FIG. 36 is a perspective view of the lower surface 2a of the cover 2 with an undersized upper surface 2b with the fillet 2c microneedle array inserted on the underside of the recessed cover, so that the microneedles 6 extend beyond sleeves. Bodily features 31 are interspersed. The fillet 2c, slope 2d, conductive trace 32 are also shown.

Figure 37:
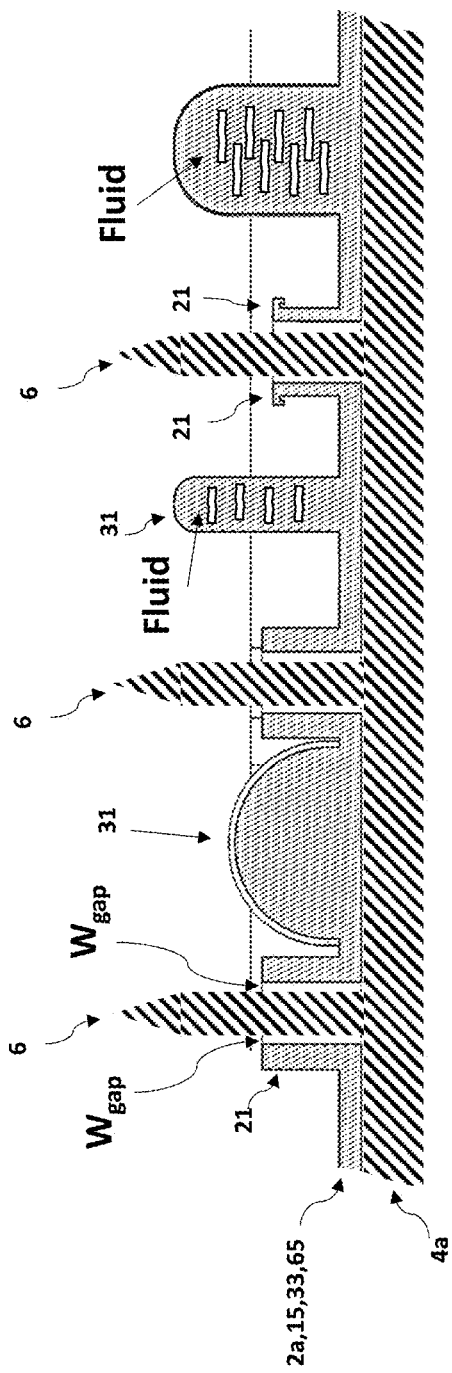
FIG. 37 is a section view of a portion of an embodiment of a cover with cover enhancements including bodily features loaded with fluid and sleeves, and a microneedle inserted into the set of first openings, with the gaps between microneedles and the sleeves unfilled prior to application of the curable resin.

Cross sections show additional detail. FIG. 37 is a side section view of a portion of the cover (either 2, 15, 33, 65) having enhancements. The gap between the outer diameter of the microneedles 6 and the inner diameter of the sleeves is $W_{gap}$. Bodily features 31 are shown holding fluid. The sleeve furthest to the right has arms which extend outward from the sleeve.

Figure 38:
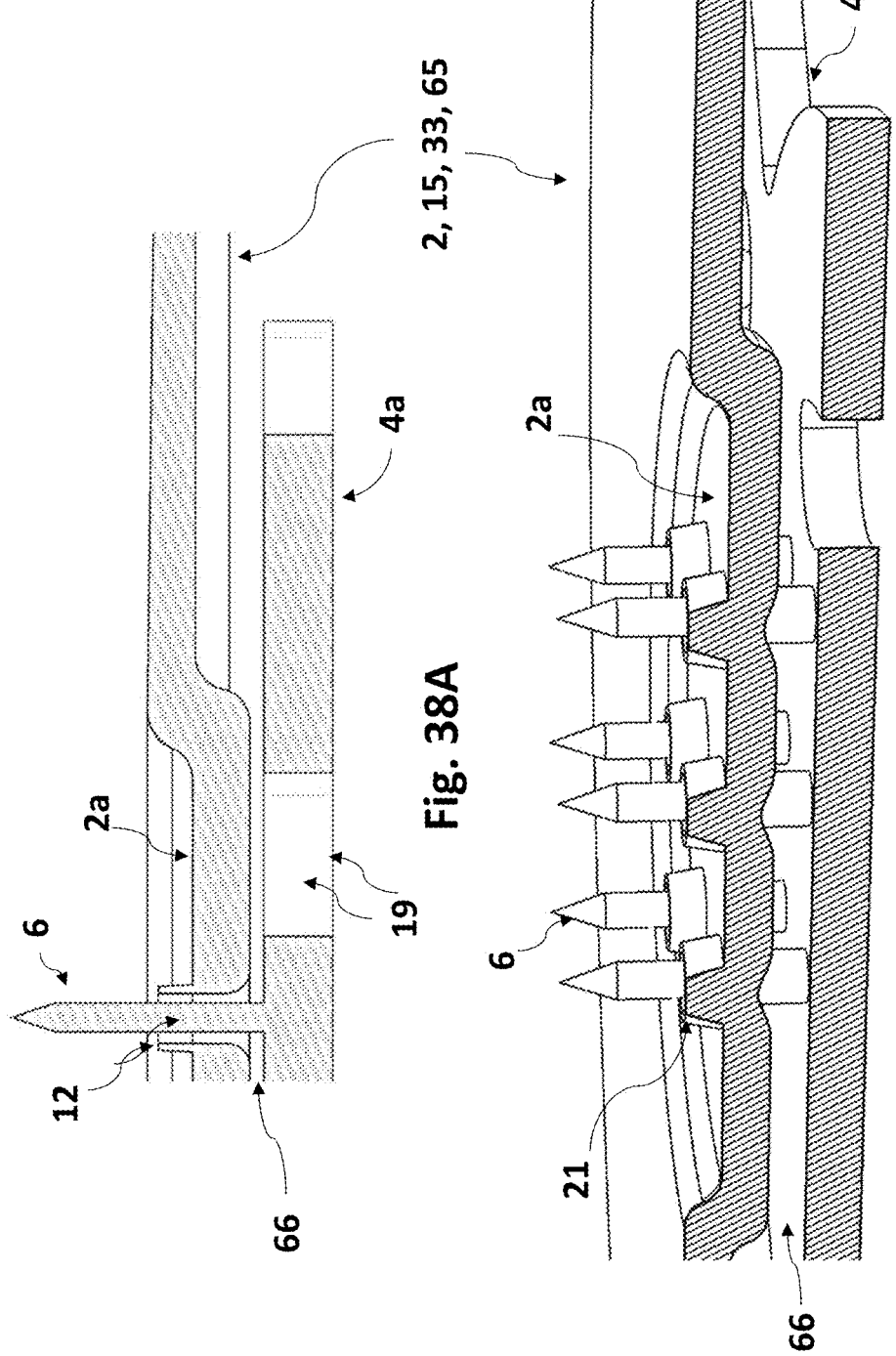
FIGS. 38A and 38B are section views of one embodiment of a portion of the microneedle array inserted into the first openings of a cover showing a gap between the two prior to application of the curable resin and without microfluidic channels.
Figure 39:
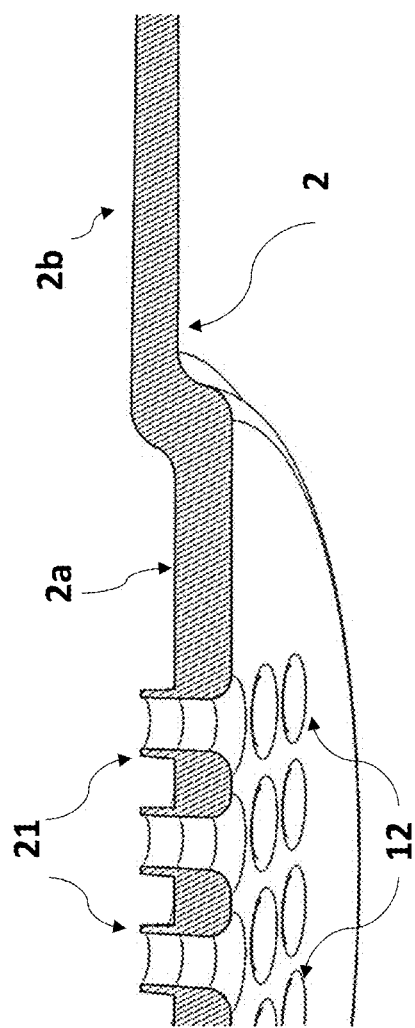
FIG. 39 is a perspective view underneath a portion of one embodiment of a recessed cover showing the set of first openings, sleeves and the lower and upper surfaces of the cover.

FIG. 38A is a section side view of a recessed cover 2 with one microneedle 6 extending through a first opening before curable custom resin flows into $W_{gap}$ through, for instance, a second opening for resin 4e in the microneedle array 4. Alternatively, the curable custom resin is applied to the top of the microneedle array or the bottom of the cover before the two pieces are coupled together. Here, there is a gap 66 configured to be between the cover 2, 15, 33, 65 and microneedle array 4a so that curable resin can flow through (without the need for microfluidic channels) and secure the cover to the microneedle array, and also to seal the $W_{gap}$. The curable resin, once cured, provides strength and protection of the underlying electronics from fluids. FIG. 38B is a perspective view of a larger portion of the recessed cover than in FIG. 38A. FIG. 39 is a section perspective view of a portion of the underside of the cover 2, 15, 33, 65 showing the first openings 12 surrounded by sleeves 21.

Figure 40:
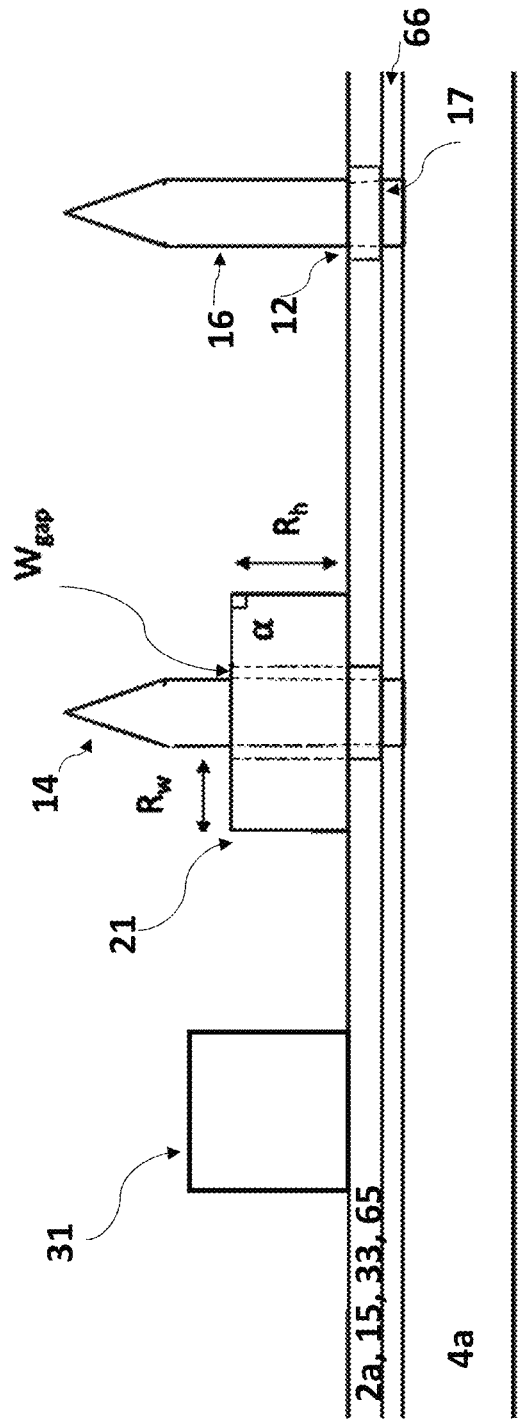
FIG. 40 is a section view of a portion of one embodiment of a microneedle array inserted through a cover with enhancements including a bodily feature and a sleeve, also showing the gap between the openings and the microneedles prior to application of the curable resin. No microfluidic channels are present so there is a gap between the cover and the microneedle array.

FIG. 40 is a section view of a portion of the cover 2, 15, 33, 65 with a sleeve 21 surrounding a portion of the microneedle body 16 and the base 17 and leaving a portion of the body and the tip 14 exposed for insertion into the user's skin. One of the microneedles has no sleeve. A bodily feature 31 is also shown. In the improved cover shown e.g. in FIG. 40, there is a wide range of features and functions that stem from different combinations of variables of the radius width ($R_w$), the width of the gap between the sleeve and the microneedle ($W_{gap}$), and the height of the radius ($R_h$), and the angle α. For example, the angle α in FIG. 40 is a right angle but increasing it to 135 degrees on the entire annulus would contribute to easier insertion. The properties of the materials of the sleeves and improved cover itself that can be distinct from the materials used in the microneedle array all of which are described herein. A bodily feature 31 can be either mechanical or chemical in nature. When mechanical, it deforms the skin by stretching or pinching the skin near one or more microneedles in order to make the microneedles pierce the skin more easily. When chemical, iontophoresis can be used to improve conductance of compounds loaded in the bodily feature, and the compounds can cross the skin more easily than without application of the voltage. The compounds can be in solution, gels or semi-solids. Also, bodily features can be chemical and mechanical at the same time. Reproducibility of sealing the microneedles is enabled in the improved cover with sleeves if further enhanced by adjusting the height of the sleeve to fine tuning of the available electrochemical surface area on the microneedles by mainly adjusting the height (Rh) among all sleeves. The microfluidic channel (adjustable by $W_{gap}$) between the interior wall of the sleeve and the microneedle creates a microfluidic pathway for the insulating resin which covers the base of the microneedle until it reaches the top of the sleeve.

Figure 41:
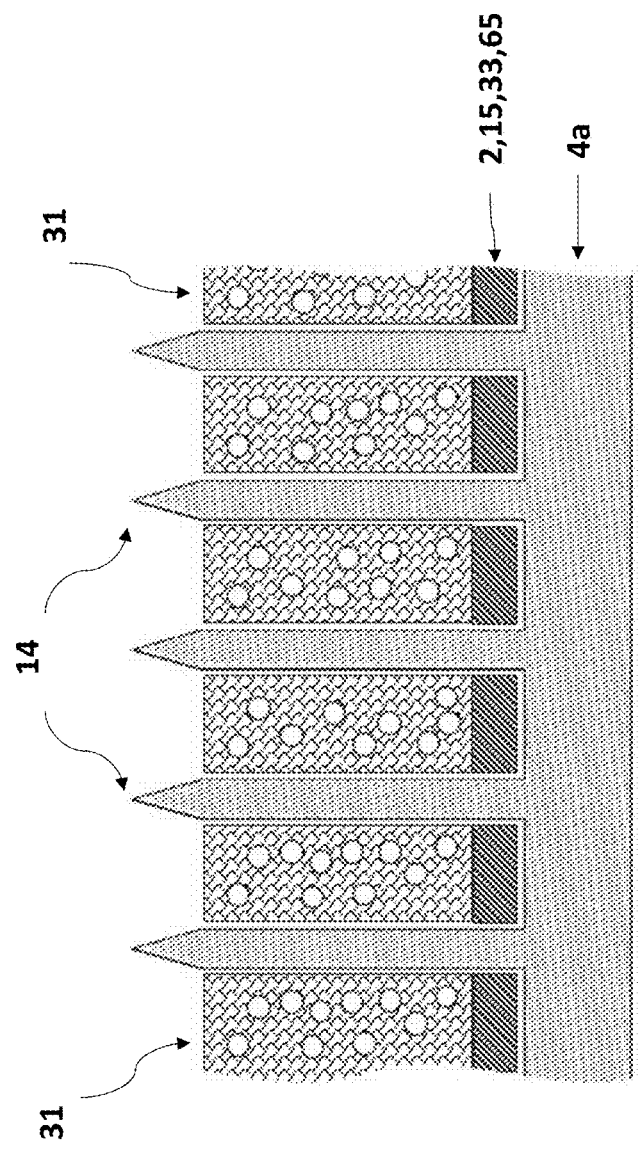
FIG. 41 is a section view of a portion of the microneedle array inserted through a cover bodily features holding compounds dissolved in fluid.

FIG. 41 is a section view of a microneedle array 4 and a cover 2, 15, 33, 65 with spongy, elastic and absorbable bodily features 31 impregnated with fluid containing compounds selected from the group consisting of pharmaceuticals, salts, anti-inflammatory compounds and the like. These compounds can be intended for absorption by the skin or for combatting biofouling of the microneedles to extend their lives.

Figure 42:
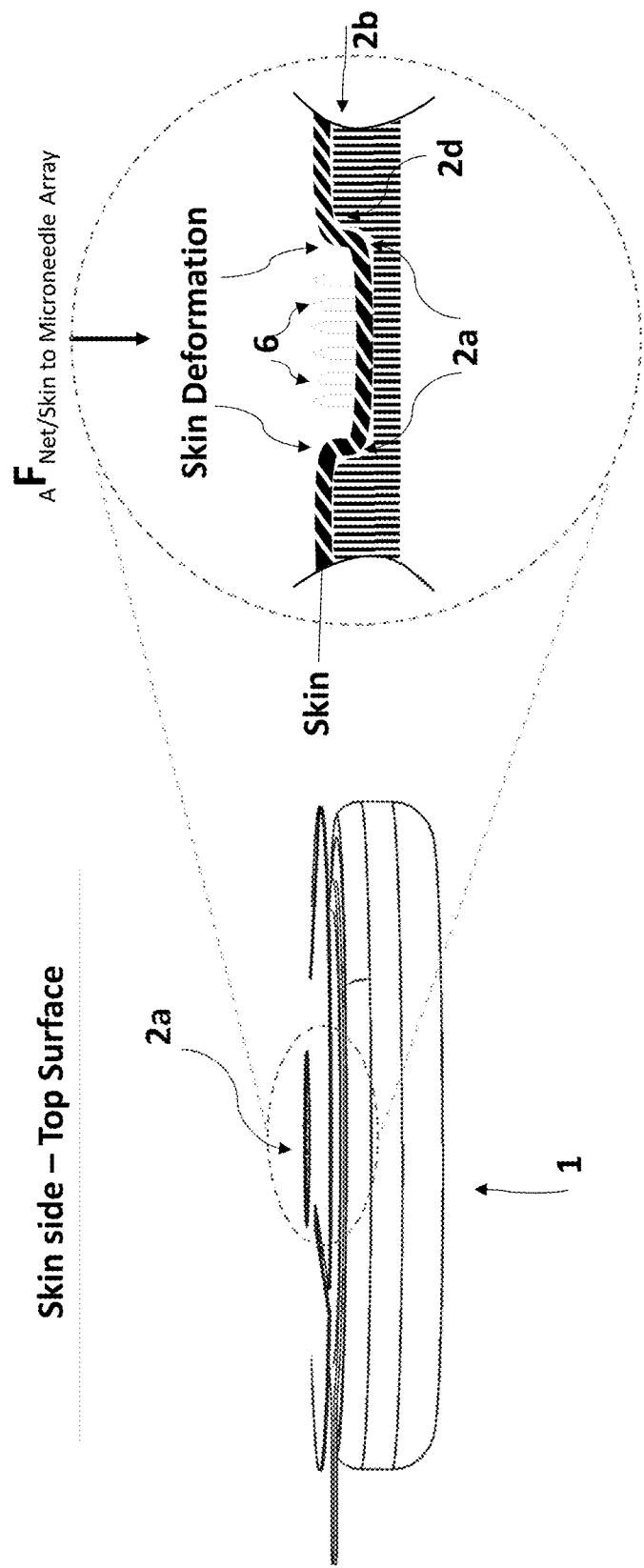
FIG. 42 is a side view of an embodiment of the wearable device with a recessed cover and an enlarged section view of a user's skin being deformed at the slope and boundary between the lower and upper surfaces of the cover.
Figure 43:
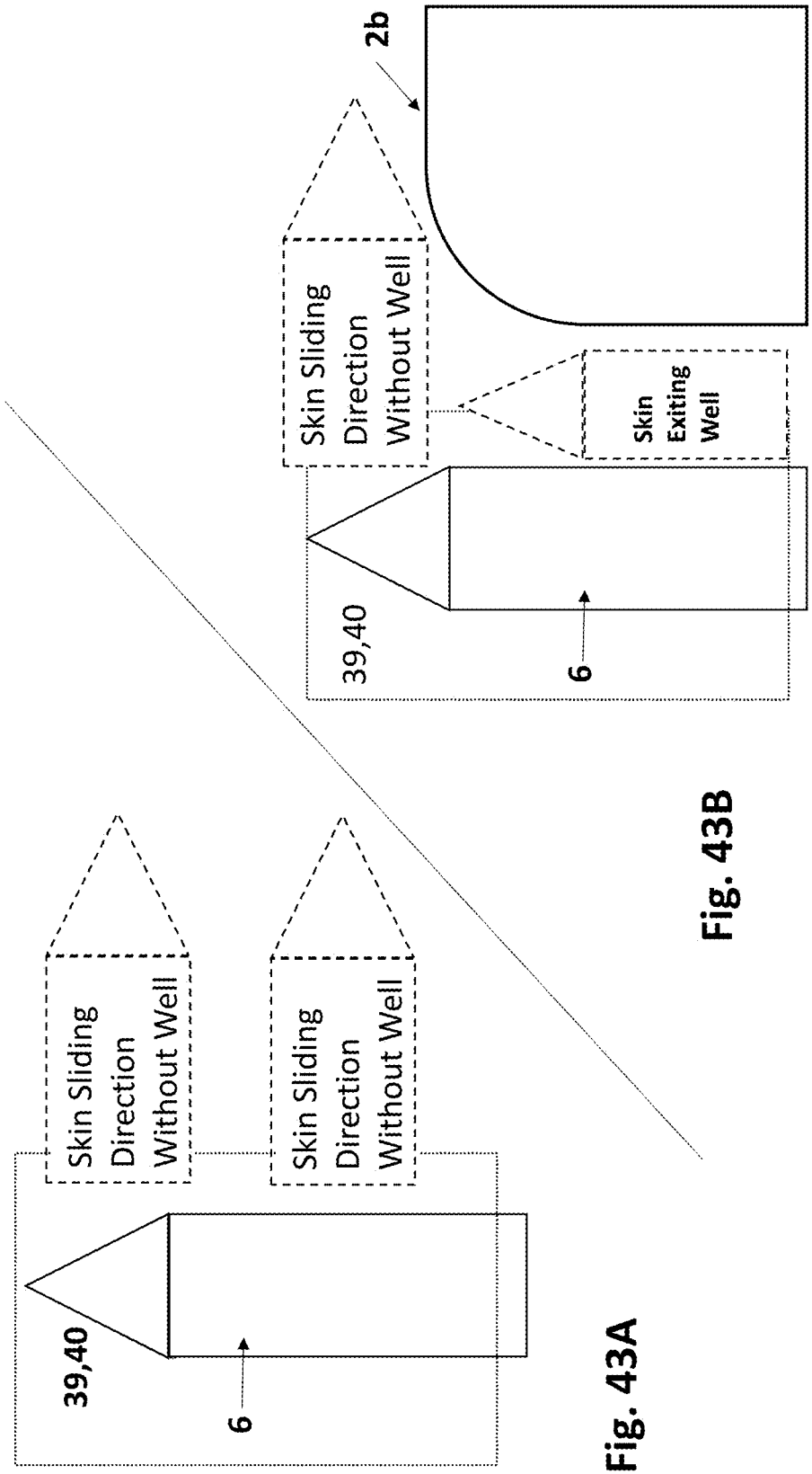
FIG. 43A-B are schematics of the forces on the skin in FIG. 42.

FIG. 42 is a side view of the wearable biosensor device 1 of the embodiment with two modules 18, 18a and an enlarged section view of the user's skin being deformed where the microneedles 6 have pierced the skin in the area defined by the fillet 2c and the downward slope to the lower surface 2a of the recessed cover or the separate cover 15. As shown in FIG. 42, the microneedle array recessed below the upper surface of the cover, which causes the deformation of the skin at the downward slope 2d (acting as a negative fillet) which, due to the inherence elasticity of the skin, provides constant and passive microneedle pressure against the skin while the wearable device is adhered to skin. That is, when the area surrounding the microneedle array is depressed more into the skin, such as with a ring-protrusion surrounding the microneedle. This constant passive pressure at the raised areas causes the skin to stretch into the recess below the fillet, thereby immobilizing the skin from moving from normal-to-microneedle-tip insertion of the microneedle to the skin. Said differently, the well prepares the skin for a smooth microneedle insertion by 1) stretching the skin, 2) immobilizing the skin from the sides during microneedle insertion, 3) causing a constant compression force from the skin to the microneedle due to the constant pinching of the elastic skin induced by the raising of the surface from the lower surface 2a to the upper surface 2b, and 4) further mechanical protection of the microneedles at all microneedle/skin interaction including the initial application of the sensor on body and microneedle/skin insertion, during wear, final removal, and incidental sliding of the microneedle on body primarily by shifting the fracture inducing normal stress from the lower body of the microneedle, in the lack of a well, to the rather bending inducing normal stress to the body to the upper body of the microneedles. This is shown in FIG. 42 and FIGS. 43A and 43B. The two parallel arrows in 43A show unimpeded lateral movement without a change in elevation on the cover. In 43B the arrow pointing up shows the pinching of the skin because it cannot move laterally because of the elevation change from the lower surface 2a to the upper surface 2b. The microneedle array illustrated from top view, left, and side view, right, with drawing of the skin formation after application of the device to the skin. FIG. 43A depicts the skin sliding sideways without a well wall but FIG. 42 shows the skin is pinched and rises to the top of the well wall. Pinching force shown in FIG. 43A where the skin sliding stress is applied through the entire body of the microneedle array and FIG. 43B with well where the skin skidding force induces skin-exiting-well stress to shift the forces away from the bottom of the microneedle array to the surface while skin is being exited out of the well.

Figure 44:
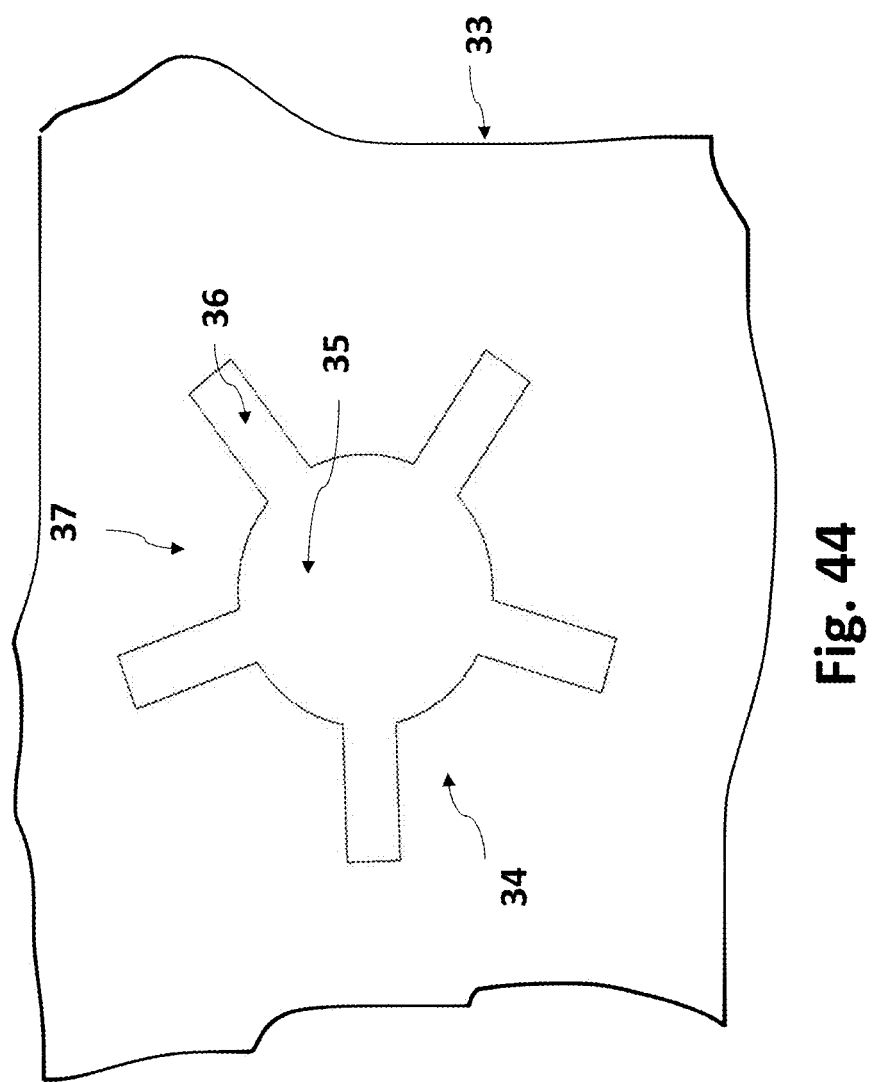
FIG. 44 is a top down view of one embodiment of a complex opening in portion of a foldable cover.

FIG. 44 is a top down view of a single complex opening of a foldable cover 34. A center opening 35 is surrounded by radiating openings 36 and petal-like sleeves 37.

Figure 45B:
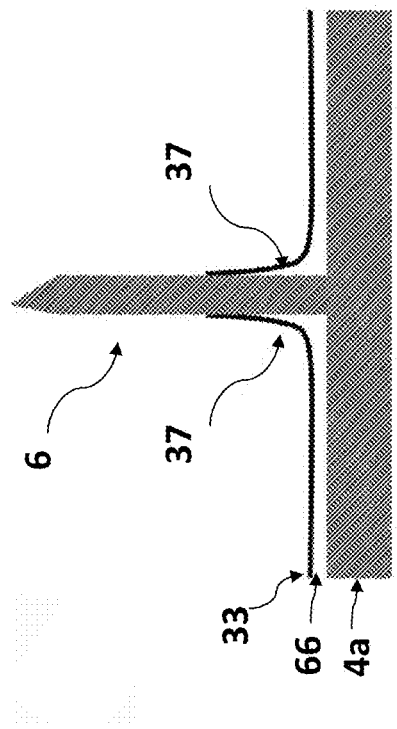
FIG. 45A is a top down view of a foldable cover and 45B is a portion of a section view of a microneedle inserted through a complex opening showing the folding of the petal-like sleeves around the base and a portion of the body region of the microneedle. Curable resin has not been applied.
Figure 45A:
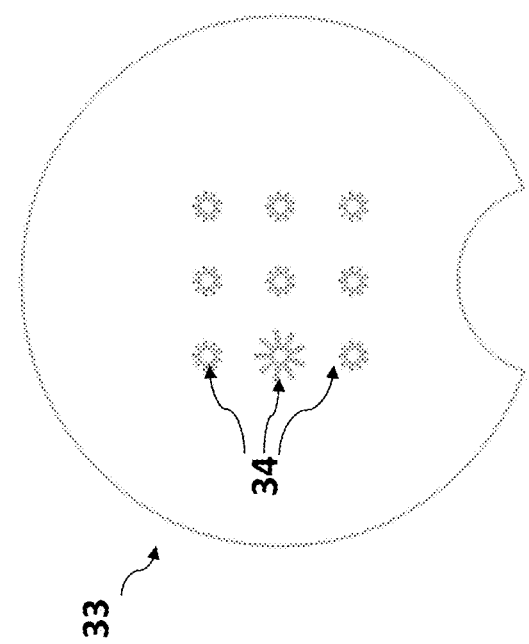

FIG. 45A is a top-down view of another embodiment of a foldable cover 33, here with nine complex openings 34, which significantly improve the functionality of a microneedle array 4a. FIG. 45A is a section view of a portion of the foldable cover showing how petal-like sleeves fold around a microneedle, as discussed further herein, even though a gap 66 remains for the flow of curable resin. Without having actual vertical channels at the base of the microneedle, the petal-like sleeves of the foldable cover work as microfluidic channels as the curable resin flows upward. That is, the petals guide the curable resin upward and, at their ends, help stop the capillary flow of resin. Like the other embodiments of the cover, the foldable cover helps isolate the microneedle array from unwanted electrical interference and also ensures a reproducible passivation process that enhances the array's durability and performance consistency and manufacture at scale. The foldable cover contributes to the mechanical stability of the microneedles, reducing the risk of structural failure when subjected to regular use. It serves as a barrier against fluids, preserving the integrity of the electrochemical environment necessary for accurate biosensing or the controlled delivery of pharmaceuticals. The foldable cover's properties prevent interference from external fluids, direct contact of the microneedle's non-passivated areas to the skin or other unwanted materials, and stabilizes the microneedles to yield consistent, reliable measurements.

Foldability allows for a customizable and precise fit over the microneedle array, providing a tailored isolation layer that conforms to the intricate topography of the microstructures. This ensures complete coverage without compromising the functionality of the microneedle tips. The material chosen for the cover is foldable either inherently or by adjusted aspect ratio (thin-enough), allowing for a compact design that can be easily deployed or retracted, facilitating both the assembly process and the user experience.

Like the other covers, the foldable cover is positioned over the top surface of the microneedle array. The foldable cover is fabricated from a biocompatible material which is foldable selected from the group consisting of polyimide, polycarbonate, acrylic, PET and PETG. In some embodiments the foldable cover can also include microfluidic channels 200. This design not only maximizes the array's lifespan but also enhances the quality and accuracy of the data collected.

The design of the foldable cover incorporates several characteristics and aspects that contribute to its functionality. These include its material composition, which is selected for its durability, flexibility, and biocompatibility, ensuring that it can withstand the physical demands of application while being safe for use in contact with human skin. Additionally, the foldable nature of the sheet allows for easy assembly and disassembly, facilitating the preparation of the microneedle array for use and its subsequent storage. This feature also allows for the cover to adapt to various microneedle geometries and configurations, making it a versatile solution for a wide range of applications.

As depicted in FIG. 45A the foldable cover comprises a set of complex openings 34 comprising a center opening 35 and radiating openings 36 around the center opening. The set of complex openings is configured to correspond to the microneedles on the microneedle array. Petal-like sleeves 37 surround the center opening and separate the various radiating openings. The petal-like sleeves surround a center opening of the complex hole for insertion of a curable resin. In various embodiments, thickness and diameter of the foldable cover ranges from approximately 0.5 um to 1 mm, and 150 um to 4 mm respectively, although other dimensions are possible. In some embodiments of the invention, both the bottom surface of the foldable cover interfacing the microneedle array and the top side are morphologically and structurally engineered for optimal curable resin flow and biocompatibility. This can include embodiments with one or a combination of microfluidic channels engraved on the microneedle or cover surface side, deliberately added surface roughness, and chemical functionalization of the surface to optimize the surface hydrophilicity. This aspect also enables reproducible passivation: curable resin flows through the complex openings 12 allowing formation of a passivation layer on the microneedles' thin metallic layer in a reproducible way by flowing through the gap between the microneedle and cover, or through microfluidic channels, and reaching the complex openings the curable resin rising upwards to the tips of the petal-like sleeves which act as a cut-off line 8 in stopping the upward flow.

Multi-layered Design: in some embodiments, multiple layers for the foldable cover are used to provide differentiated passivation zones, with each layer tailored to a specific function, such as fluid resistance, mechanical stability, or adhesive properties. For instance, the exposed surface area of the working electrodes can differ from those of the counter electrodes or the reference electrode by simply decreasing the cutting length or diameters around the microneedles. Another example is the addition of a double sided medical adhesive on top of the foldable cover which will act as an adhesive sticking the cover and skin together for a more robust microneedle insertion into the skin.

By using at least two electrodes (directly or capacitively coupled), the skin's impedance can be measured. Bioimpedance measurements are taken by applying an electric stimulation to the skin and measuring the body's electrical response. The fundamental frequency of the stimulation can take various forms which can be altered for different monitoring techniques—DC up to 1 MHz. An example of this is monitoring electrodermal activity (EDA), by which a DC or low frequency signal is applied to the skin to measure electrical characteristics of the skin (e.g., changes in skin conductance).

The conductive trace 32 can be patterned to form a temperature sensor, leveraging the thermal properties of one or more materials (e.g., Pt, Cr, Ag) to form sensors such as resistive temperature detectors (RTDs) and thermistors. The conductive material of this sensor is electrically insulated from the skin. This forms a skin temperature monitor. Temperature data can be used in conjunction with amperometric biosensor data to compensate for drift.

Multiple sensing modalities can be used in conjunction with chemical biosensing to identify and capture physiological state. For example, in one embodiment of the invention, EDA and skin-temperature monitoring provided by the electronic microneedle cover can be combined with sensing the analyte cortisol by the microneedles to identify states of stress for the device wearer.

Additional electrochemical sensors can be functionalized with electrodes on the microneedle cover.

Figure 46:
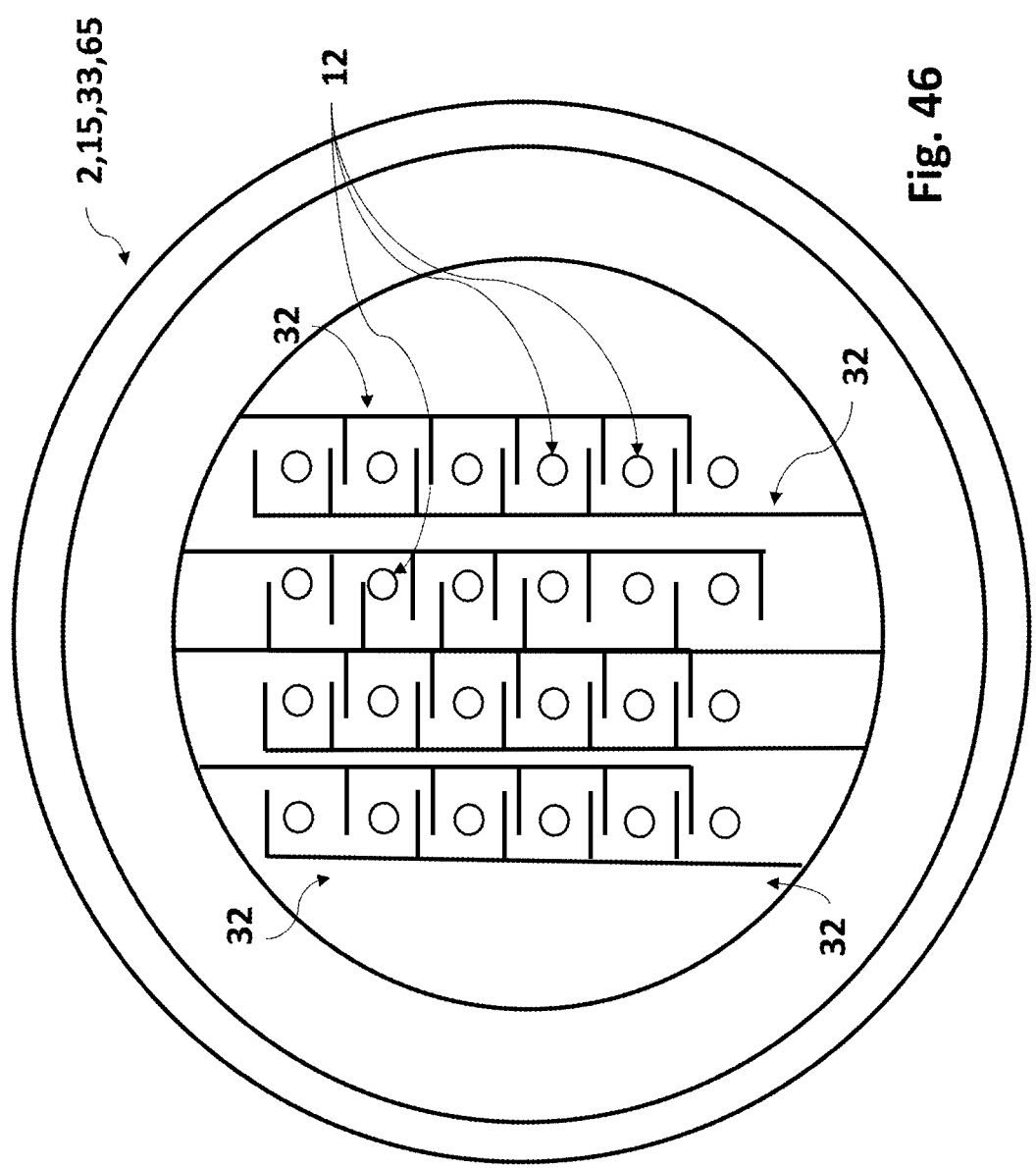
FIG. 46 is a top down view of one embodiment of a cover with conductive traces surrounding the set of first openings.

In another embodiment, the cover can also have a set of conductive traces 32 on the top surface (skin-facing side) which have important functions also discussed herein. FIG. 46 is a top down view of a cover 2, 15, 33, 65 (or, a portion of a larger cover) in which the first openings are dispersed among the conductive trace 32.

The improved cover in some embodiments may be electronic for skin-based sensors, integration of modalities, and robust electrochemical sensing. After insertion, the microneedle cover lies against the skin. This allows for skin-based (in addition to ISF-based) sensing modalities and techniques to be integrated into the wearable device. Moreover, skin-based stimulation techniques can be leveraged to improve reliability of ISF-based biosensing.

Electronics Unit

The electronics unit can be disposable or reusable in different embodiments, so the descriptions of it herein can apply to any embodiments of the electronics unit.

Figure 47:
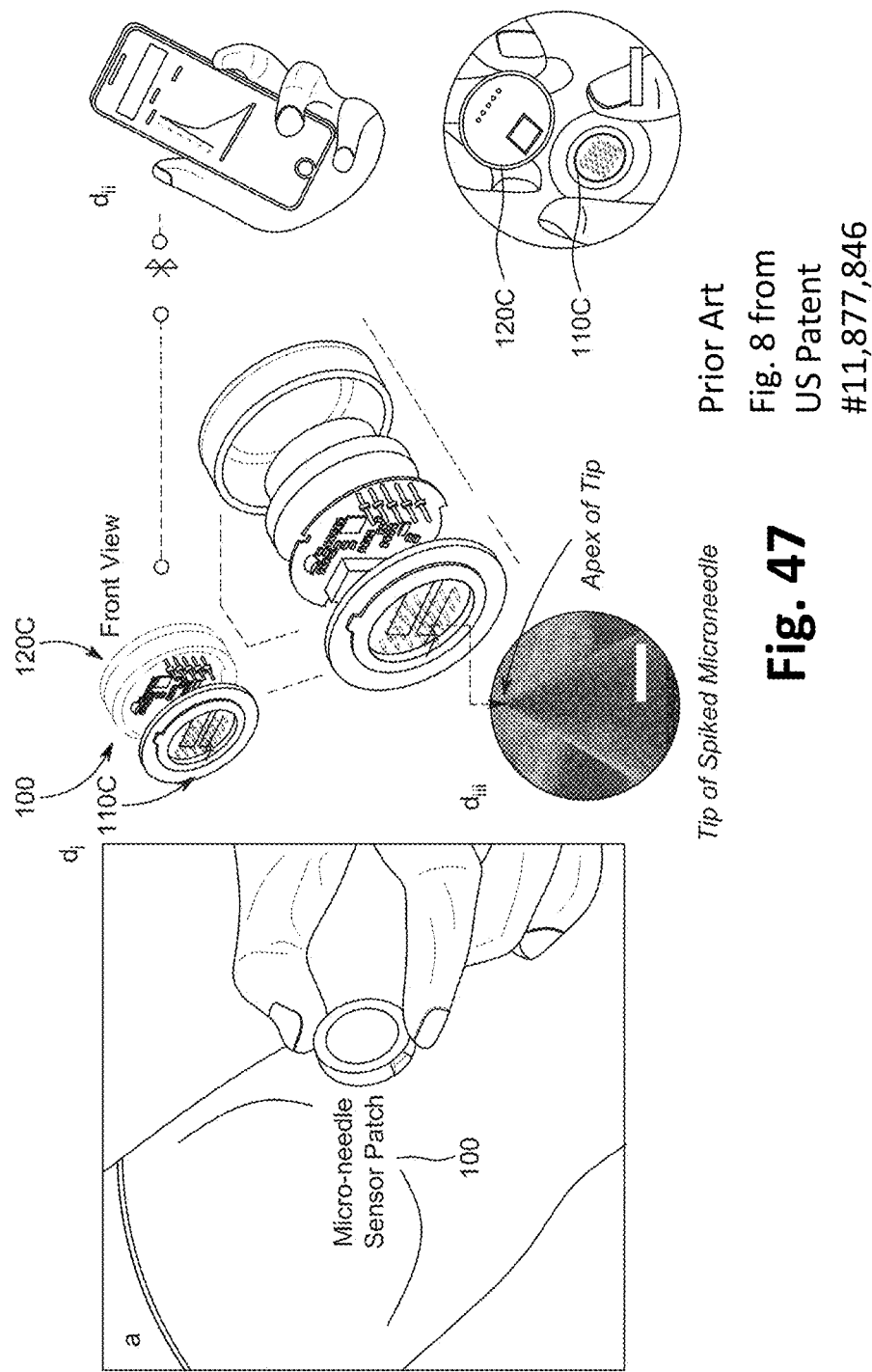
FIG. 47 (FIG. 8 of U.S. Pat. No. 11,877,846) includes exploded views and perspective views of the wearable device and its relation to an external computing device (smart phone).

Molecular level electrochemical signals from the wearer's ISF are continuously and selectively gathered by the inserted microneedle tips and are carried through the low-noise, reusable sensor-electronics (reusable electronics unit 120) through a between disposable sensor component 18*a* and reusable module 18*b*, and which can be wirelessly transmitted to an external computing device (e.g., a smartphone/mobile device) for data processing, e.g., via a software application (app) executable on the mobile device 130 and FIG. 47 (FIG. 8 of the '846 patent), panel ($d_{ii}$)), e.g., for visualization and analysis of the real-time monitoring of analytes. The accompanying app on the mobile device enables control of certain operations of the wearable device.

Figure 48:
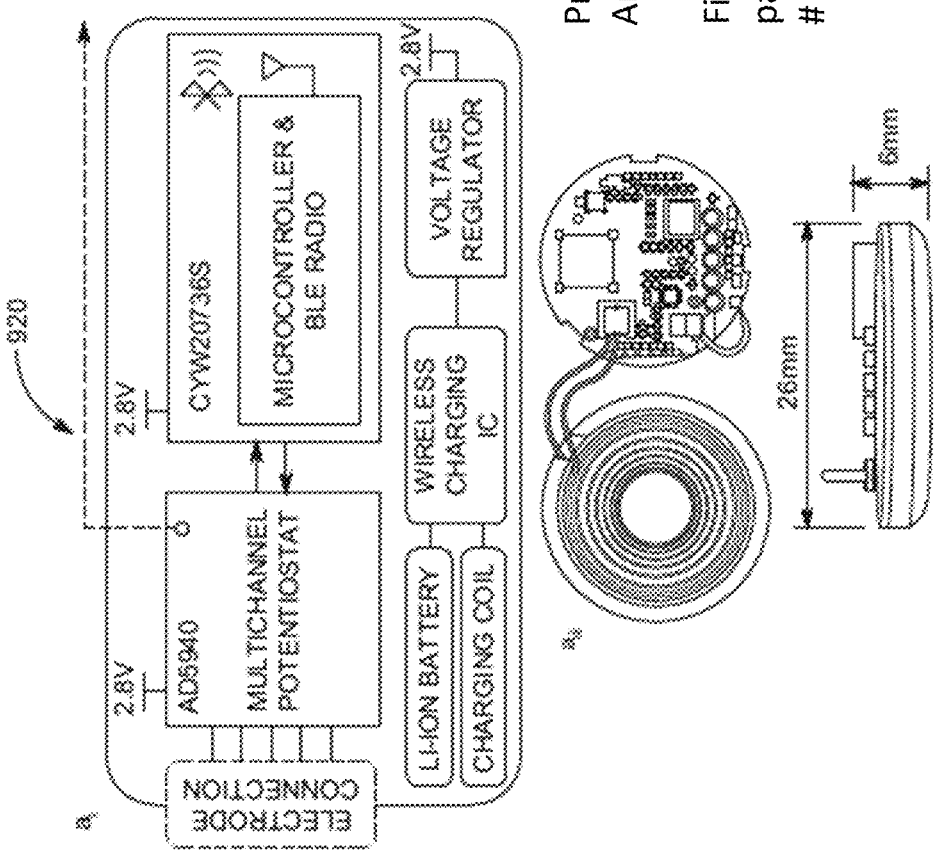
FIG. 48 (FIG. 9 of U.S. Pat. No. 11,877,846) shows aspects of one embodiment of the electronic unit.
Figure 49:
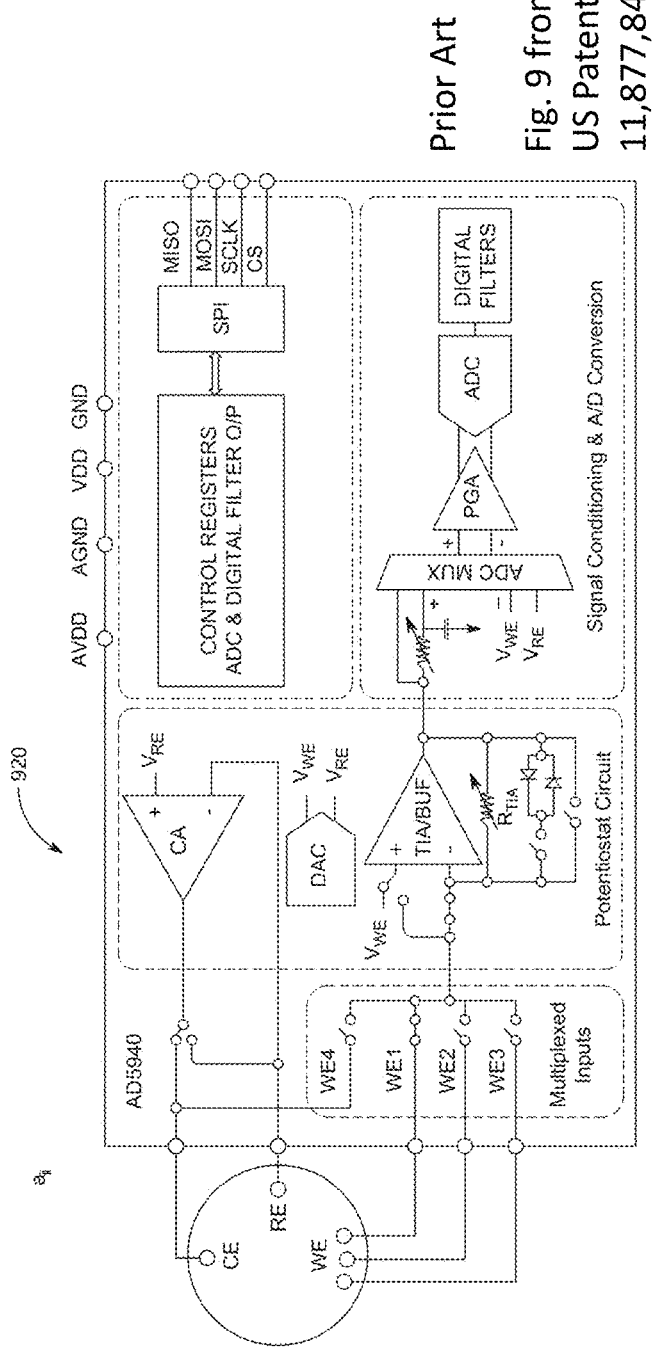
FIG. 49 (FIG. 9 of U.S. Pat. No. 11,877,846) shows additional aspects of one embodiment of the electronic unit.

FIG. 48 (FIG. 9 of the '846 patent) shows schematics depicting an example embodiment of the disposable sensor component 110C and the reusable electronics unit 120C shown in FIG. 47, e.g., used in the example implementations. FIG. 48 shows schematic diagrams illustrating the example electronics and sensor architecture for the disposable sensor component 110C and the reusable electronics unit 120C, labeled 920 in FIG. 48, where panel ($a_i$) shows a functional block diagram of example components in an architectural configuration of the reusable electronics unit 120C; FIG. 49 shows a functional block diagram of an example signal processing circuit (AD5940, Analog Devices) electrochemical analog front end (recreated from the component's datasheet); panel ($a_{iii}$) shows an image depicting an example of the electronic system PCB connection to a battery (e.g., through a low-profile connector) and to the charging coil (e.g., through large solder pads); and in FIG. 50 panel ($a_{iv}$) shows a diagram showing example components of the reusable electronics unit 120C, including example electronic interface connection pins 911 and a break-out diagram 912 demonstrating how the disposable electronic unit 120C interfaces to the disposable sensor component 110C (i.e., microneedle array 4) via the connection pins 911—which, in this example, insert into conductive holes ("E-connection Hole" in the diagram 912) on the sensor base (e.g., where such holes can be made conductive by sputter deposited metal within CNC milled holes), and where mechanical guides at the base of the conductive pins 911 provide mechanical retention to the example electronic system PCB.

Figure 50:
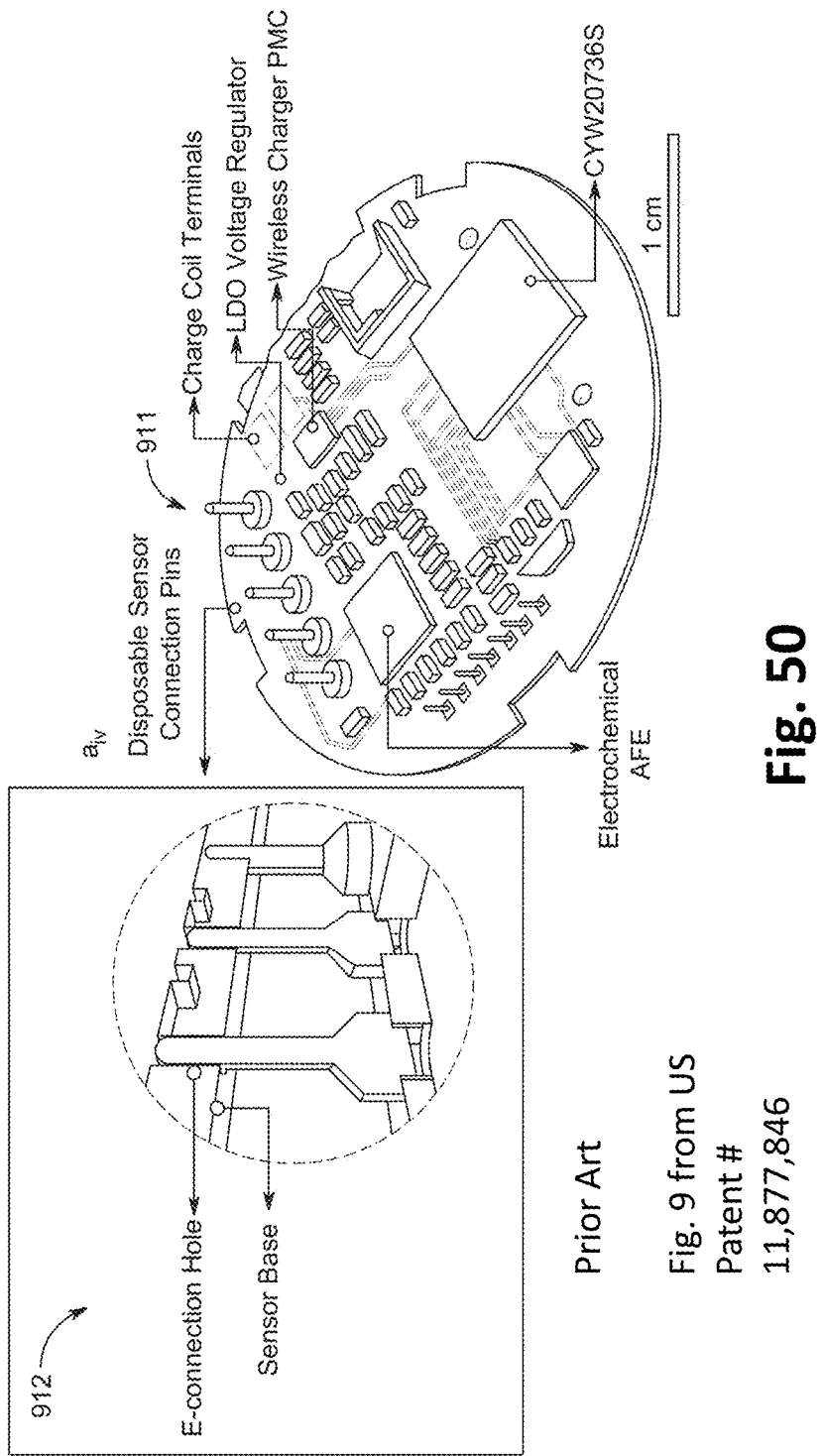
FIG. 50 (FIG. 9 of U.S. Pat. No. 11,877,846) shows additional aspects of one embodiment of the electronic unit.

The schematics and images in FIG. 48-50 demonstrate an example embodiment of the disclosed wearable biosensor device 100. For example, to acquire electrochemical signal data and subsequently transmit it, the example reusable electronic unit 920 of the device in FIG. 50 utilizes two integrated circuits: an electrochemical analog front end (AFE) and a Bluetooth Low Energy (BLE) system-in-package (SiP). In this example, the AFE provides the circuitry for multiplexing between up to four independent working electrodes, signal conditioning (amplification and filtering), and signal digitization, while the BLE SiP provides a low power microcontroller for processing the digitized signals, as well as a BLE radio and embedded antenna for data transmission. Powering these components, in this example, is accomplished by a lithium-polymer battery (through a voltage regulator), which is inductively charged through a wireless charging IC and charging coil (e.g., see FIG. 15 of the '846 patent). Additionally, power optimizations for the AFE and BLE SiP can enable 30 days of battery life while maintaining a relatively small battery size (e.g., see FIG. 16 of the '846 patent). Minimizing the number of necessary ICs to only four (2 for signal acquisition/transmission and 2 for voltage regulation/recharging), in addition to the power optimizations, can allow for a compact design (e.g., see FIG. 50, panel ($a_{iv}$)).

An example fabrication and assembly process for the example electronic system is described here. The example components of the electronic system used in the example implementations (e.g., discussed in connection with FIGS. 8-13 of the '846 patent) were assembled onto a 4-layer FR4 printed circuit board (PCB), e.g., which measures 0.5 mm in height and 5.3 cm2 in area (r=13 mm). Fabrication and assembly were performed by PCBminions (Princeton, N.J., USA & Shenzhen, China). Components were sourced from Digi-Key Electronics (Thief River Falls, Minn., USA). Example components include the AD5940 electrochemical analog front end (AD5940BCBZ-RL, Analog Devices, Inc., Wilmington, Mass., USA), the CYW20736S, Bluetooth Low Energy (BLE) system-in-package (SiP) module (CYW20736S, Cypress Semiconductor Corporation, San Jose, Calif., USA), a 2.8V low-noise, low quiescent current low-dropout (LDO) regulator (LP5907UVX-2.8/NOPB, Texas Instruments, Dallas, Tex., USA), a wireless Li-ion battery charger (LTC4124EV #TRMPBF, Analog Devices, Inc., Wilmington, Mass., USA), a wireless charging coil (WR202020-18M8-G, TDK, Chuo City, Tokyo, Japan), and a 110 mAh Li-ion coin cell battery (RJD2430C1ST1, Illinois Capacitor, Des Plaines, Ill., USA). The electrode connection includes five gold plated nickel, 0.508 mm diameter pins (0508-0-00-15-00-00-03-0, Mill-Max Manufacturing Corporation, Oyster Bay, N.Y., USA).

Aspects of an electrochemical sensing operation for an example electronic system are described herein. The AD5940 electrochemical analog front end (AFE) integrates multiple circuits for performing electrochemical analysis, which are functionally grouped into circuitry for multiplexed input selection, potentiostat operation, signal conditioning and digital conversion, and data communication. The AFE interfaces with the sensor array through the five gold-plated pins. Four of the pins are used as multiplexed input channels when operating in a 2-electrode configuration (labeled WE1, WE2, WE3, and WE4), with the fifth pin used for a combined counter/reference electrode. When operating in a 3-electrode configuration, three working electrodes are available for multiplexing (WE1, WE2, WE3), and the fourth and fifth pins are used for the counter and reference electrodes. Each working electrode input can be individually addressed to connect the electrode to the potentiostat circuit for electrochemical analysis.

The potentiostat circuit includes a control amplifier (CA), a transimpedance amplifier (TIA), and a 12-bit dual output digital-to-analog converter (DAC) which sets the common mode reference electrode potential (VRE) and working electrode potential (VWE). The TIA converts input current IIn into a voltage to be measured by the ADC. The potential difference (VWE-VRE), set by the DAC, is applied to a connected electrochemical cell through the control amplifier and TIA. The operational range for the applied potential is +/−1.0 with a resolution of 0.537 mV (12-bit DAC, VRef=2.2V).

Signals from the TIA feed into the signal conditioning and digital conversion circuitry, which include a programmable analog RC filter, a differential multiplexer (labeled ADC MUX), a programmable gain amplifier (PGA), a 16-bit analog-to-digital converter (ADC) for digitizing signals into measurement data, and cascaded digital sinc3 and sinc2 filters. Both the TIA and PGA feature programmable gain values. The ADC was configured to measure the differential voltage between the amplifier output and VWE via the ADC MUX.

The AFE also contains data registers to store configuration information and for storing measurement data from the ADC or digital filters. Data communication with these data registers occurred through the AFE's SPI interface.

Signal filtering on the AFE, which is used to suppress random electronic noise and electrochemical noise, is accomplished in both the analog and digital domains. A single pole low pass analog filter is formed by a programmable resistor and a 1 µF capacitor located at the output of the TIA/BUF amplifier. The resistor is set to 20 kΩ, resulting in a 3 dB cutoff frequency of 7.96 Hz, which was chosen suppress noise whilst not allowing the filter's settling time to cause measurement inaccuracies for the capacitive currents found in amperometry tests. The ADC output connects to a digital sinc3 filter followed by a sinc2 filter. Configuring the bandwidths of these filters is done by digitally setting their oversampling ratios, which are set to 5 and 1333 for sinc3 and sinc2, respectively (the maximum setting on the AFE). This produces an overall filter 3 dB bandwidth of 38.32 Hz at a sampling rate of 800 kSPS (found through simulation). Note that the frequency response of digital sinc filters is similar to that of averaging/integration methods commonly used in electrochemical analysis. An additional 60 Hz/50 Hz mains filter is used after the sinc filters.

Signal amplification is performed by the TIA and PGA to ensure that their levels are always within the detectable limits of the ADC over a wide range of input current. An autoranging system is employed to dynamically adjust the TIA and PGA gains during tests to do so. The system algorithm recursively tests different transimpedance values until the signal level is within 20% to 80% of the ADC's full range. Each gain level covers 12.04 dB of range, except for the highest transimpedance level which covers 73.1 dB from 16.2 nA down to 3.6 pA (e.g., the limit of detection for the electronic system), and the lowest transimpedance gain level which extends from 0.83 mA up to 2.15 mA for a range of 8.3 dB. The autoranging system allows the electronic system to support a range of 2.15 mA to 3.6 pA (175 dB of range). Note that a diode pair is connected to the TIA's feedback path to not disturb the cell biasing (allowing current to flow) while switching between RTIA values.

Bluetooth Operation. The CYW20736S BLE SiP module features an ARM Cortex-M3 microcontroller (MCU), a BLE radio, and an embedded planar inverted-F antenna. The module is programmed to control all electronic system functionality, namely configuration of the AFE through its SPI bus, control of electrochemical measurement data acquisition, and wireless communication with a mobile device over BLE.

Wireless BLE operation of the electronic system is described, as an example. The electronic system in the some of the example implementations was configured as a Bluetooth Generic Attribute Profile (GATT) server and hosts custom services and characteristics which a GATT client—the smartphone—can interact with. The BLE GATT can be organized into "services" which group together pieces of data referred to as "characteristics." Two services were used for electrochemical tests: a configuration service and a measurement data service. The configuration service contains characteristics for setting test parameters (e.g., applied potential for amperometry). The measurement data services can act as unique data channels for transmitting data, and trivially contains a characteristic for measurement data. Prior to transmission, measurement data acquired through the ADC is converted to relevant measurement units—current in pA for amperometry.

Power Management and Wireless Recharging. The power management and wireless recharging circuitry on the electronic system include a wireless recharger IC, a 2.8V LDO, and a wireless charging receive coil. For example, power for the electronics was sourced from the rechargeable Li-ion battery—a 2430 type (e.g., 24 mm in diameter, 3.0 mm in height) coin cell. The example battery, receive coil, and PCB were adhered to each other with double-sided tape, resulting in a total device height (e.g., from the top of the battery connector to the bottom of charging coil) of 6 mm and a diameter of 26 mm.

Under normal operation, power is sourced from battery, through the wireless recharger IC, and into the LDO. The LDO then regulates the battery voltage (~3.7V) down to 2.8V, which is supplied to the AD5940 and CYW20736S. The electronic systems begin inductively charging the battery when it is placed on a transmitter pad. Charging is regulated by the wireless recharging IC, which features over-discharge protection and constant current/constant voltage charging capability to quickly charge the battery without overcharging.

Power Optimizations. Both the AD5940 AFE and CYW20736S BLE module feature "sleep" modes to reduce average power consumption by power-gating and/or clock-gating circuit blocks. This is leveraged on the AFE by turning the ADC and digital filters on solely for periodic sampling events and turning them off outside of these events. Furthermore, the microcontroller and BLE radio on the CYW20736S are deterministically gated between sampling events. Note that throughout an entire electrochemical test, the DAC, control amplifier, and TIA/BUF amplifier are left on to maintain the reference electrode potential and maintain/measure the working electrode potential for potential-controlled/potentiometry tests.

In the example implementations, the instantaneous current consumption before, during, and after a single sampling event included the following. An increase in current to ~10 mA was observed at t=0.4 s, indicating that the microcontroller, ADC, and digital filters have been turned on to begin a sampling event. The current drops down shortly after, indicating that data had been sampled and the microcontroller, ADC, and digital filters have turned off. Next, the current spikes to ~20-30 mA, indicating that the BLE radio and microcontroller have turned on, which occurs for 3 sequential BLE connection events. During the first, data was transmitted to a mobile device. Next, the electronic system received a confirmation from the mobile device that the measurement data had been properly received. Lastly, the electronic system received an empty BLE packet from the mobile device, telling the electronic system that no further BLE communication will take place, allowing the BLE radio to be kept off until the next sampling event. Before and after these events, the low current levels labeled "Sleep" verify that ICs were successfully placed into low power modes. Small spikes of ~5 mA appear every 100 ms—this is the CYW20736S periodically waking up to briefly to perform basic system operations, such as flashing the electronic system's LED, taking battery level measurements, or checking if data needs to be retransmitted due to a BLE disconnect.

The average current consumption of a 60 s amperometry test (sampling interval=1 s) and the instantaneous current of three sampling events during this test for reference was considered. The average current lied close to the "Sleep" current found between sampling events, as the electronic system remains primarily in sleep mode given the long sampling interval.

Current consumption decays back to 1.06 mA as the sampling interval was increased back to 1 s, resulting in a battery life of 4 days and 7.6 hours. Additionally, the electronic system can be placed into an ultra-low power mode via a BLE command whereby all components are turned off for a preset duration of time. In this mode, the electronic system consumes 53.5 pA. Duty cycling this ultra-low power mode with continuous sampling allows for significant battery life gains. For instance, 10% duty cycling with 1 minute of continuous sampling mode (e.g., sampling interval=1 s) followed by 9 minutes of ultra-low power mode results in average current consumption of 154 µA and a battery life of approximately 30 days.

Firmware Programming. Programming and reprogramming procedure for the electronic system used in at least some of the example implementations are described. The programming used UART connections (Tx, Rx, VCC, GND), and required a physical connection between the electronics and a personal computer which hosts the firmware. This was accomplished by first connecting the electronics to a Cypress BCM92073 X_LE_CIT development kit through a 6-pin Molex PicoBlade cable, and connecting the kit to the personal computer using a micro-USB cable. The development kit was needed specifically for its on-board FTDI USB-UART interface chip, which converts serial UART signals into serial USB signals. Initial programming the electronics is accomplished using Cypress' WICED SMART, a software development kit (SDK) which provides an Eclipse-based integrated development environment (IDE) for building firmware and downloading it to the electronics. Thereafter, the programming header of the electronics (which has no active components) is cut off, making the electronic system ready to be integrated with the sensor array.

Reprogramming can be done through over-the-air (OTA) updates via BLE. Afterward, programming is done wirelessly via BLE through Over-the-Air (OTA) updates. This enables rapid deployment of firmware updates in line with today's agile software development environments.

Force Touch Sensor

The present invention is a wearable biosensor device system in one aspect for reliably and repeatably inserting submillimeter microneedles in a microneedle array in a wearable biosensor into the outermost layer of the skin—the epidermis—to facilitate accurate biomolecular monitoring in a biofluid such as interstitial fluid (ISF), blood and cerebrospinal fluid. The invention enables better placement of the microneedle array with a force touch sensor and feedback indicator which guide the user in applying an adequate amount of pressure (force) onto a device composed of microneedles to ensure proper insertion and provides real-time feedback. Placement includes not only the initial placement of the device but also a continuous monitoring that correct placement has been maintained throughout the life of the wearable biosensor device. The system also includes a bioelectronic measurement component which compares electrical signals for the microneedles to notify the wearer that the microneedles have reached a biofluid in the body. The feedback can be in different ways through, for example, vibrations, sounds, flashing lights on the wearable device and notification through Bluetooth or similar signals to a mobile device containing an app.

The microneedle array may include a group of microneedles to detect a first analyte, a second group of microneedles to detect a second analyte, and a third portion of microneedles to detect a third analyte. The microneedle array may be configured to detect any suitable number of analytes (e.g., 1, 2, 3, 4, 5 or more, etc.). Suitable target analytes for detection are selected from the group consisting of glucose, ketones, lactate, and alcohol.

The wearable biosensor device 1 comprises a microneedle array having a substrate with microneedles disposed on the substrate, wherein at least one of the microneedles is configured as a working electrode to detect an electrical signal from a reaction with a target analyte exposed to the microneedle array in a biofluid of a body of a wearer, and the working electrode is functionalized with at least one chemical layer positioned on at least one of the microneedles and is configured for producing an electrical signal from a reaction with the target analyte; an electronics unit underneath the substrate connected to the microneedles by a plurality of electrical connections; a force touch sensor configured to measure force applied during placement or anytime during the life of the device of the microneedle array into skin of a user, the force touch sensor connected electrically to the electronics unit; the electronics unit configured as a placement validation system is configured to detect a change in conditions using bioelectronic measurement among microneedles outside the body and in a biofluid, and a feedback indicator connected electrically to the electronics unit and configured to provide to the wearer a notification of excessive force in placement and/or of proper placement in the biofluid. The electronics unit comprises a data processing unit in communication with a signal processing circuit, the data processing unit comprising a processor and a memory and configured to process the electrical signal as data representative of one or more parameters of the target analyte, and the signal processing circuit is configured to process the electrical signal by one or more of amplifying the electrical signal, filtering the electrical signal, or converting the electrical signal from analog to digital, and the data processing unit is configured to process the electrical signal after processing by the signal processing circuit. The electronics unit further comprises a wireless communication unit in communication with one or both of the signal processing circuit and the data processing unit, the wireless communication unit comprising a wireless transmitter or wireless transceiver to at least transmit one or both of the electrical signal and the data to an external computing device.

The at least one chemical layer comprises a material selected may be from the group consisting of an enzyme, an ionophore, an antibody, a peptide nucleic acid (PNA), a DNA aptamer, a RNA aptamer, a molecularly imprinted polymer (MIP), and a cell. The microneedles of the wearable biosensor may be targeted for a single analyte in the biofluid, or may be separated into groups which are electrically segregated, and the chemical layer for each of the groups is different to a unique analyte.

The force touch sensor may be selected from the group consisting of pressure, strain gauge, piezoelectric, piezoresistive, resonant, electromagnetic, capacitive, and diaphragm-based MEMS sensors operating individually or in combination with each other, and the force touch sensor is configured to transduce an applied force into an electrical parameter selected from the group consisting of resistance, current, capacitance, inductance, frequency or phase shift, voltage variability, optical or thermal changes and magnetic field variations.

The placement validation system can comprises a single or multiplexed two-, three- or four-electrode electrochemical system comprising the microneedles, and the bioelectronic measurement system is configured to use electrochemical techniques selected from the group consisting of impedance spectroscopy, voltammetry, potentiometry and amperometry.

The feedback indicator comprises hardware or software configured to generate a notification selected from the group consisting of a microelectromechanical system (MEMS) speaker, a vibration actuator, and a light-emitting diode (LED) on the wearable device and a notification through Bluetooth or similar signals to a mobile device containing an app.

The vibration actuator is selected from the group consisting of an eccentric rotating mass actuator (ERM), a linear resonant actuator (LRA), a piezoelectric actuator, electroactive polymers (EAPs), microelectromechanical systems (MEMS), a tactile haptic-based oscillation/resonance actuator and a voice coil actuator. The driving signal of the vibration actuator is selected from the group consisting of amplitude, frequency and on/off keying.

The indication to the wearer is selected from the group of a sound, a light, a vibration or a message delivered to the app on the mobile device.

The force touch sensor can also be configured as a switch to turn the device on or off.

The improved aspects for placement are configured in a device with a microneedle array comprising a nonconductive polymer coated with an electrically conductive layer and positioned underneath the chemical layer, or a microneedle array comprising a semiconductor material having various material layers applied and shaped using microelectromechanical systems (MEMS). In one embodiment of the invention, a force touch sensor is integrated into a wearable biosensor device such as those in the '846 patent and is connected to a printed circuit board (PCB), underneath the microneedle array and substrate, translating the forces among the microneedles and the skin to a measurable signal. The force touch sensor in different embodiments is selected from the group consisting of pressure, strain gauge, piezoelectric, piezoresistive, resonant, electromagnetic, capacitive, and diaphragm-based MEMS sensors operating individually or in combination with each other.

In various embodiments, the feedback indicator is also integrated into the microneedle sensor device electrically connected to the electronics unit. In another embodiment the feedback indicator can be mounted to the microneedle array and have electrical connections to the electronics unit. It can also be mounted to an enclosure and electrically connected to the electronics unit. Embodiments of the feedback indicator comprise devices selected from the group consisting of a microelectromechanical system (MEMS) speaker, a vibration actuator, and a light-emitting diode (LED).

Figure 51:
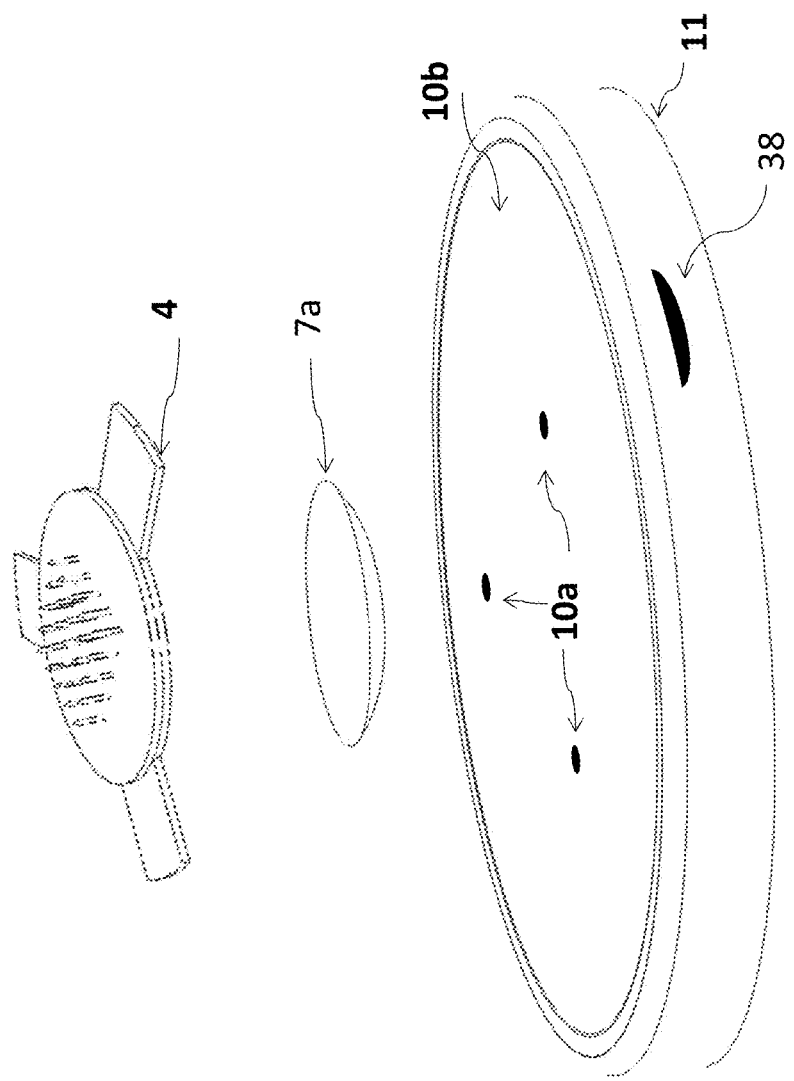
FIG. 51 is a perspective view of the positioning of the force touch sensor between a microneedle array and the electronics unit.
Figure 52:
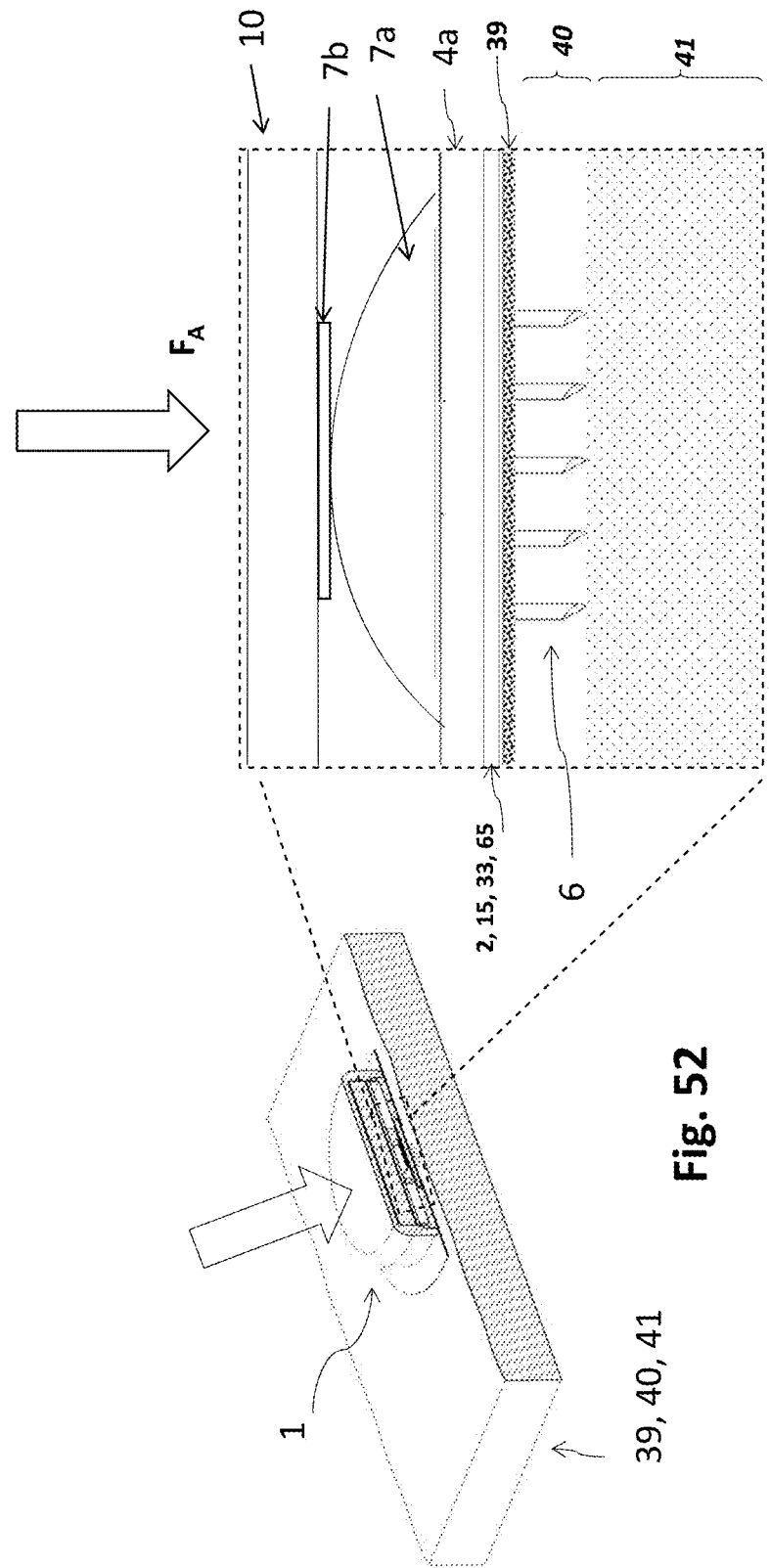
FIG. 52 is a section view of one embodiment of the wearable device applied to the skin of a user, with an enlarged view showing a force touch sensor.

Interplay between the force touch sensor and feedback indicator and the "mode" of user interaction can be realized in various ways. The following describes an exemplary operation mode for the feedback and implementation in the wearable biosensor device 1. As shown in the embodiment in FIG. 51 and FIG. 52, the force touch sensor 7 is a two component resistance-based pressure sensor 7a placed behind the microneedle array 4 (i.e., opposite the top of the microneedle array tips), with the complementary conductive trace 7b behind the electronics unit, e.g., a PCB or ASIC. FIG. 51 is an exploded view of the wearable biosensor 1 with a pressure sensor under the microneedle array 4 in two parts, an elastic conductive pad 7a and contacts 10 a for the electronics unit (PCB or other covered by plastic sheath 10b, which is connected electrically to the electronics unit 10. In this embodiment, a feedback indicator 38 (e.g., a micro speaker) is located on the outside of the biosensor device. FIG. 52 is a cross-sectional view of the sensor 1 on the stratum corneum (outer layer of skin) 39 with the user pressing the wearable sensor (shown left in cross-section). Pressure sensor components 7a, 7b are underneath the device substrate 4a, the microneedle array 4, the cover 2, 15, 33, 65 the stratum corneum (skin's dead keratinocytes) 39 and the epidermis 40 and dermis layers 41 underneath it (Right). Arrows FA show the direction of force.

Figure 53:
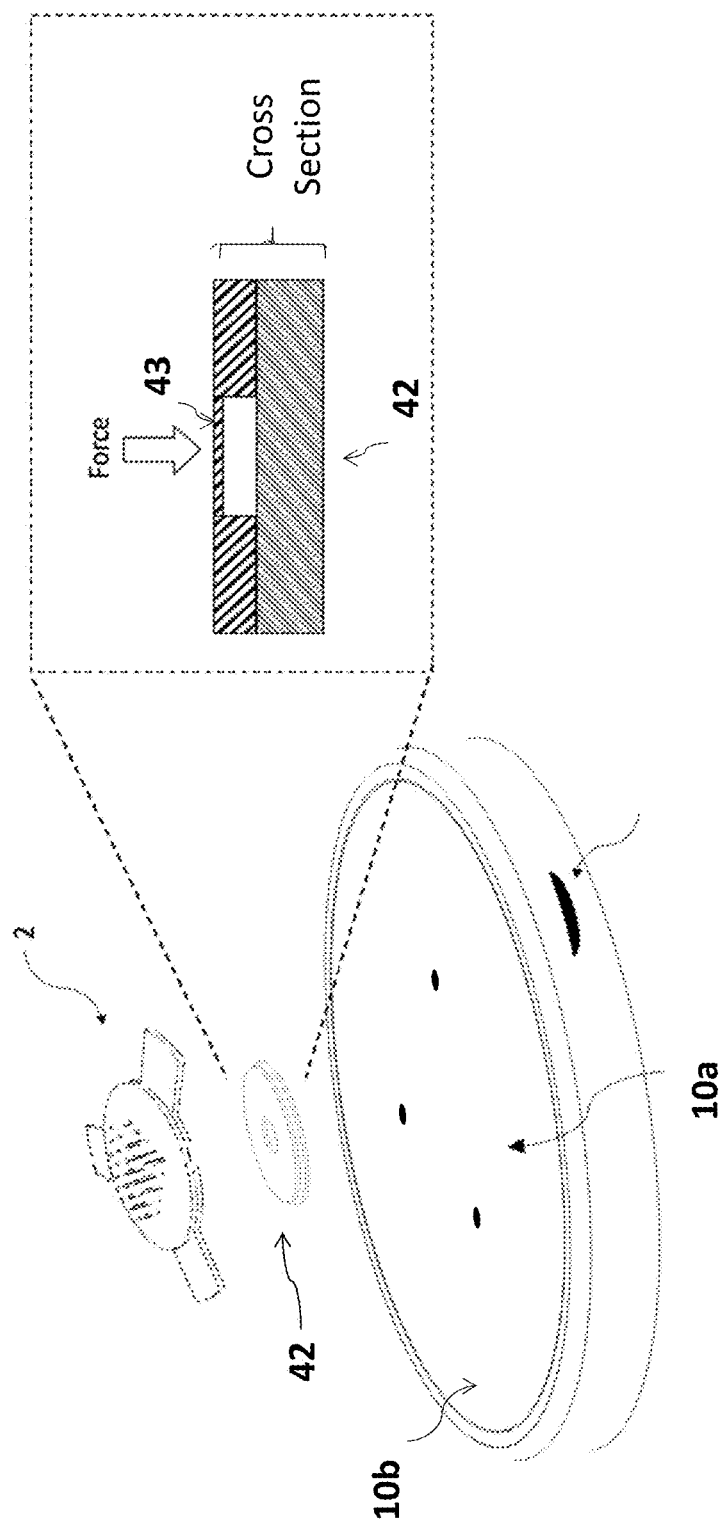
FIG. 53 is a perspective view of a MEMS diaphragm sensor in relation to the microneedle array and the electronics unit (not pictured under a sheath and in the lower enclosure). A cross section of the MEMS diaphragm is also included as enlarged.

FIG. 53 shows a further embodiment of the present invention, a Micro-Electro-Mechanical Systems (MEMS) pressure sensor 42 (e.g., capacitive pressure sensor). The MEMS pressure sensor is situated to maximize its operational efficacy, either positioned directly between the microneedle array 4 and the substrate or base or in conjunction with the electronics unit, such as a PCB or an ASIC. The MEMS pressure sensor 43 in this embodiment is distinguished by a diaphragm crafted from silicon or a similarly behaving material. This diaphragm, shown in the callout to the right, is meticulously calibrated to deform within a specific pressure range, precisely from 1 Newton (N) to 50 Newtons (N). The design ensures that the sensitivity of the diaphragm is finely tuned, inversely correlating with its dimensional proportions. Upon application of the microneedle array to a patient's skin, and subsequent exertion of pressure, the MEMS pressure sensor 42 is activated. The diaphragm 43 deforms responsively, influencing the piezoresistive elements that are integrally embedded within it. These elements, highly sensitive to deformation, undergo a change in electrical resistance that directly corresponds to the magnitude of the applied pressure. This change is accurately captured and processed by the embedded electrical circuitry, such as the Wheatstone bridge network, described further herein, which is specifically configured to amplify and refine the signal for enhanced precision. The Wheatstone bridge, a fundamental circuit in pressure sensing applications, is adept at precisely measuring minute changes in resistance, making it ideal for translating the mechanical deformations of the diaphragm into reliable electrical signals. Subsequently, the processed signal undergoes a transformation from an analog to a digital format.

Figure 54:
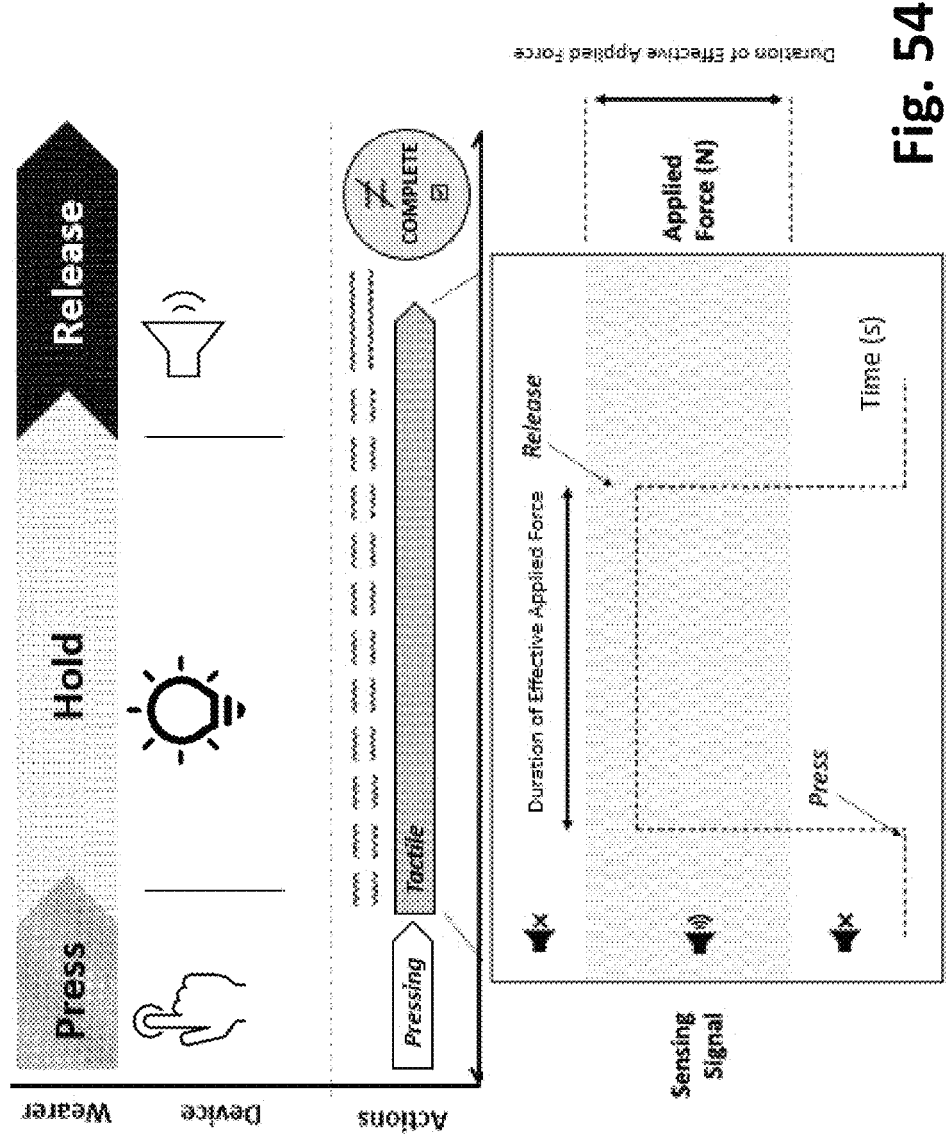
FIG. 54 is a diagram of steps and outcomes for a skin-insertion force reduction aspect of the device which validates with a micro speaker the placement of the microneedle tips in a suitable portion of the skin.

FIG. 54 depicts operation of one embodiment of the force touch sensor 7, 7a, 7b of the device. The diagram shows a basic mode of press/hold/release phases with the corresponding exemplary graph of a pressure sensor and duration and magnitude of the applied force using a pressure sensor as the force touch sensor, and a speaker emitting a sound such as a beep. FIG. 54 depicts the feedback indicator 38 in an embodiment as a micro speaker. Here, the user applies the device 1 to her skin and presses the back end of the device (with the microneedle tips facing the skin). Upon applying the pressure, the micro speaker begins providing feedback in the form of beeping to guide the applied pressure in magnitude and duration. In one embodiment, a 0.5 second on/0.5 second off beeping regime occurs when the user applies a "correct" magnitude of force to the device and continues for 6 seconds to guide the duration, after which a continuous beep (a single tone for 3 seconds followed by muting) is emitted to indicate that the microneedles have been inserted correctly and the application process is complete. In one embodiment, a correct magnitude of force is within a range of 5-50 newtons and in another embodiment 15-35 newtons. Pauses in beeping can indicate insufficient magnitude and therefore the need to reposition the device. All beeping (or any other feedback) occurs in real-time.

Figure 55:
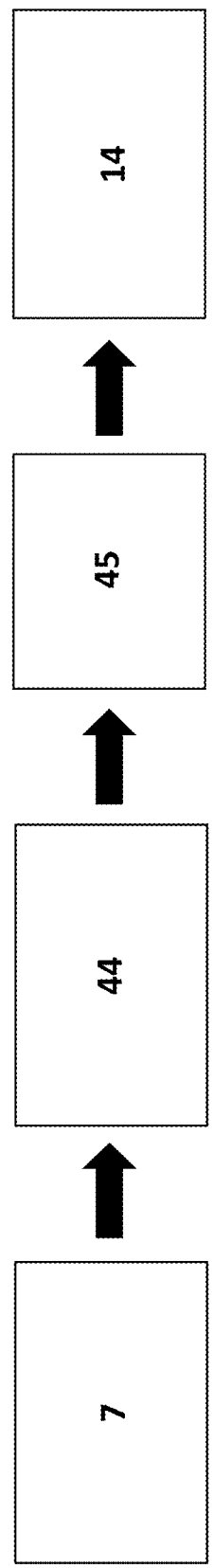
FIG. 55 is a functional block diagram for the force touch sensor data measurement.

A functional block diagram for the force touch sensor data measurement is depicted in FIG. 55, which in one embodiment comprises a force touch (pressure) sensor 7, signal processing circuitry 44, an analog-to-digital converter (ADC) 45, and a microcontroller 46.

In another embodiment, the signal processing circuitry may provide electrical biasing to the force touch sensor for proper operation.

In one embodiment, the force touch sensor can be used as a switch to turn the entire sensor on or off, where the two separate conductive elements usually resulting in a change in resistance or a closed circuit signals a button being pressed.

In yet another embodiment, the signal processing circuitry may provide signal conversion (e.g., transimpedance or current-to-voltage conversion), signal filtering (e.g., passband filter), and/or signal amplification to condition the signal for acquisition (i.e., quantization or digitization) by the analog-to-digital (ADC) converter with a high signal-to-noise ratio.

In other embodiments, the ADC may have a single-ended input or a differential input.

In some embodiments, an analog multiplexor may be used at the input of the ADC to utilize the ADC for acquiring multiple signals.

The microcontroller may be used to interpret the electrical signals coming from the output of ADC with suitable algorithms or mathematical equations/transformations (e.g., convert a raw quantized bit-stream into an integer value representative of the acquired signal).

Additional digital signal processing circuitry may be utilized after the digitization of acquired data through digital circuits (e.g., a cascaded integrator-comb (CIC) filter) to improve the signal-to-noise ratio.

Figure 56:
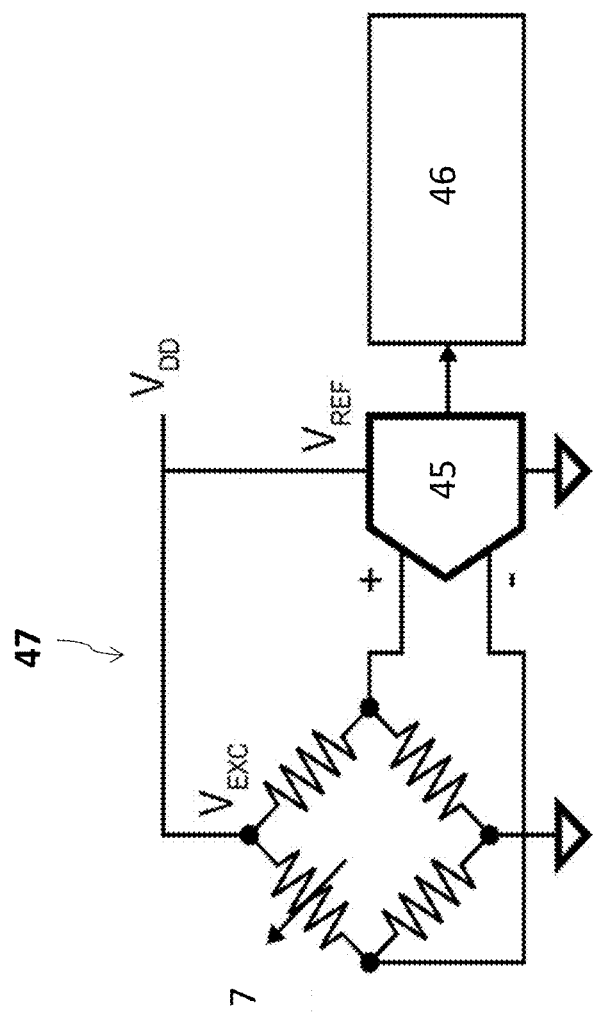
FIG. 56 is a circuit diagram of one embodiment of a Wheatstone Bridge circuit for a force touch sensor.

One embodiment of the circuit implementation of the force touch sensor data measurement capability is depicted in FIG. 56. Here, the force touch sensor 1 is represented as a sensor whose resistance is sensitive to applied force, such as a force sensing resistor (FSR), which exhibits a decrease in presented resistance in response to increase in applied force. A Wheatstone Bridge circuit 47 is employed to convert a resistance change into a voltage change, which can then be acquired (quantized/digitized) by the analog-to-digital converter (ADC) 45. The supply voltage, $V_{DD}$, is used as both the excitation voltage ($V_{EXC}$) for the Wheatstone bridge and the ADC reference voltage ($V_{REF}$), which keeps the Wheatstone bridge common-mode voltage output always within the common-mode input range of the ADC. In certain embodiments, power to the Wheatstone Bridge and the ADC can be duty cycled to limit power consumption. In this embodiment, the differential output of the Wheatstone bridge is measured by a differential ADC. The ADC quantizes this differential voltage and provides a bit stream of quantized data to the microcontroller 46 through a digital bus. The microcontroller performs a mathematical transformation on the bit-stream and converts it into an integer value of the applied force.

A schematic of one embodiment of a skin-insertion force reduction capability herein utilizes a force touch sensor and a vibration actuator in order to translate force applied by the user into electronically-controlled vibration of the microneedle electrode(s) to lower the minimum force required for reliable/repeatable microneedle electrode insertion into the epidermis. Minimizing force applied to the skin 1) localizes and minimizes damage to the surrounding skin tissue, 2) minimizes local inflammatory response and resultant biofouling, and 3) improves short-term response (reduced "warm-up" period duration) and 4) improves the long-term stability of the sensor within the skin.

The force touch sensor can be integrated into the microneedle array and/or the electronics unit (e.g., PCB) and can be placed behind the microneedle base (opposite the microneedle tips) with a conductive complementary trace behind the PCB. Additionally the force touch sensor is electrically connected to the PCB. Other embodiments include implementing this on the microneedle array itself, on the enclosure of the microneedle array, all on a single ASIC chip, or on a PCB as an electronic component.

The force touch sensor can be strain, piezoelectric, or capacitive in nature (among other types described herein) which transduces an applied force into an electrical parameter selected from the group consisting of resistance, impedance, potential, current, capacitance, inductance, frequency or phase shift, voltage variability, optical or thermal changes and magnetic field variations.

The feedback indicator, e.g., vibration actuator, can be electrically connected to the electronics unit such as a PCB. The microneedle array and PCB can also be mechanically integrated with the device housing. This allows the vibration actuator, when mechanically bonded to the PCB, to be mechanically coupled to the microneedle array. In various embodiments, force applied onto the force touch sensor can modulate the vibration actuator driving signal, therefore modulating vibration characteristics. The driving signal of the vibration actuator is selected from the group consisting of amplitude, frequency, and on/off keying. A combination of these types can also be used. The force touch sensor output can be filtered such that there is no feedback interference caused by vibration actuator while acquiring force-touch data.

Figure 57:
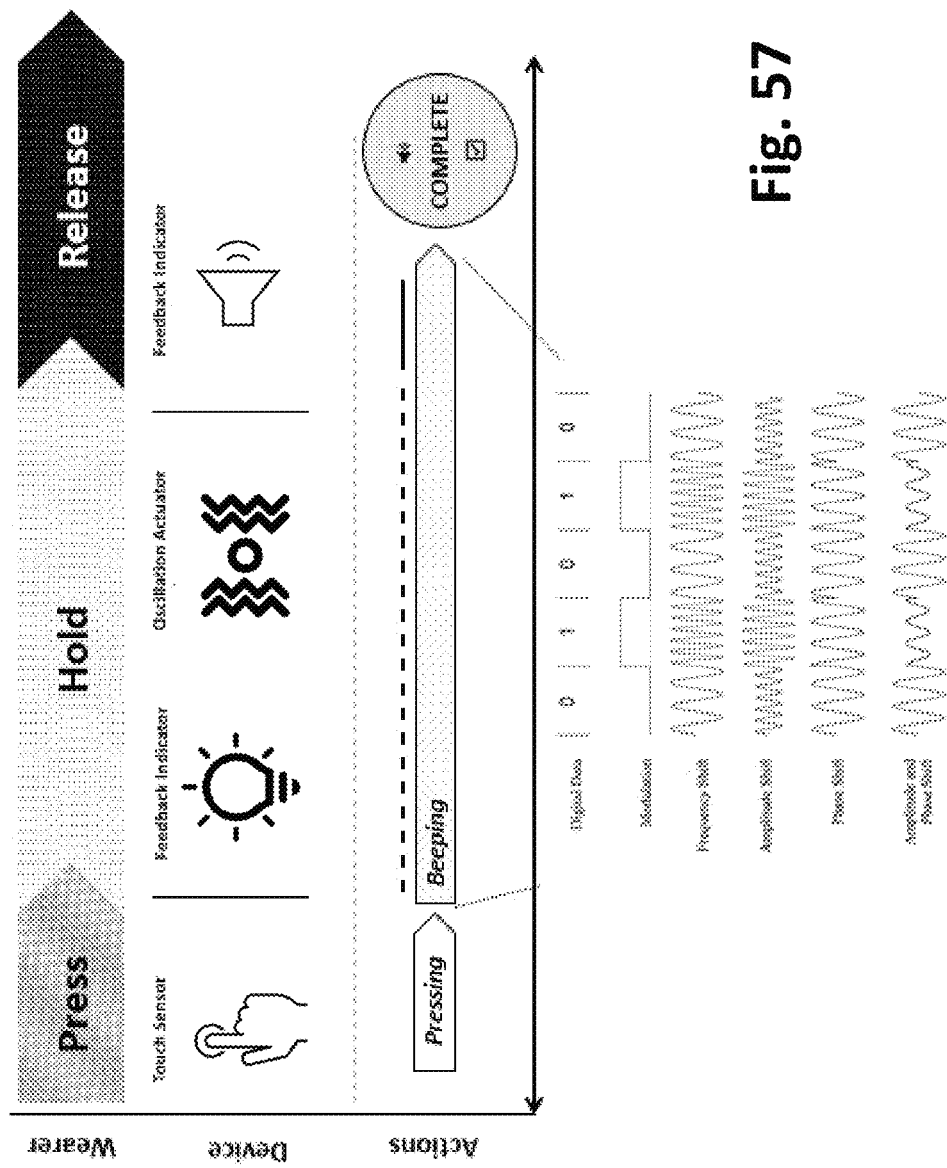
FIG. 57 depicts a skin-insertion force reduction aspect of the device with a corresponding exemplary graph of the pressure sensor duration the magnitude and duration of the applied force.

The force touch sensor and vibration actuator, the interplay between the devices, and an operation mode for user interaction can be used in various ways. The following describes an embodiment of the operation mode for this device. The sensor can be a two-component resistance-based pressure sensor with one component placed behind the microneedle array and another on the electronics unit (as in FIG. 51), and a tactile haptic-based oscillation/resonance actuator in a PCB-mounted resonance-utilizing vibration device electrically connected to the PCB. The oscillation/ resistance actuator is selected from the group consisting of linear, rotary and tactile haptic. The user applies the sensor on her skin and presses the back end of the device with the microneedle tips facing the skin. Upon applying the pressure, the actuator begins to resonate with a predefined frequency, magnitude and modulation appropriate for low-force insertion of the microneedle tips through the skin. FIG. 57 depicts a skin-insertion force reduction aspect of the system, with the diagram showing a basic mode of press/hold/release phases with the corresponding exemplary graph of the pressure sensor duration the magnitude and duration of the applied force.

Figure 58A:
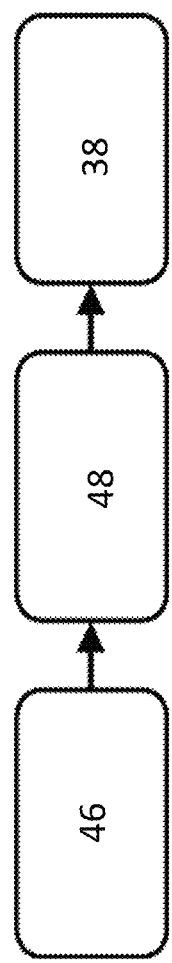
FIG. 58A is a functional block diagram of the vibration actuator control system.

A functional block diagram of the vibration actuator control system is depicted in FIG. 58A. It comprises a microcontroller 46, an actuator driver 48, and an actuator 38 that produces vibration of the device.

Vibration actuators are selected from the group consisting of an eccentric rotating mass actuator (ERM), a linear resonant actuator (LRA) 59, a piezoelectric actuator, electroactive polymers (EAPs), microelectromechanical systems (MEMS), a tactile haptic-based oscillation/resonance actuator and a voice coil actuator.

The actuator driver outputs a signal whose fundamental frequency is within the operational range of the actuator to cause the vibratory motion of the actuator. The actuator driver, in part, provides amplification to its input signal (from the microcontroller) to provide sufficient current and voltage to cause the actuator to vibrate at the desired magnitude. The actuator driver circuitry may include filtering or employ waveform engineering (e.g., leveraging non-linear characteristics of active components) to produce the desired signal at the actuator's input.

Figure 58B:
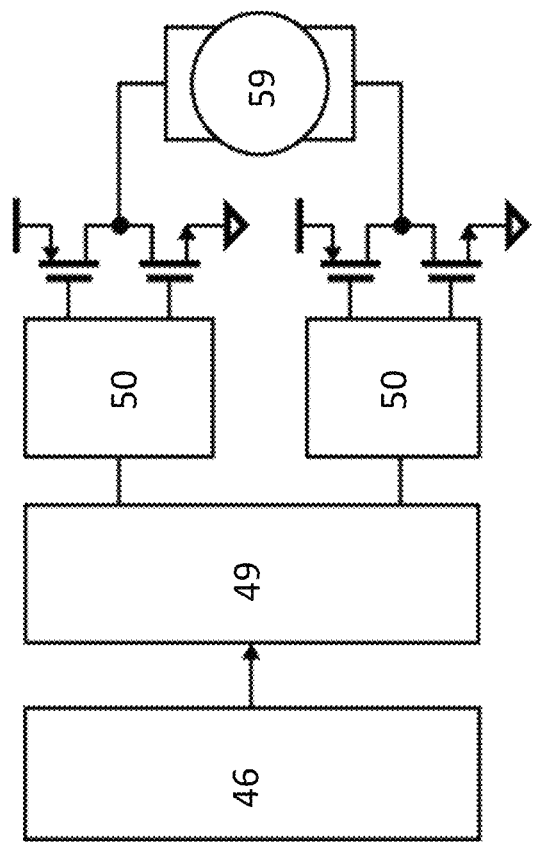
FIG. 58B is an example circuit implementation of the vibration actuator control system.

An example circuit implementation of the vibration actuator control system is depicted in FIG. 58B. In one embodiment, the vibration actuator 48 is implemented with a linear resonant actuator (LRA) 59, and the actuator driver is implemented with a class D amplifier which comprises a logic circuit, gate drivers 50, and output transistors and which operates via pulse-width-modulation (PWM). The microcontroller 46 communicates with the logic circuit 49 (over a digital bus) the desired amplitude of the driver output signal. The logic circuit creates a corresponding PWM signal applied to the switching transistors via gate drivers to ultimately drive the LRA at the desired amplitude at the actuator's resonant frequency.

Figure 59:
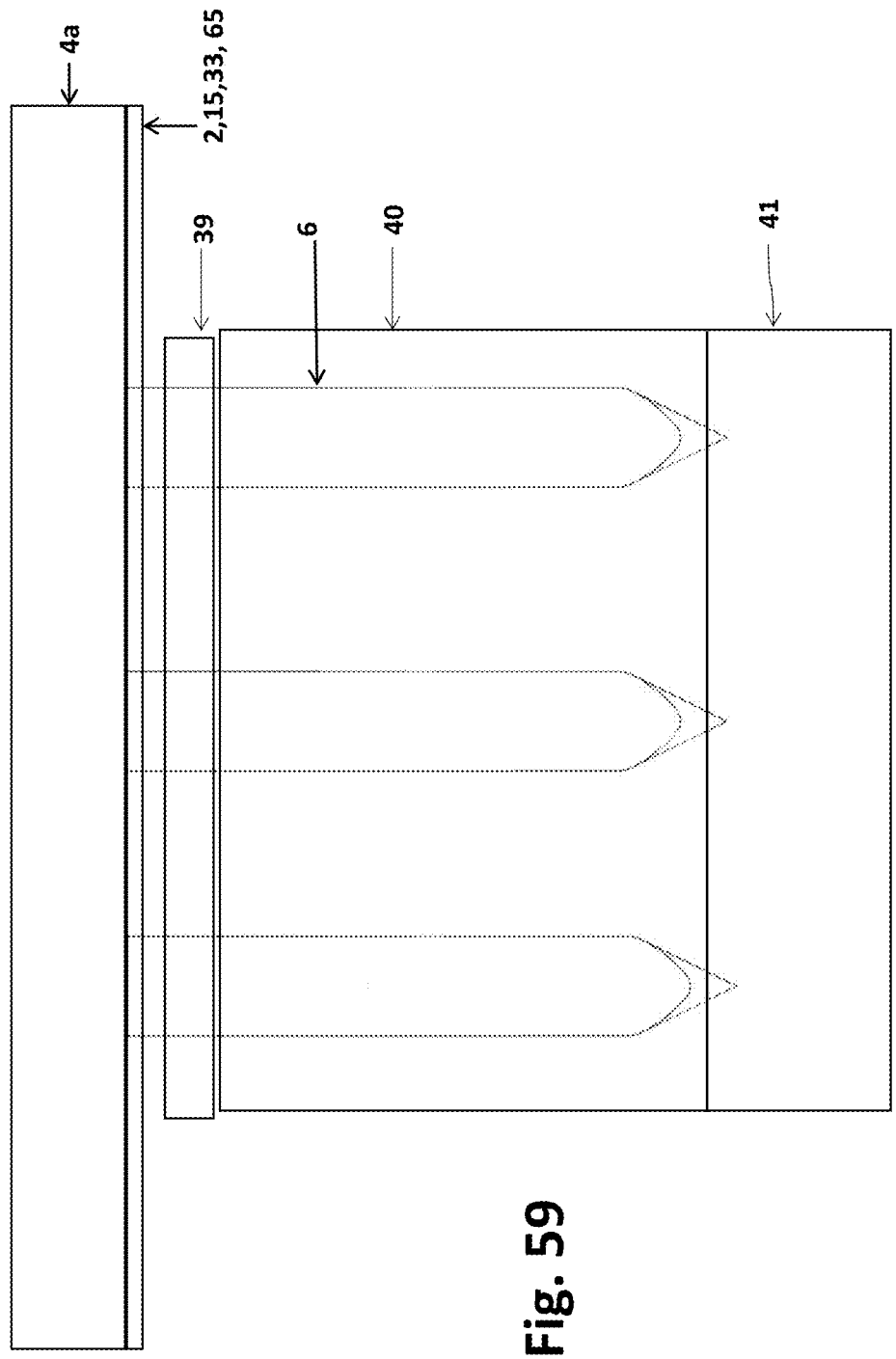
FIG. 59 is a section view of microneedle tips inserted near the border of the epidermis and dermis.

Bioelectronic measurement by the microneedle array in combination with the electronics unit also enables verification that the microneedles are properly placed initially and throughout the life of the wearable biosensor device. This protects from excessive or insufficient force during initial placement, and also provides data for notification to the wearer continuously during the life of the device. Microneedles enable accurate biomolecular monitoring by providing continuous access to the ISF beneath the epidermis, whose biomolecular concentration and temporal profiles closely match those of blood. To access and be immersed in ISF, the microneedles 6 must pierce through the outermost layer of the skin, the stratum corneum 39 (~20 μm thickness), and become embedded in the viable epidermis 40 and dermis 41 (~200 μm and ~2 mm thickness, respectively). This is depicted in FIG. 59. It is only after the microneedles are immersed in ISF that accurate biomolecular monitoring occurs. FIG. 59 is a section view of the microneedle array with the microneedles piercing the skin to reach to the border of the dermis and epidermis. This arrangement enables a placement validation system utilizes a bio-electronic measurement in communication with a feedback indicator. The placement validation system informs the user through the feedback indicator when the microneedles have successfully (or unsuccessfully) been embedded into the epidermis (beneath the stratum corneum) and immersed in ISF to facilitate accurate biomolecular monitoring. The feedback indicator, in various forms further described herein, is selected from the group consisting of a vibration actuator, a sound, and/or a flashing light that originate from the device, or a notification through Bluetooth or similar signals to an app on a mobile device of the wearer, which are delivered in response to real-time bioelectronic measurements taken through the tips of the microneedles. Details about the system and the device which implements the system follow.

The bioelectronic measurement system includes the microneedle array described herein which is electrically interfaced with the electronics unit, in one embodiment a PCB. It can be a single or multiplexed two-, three-, or four-electrode electrochemical system utilizing microneedles as electrodes.

The two microneedle electrode configuration is a working electrode (WE) vs. reference electrode combined with counter electrode (RE/CE), and the three microneedle electrode system is configured as WE vs. CE vs. RE. A four-electrode system is configured as working sense electrode (WSE) vs. WE vs. CE vs. RE.

The validation placement system can use electrochemical measurement techniques selected from the group consisting of impedance spectroscopy, potentiometry, voltammetry, and amperometry.

The feedback indicator is integrated into the microneedle sensor device and connected to the PCB. Embodiments of the feedback indicator include a microelectromechanical system (MEMS) speaker, an electrical actuator, and an LED.

Figure 60:
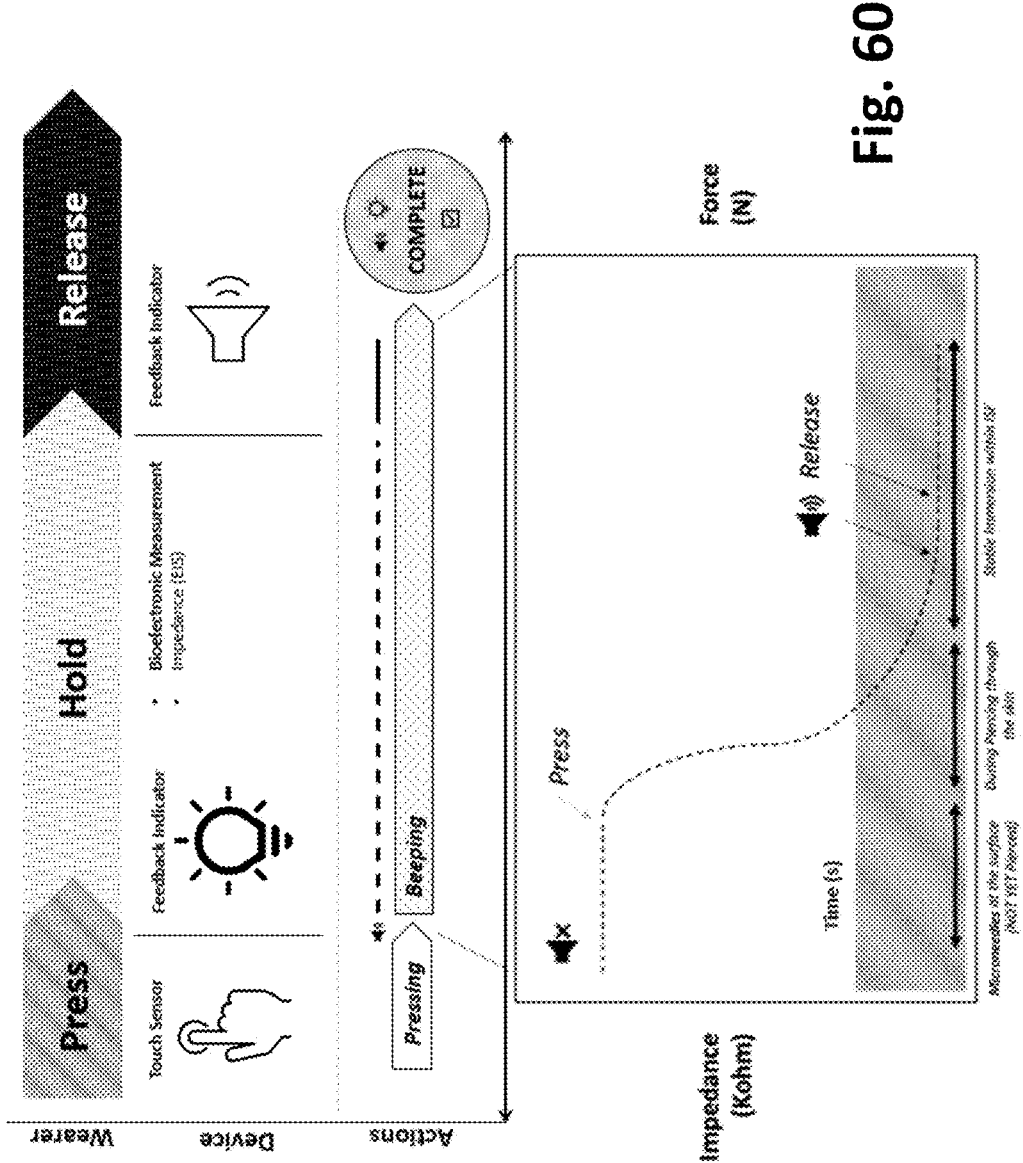
FIG. 60 is a diagram of impedance vs. applied force curve for microneedle electrodes for three phases during insertion through the dermis to the epidermis.

The bioelectronic measurement system and feedback indicator devices, the interplay between the devices, and the operation mode can be realized in various ways. The following describes an embodiment of the operation mode for the feedback and implementation in the device: the placement validation system uses the bioelectronic measurement to perform real-time impedance measurement among electrodes in real-time upon applying a particular magnitude of force on the back side of the sensor device with the microneedle tips facing the skin. As force is applied to the device the pressure sensor, acting as a switch, triggers a start of the impedance measurement and, due to the conductivity shift from the surface of the skin to the dermis soaked with interstitial fluid, the impedance measured among the electrodes will change (i.e., a much larger impedance measured at the microneedle contact with the dermis with less fluid content; and a much lower impedance at the microneedle immersed in the ISF). FIG. 60 illustrates the trend of this change—impedance decreases as applied force increases. The impedance drops suddenly once the microneedle electrodes have reached ISF. The impedance is monitored by the bioelectronic measuring system in real time to identify when this drop occurs by comparing the impedance in real-time against a threshold. Once the impedance crosses this threshold, and continues to stay past this threshold during the hold time for a pre-set time, a "release" signal is delivered by the feedback indicator in the form of, for example, a buzzing and/or a green light. The buzzing validates to the user that the microneedle electrodes have accessed ISF. FIG. 60 depicts impedance vs. applied force curve for microneedle electrodes for three phases during insertion through the dermis to the epidermis.

Figure 61:
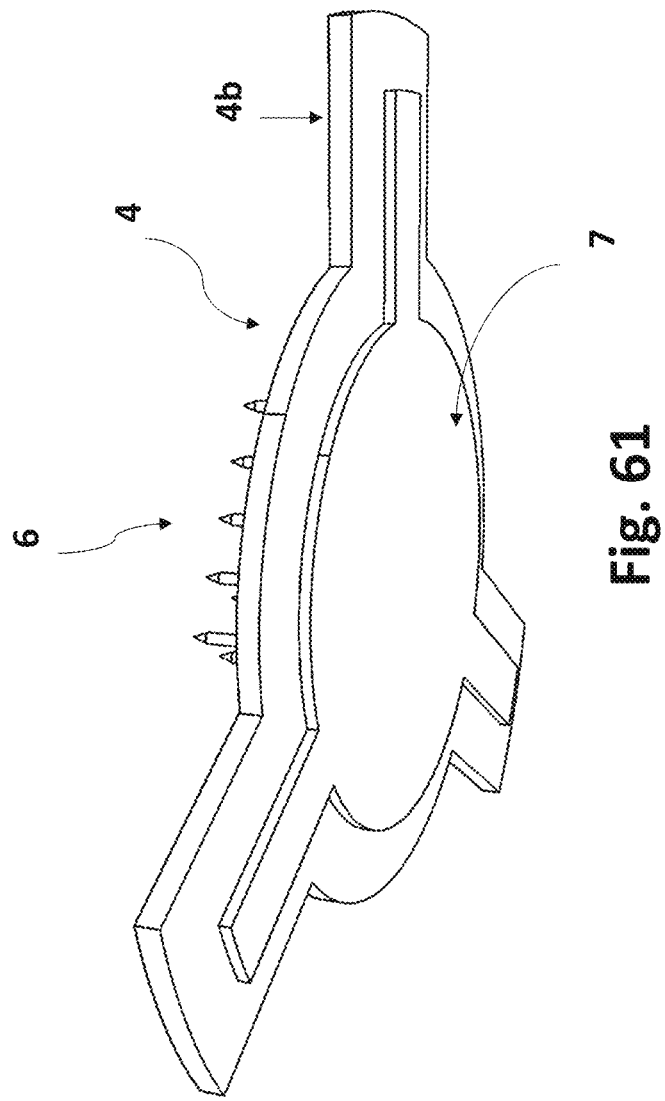
FIG. 61 is a perspective view underneath of one embodiment of a microneedle array with cantilevered arms and a force touch sensor.

FIG. 61 is a perspective view from underneath the microneedle array 4 showing the cantilevered arms 4b and a force touch sensor 7, here a strain gauge. The tips 14 of microneedles, and the body regions 16, are shown. A strain gauge (pressure sensor, or a touch sensor) on the back of the microneedle array and all of its cantilevered arms 4b. Using this configuration, the invention can electronically monitor the strain placed on the cantilever arms to approximate the force incident upon the microneedle array from the skin. These measurements can be used to digitally remove artifacts caused by forces placed upon the microneedle array which are more static in nature, such as if the user rests on the integrated sensor while sleeping. The strain gauge here is mechanically coupled due to the compression positive force at the skin and microneedle caused by movement of the cantilever arms.

Properties of the Microneedles

In some embodiments, for example, the microneedles 6 are at least partially functionalized by a chemical layer 51. For example, in some embodiments, the chemical layer can be deposited on just a portion of a microneedle 6, e.g., such as the tip; or in other embodiments, the chemical layer 51 can be coated on the tip and outer wall of the body of the microneedle 6. The chemical layer 51 is configured to chemically facilitate an electrochemically detectable reaction with a target analyte.

The innermost layer of the sensor is engineered to effectively reject environmental and operational interferences, ensuring the purity and accuracy of the signal. This layer is composed of advanced polymers known for their exceptional chemical stability and insulating properties. Some examples are poly-o-phenylenediamine (PPD), polyvinylidene fluoride (PVDF), polyvinyl chloride (PVC), polyurethane (PU), cellulose acetate and its derivatives, polyether sulfone and its derivatives, and polyvinyl acetate. The choice of polymers can be tailored based on the specific application needs. This layer acts as a foundational barrier, protecting the sensor's core from detrimental external influences while maintaining its structural integrity.

Following the interference-rejecting layer is a critical component of the sensor: the layer comprising the immobilized recognition element. This layer is designed to specifically bind or interact with the target analyte, enabling precise detection and quantification. The recognition elements can include enzymes, aptamers, antibodies, ionophores, and nanozymes, each selected based on the target analyte's nature and the desired specificity and sensitivity. The immobilization medium and preparation processes are carefully chosen to preserve the recognition element's functionality while ensuring its optimal exposure to the analyte. This design consideration allows for the direct and efficient capture of the target, facilitating accurate and reliable sensor responses.

Encasing the sensor is an outer protective layer comprising polymers such as polyvinyl chloride (PVC), polyurethane (PU), Nafion, poly-o-phenylenediamine (PPD), polyvinylpyrrolidone (PVP), and similar materials. These polymers are selected for their durability within biological media, biochemical resistance, and ability to offer robust protection against physical damage, chemical degradation, and environmental factors such as humidity and temperature fluctuations. The composition of the outer protective layer is optimized to regulate the diffusion of the target analyte. This protective layer serves to extend the sensor's operational lifespan and maintain its performance characteristics over time.

Each layer of the sensor structure offers opportunities for further optimization through the addition of various additives. These enhancements can include surfactants, additional polymers, nanoparticles, carbohydrates, and auxiliary elements, each contributing to the sensor's overall efficiency and effectiveness. The inclusion of surfactants can improve the interface between the layers and the target analytes, enhancing the sensor's sensitivity and selectivity. The integration of other polymers and nanoparticles can provide structural support and increase the surface area for interaction, respectively. Carbohydrates can be utilized for their biocompatibility and specific binding properties, while auxiliary elements may be added to enhance signal transduction or stability. Furthermore, the design of the sensor is adaptable, allowing for the incorporation of additional layers as required. These extra layers can be tailored to address specific challenges or to further enhance the sensor's properties, such as its responsiveness to particular analytes, its operational lifespan, or its resilience to environmental conditions. This modular approach ensures that the sensor can be finely tuned to meet the exact needs of its intended application, making it a highly versatile and customizable tool in the field of sensing technology.

Preparation of biosensors. oPD monomer solution (5 mM) was prepared in an acetate buffer (I=0.2 M, pH 5.2) and electrodeposited at 0.65 V (vs Ag/AgCl) for 15 min. The enzyme solutions GOx (20 mg ml-1), LOx (12 mg ml-1) and Aox (10 mg ml-1) were prepared in chitosan (1 wt % in 1% HOAc) in optimized volume ratios of 1:2, 1:10 and 1:1, respectively. A volume of 2 ml of each enzyme solution was used to modify the corresponding biosensor by covering the microneedle array, followed by crosslinking with 1 ml of PEGDE (1%). The electrodes were then modified by casting chitosan solution (1, 2 and 1 ml for glucose, lactate and alcohol biosensors, respectively). Finally, a 2% PVC solution prepared in THF solvent and containing 1 mM Triton X-100 was cast onto the microneedle (i ml for the glucose and lactate biosensors, and 1.5 ml for the alcohol biosensor) and chilled for 4 h at 4° C. for further experimentation.

Biosensing chemistry and in-vitro characterizations can be performed as follows. Lactate, alcohol and glucose biosensors were developed on the tip of the microneedles. The developed protocol relied on electrodepositing an innermost interference-rejecting polymer layer, poly-o-phenylenediamine (PPD), followed by immobilizing the respective oxidase enzyme intermingled in chitosan polyelectrolyte layer and finally, forming non-ionic surfactant-containing polyvinyl chloride (PVC) as the diffusion-limiting outer film. While the hydrophobic PVC component limits glucose diffusion to the electrode surface and allows facile oxygen transport, its surfactant imparts a degree of hydrophilicity that allows a tailored glucose flux and minimizes surface biofouling. Before in vivo testing on human participants, the in vitro analytical performance of each biosensor was investigated in an artificial solution that closely mimics the physiological ISF composition. The developed microneedle biosensors exhibited excellent capabilities in detecting the three target analytes within wide dynamic ranges. The dynamic ranges were obtained as 0-40 mM for glucose, 0-28 mM for lactate and 0-100 mM for alcohol, with limits of detection (calculated on the basis of signal/noise=3) of 0.32, 0.15 and 0.50 mM, respectively. Stability tests showed negligible losses in the enzyme functionality over 12 h of continuous operation, reflecting the robust enzyme immobilization and the protective characteristics of the outer PVC polymer membrane. While it is challenging to exactly simulate the dynamic in vivo medium under in vitro laboratory conditions (considering uncontrolled variations in the oxygen levels, temperature and so on), which can affect the sensor response during on-body monitoring performance, the on-body operation illustrates high accuracy under extended in vivo testing. Further optimization of the applied sensor chemistries and coatings is expected to extend the stability of the microneedle biosensors. In addition, the selectivity of the microneedle biosensors was tested using common electroactive interfering molecules (for example, ascorbic acid, uric acid, acetaminophen) within their normal physiologic or therapeutic ranges. Despite the relatively high operating potential (0.6 V), the obtained data illustrate excellent selectivity of the biosensors, reflecting the effective interference-rejecting performance of the applied multilayered sensing chemistry.

In some embodiments, the working electrode is functionalized using an electropolymerization of o-Phenylene diamine (OPD)/Glucose oxidase (GOx) mixture physically immobilizing the GOx within the PPD layer. The PPD layer is then covered with a precisely controlled thick films of Polyvinyl chloride (PVC) and polyurethane (PU) which act as antibiofouling layers.

Antibiofouling properties of the microneedles is of utmost importance when it comes to the continuous monitoring. Therefore, specific antibiofouling coatings of a unique combination of polymers such as Polyvinyl chloride (PVC), p-Phenylenediamine (PPD), Polyurethane (PU) and chitosan or zwitterionic polymers with excellent antibiofouling properties, and cross linkers such as Polyethylene glycidyl diether (PEGDE) and Glutaraldehyde (GA) are developed towards keeping the enzymes in a stable environment while keeping the sensitivity and detection range of the sensors within ideal. A unique sequence of immobilization techniques such as dip casting, electrochemical deposition and drop casting using uniquely fabricated immobilization cells are used to implement uniformly reproducible immobilization protocols for each sensor in a scalable fashion.

Figure 62:
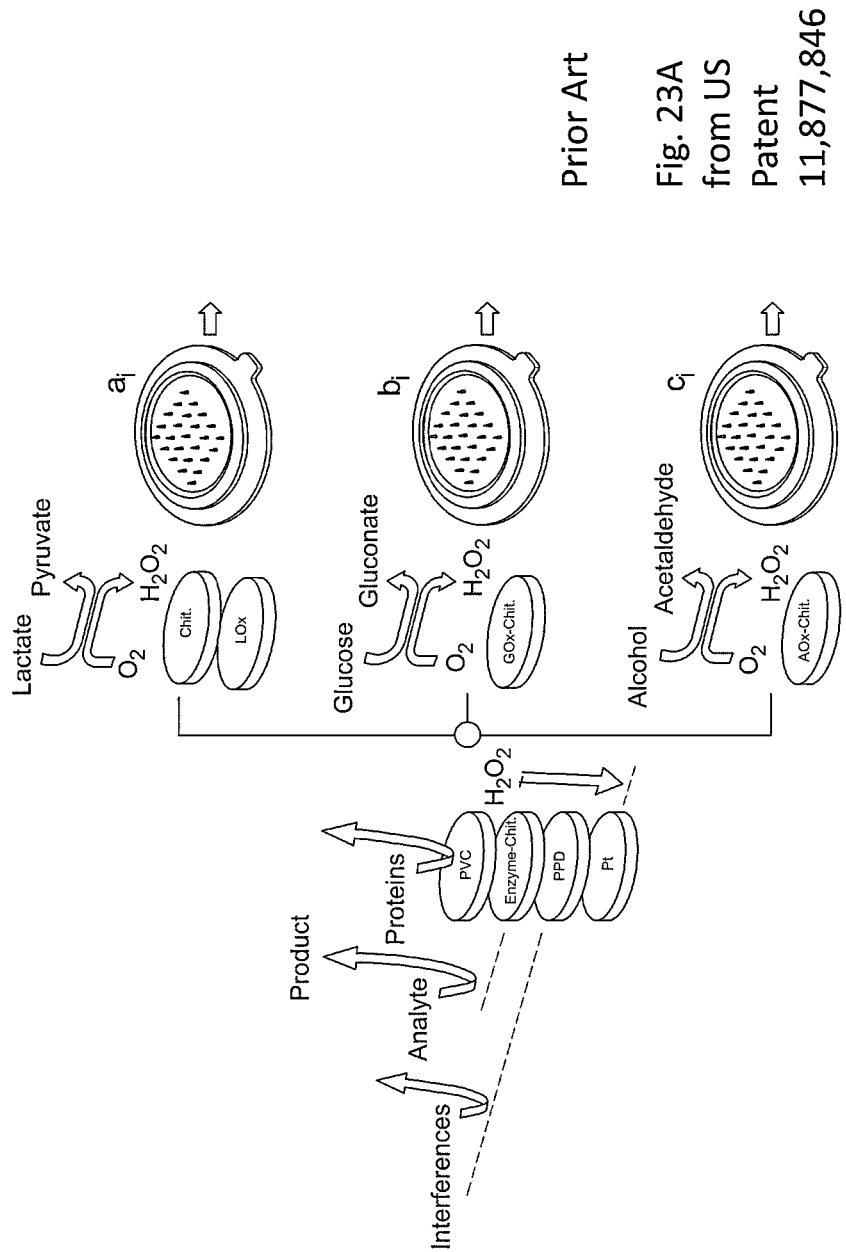
FIG. 62 (FIG. 23A of U.S. Pat. No. 11,877,846) is a schematic showing one embodiment of layers added on the electrically conductive layer of microneedles.

In example implementations diagrammed in FIG. 62 (FIG. 23A of the '846 patent), lactate, alcohol, and glucose biosensing contingents (e.g., different chemical layers) were developed on the tip of the microneedles. To create the biosensing contingents on the microneedles, the protocol utilized electrodepositing an innermost interference-rejecting polymer layer, poly-o-phenylenediamine (PPD), followed by immobilizing the respective oxidase enzyme intermingled in chitosan polyelectrolyte layer and finally, forming non-ionic surfactant-containing polyvinyl chloride (PVC) as the diffusion-limiting outer film. Enzyme loadings and the thickness of each polymer layer were carefully optimized to enable accurate continuous monitoring for each biomarker with excellent selectivity and stability while mitigating biofouling and 'oxygen-deficiency'.

Preparation of Example Biosensors. A o-PD (5 mM) solution was prepared in an acetate buffer (I=0.2 M, pH 5.2) and electrodeposited at 0.65 V (vs. Ag/AgCl) for 15 min. The enzyme solutions GOx (20 mg/mL), LOx (12 mg/mL), and AOx (10 mg/mL) were prepared in chitosan (1 wt % in 1% HOAc) in optimized volume ratios of 1:2, 1:10, and 1:1, respectively. For example, 2 mL of each enzyme solution was used to modify the corresponding biosensor by covering the microneedle array, followed by crosslinking with 1 mL of PEGDE (i %). The electrodes were then modified by casting chitosan solution (e.g., 1 mL, 2 mL, and 1 mL for glucose, lactate, and alcohol biosensors, respectively). Finally, a 2% PVC solution prepared in THF solvent and containing 1 mM Triton X-100 was cast onto the microneedle (e.g., 1 mL for the glucose and lactate biosensors, and 1.5 mL for the alcohol biosensor) and chilled for 4 h at 4° C. for further experimentation.

The example wearable, non-intrusive microneedle electrochemical sensor patch was configured to include one or more reagent sensing layers (on the microneedle microelectrode sensor) for single- or multi-analyte sensing, including but not limited to lactate/glucose, alcohol/glucose, lactate/glucose/alcohol, glucose/ketone bodies, lactate/ketone bodies, lactate/sodium, or any individual or combination of lactate, glucose, alcohol, ketone bodies (e.g., beta-hydroxybutyrate), or salt ions (e.g., sodium) for continuous single- or multi-analyte monitoring. In example implementations for glucose monitoring, the example wearable, non-intrusive microneedle electrochemical sensor patch was configured by electrodepositing poly-o-phenylene diamine (PPD) as the inner layer of the sensor, followed by drop casting an optimized composition of the mixture glucose oxidase (GOx)-Chitosan and glutaraldehyde crosslinker (and/or polyethylene glycol diglycidyl ether (PEGDE) crosslinker); and where a final step included coating the sensor with an outer polymer layer of polyvinyl chloride (PVC) containing an optimized amount of a non-inionic surfactant (e.g., Triton x-100). In example implementations for lactate monitoring, the example wearable, non-intrusive microneedle electrochemical sensor patch was configured by electrodepositing poly-o-phenylene diamine (PPD) as the inner layer of the sensor, followed by drop casting an optimized amount of the enzyme lactate oxidase (LOx) and a crosslinker (e.g., PEGDE or glutaraldehyde), which was followed by sequential drop-casting of Chitosan and PVC-surfactant polymer membranes. In example implementations for alcohol monitoring, the example wearable, non-intrusive microneedle electrochemical sensor patch was configured by electrodepositing PPD as the inner layer of the sensor, followed by drop casting an optimized composition of the mixture alcohol oxidase (AOx)-Chitosan, and where a final step included coating the sensor with an outer polymer layer of PVC containing Triton x-100 surfactant.

In example implementations for ketone monitoring, the example wearable, non-intrusive microneedle electrochemical sensor patch was configured by the following. A beta-hydroxybutyrate dehydrogenase (HBD) enzyme and a ferrocene derivative molecule are both covalently attached to a branched polyethyleneimine (PEI) on the surface of carbon coated microneedles, followed by glutaraldehyde crosslinking and coating by a biofouling resistant outer polymer layer, PVC including a specific concentration of a non-ionic surfactant, triton X-100.

In example implementations for hydration monitoring via target salt ions (e.g., sodium), the example wearable, non-intrusive microneedle electrochemical sensor patch was configured by the following. Sodium ionophore, ion exchanger, plasticizer and PVC polymer are mixed in tailored optimized ratios and dissolved in tetrahydrofuran solvent to form the sodium sensitive cocktail layer on the surface of carbon coated microneedles.

All dimensions and ranges herein are approximate. In some embodiments, the microneedles 6 of the array include a total height (from bottom base to tip) ranging from 400 μm to 4,000 μm. The example wearable device is configured to have solid microneedles designed in an array for modifications of reagent sensing layer(s) and with specific geometric ranges and configurations in a single patch. For example, solid microneedles can be structured to include 850 μm to 1,000 μm height and a width of 70-300 μm. The microneedles can be arranged in a single patch for dual and single sensing, with spacing between the sensing regions for the dual sensors can be adjusted to 7-20 mm towards minimizing the cross-talk between the sensors.

Data collected with the microneedles' tips is believed to have been approximately in the area near the border between the dermis and epidermis, but the depth of this border area can vary from person to person. Also, the microneedle tips can be placed shallower or deeper in some embodiments, so the location of the microneedle tips in the skin can vary significantly.

In some embodiments of the wearable biosensor device 1, for example, the conical microneedles 6 can be configured to have a height (from body base to tip apex) in a range of 800 μm to 4,000 μm (0.8 mm to 4 mm). In some embodiments, for example, the tip of the microneedles 6 can be configured to have: (i) tip height in a range of 100 μm to 200 μm, (ii) tip base diameter or thickness in a range of 50 μm to 450 μm, and (iii) tip angle (at apex to tip base) in a range of 40° to 85°. In some embodiments, for example, the body of the microneedles 6 can be configured to have a diameter or thickness (e.g., horizontal length or girth) in a range of 50 μm to 450 μm. In some embodiments, for example, the microneedles 6 can be configured to have an overall height-to-thickness aspect ratio in a range of 4:1 to 20:1.

In some embodiments, the microneedle 6 of at least some of the microneedles includes (i) a body region with one cylindrical exterior wall such that the microneedle body is of a cylindrical shape, and (ii) a tip region with one conical exterior wall such that the microneedle tip is of a conical shape.

There are a number of different embodiments of the microneedle in addition to the cylindrical microneedle depicted in FIGS. 63A and 63B, such as a prism with variable numbers of sides or an oval or squoval. Several embodiments of the off-center tip in which the needles are non-cylindrical are shown in FIGS. 63A-63B depict one embodiment of properties and aspects of a cylindrical microneedle design including structural features for skin insertion and for interlocking. FIG. 63A is a perspective view of the substrate 4 and the microneedles 6 integral with the substrate comprising an electrically nonconductive material selected from the group consisting of nonconductive polymer, composite, ceramic and the like. Some features of the substrate are omitted in this view, such as the channels which separate the microneedle regions and the microfluidic channels containing a custom resin which has been flowed and cured. FIG. 63A is an enlarged side view of one of the improved microneedles 6 from a base 17, through a body region 16 and to an asymmetrical tip region 60 comprising an off-center tip 57 and a section view of the substrate 4. The off-center tip can be positioned anywhere between the outer edge 54 of the microneedle and the center C (or c), shown in dotted line in FIG. 67, and the off-center tip is accompanied by at least one major surface 52 and at least one minor surface 53. The off-center tip 57 improves skin insertion by reducing the amount of force needed and by minimizing tissue damage and an immune response at the insertion site. Here, Ht is total height of the microneedle tip above the upper surface of the substrate, and Hoc is the height of the tip to the lowest point of a minor surface 53 of the tip region. L is the width of the off-center tip to the edge 54 on the side of the major surface, and Loc is the distance from the off center tip to the edge 57 joining the minor surface. Embodiments of the microneedle which are cylindrical comprise a single major surface and a single minor surface, while multiple major and minor surfaces are added in additional embodiments, especially where the body region is not cylindrical.

Figure 1:
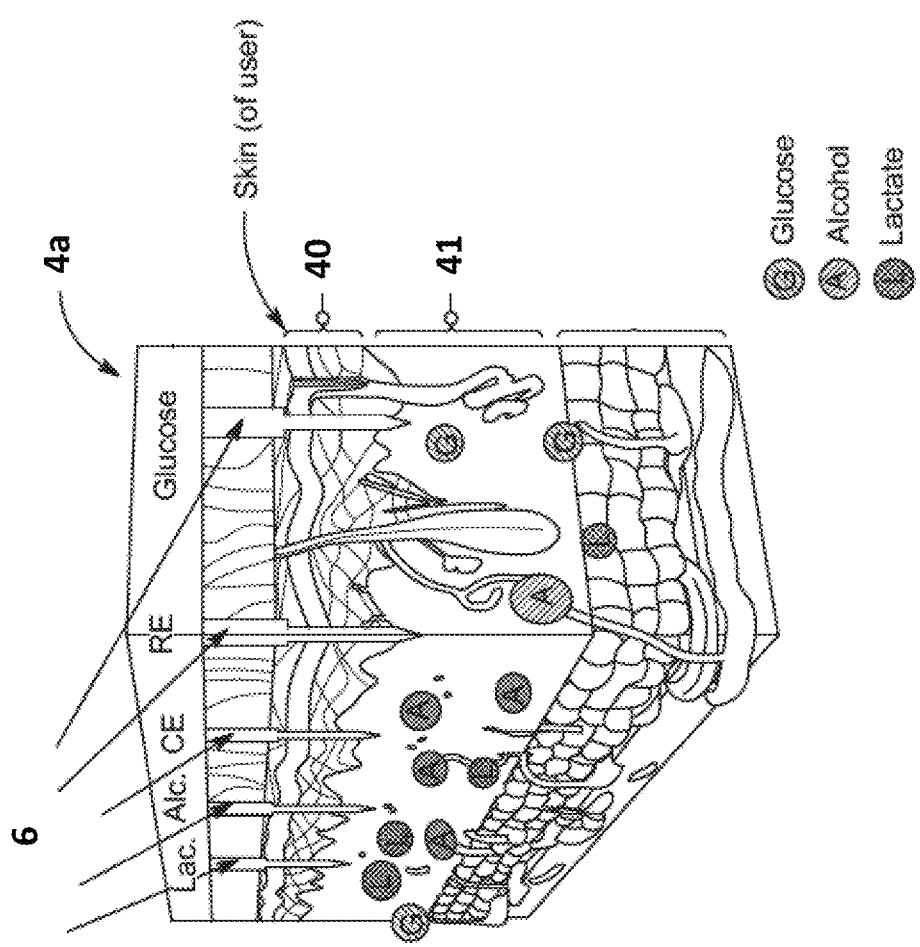
FIG. 1 is a schematic of microneedles inserted into skin.

FIGS. 64A-64C are respectively microneedles in the shape of triangular, pentagonal and hexagonal prisms. FIG. 64C-1 shows two cross-sections of a hexagonal bottom, and a circle top cross-section. The major and minor surfaces of the off-center tip may exist in a number of embodiments selected from the group consisting of curved, flat and/or textured surfaces. In some embodiments, the off-center tip comprises curves on the major and minor surfaces and in other embodiments the major and minor surfaces are flat or textured. In other embodiments the major and minor surfaces comprise a combination of curved, flat and/or textured surfaces. The shape of the curves can vary greatly. The textured surfaces are described elsewhere herein.

Insertion of the improved microneedles herein just below the dermis layer of the skin is the first step for using a device with a microneedle array, and the performance and life of the microneedle array can be affected by the insertion itself. Insertion subjects the microneedles to stresses which can damage them and the tissue region at the insertion site. To produce a better outcome, the present system comprises novel microneedle features not seen in the prior art.

In various embodiments the improved microneedle array improves skin insertion and locking into a stable position in living tissue. In one embodiment each microneedle comprises an electrically insulative material such as a nonconductive polymer configured to bend slightly during insertion as a result of novel features including an off-center tip, an indention near the base of the body of the microneedle and, in some embodiments, cavities in the microneedles. Also, in some embodiments sills extend outwardly from the body of the microneedle. As discussed in this application, the off-center tip and an indention together assist with bending upon insertion but then, after insertion, a return of the microneedle to an approximately perpendicular position relative to the substrate. The sills extending from the microneedle assist with locking the microneedle in place after insertion.

As discussed herein, the bending and locking provide many beneficial effects for performance of the microneedle over time. The benefits of the bending and locking occur in a chain: lower shear force is needed for insertion resulting in an easier cut of the skin, lower force required to rip the skin, less trauma to the skin, less bodily reaction, lower inflammatory response at the insertion area, lower biofouling at the tip, and less warm-up time resulting in longer, more stable operation of the microneedles.

Figure 66:
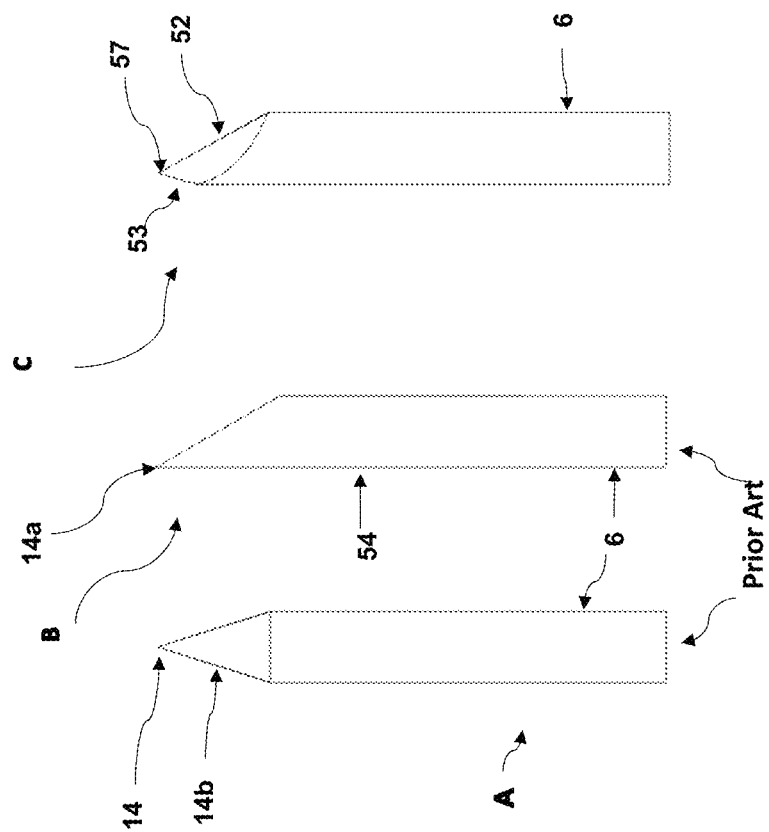
FIGS. 65-66 are perspective and 3D views of prior art cylindrical microneedles and one embodiment of a cylindrical microneedle herein with an off-center tip and major and minor surfaces.
Figure 65:
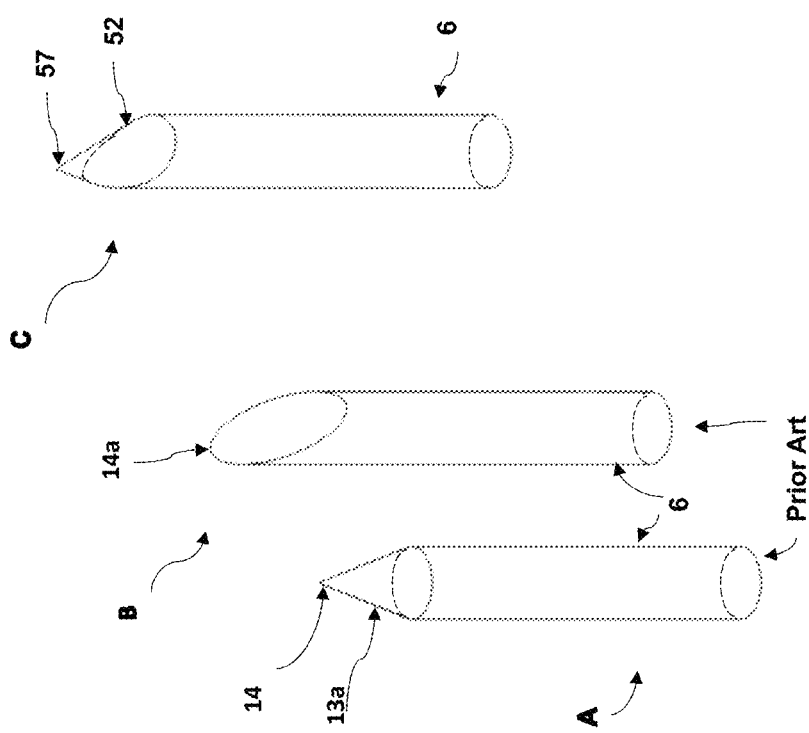

As also shown in FIGS. 65-66, the off-center tip is a significant improvement respectively over both a prior art conical tip 14 (items A and B in a perspective view in FIG. 65) having a conical slope 13a and a prior art single-bevel, non-conical tip 14a (items A and B in a side view in FIG. 66) (i.e., where 0≤loc<c and loc is the normal distance from the outer edge 54 to the axis crossing the off-center tip 57 and C is the center of the microneedle). In contrast, the prior art, single bevel tip is located at the outer edge 54 of the microneedle. As shown, the off-center tip provides an intrinsic deflection-ability to the microneedle body during the insertion and further reducing insertion forces as discussed herein. The indention is not shown here. In FIG. 67 a cross-section of microneedle labeled C in FIGS. 65-67, the dotted line 59 is the vertical axis passing through the off-center tip, and the dotted line 58 originating from C is the vertical axis of the center of the microneedle and r is the radius of the body region of the microneedle.

Figures 68A, 68B:
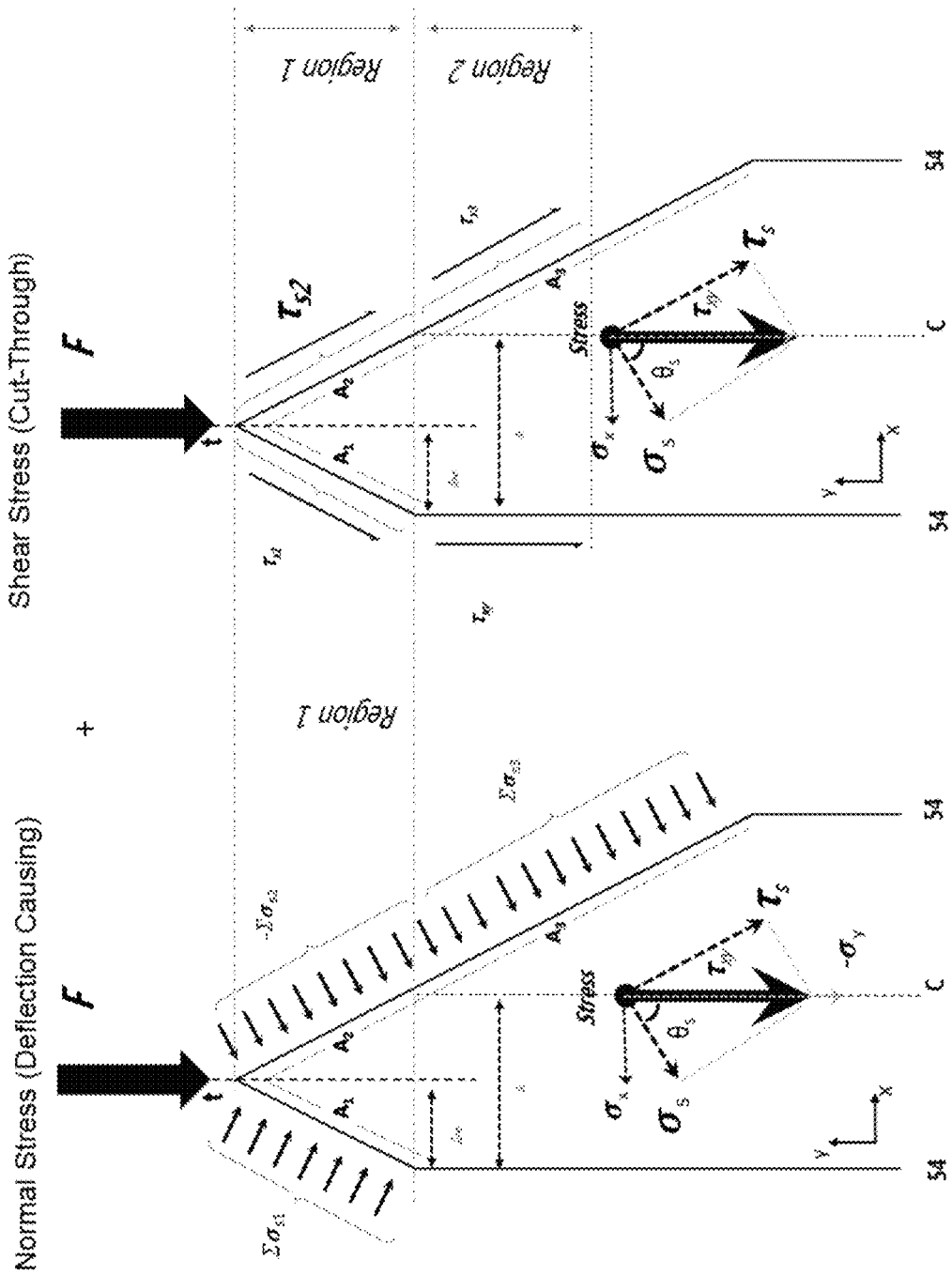
FIGS. 68A-68B show normal and shear stresses on regions one and two of an off-center tip during placement.

The movements enabling the off-center tip to reduce insertion force as well as the deflection mechanism is explained further in FIGS. 68A-C1-3. During the insertion of the off-center tip, a skin-insertion applied force of 'F' converts into two primary stresses of shear stress (τ) which is responsible for the microneedle cutting through the skin, and normal stress (σ) which is responsible for both the deflection of the microneedle body, and the penetration of the microneedles into the skin. With an off-center tip, there is a region one in which the major and minor surfaces pierce the skin in an approximately symmetrical fashion and, after the tip has pierced region one, region two with the longer surface, (i.e., the major surface) is now passing into the skin causing greater shear stress.

In FIGS. 68A-C1-3, and elsewhere herein, the following terms apply:

F/A=Stress
σ=Normal Stress=±Fn/A
τ=Shear Stress=±Fp/A
dlt=displacement of the tip
F=Force applied
A=Surface area
Fp=Force parallel to A
Fn=Force normal to A
Loc=normal distance from edge plane to axis crossing tip of microneedle
Lc=normal distance from edge plane to axis crossing center of microneedle cross section
σs=Normal to plane stress=F·cos(θs)/A
σx=Deflection causing stress=Ftorch/(A·Sin(θs))
τs=F·sin(θs)/A
τxy=cutting-through stress
cos(90°−θs)=τs/τxy
τxy=τs/sin/(θs)
cos θs=sin(90−θs)

FIG. 68A is an enlargement of the tip region comprising an off-center tip and upper body of the microneedle in 68A 69A showing normal stress/deflection causing forces in regions one and two of insertion. FIG. 68B is an enlargement of the tip region and the off-center tip and upper body of the microneedle in 68A showing shear stress/cut through forces in regions one and two. FIGS. 68C1-68C3 contains three diagrams showing the above movements in X and Y axes showing microneedle tips schematically from the side. The bottom rectangle in FIG. 68C3 represents the force from normal stress on region one. The top rectangle in FIG. 68C2 represents the direction of shear stress from region two's entry into the skin.

Normal Stress (σ) or Deflection-Causing/Penetration Stress: The applied insertion force of F at region one, as seen in FIGS. 68A and 68B, converts into equally opposing normal stresses (Σσsy) at the X axis and dual positive normal stresses on the Y axis (Σσsy). The equally opposing normal stresses, neutralize each other (i.e., |Σσs|=|Σσx1|−|Σσx2|=0) resulting in a net deflection stress at the X axis equal to zero (ΣxNET=0). Dual positive stresses result into a net penetration stress at the Y axis larger than zero (i.e., |Σσs|=|Σσy1|−|Σσy2|>0) which, causes the penetration of the microneedle into the skin. This means that at the first moments of microneedle insertion, with respect to the normal stress effect on the off-center tip 57, there is no deflection to the body of the microneedle and insertion takes place parallel to the Y (vertical) axis because the normal stress on areas A1 and A2 are equal and in opposite direction on the X axis. At region two, however, as a result of the geometry-based removal of normal stress on the left edge 54 of the microneedle, there is zero opposing deflection force to neutralize deflection forces on area A3. Thus, a net deflection force of σxNET=−Σ(σs3)·sin θs from the major surface will cause displacement of the microneedle tip/body in the x axis and in a negative direction ((|dlx|>0) to the left as shown, for example in FIG. 68B. Therefore, the off-center tip causes a dynamic deflection in region one of insertion versus region two. The magnitude of the deflection during the insertion stage is dependent upon the loc which ranges from 0≤loc<c, (i.e., dlx∝σxNET∝(lc/loc), 0<(lc/loc)<1), i.e., anywhere between the edge plane and the center of the microneedle.

Shear Stress (τ) or Cut-through-stress: In FIG. 68B the applied insertion force of F at region one also translates into equal shear stresses (i.e., τs1 and τs2) acting on the same −y axis direction, causing a positive stress that is responsible for cutting through the outermost layer of the epidermis (|Στxy|=|τs1+τs2|/|Sin θs|, >0). At region one, the magnitude of the shear stress is moderate and significantly increases throughout region two as, again, the off-center tip 57 is moved to the left as shown in FIG. 68B. During microneedle insertion, when the off-center tip 5a of the tip region 5 reaches region two, there is a pure shear force from the left, non-angled side of the microneedle (τxy) that adds to the shear force applied to the A3 (τs3/|Sin θs|) which are responsible for the significant increase of the shear stress at region two (i.e., Στxy|=|τxy+(τs3/|Sin θs|, therefore |τxyNET|>>0, therefore: |τxynet of Region 2|>>|τxynet of Region 1| This means that region two total shear stress is greater than for region one. The relationship between loc and the cut-through stress, as well as the loc to the applied force required is established to be τxyNET∝(lc/loc), and Fins-required a (lc/loc), respectively. This means that manipulation of the loc, within the boundary conditions of 0≤loc<c, allows optimizing of the practical requirements such as microneedle array insertion force and materials properties capable of producing a large enough safety factor.

Shear Stress (τ)/Cut-through-stress: In FIG. 68B the applied insertion force of F at region one also converts into equal shear stresses (i.e., τs1 and τs2) acting on the same −y axis direction, causing a positive force that is responsible for cutting through the outermost layer of the epidermis (|Στxy|=|τs1+τs2|/|Sin θs|, >0). At region one, the magnitude of the shear stress is moderate but significantly increases throughout region two as described mathematically and, again, the tip is moved to the left as shown in FIG. 68B. During microneedle insertion, when the off-center tip 57 of the asymmetric tip region 60 reaches region two, there is a pure shear force from the left, non-angled side of the microneedle (τxy) that adds to the shear force applied to the A3 (τs3/|Sin θs|) which are responsible for the significant increase of the shear stress at region two (i.e., Στxy|=|τxy+(τs3/|Sin θs|, therefore |τxyNET|>>0, therefore: |τxynet of Region 2|>>|τxynet of Region 1| This means that region two shear stresses are much greater than for region one. The relationship between loc and the cut-through stress, as well as the loc to the applied force required is established to be τxyNET∝(lc/loc), and Fins-required∝(lc/loc), respectively. This means that manipulating loc, within the boundary conditions of 0≤loc<c, allows optimizing of the practical requirements such as microneedle array insertion force and materials properties capable of producing a large enough safety factor.

Tip design affects the microneedle safety factor. The safety factor (SF) of a design or a material is defined as the ratio between the strength (ultimate strength or the yield strength) of the material and the maximum stress in the part. The SF indicates, in a specific area of the model, whether the stress is higher than the strength the material can bear. Yield strength of the material is the reference point for calculating the safety factor of the microneedles. This is because elastic deformation (i.e., non-permanent deformation) of the microneedles during the life of the device is important.

Safety Factor=(Yield Strength)/(Working or Design Stress)

or

Safety Factor=(Ultimate Strength)/(Working or Design Stress)

An aspect of the off-center tip that enables a higher SF purely based on the two-region geometry of the microneedles is partial transfer of the given insertion force applied (F) to be consumed for producing a deflection to the body of the microneedle starting from region two. This reduces the overall design stress on the body of the microneedle and therefore increases the SF purely based on the design (i.e., SF∝[1/(Design Stress)]).

FIGS. 69A-B illustrate an example of the safety factor distribution throughout the body of the microneedle at an applied insertion force of 1N/microneedle with PMMA-like materials, where N represents Newton. Aside from the design features, the SF of the microneedle can be greatly optimized based on the microneedle counts on an array, materials used, and design specifications (i.e., microneedle height, cross-sectional diameter, etc.) W1/W2 and the impact on the Safety Factor of the microneedle body. To clarify this phenomenon, the off-center tip in FIG. 69B is compared with the prior art centric conical microneedle in FIG. 69A. At the given insertion force F, due to the smaller cross-sectional area of W1 in FIG. B, where W is width of the microneedle, the stress on the model in FIG. 69B (F/Wb1) is more than the stress on the FIG. 69A region one (F/Wa1), and therefore the required skin insertion F will be lower in FIG. 69B (or the smaller force is needed to produce the same result for insertion). This requires less Force for the region two of the model in FIG. 69B and therefore produces a higher safety factor at the body of the microneedle in FIG. 69B. Therefore, for this model with 0≤W1/W2<1, the smaller the ratio of (1) (W1/W2) (at a constant W2) then the larger the safety factor. The off-center tip in FIG. 69B, more or less, acts as a needle with a smaller cross-sectional area (a smaller needle gauge inside of a larger needle gauge) along region one, while keeping the larger cross-sectional area at the body.

Figure 71E:
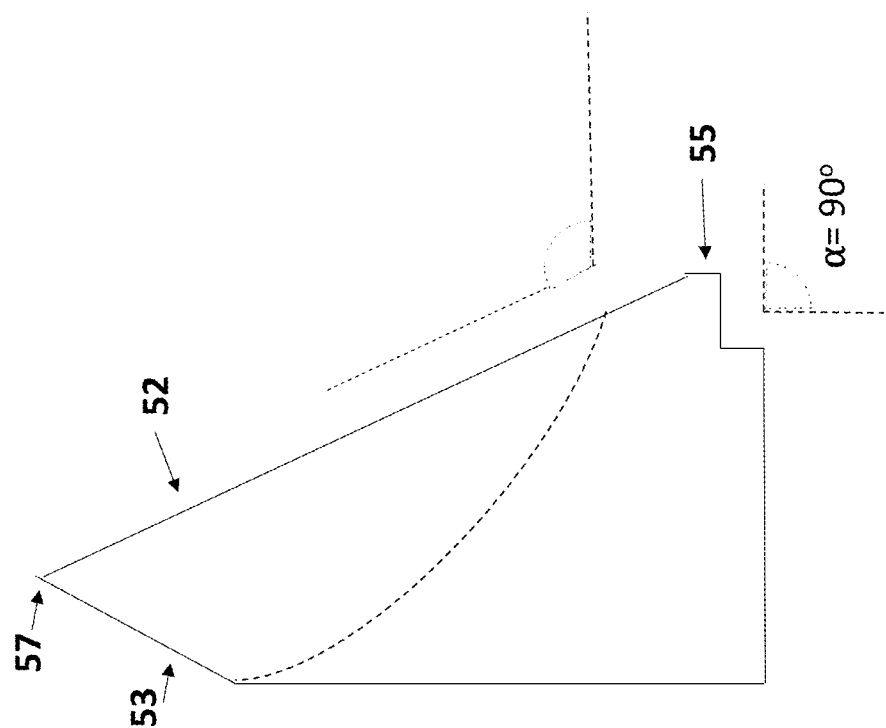
FIG. 71E is a closer view of an off-center tip and tip region with a top most sill as a continuation of the major surface.

The major and minor surfaces can be designed and fabricated to be a doubly curved surface. The doubly curved surface enhances the angular stress or overall shear stress at the microneedle/skin interface which is responsible for cutting through the skin, and therefore requires less insertion force and thus the user will notice it less. FIG. 70 is a drawing of the doubly curved surface and the major surface 52 and off-center tip 57, and Skin locking includes the novel tip geometry and locking mechanism described herein including the indentation and the locking sills. Sills extend outward from the edge 54 of the microneedle, and have a curved or slanted surface to aid with insertion; otherwise the sills may be shaped differently than those depicted herein. The off-center tip means the applied pressure during the skin insertion induces deflection at the microneedle body while being inserted into the skin. The deflection resulting from this geometry plays a role in a skin-locking mechanism distinct from aspects of the tip geometry and is described further herein. FIGS. 71A-D are four views of a cylindrical microneedle with the off-center tip, the indention and the sills described herein. FIG. 71A is a perspective 3D view, FIG. 71B is a side view, FIG. 71C is a back view and FIG. 71D is a front view. The skin locking mechanism also includes at least one sill (within a range of approximately 1-10) on the body of the microneedle as shown in FIGS. 71A-71D. In this embodiment the sills start from the intersection between the microneedle tip region two and the microneedle body on the side with the major axis. These sills enhance the skin/microneedle-body interlocking and therefore help to reduce the non-analyte signals such as, for example, the user's bodily movements. In the cross section in FIG. 71E, the major surface with a larger contact angle of $\gamma=135°$ promotes sliding of the skin surface during microneedle insertion and a locking angle of $\alpha=90°$ which promotes applied forces beyond the normal microneedle physical oscillations. A sill 55 here extends the slope of the major surface 52.

Figure 72B:
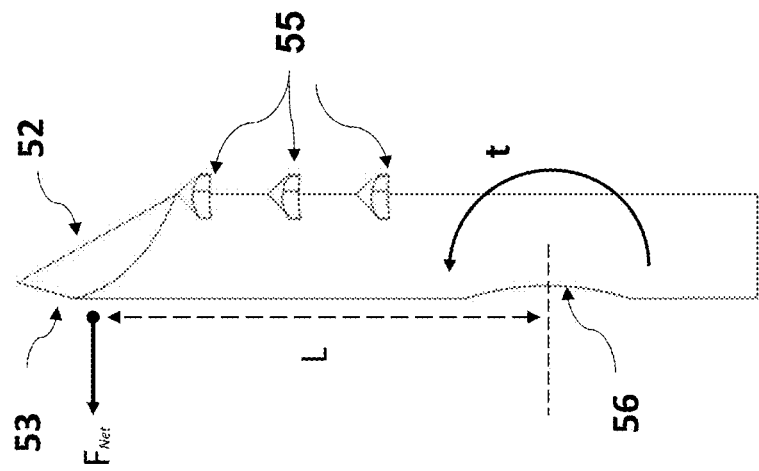
FIGS. 72A-72B show rotational forces of an embodiment of a microneedle herein as a result of bending at an indention near the base and/or lower body region of a microneedle.
Figure 72A:
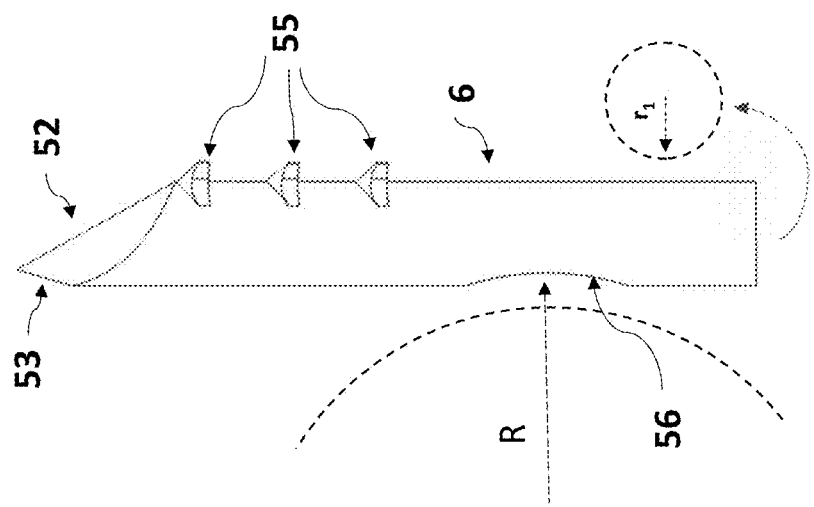

In some embodiments, in order to guide deflection during insertion, the body of the microneedle has an indention 10 (semi-circular in one embodiment) placed on the lower body of the microneedle 2, as shown in FIGS. 72A-B, to both guide the direction of the bending deformation during skin insertion and to regulate the magnitude of the microneedle body region deformation during microneedle insertion into the skin. The ratio of indention radius (R) to the radius of the microneedle bodily cross section (r1) has a direct relation with the dl of the tip (deflection magnitude). The higher the ratio, the larger the bending deformation will be during insertion and thus the more angled the skin insertion (i.e., more parallel to the skin surface). In FIGS. 72A-B, the placement of the indention 56 to guide deformation is closer to the microneedle base and creates a creates a Length (L). The magnitude of L is directly proportional to the Torque (t=FNet·L). Torque is the net force (FNet) multiplied by the Length (L), where the net force is the Normal force, generated across the microneedle body. Like R/r, the larger the L, the larger the t and the more angled the skin insertion (i.e., the more parallel is the insertion to the skin surface as compared to normal stress to the skin surface) at a constant FNet. The topmost sill in this embodiment is in the body region below the tip region.

Figure 73C:
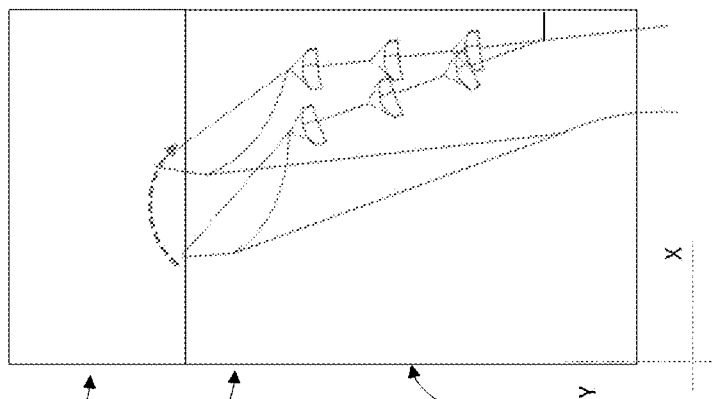
FIGS. 73A-73C show side views of a microneedle with an off-center tip, sills and indention showing respectively pre-insertion, during insertion and post-insertion.
Figure 73B:
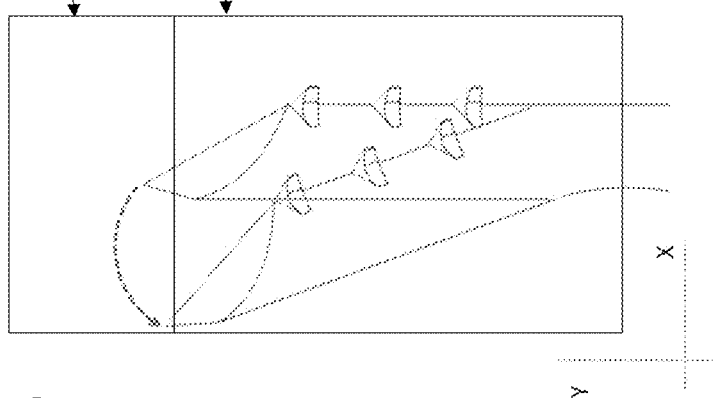
Figure 73A:
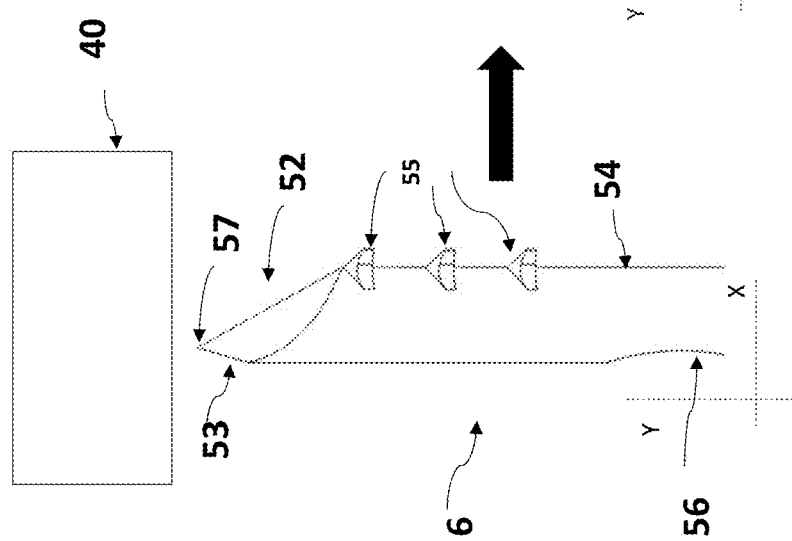

The dynamics and mechanism of the skin lock mechanism function can be shown in three different views. FIG. 73A is pre-insertion in a zero-force state. FIG. 73B shows the force-based deflection during insertion. As a result of the off-center tip as well as the indention, as shown in FIG. 73B, the net applied stress on the microneedle(s) during insertion causes a torque that causes deflection of the microneedle during insertion. The position of the microneedle, before deflection, is shown in in 73A and 73B, and 73B also shows the "leaning to the left" position during insertion and deflection, and the movement to the left in the dotted line arc. FIG. 73C, demonstrates the movement of the needle post-insertion from "leaning to the left," with a dotted line arc showing movement back to its passive force before insertion. After removal of the applied insertion force, and due to the intrinsic elasticity (i.e., spring-like quality) of the microneedle, there is a net retraction torque that not only springs back the microneedle (shown by the rotation direction in FIG. 73C) but also enhances microneedle-skin interface interaction/locking at the microneedle sills. After insertion and bending have occurred, the skin-locking of the sills 55 helps minimize movement within the tissue during the insertion life of the microneedle, and thus reduce electrochemical noise during sensor operation.

An indention 56 on or near the base 17 weakens one side of the microneedle on the side with the off-center tip to allow the microneedle to guide deflection of the microneedle to the side of the indention during skin insertion. In the embodiment of FIG. 73A-C three sills 55 are depicted starting just below where the major slope of the off-center tip intersects with the microneedle body, but any number of sills can be used. The topmost sill may also be a continuation of the major surface. In the embodiment of FIG. 73A-C, the sills are on the edge 54 of the microneedle opposite the off-center tip and the indention. These sills extend outward from the body of the microneedle with a downward slope to complement the slope of the off-center tip. The slope of the sills, in various embodiments, are on the upper portion of the sills nearest the tip but not on the lower portion nearest the base. Thus, the sills are relatively more easy to insert than to remove and in this way, the sills help to lock the microneedles into place after insertion. It should also be noted that, after the flexing during insertion as shown in FIGS. 73B and 73C, the microneedle will return to an approximately perpendicular position (as in FIG. 73A before insertion) and, as the sills move, they will position the microneedles more firmly into the tissue.

A spiral protrusion is disclosed in FIGS. 34A-34D of the '846 patent, and the numbers in this paragraph pertain to those figures. FIG. 34C is a diagram depicting an example embodiment of the microneedle in accordance with the embodiments of the microneedle 3411 shown in FIG. 34A, where the protrusion 3412 of the microneedle 3411 includes a terminus portion 3412X directed downward away from the apex 3411A to form an interlocking edge 3412E on the protrusion. In implementations of a microneedle sensor device comprising the example microneedle shown in FIG. 34C, the device is capable of reducing noise and thereby enhancing the detectable electrical signal associated with the target analyte in the biofluid to be detected. The example protrusion 3412 shown in FIG. 34C is a spiral protrusion, but it is understood that other embodiments of the protrusion 3412, including a vertical protrusion or a lateral protrusion can be configured to include the terminus portion 3412X directed downward away from the apex 3411A to form the interlocking edge 3412E on the protrusion 3412. For example, the structure of the interlocking edge 3412E with the terminus portion 3412X can support the microneedle 3411 while inserted in the skin, which consequently can reduce noise in the detected measurements. Also, for example, the structure of the interlocking edge 3412E with the terminus portion 3412X may facilitate a reduced or pain-free insertion, wearing, and/or removal process. Furthermore, for example embodiments of the microneedles that include the winding protrusion structures, a spiral body of the microneedle can be formed by using a two-flute micro-CNC microbit followed by an inverted T micro-bits to form the spiral structure of the spike body, e.g., at the abovementioned example machining parameters.

In various embodiments, the microneedles herein also have other improvements over the prior art. These improvements are micro-anomalies in the microneedles selected from the group consisting of knobs 61, regular-shaped cavities 62A and amorphous cavities 62B, and solid additives 63 selected from the group consisting of spheres, sheets and fibers. Anomalies are produced as well by liquid additives to material before it is molded or printed or made solid by other methods.

As shown in one embodiment in FIG. 74, knobs 61 on the microneedle body at the optimal area surface density and shape can vary the mechanical properties of the microneedles. In one embodiment they can reduce the microneedle/skin insertion forces by reducing the microneedle body/skin friction and enhancing the sliding of the microneedle through the skin. Knobs 61 can be created in several ways including: 1) adding solid particles into the liquid material before molding or printing, 2) spraying solid particles onto the microneedles before they are fully cured allows the particles to create a bond with the microneedle after curing, and 3) applying an adhesive to the microneedles and then spraying solid particles onto the microneedles. All of these methods produce a random pattern of knobs.

Figure 76:
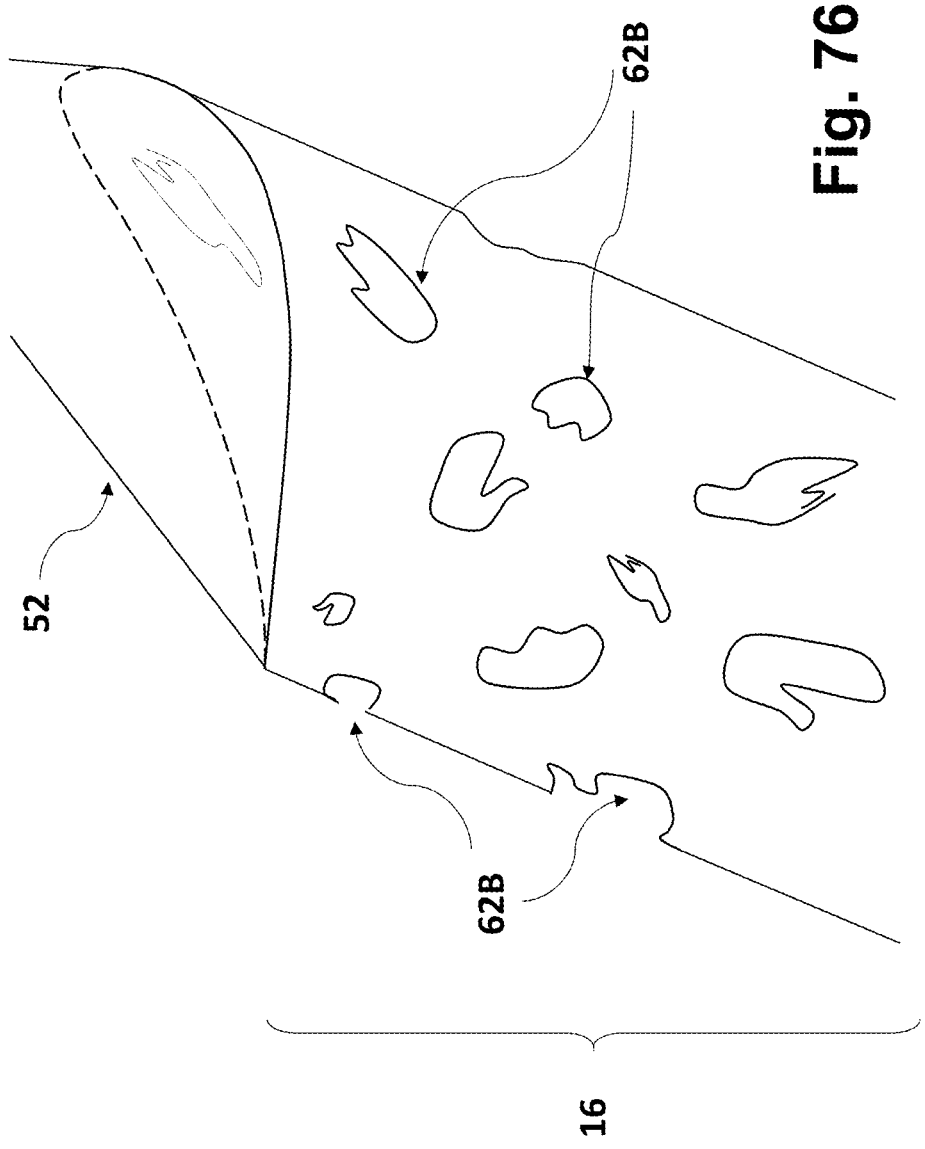
FIG. 76 is similar to FIGS. 74-75 but instead shows amorphous cavities on the surface of the upper body region and the tip region.

FIG. 75 is one embodiment of a portion of a microneedle body with regular-shaped cavities 62A at the surface of the microneedle. Cavities can either be a regular-shaped 62A as in FIG. 75 or amorphous 62B as in FIG. 76, a partial microneedle body illustrated with amorphous cavities. Cavities 62A, 62B allow for more anchoring surface for the subsequent sensing (for sensing applications) and/or drug loading (for drug delivery application) layers immobilized on the surface of the microneedle tip region and body. A greater volume of regular-shaped or amorphous cavities can increase anchoring and loading of the desired materials, reagents, drugs and more. Cavities can also increase the flexibility of a microneedle, especially near the indention 56. The cavities can be superficial or extend to the core of the microneedle. The depth/extent and shape of regular-shaped and amorphous cavities throughout the microneedle can be engineered by nano-surface engineering of the sacrificial component to the structure of the microneedle.

In some embodiments, regular-shaped cavities 62A are created by adding solid additives to the liquid polymer, for example, polystyrene spheres, or reactive metals or metal oxides such as magnesium microparticles or aluminum oxide microparticles. These spheres as they contact the edge of the microneedles after molding can be removed by exposure to a chemical such as an acid or alcohol, leaving an opening with the shape of the sphere. All of the cavities disclosed herein are randomly distributed, unlike pores described in the '846 patent created by a CNC process. In various embodiments such as FIG. 76, amorphous cavities 62B are created by adding liquids or irregularly shaped material into the liquid polymer prior to molding, and after molding and curing then submerging the microneedles into chemicals (e.g., acetone or acid) etches away the additive and leaves an amorphous cavity, and these cavities are randomly distributed.

Another method of producing the cavities comprises the following steps: adding one or more types of additives (e.g., polymer, ceramic, metal, metal-oxide, sugars, and/or sacrificial material whether amorphous or crystalline, 0.1-10 micron in diameter) in suspensions/colloids to a biomedical-grade non-cured polymeric medium, mixing, sometimes aging for a certain time, pouring the mixture into a substrate/microneedle mold, followed by de-bubbling, curing (e.g., photo-crosslinking, heating, etc.) of the liquid, removal from the mold, and exposing the microneedle to a suitable solvent for a specific time to remove or desirably impact the additive to achieve the desired property. The cavity sizes and densities on the surface and/or in the microneedle body are adjusted by methods including without limitation the methods described herein.

Another method of forming cavities on the surface of the microneedle is plasma bombardment during which a plastic material such as PMMA is exposed to a high-energy plasma field. This plasma containing components selected from the group consisting of ions, electrons, and reactive species, and the plasma interacts with the PMMA surface, etching away material and creating a textured landscape of cavities at the nanometer to micrometer scale. The specific characteristics of these amorphous cavities—such as their size, shape, and distribution—are governed by the parameters of the plasma treatment, which include the type of gas used (e.g., oxygen, nitrogen, or argon), the plasma power, exposure time, and the presence of any additional reactive agents. The energetic particles in the plasma effectively break the molecular bonds in the surface layers of the PMMA, removing material and leaving behind a structure with cavities which enhance the surface properties, such as increased hydrophilicity, biocompatibility, or permeability, and expanding the material's sensing characteristics such as better anchoring/adhesion and loading of the chemical element.

Figure 77:
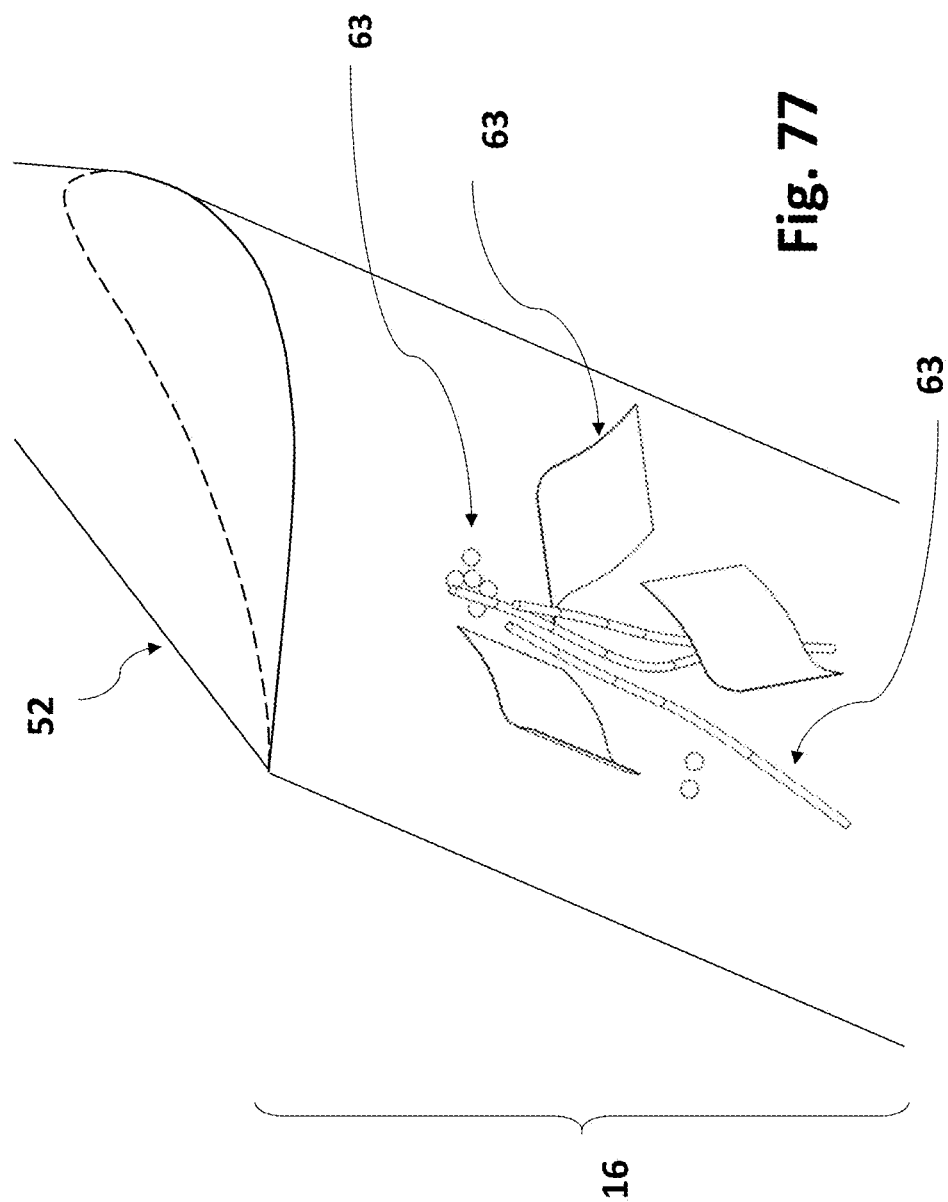
FIG. 77 is similar to FIGS. 74-76 but instead shows solid additives on the surface or in the upper body region.

Additives in the manufacturing process are retained within the body region and/or on the surface of the microneedle to add properties and capabilities inside or on the surface of the microneedle in order to optimize the performance for sensing or drug delivery. Electrical properties of the microneedles can be tuned as desired. For instance, the conductivity of the microneedle body can be manipulated by introduction of additives such as solid particles 16c such as polymers, fibers, sheets and/or conductive or non-conductive liquid materials can produce highly conductive, semi-conductive, or non-conductive microneedle electrodes, in one embodiment as shown in FIG. 14 with spheres, sheets and fibers. Additives are selected from the group consisting of conductive polymers selected from the group consisting of PEDOT:PSS (poly(3, 4-ethylenedioxythiophene) polystyrene sulfonate) and non-conductive elastic polymers selected from the group consisting of PDMS (Polydimethylsiloxane). FIG. 77 is a partial microneedle body illustrated with solid additives 63 selected from the groups consisting of spheres, sheets and fibers.

Engineering of the electrochemical properties of the microneedle by changing the surface morphology includes increasing surface area on the individual microneedles with micro-anomalies such as cavities. This benefits electrochemical sensing performance by: (A) enhancing the electrochemical sensitivity by increasing the surface of the microneedles with the surface of the cavities exposed to the surface which allow higher loading of the recognition element or drug to be delivered at a given microneedle; (B) improving immobilization of the sensing or drug delivery layers by increasing anchorable surface area with the added surface of the cavities; (C) increasing the stability and wear-time of the microneedle from both of the "A" and "B" phenomena occurring subsequently.

Cavities in the microneedle can enhance the stability of the electrochemical response of the microneedle through the following. First, surface cavities on the working electrode microneedle can hold and retain different layers of the sensing chemistry. Encapsulation of the biorecognition layer inside these cavities increases the anchoring and surface adhesion of the sensing or drug layers and protects the layer against mechanical delamination when inserted into the body. Additionally, the enhanced surface adhesion diminishes the leaching of the layer. Next, for the reference electrode microneedle, the cavity structure also diminishes the leaching of the solid electrolyte (a hydrogel polymer containing a saturated concentration of a salt such as sodium chloride) and therefore diminishes the potential drift of the reference electrode over time and enhances the stability. Additionally, in the case of drug delivery applications, cavities enhance the drug loading at the surface of the individual microneedles which in turn enhances the effective drug releasing wear time on a given microneedle.

Engineering of the mechanical properties of the microneedles can be engineered by additives which, in differing embodiments, include at least one type of different particles, precipitates, and inclusions. The resin/additive mixture creates a composite like material with highly tunable mechanical properties towards desired wearing applications.

Like the other properties, the chemical properties of the microneedle can be greatly impacted by introduction of micro-anomalies to the microneedle resin before curing. An example is the tailoring of the catalytic activities of the microneedle electrode to the desirable sensing application with materials selected from the group of carbon based materials such as graphene, carbon nano tubes (CNT) and ultrafine amorphous graphite for carbon based catalytic sensing applications; organo-metallic complexes such as Prussian blue; metal oxides such as iron oxide and iridium oxide; and metal nano particles selected from the group consisting of platinum, gold and iridium.

As shown in FIG. 34 of the '846 patent, moreover, for example, pore structures can be created by the tip of the V groove CNC micro-bit on the surface of the cone feature using the above example machining parameters. In some embodiments, the microneedle 3411 can include a plurality of pores 3411TP (e.g., microscale-sized pores, "micropores", which can be in a range of 0.5 µm to 20 µm, or in a range of 0.5 µm to 10 µm) distributed on the tip region 3411. In some implementations, the pores 3411 are configured to attach one or more chemical compounds to provide the functional layer 116 configured to interact with a target analyte in the biofluid. For example, the pores 3411 can attach the one or more chemical compounds (e.g., reagents) to facilitate an electrochemical reaction involving the target analyte in the biofluid exposed to the microneedle 3411 to cause production of an electrical signal detectable at an electrode portion of the microneedle 3411 (e.g., the sensor electrode portion including an electrically conductive material at the tip region 3411T or the tip region 3411T and the upper segment 3411BU of the body region 3411B).

In some embodiments the present invention includes aspects for extended-life of the microneedles. The extended-life results from a combination of microneedle design and advanced sequential activation techniques, which extend the life of the microneedles to maintain accurate and reliable readings over a period (greater than without these aspects) by gradual exposure of the sensing microneedle electrodes to the biofluid over time. Microneedles exposed directly to the biofluid will begin their life, and microneedles not exposed immediately will delay the beginning of their active life, and thus be active longer than those exposed upon implantation. The extended-life is achieved by one of the following features, or by a combination of two or more of these features.

The first extended-life feature is sequential release by biodegradable protective/passivation coating ("enteric coating") on top of the chemical layers of the microneedles configured as working electrodes. The enteric coating protects the chemical layer (or layers) of the microneedles from degradation or damage during insertion and during the sensing period. The enteric coating degrades in a controlled manner, breaking down into small, non-toxic particles that can be safely absorbed by the body. This enteric coating improves the accuracy of the wearable biosensor over time and reduces the risk of adverse reactions, in that the effective life of working electrodes may be staggered by the depth and make up of the enteric coating. The sensing over time after the enteric coating is removed from one or more of the working electrodes occurs as a result of the staggered exposure of the electrodes to the environment. Once the protection provided by the enteric coating is removed, the chemical layers are exposed to the electrical signals in the tissue, allowing them to be sensed and monitored. The working electrodes in the microneedle sensor are made from conductive materials, such as metals or conductive polymers that are capable of detecting and transmitting electrical signals. When the working electrodes are exposed to the electrical signals from chemical layer reactions with the biofluid, they will generate a corresponding electrical signal that can be transmitted wirelessly to an external device.

Enteric coatings herein are biocompatible and able to withstand the harsh environment of the such as gastrointestinal tract, and are selected from the group consisting of cellulose acetate phthalate (CAP), hydroxypropyl methylcellulose phthalate (HPMCP), polyvinyl acetate phthalate (PVAP), methacrylic acid copolymer (Eudragit®), and sodium alginate. The degradation time of an enteric coating is controlled by adjusting the properties of the coating material, such as its composition and thickness. The thickness of the enteric coating is adjusted to control the degradation time. A thicker coating will provide more protection and take longer to degrade, while a thinner coating will degrade more quickly. The composition of the coating material is adjusted to control the degradation time. For example, a biodegradable polymer slows the degradation time, while a water-soluble material can accelerate the degradation time. For example, pH-sensitive coatings are designed to dissolve at a specific pH such as that of the small intestine. The degradation time of a pH-sensitive coating can be controlled by adjusting the pH at which the coating dissolves. Release-controlling agents, in some embodiments, are added to the enteric coating to control the degradation time. The specific release-controlling agents used and the amount added depend on the intended use and the desired outcome. Swelling agents, such as gums and hydrocolloids, are added to the enteric coating to control the rate of swelling and the release of the active ingredient. Swelling agents can be used to slow down the rate of degradation and extend the sensing period. Disintegrants, such as starch and cross-linked polyvinylpyrrolidone, are added to the enteric coating to control the rate of degradation and the release of the active ingredient. Disintegrants can be used to accelerate the rate of degradation and shorten the sensing period. In some embodiments, pH-sensitive materials, such as polymers and copolymers, are added to the enteric coating to control the rate of degradation based on the pH of the environment. pH-sensitive materials extend the sensing period in an acidic environment and accelerate the degradation time in an alkaline environment. Enzymes, such as proteases and lipases, may be added to the enteric coating in some embodiments to control the rate of degradation based on the presence of specific substances in the environment. Enzymes are used to extend the sensing period in the absence of the specific substances and accelerate the degradation time in their presence.

In other embodiments, additional agents can be added to the enteric layer. Anti-fouling agents can also be added to the enteric coating to prevent the buildup of biological material, such as proteins and cells, on the surface of the electrodes. This can improve the accuracy and reliability of the sensors over time and reduce the risk of infection. Antimicrobial agents, such as antibiotics and antifungals, can also be added to the enteric coating to prevent the growth of bacteria and other microorganisms on the surface of the electrodes. This improves patient safety and reduces the risk of adverse reactions. Peptides, such as cationic peptides and antimicrobial peptides, can be added to the enteric coating to prevent the buildup of biological material on the surface of the electrodes. Peptides can also have antimicrobial activity, reducing the risk of infection. Polymers, such as polyethylene glycol and polyvinyl alcohol, can be added to the enteric coating to prevent the buildup of biological material on the surface of the electrodes. Polymers can also have antimicrobial activity, reducing the risk of infection. Nanoparticles, such as silver and zinc oxide nanoparticles, can also added to the enteric coating to prevent the buildup of biological material on the surface of the electrodes. Nanoparticles can also have antimicrobial activity, reducing the risk of infection.

In various embodiments, the invention uses several electrochemical techniques to extend the life of the device by reducing biofouling of implanted working electrodes. Anodic protection includes application of a small electrical current to the working electrodes to slow the rate of corrosion and biofouling. The current creates a protective layer on the surface of the electrodes to prevent the buildup of biological material. Various kinds of electrodes with current ranges will suffice: platinum electrodes in the range of 100-1000 $\mu A/mm^2$; gold electrodes in the range of 50-500 $\mu A/mm^2$; titanium electrodes in the range of 100-1000 $\mu A/mm^2$; stainless steel electrodes in the range of 50-500 $\mu A/mm^2$. All of these refer to the kind of electrically conductive layer; that is, they are not solid metal electrodes.

Electrochemical cleaning involves using a small electrical current to remove biofouling from the surface of the electrodes. The current breaks down the bonds between the biofouling material and the surface of the electrically conductive layer on the electrodes, allowing the biofouling material to be removed. In alternating current (AC) cleaning, the frequency of the AC current can range from 10 Hz to 1 MHz, and the magnitude of the current can range from 10-100 $\mu A/mm^2$. In pulsed direct current (PDC) cleaning: The duration of the pulses can range from microseconds to milliseconds, and the magnitude of the current can range from 10-100 $\mu A/mm^2$.

In various embodiments the microneedle array of the present invention is warmup-free for rapid and accurate detection of biomolecules, making it suitable for time-sensitive applications, such as sepsis diagnosis and management, where monitoring lactate, pH, and other biomarkers quickly is crucial.

The warmup free aspect achieves its rapid response by addressing the factors that typically necessitate a warmup period in these sensors, such as stabilization, calibration, and hydration. This may be accomplished in various embodiments through pre-hydration. The sensor is pre-hydrated within a hydration chamber before application to the skin, allowing for faster equilibration with the biofluid and eliminating the need for a warmup period. Pre-hydration methods include immersion of the sensor in a hydration solution, such as phosphate-buffered saline (PBS), for a specified period before insertion.

Figure 78:
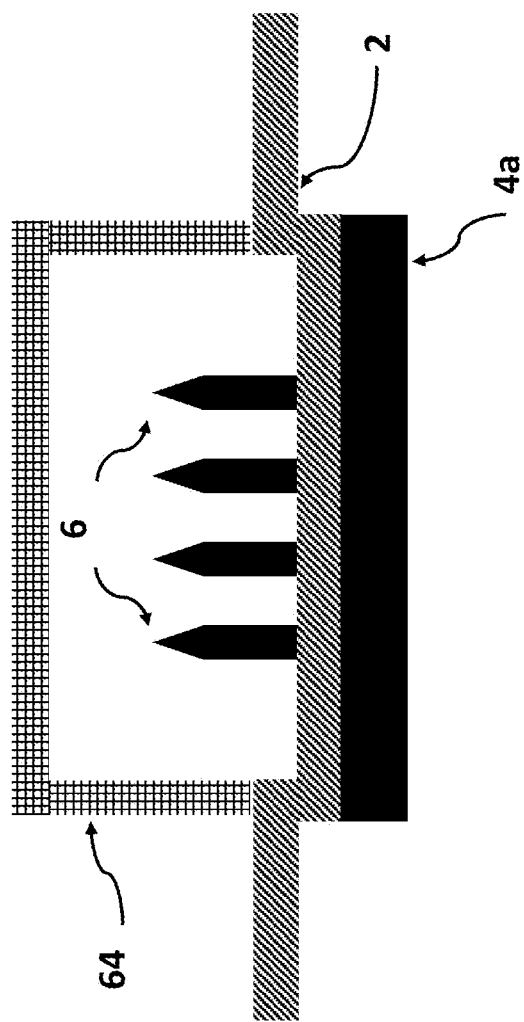
FIG. 78 is a schematic side view of a hydration chamber for the microneedles.

Another example is exposure of the sensor to a controlled humidity environment, ensuring that the polymer coating absorbs the necessary moisture before use. In this pre-hydration method, the sensor is exposed is surrounded by a hydration chamber 64 enclosing a controlled humidity environment to allow the polymer coating on the microneedles to absorb the necessary moisture before use. One embodiment of this hydration chamber is found in FIG. 78. The hydration chamber is designed to maintain a specific humidity level, typically within the range of 40-90% relative humidity, depending on the desired moisture content and the specific polymer used for the coating. The hydration chamber can be equipped with a humidity sensor, such as a capacitive or resistive sensor, which continuously monitors the internal humidity levels. A microcontroller or a feedback control system is integrated into the hydration chamber to actively regulate the humidity levels by introducing moisture or drying the air as required. This can be achieved by incorporating a humidification system, like an ultrasonic or evaporative humidifier, and a dehumidification system, such as a desiccant-based or thermoelectric dehumidifier, within the hydration chamber. The duration of exposure to the controlled humidity environment is determined based on the specific polymer coating, its water absorption capacity, and the desired moisture content for optimal sensor performance. The exposure duration can range from a few minutes to several hours, depending on these factors. During the pre-hydration process, the sensor is placed inside the hydration chamber, allowing the polymer coating on the microneedles to absorb moisture from the surrounding air. The hydrated polymer coating facilitates faster equilibration with the interstitial fluid upon application to the skin, eliminating the need for a warmup period. To ensure consistent and reliable sensor performance, the hydration chamber must be well-sealed to prevent any potential contamination from external sources. Moreover, the hydration chamber should be regularly monitored and maintained to ensure that the humidity levels remain within the desired range and that the pre-hydration process is effective.

Another warm-up free embodiment incorporates a hydrogel layer on the sensor surface, which retains moisture and enables rapid equilibration upon insertion. Encapsulation of the microneedle in a hydrogel matrix, such as polyvinyl alcohol (PVA) or agarose, which retains moisture and ensures constant hydration of the microneedles. To ensure pre-hydration, the microneedle array can be encapsulated in a hydrogel matrix made from biocompatible materials like polyvinyl alcohol (PVA) or agarose. These hydrogels have excellent water retention capacity, biocompatibility, and mechanical properties. The hydrogel encapsulation process involves embedding the microneedle array within the hydrogel material. This can be achieved through various techniques, such as in situ polymerization, UV crosslinking, or solvent casting. The hydrogel matrix will maintain the hydration of the microneedles, allowing for immediate use upon application to the skin. Moreover, the hydrogel encapsulation can also provide a protective barrier against external contaminants and reduce the risk of infection during use.

Another example embodiment is incorporation within the biosensor device of a hydrating chamber that contains a hydrating solution (e.g., PBS) and continuously delivers it to the microneedle array during use. A hydrating chamber can be integrated within the wearable biosensor to maintain the hydration of the microneedles. The hydrating chamber contains a hydrating solution, such as phosphate-buffered saline (PBS), which is continuously delivered to the microneedle array through microchannels. The hydrating chamber can be fabricated using soft lithography techniques or 3D printing technology. To control the flow of the hydrating solution, a micro-pump, such as a piezoelectric or peristaltic pump, can be integrated into the system. This pump can be connected to a power source, such as a small battery or an energy harvesting module, allowing for continuous hydration of the microneedle array and eliminating the need for a warmup period.

Another warm-up free embodiment incorporates a gas microchamber that maintains a controlled humidity around the microneedles, ensuring constant humidity/hydration while minimizing the risk of contamination. In one embodiment the gas microchamber comprises a semi-permeable membrane that allows water vapor to enter while keeping contaminants out. The membrane can be made of materials such as polydimethylsiloxane (PDMS), which is known for its excellent gas permeability and biocompatibility. The humidity inside the gas microchamber can be regulated using a miniaturized humidity sensor and an active control system, such as a microcontroller, which adjusts the humidity level by releasing or absorbing water vapor as needed. This system ensures constant hydration of the microneedles, promoting faster equilibration with the interstitial fluid and eliminating the need for a warmup period, while simultaneously minimizing the risk of contamination from external sources.

Microneedle design can also contribute to warm-up free sensing. Smaller or differently shaped microneedles can reduce the impact of tissue trauma or inflammation upon insertion, minimizing the need for a warmup period. Examples of microneedle designs include tapered microneedles with high aspect ratios, which penetrate more easily and reduce tissue damage. Tapered microneedles with high aspect ratios refer to those with a slender and elongated conical shape, allowing for easier penetration into the skin with minimal tissue damage. This design reduces the force required for insertion and distributes the stress along the needle's length, minimizing tissue trauma and inflammation. A high aspect ratio (needle height to base width) is essential for improved mechanical stability and penetration depth. For example, an aspect ratio of at least 1 implies that the needle height is equal to or greater than its base width. Materials such as silicon, stainless steel, or biodegradable polymers like polylactic acid (PLA) and polyglycolic acid (PGA) can be used to fabricate these tapered microneedles. Manufacturing methods include microfabrication techniques like photolithography, deep reactive-ion etching (DRIE), or laser ablation.

Prior art devices employ a long needle applicator to affix a continuous glucose monitor to the user's arm, which can lead to local tissue damage and inflammation. This inflammation, in turn, contributes to the warmup time, as the sensor needs to stabilize and adapt to the physiological changes induced by the application process.

The present invention offers an alternative method of application that minimizes trauma and inflammation at the site of attachment. The biowearable device is applicator-free and instead, it can be applied by a mild finger pressure up to 15 s, monitored and confirmed by an embedded pressure sensor. By eliminating the applicator, trauma and inflammation are reduced at the application site. By reducing the initial tissue disturbance, the sensor can more rapidly achieve a stable and accurate reading. This approach not only enhances user comfort but also plays a vital role in eliminating the warmup time typically associated with prior art devices.

Emergent Properties of the Device

As described in the '846 patent the basic cover 15, and the other cover embodiments herein, provide a) electrical isolation to the metalized surface of the microneedle array base, b) sealing and insulation against moisture (i.e., fluids and or gas vapors such as liquid or vaporized sweat, water) created by filling of the microneedle cover vacant micro-interface by a curable resin, and c) mechanical strength to the base of each individual microneedle.

The disposable module 18*a* disclosed herein is skin-conforming and in various embodiments can have four distinct mechanisms and characteristics which enable flexibility and conformability to skin:

Conformal skin-facing materials. The skin adhesive layer 3 of the disposable module is made from a flexible material with the proper (approximately 0.05-1 mm) thickness to allow for conformability. The surface area which makes contact with the skin is maximized in proportion to rigid material, resulting in a high flexible-to-rigid ratio for surface area, FIG. 2.

Degree of free motion. This is assisted by the elastic insulative base contact to the rigid electronics body. An elastic non-conductive rubber insulative base 24 forms the contact between the reusable electronic module 18a and the rigid base 23. By mechanically connecting the two pieces with an elastic material, the mechanical coupling between the two modules is designed to be loose.

Maneuvering gap. The maneuvering gap 28 mechanically decouples the rigid base 23 from the flexible piece. There is a small air gap between the bottom of the conformable skin adhesive and the top of the reusable electronic housing, which is created by the height of the rigid base and its clips. This space allows the rigid lower housing 11 to tilt without making contact with the skin. This is done to mitigate the likelihood of mechanical coupling between the rigid lower enclosure and the skin. This aspect forms a "floating piece" design.

Counterbalance/cantilever microneedle array arms. The microneedle array 4 in some embodiments has cantilevered arms 4b which protrude outwards from the center of the array. An embodiment with three arms is depicted in this disclosure but in other embodiments there can be one or more arms). These cantilevered arms 4b provide a) electrical contact points for the elastic conductive rubber contacts (that sit on the top side of the array-piece), and b) provide mechanical contact with the electronics unit (which is located beneath the array-piece). Directly underneath the microneedles themselves is a cavity. The arms, however, sit atop an electronic unit. In the integrated device, when a downward force is applied to the microneedles (e.g., from skin being pushed onto the microneedles), the flexible arms are loaded against the electronics unit which in turn causes an upward force to mechanically stabilize the microneedle array.

There are several structural features for microneedle/skin motion artifact interference via dynamic coupling through three distinct mechanisms. The integration and stacking of the disposable piece multilayers create a) flexibility and conformability of the disposable piece, b) insulation against the water, moisture, vapor, dust, and the like, c) single step disposability of the entire disposable embodiment, and d) mitigated motion artifacts. Following is a description of each subcomponent and the structural features as well as the materials properties which support the mechanisms mentioned above.

First, the sloping skin-side of the upper surface 2b of the recessed cover provides a constant skin insertion force while adherence to the skin (constant pushback of the skin/a natural spring on the microneedle array). When the wearable device is first attached to the skin using the adhesive, the skin curves with the surface of the domed surface. Due to the elastic properties of the skin, the skin tries to pull itself back to the body to become flat again. This pulling action is seen towards the edges of the domed surface, with larger pulling forces being caused by greater surface angle, $\alpha$. This pulling from the outer edges causes a net pushing force of the skin found at the center of the dome toward the microneedle array, thus facilitating robust skin-microneedle contact, as shown in FIG. 27, a skin-facing rigid base curving away from the skin along its perimeter at angle $\alpha$.

Next, cantilevered arms 4b of the microneedle array provide the second level of spring-like push-back force from the microneedle base towards the skin that enhances the coupling of the microneedle and skin at the microneedle/skin interface. Accordingly, the mechanical fluctuations/micro-movements caused by the wearer's physical motion are compensated for by the microneedle spring-like base where the elastic stress caused by the pinched skin loads the microneedle cantilevered arms and produces a reaction by the microneedle spring force back to the microneedle and keeps the two being in constant coupling interaction during the wearing of the sensor. Said differently, the process for these forces is as follows: Adhesive keeps the two pieces of skin and microneedle together and the skin depression at the well combines with the domed/curved surface of the rigid piece to create a bump on the skin with a net compression force towards the microneedle which loads the spring arms of the microneedles (strain gauge on the back) and creates a positive net force from the base of the microneedles to the skin. All of this creates the 3rd level mechanism of skin/microneedle coupling. Here, any force incident upon the microneedle array (which has no backing behind it), will load or strain the spring arms, which are backed by ledges found on the electronics unit. This loading will produce an upward force of the array onto (into) the skin.

Immobilization anchoring is enabled by the invention. As a critical component for long term stability of the microneedle functional groups, the surface groups on the sleeve, various embodiments, are modified to optimize the uniformity and thickness of the first immobilization polymer layer. The surface groups therein act as anchors and create specific and non-specific bonding interactions with the immobilized layers. This anchoring also enhances the robustness of sensor and avoids delamination of the layers.

The surface of the cover can be highly manipulated to serve desired outcomes by incorporating materials distinct from the microneedle materials, thus having distinct properties. A schematic of this aspect is shown in FIG. 37. Foam-like, squeezable long sleeves and bodily features 31 can be loaded with drugs or other compounds for many purposes including improved multiplexed sensors (e.g., glucose and lactate), because the diffusion of hydrogen peroxide as by-products between the sensors highly diminishes the accuracy of the measurements. In different embodiments surface hydrophobicity of the sleeve can be adjusted to optimize the uniformity and thickness of the immobilized layers. Foam-like, spongy and porous structure allows loading of materials such as water for skin hydration, pharmaceuticals or other compounds that impact the sensing mechanism constructively. To aid in protecting or concealing the microneedles, for example, foam-like squeezable long sleeves 21 can surround the microneedles. In or on the sleeves, reagents can be loaded which decompose the produced hydrogen peroxide and thus avoid their diffusion between different sensors. One example of hydrogen peroxide decomposing reagents is the enzyme catalase which produces oxygen and ameliorates the common issue of oxygen deficit in oxidase enzyme-based sensors.

In one embodiment the sleeve of the microneedle comprises a polymer comprising cavities containing solutions such as buffers to keep the microneedle sensing layers swollen and hydrated throughout their shelf life. This increases the stability and lifetime of the sensors. The already-hydrated polymer layers on the microneedle sensors reduce warmup times upon their application to the body.

Sleeves greatly improve the mechanical robustness of microneedles due to the bigger stem diameter where sleeve covers the microneedle.

Anchoring from the cover body to the skin reduces noise artifacts caused by wearer's movements and sensors' micromovements on the body. A wide range of anchoring shapes and design are provided in various embodiments.

In various embodiments, pores and cavities may be created on the surface of or in the sleeve or the cover. These cavities can be loaded with reagents that aid in minimizing the biofouling and therefore imparting longer life span to the microneedle-based sensors. Some examples of anti-biofouling reagents are dexamethasone and nitric oxide-releasing chemistry. Upon piercing the skin, microneedles are in contact with the ISF in the epidermis. Some small flow of ISF can occur toward the skin and extend to the microneedle base which causes the formation of a thin layer of fluid being in contact with the cover. Thus, anti-biofouling reagent can diffuse to the fluid and the concentration gradient can cause it to diffuse toward the skin's inner layers. In embodiments such as FIG. 38, the bodily features 31 can be spongy and loaded with a solution containing compounds for many purposes. The spongy features depress and release their contents fully upon pressure to assist the microneedles to pierce the skin.

Gradual release of various agents can be achieved through enteric coating. The anti-biofouling reagent-loaded cavities in some embodiments are coated with biocompatible polymer enteric coatings. Upon contact with the interstitial fluid, the enteric coating gradually dissolves which causes the gradual release of the reagents and their diffusion into the epidermis.

ADDITIONAL EXAMPLES

The invention has many other embodiments besides those disclosed above, including examples 1-49 and others contained herein.

Example 1 is a wearable biosensor device comprising a microneedle array comprising a substrate with microneedles disposed on a top surface of the substrate, said microneedle array comprising an electrically insulative material, and at least a portion of the microneedle array being coated with an electrically conductive layer, wherein at least one of the microneedles is configured as a working electrode to detect an electrical signal from a reaction with a target analyte in a biofluid exposed to the microneedle array, wherein at least one of the microneedles is a working electrode functionalized with at least one chemical layer positioned on top of the electrically conductive layer and configured for producing the electrical signal from a reaction with the target analyte in a biofluid, and the microneedles comprise a base, a body region, and a tip in a tip region, a cover comprising the electrically insulative material coupled with the substrate, the cover having a top surface facing a user's skin and the cover and a set of first openings beyond which the tip region and at least a distal portion of the body region of the microneedles extend, and wherein a cured custom resin is positioned between the microneedle array and the cover and also surrounds the bases of at least some of the microneedles, the cured custom resin insulating and securing the cover to the substrate and the microneedles, and an electronics unit positioned underneath the substrate and connected to the electrically conductive layer by a plurality of electrical interconnections.

Example 2 includes the device of any of examples 1-49 in which the microneedles are differentiated into at least two sensing regions wherein each of the sensing regions comprises at least one of the working electrodes functionalized for a different one of the target analytes.

Example 3 includes the device of any of examples 1-49 in which a bottom portion of the cover and/or the substrate comprise microfluidic channels containing the cured custom resin.

Example 4 includes the device of any of examples 1-49 in which there is a cutoff line on at least some of the microneedles, and the cured custom resin extends upward to the cutoff line of a respective microneedle Example 5 includes the device of any of examples 1-49 in which the body region and the tip region are symmetrical and the tip is off-center.

Example 6 includes the device of any of examples 1-49 in which the tip region comprises at least one major surface and at least one minor surface.

Example 7 includes the device of any of examples 1-49 in which the at least one major surface and minor surface are selected from the group consisting of curved and flat.

Example 8 includes the device of any of examples 1-49 in which an indention is located on a side or area of the microneedles on or near the base, and the indention is configured to guide deflection of the microneedles during insertion of the microneedles into a tissue.

Example 9 includes the device of any of examples 1-49 in which the microneedle array comprises micro-anomalies selected from the group consisting of knobs, cavities, liquid curing to an etchable solid and solid additives.

Example 10 includes the device of any of examples 1-49 in which the body region further comprises at least one sill on a side of the microneedle near the tip region.

Example 11 includes the device of any of examples 1-49 in which at least some of the microneedles have an asymmetric shape.

Example 12 includes the device of any of examples 1-49 in which a force touch sensor is configured to measure force applied during placement or anytime during the life of the device of the microneedle array into skin of a user, the force touch sensor connected electrically to a placement validation circuit within the electronics unit and configured to detect changes in conditions using electromechanical measurement among the microneedles outside the body before insertion and in, during or after insertion within the biofluid, and a feedback indicator connected electrically to the electronics unit and configured to provide to the wearer a notification of excessive or insufficient force in placement and/or of proper placement in the biofluid.

Example 13 includes the device of any of examples 1-49 in which the force touch sensor is selected from the group consisting of sensors for pressure, strain gauge, piezoresistance, resonance, electromagnetic force, capacitive, and a diaphragm-based MEMS sensor operating individually or in combination with each other.

Example 14 includes the device of any of examples 1-49 in which the force touch sensor is configured to transduce an applied force into an electrical parameter selected from the group consisting of resistance, current, capacitance, inductance, frequency or phase shift, voltage variability, optical or thermal changes and magnetic field variations.

Example 15 includes the device of any of examples 1-49 in which the placement validation circuit is configured to use electrochemical techniques selected from the group consisting of impedance spectroscopy, voltammetry, potentiometry and/or amperometry.

Example 16 includes the device of any of examples 1-49 in which the feedback indicator comprises a physical or virtual device configured to generate a notification selected from the group consisting of a microelectromechanical system (MEMS) speaker, a vibration actuator, and a light-emitting diode (LED) on the wearable device and a notification through Bluetooth or similar signals to a mobile device containing an app.

Example 17 includes the device of any of examples 1-49 in which the vibration actuator is selected from the group consisting of an eccentric rotating mass actuator (ERM), a linear resonant actuator (LRA), a piezoelectric actuator, electroactive polymers (EAPs), microelectromechanical systems (MEMS), a tactile haptic-based oscillation/resonance actuator and a voice coil actuator.

Example 18 includes the device of any of examples 1-49 in which a driving signal of the vibration actuator is selected from the group consisting of amplitude, frequency and on/off keying.

Example 19 includes the device of any of examples 1-49 in which the notification is selected from the group of a sound, a light, a vibration or a message delivered to the app on the mobile device.

Example 20 includes the device of any of examples 1-49 in which the force touch sensor is also configured as a switch to turn the device on or off.

Example 21 includes the device of any of examples 1-49 in which the cover further comprises sleeves positioned on the top surface around at least a portion of the first openings, and there is a gap between an inner surface of each of the sleeves and an outer surface of the microneedles, the cured custom resin filling the gap, surrounding the base of the microneedle, sealing the gaps and strengthening the microneedle array, and creating passivation of the microneedles leaving reproducible surface area of the electrically conductive layer on the microneedles.

Example 22 includes the device of any of examples 1-49 in which each of the sleeves has a width, a height and an angle configured to modify insertion of the microneedles into the user's skin.

Example 23 includes the device of any of examples 1-49 in which the cover further comprises at least one bodily feature positioned on the top surface extending toward the user's skin.

Example 24 includes the device of any of examples 1-49 in which the at least one bodily feature comprises an absorbable, elastically deforming and spongy material.

Example 25 includes the device of any of examples 1-49 in which the at least one bodily feature is impregnated with a fluid which may be released when pressure is applied.

Example 26 includes the device of any of examples 1-49 in which the top surface of the cover further comprises at least one conductive trace.

Example 27 includes the device of any of examples 1-49 in which n the conductive trace is configured as a non-analyte sensor to sense non-analyte conditions selected from the group consisting of perspiration, force touch, heat and shock, and further configured to send the non-analyte information to the signal processing circuit of the electronics unit for modification of the electrical signals associated with analyte reactions detectable at the working electrode.

Example 28 includes the device of any of examples 1-49 in which the conductive trace is configured as an additional analyte sensor, and is further configured to send additional analyte information to the signal processing circuit of the electronics unit for modification of the electrical signals associated with analyte reactions detectable at the working electrode.

Example 29 includes the device of any of examples 1-49 in which the cover is a recessed cover comprising an upper surface integral with and surrounding a lower surface comprising the set of first openings.

Example 30 includes the device of any of examples 1-49 in which the upper surface and the lower surface are joined by a slope.

Example 31 includes the device of any of examples 1-49 in which the recessed cover further comprises a fillet at an inner boundary of the upper surface configured to pinch the user's skin, to stretch the user's skin where the microneedles are inserted into the skin and to secure the microneedles at an insertion location of the user's skin.

Example 32 includes the device of any of examples 1-49 in which the upper surface of the recessed cover is higher at the fillet than at an outer edge of the recessed cover.

Example 33 includes the device of any of examples 1-49 in which the slope between the upper surface and the lower surface of the recessed cover comprises one or more gradients.

Example 34 includes the device of any of examples 1-49 in which the cover is an elevated cover wherein the set of first openings is positioned within a raised panel, the raised panel being integral with and surrounded by a bottom panel, and an outer border of the raised panel is configured to pinch the user's skin, to stretch the user's skin where the microneedles are inserted into the skin and to secure the microneedles at an insertion location of the user's skin.

Example 35 includes the device of any of examples 1-49 in which some of the microneedles are coated with an outer enteric layer.

Example 36 includes the device of any of examples 1-49 in which the outer enteric layer on some of the microneedles varies in composition and thickness from the outer enteric layer on other of the microneedles.

Example 37 includes the device of any of examples 1-49 in which an electrical protective system for the microneedles is configured to prevent biofouling, wherein the electrical protective system comprises circuitry for anodic protection or alternating current delivered to at least some of the microneedles.

Example 38 includes the device of any of examples 1-49 in which the microneedles prior to insertion into the skin are enclosed within a hydration chamber configured to maintain an internal humidity level.

Example 39 includes the device of any of examples 1-49 in which the hydration chamber comprises a moisture system comprising a moisture sensor configured to monitor the internal humidity level, a pump and a reservoir for one or more additives to circulate within the hydration chamber.

Example 40 includes the device of any of examples 1-49 in which the microneedles are coated with a hydrogel layer prior to insertion.

Example 41 includes the device of any of examples 1-49 in which at least some of the microneedles are tapered having an aspect ratio of at least one.

Example 42 includes the device of any of examples 1-49 in which the microneedles are implanted by pressure applied manually without the assistance of a mechanical applicator.

Example 43 includes the device of any of examples 1-49 in which at least one foldable cover is overlaid onto the microneedle array comprising a foldable nonconductive polymer and complex openings, and each of the complex openings is configured to allow one of the microneedles to extend above the foldable cover.

Example 44 includes the device of any of examples 1-49 in which each of the complex holes comprises a center opening and radiating openings from the center opening, the radiating openings defined by petal-like portions positioned around the center opening of the complex hole.

Example 45 includes the device of any of examples 1-49 in which the petal-like portions of one of the complex holes are folded upward around one of the microneedles and provide the cutoff line for cured resin.

Example 46 includes the device of any of examples 1-49 in which each of the electrical connections comprises a contact terminus comprising an electrically-conductive and mechanically frictionous contact pad on walls of a hole in or on the substrate, and wherein the frictionous contact pad is electrically connected to the electrically conductive layer, and a rigid or flexible conductive pin is connected with a friction fit at one end compressed to the frictionous contact pad and electrically connected at another end to the electronics unit.

Example 47 includes the device of any of examples 1-49 in which the electronics unit comprises a data processing unit in communication with a signal processing circuit, the data processing unit comprising a processor and a memory and configured to process the electrical signal as data representative of one or more parameters of the target analyte.

Example 48 includes the device of any of examples 1-49 in which the signal processing circuit is configured to process the electrical signal by one or more of amplifying the electrical signal, filtering the electrical signal, or converting the electrical signal from analog to digital, and wherein the data processing unit is configured to process the electrical signal after processing by the signal processing circuit.

Example 49 includes the device of any of examples 1-49 in which the electronics unit further comprises a wireless communication unit in communication with one or both of the signal processing circuit and the data processing unit, the wireless communication unit comprising a wireless transmitter or wireless transceiver to at least transmit one or both of the electrical signal and the data to an external computing device.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not always be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A wearable biosensor device comprising
a microneedle array comprising a substrate with microneedles disposed on a top surface of the substrate, said microneedle array comprising an electrically insulative material, and at least a portion of the microneedle array being coated with at least one electrically conductive layer, wherein at least one of the microneedles is configured as a working electrode functionalized with at least one chemical layer comprising compounds configured to interact with target analytes in a bodily tissue to produce an electrical signal, and the microneedles comprise a base, a body region, and a tip region comprising a tip,
a foldable cover comprising a foldable nonconductive polymer overlaid onto the substrate, the foldable cover further comprising a top surface facing a user's skin and a set of complex openings beyond which the tip region and at least a distal portion of the body region of the microneedles extend, and wherein a cured resin is positioned between the microneedle array and the foldable cover and also surrounds the bases of at least some of the microneedles, the cured resin insulating and securing the foldable cover to the substrate and the microneedles, and
an electronics unit positioned underneath the substrate and connected to the electrically conductive layer by a plurality of electrical interconnections.

2. The device of claim 1, wherein the microneedles are differentiated into at least two sensing regions wherein each of the sensing regions comprises at least one of the working electrodes functionalized for a different one of the target analytes.

3. The device of claim 1 wherein a bottom portion of the foldable cover and/or the substrate comprise microfluidic channels containing the cured resin.

4. The device of claim 1 further comprising a cutoff line on at least some of the microneedles, and the cured resin extends upward to the cutoff line.

5. The device as in claim 1 wherein at least some of the microneedles comprises micro-anomalies selected from the group consisting of knobs, cavities, liquid curing to an etchable solid and solid additives.

6. The device as in claim 1 wherein at least some of the body regions further comprises at least one sill on a side of the microneedle near the major surface of the tip region.

7. The device of claim 1 further comprising a force touch sensor configured to measure force applied during insertion into the user's skin or anytime during use of the device, the force touch sensor connected electrically to a placement validation circuit within the electronics unit and configured to detect changes in conditions using electromechanical measurement among the microneedles outside the body before insertion and in, during or after insertion within the bodily tissue, and a feedback indicator connected electrically to the electronics unit and configured to provide to the user a notification of excessive or insufficient force in insertion and/or of proper insertion in the bodily tissue.

8. The device as in claim 1 wherein the top surface of the foldable cover further comprises at least one conductive trace.

9. The device as in claim 8 wherein the conductive trace is configured as a non-analyte sensor to sense non-analyte information selected from the group consisting of perspiration, force touch, heat and shock, and further configured to send the non-analyte information to the signal processing circuit of the electronics unit for modification of the electrical signal at the at least one working electrode.

10. The device as in claim 8 wherein the conductive trace is configured as an additional analyte sensor.

11. The device of claim 1 wherein the foldable cover is a recessed foldable cover comprising an upper surface integral with and surrounding a lower surface comprising the set of complex openings and an outer border of the lower surface is configured to compress the user's skin, to stretch the user's skin where the microneedles are inserted into the skin and to secure the microneedles at an insertion location of the user's skin.

12. The device of claim 1 wherein the foldable cover is an elevated foldable cover wherein the set of complex openings is positioned within a raised panel, the raised panel being integral with and surrounded by a bottom panel, and an outer border of the raised panel is configured to compress the user's skin, to stretch the user's skin and to secure the microneedles in place.

13. The device as in claim 1 wherein some of the microneedles are coated with an outer enteric layer configured to degrade in a controlled manner after insertion into the bodily tissue.

14. The device as in claim 13 wherein the outer enteric layer on some of the microneedles varies in composition and thickness from the outer enteric layer on other of the microneedles.

15. The device as in claim 1 further comprising an electrical protective system for the microneedles configured to prevent biofouling, wherein the electrical protective system comprises circuitry for anodic protection or alternating current delivered to at least some of the microneedles.

16. The device as in claim 1 further comprising a hydration chamber enclosing the microneedles prior to insertion into the skin and the hydration chamber is configured to maintain an internal humidity level.

17. The device as in claim 16 wherein the hydration chamber comprises a moisture system comprising a moisture sensor configured to monitor the internal humidity level, a pump and a reservoir for one or more additives to circulate within the hydration chamber.

18. The device as in claim 1 configured for the microneedles to be implanted by pressure applied manually without assistance of a mechanical applicator.

19. The device as in claim 1 wherein each of the complex openings comprises a center opening and radiating openings from the center opening, the radiating openings defined by petal-like portions positioned around the center opening of the complex opening.

20. The device of claim 1, wherein the electronics unit comprises a data processing unit in communication with a signal processing circuit, the data processing unit comprising a processor and a memory and configured to process the electrical signal as data representative of one or more parameters of the target analyte.

21. The device of claim 20, wherein the signal processing circuit is configured to process the electrical signal by one or more of amplifying the electrical signal, filtering the electrical signal, or converting the electrical signal from analog to digital, and wherein the data processing unit is configured to process the electrical signal after processing by the signal processing circuit.

22. The device of claim 20, wherein the electronics unit further comprises a wireless communication unit in communication with one or both of the signal processing circuit and the data processing unit, the wireless communication unit comprising a wireless transmitter or wireless transceiver to at least transmit one or both of the electrical signal and the data to an external computing device.

23. The device of claim 1 wherein at least some of the microneedles are further configured to guide deflection during insertion into the bodily tissue wherein at least some of the tips are off-center within the tip region further comprising at least one major surface and at least one minor surface.

24. The device of claim 23 wherein at least some of the body regions of the microneedles comprise an indention on or near the base and opposite the at least one major surface.

25. The device of claim 1 wherein the cured resin passivates the microneedles and leaves reproducible surface area of the electrically conductive layer on the microneedles.

\* \* \* \* \*